(12) United States Patent
Peters

(10) Patent No.: US 11,873,334 B2
(45) Date of Patent: *Jan. 16, 2024

(54) METHOD OF TREATING OCULAR CONDITIONS BY ADMINISTERING AN ANTIBODY THAT ACTIVATES TIE2 AND BINDS VEGF

(71) Applicant: EyePoint Pharmaceuticals, Inc., Watertown, MA (US)

(72) Inventor: Kevin Peters, Cincinnati, OH (US)

(73) Assignee: EYEPOINT PHARMACEUTICALS, INC., Watertown, MA (US)

( * ) Notice: Subject to any disclaimer, the term of this patent is extended or adjusted under 35 U.S.C. 154(b) by 335 days.

This patent is subject to a terminal disclaimer.

(21) Appl. No.: 17/117,993

(22) Filed: Dec. 10, 2020

(65) Prior Publication Data

US 2021/0171618 A1 Jun. 10, 2021

Related U.S. Application Data

(63) Continuation of application No. 16/579,078, filed on Sep. 23, 2019, now Pat. No. 10,894,824.

(60) Provisional application No. 62/832,461, filed on Apr. 11, 2019, provisional application No. 62/735,331, filed on Sep. 24, 2018.

(51) Int. Cl.
| | |
|---|---|
| *C07K 16/22* | (2006.01) |
| *C07K 16/40* | (2006.01) |
| *A61K 9/00* | (2006.01) |

(52) U.S. Cl.
CPC ............. *C07K 16/22* (2013.01); *C07K 16/40* (2013.01); *A61K 9/0019* (2013.01); *A61K 9/0048* (2013.01); *C07K 2317/31* (2013.01); *C07K 2317/35* (2013.01); *C07K 2317/51* (2013.01); *C07K 2317/92* (2013.01)

(58) Field of Classification Search
CPC .... C07K 16/22; C07K 16/40; C07K 2317/31; C07K 2317/35; C07K 2317/51; C07K 2317/92; A61K 9/0019; A61K 9/0048
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwasaki et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,625,825 | A | 4/1997 | Rostoker et al. |
| 6,133,426 | A | 10/2000 | Gonzalez et al. |
| 6,407,213 | B1 | 6/2002 | Carter et al. |
| 7,226,755 | B1 | 6/2007 | Peters et al. |
| 7,374,758 | B2 | 5/2008 | Papadopoulos et al. |
| 7,758,859 | B2 | 7/2010 | Fuh et al. |
| 7,973,142 | B2 | 7/2011 | Rotello et al. |
| 8,258,268 | B2 | 9/2012 | Wu et al. |
| 8,349,322 | B2 | 1/2013 | Borras et al. |
| 8,524,235 | B2 | 9/2013 | Rotello et al. |
| 8,901,076 | B2 | 12/2014 | Binz et al. |
| 8,999,325 | B2 | 4/2015 | Peters et al. |
| 9,174,950 | B2 | 11/2015 | Shalwitz et al. |
| 9,403,789 | B2 | 8/2016 | Eissenstat et al. |
| 9,458,211 | B1 | 10/2016 | Bakker et al. |
| RE46,592 | E | 10/2017 | Gray et al. |
| 9,795,594 | B2 | 10/2017 | Gray et al. |
| 9,926,367 | B2 | 3/2018 | Rotello et al. |
| 9,968,674 | B2 | 5/2018 | Ioffe et al. |
| 10,035,850 | B2 | 7/2018 | Gekkieva et al. |
| 10,150,811 | B2 | 12/2018 | Peters et al. |
| 10,220,048 | B2 | 3/2019 | Peters et al. |
| 10,253,094 | B2 | 4/2019 | Peters et al. |
| 10,276,202 | B1 | 4/2019 | Jubert et al. |
| 10,329,357 | B2 | 6/2019 | Peters et al. |
| 10,463,650 | B2 | 11/2019 | Gray et al. |
| 10,464,992 | B2 | 11/2019 | Furfine et al. |
| 10,597,452 | B2 | 3/2020 | Peters et al. |
| 10,604,569 | B2 | 3/2020 | Peters et al. |
| 10,646,542 | B2 | 5/2020 | Binz et al. |
| 10,815,300 | B2 | 10/2020 | Peters |
| 10,894,824 | B2 | 1/2021 | Peters |
| 11,136,986 | B2 | 10/2021 | Peters |
| 11,180,551 | B2 | 11/2021 | Peters et al. |
| 2003/0158083 | A1 | 8/2003 | Peters |

(Continued)

FOREIGN PATENT DOCUMENTS

| | | |
|---|---|---|
| CN | 101802002 A | 8/2010 |
| CN | 107602702 A | 1/2018 |

(Continued)

OTHER PUBLICATIONS

Campochiaro PA and Peters KG (2016) Curr Diab Rep. 16(126). 11 pages. (DOI 10.1007/s11892-016-0816-5).*
Kim J, et al. (Oct. 2, 2017) J Clin Invest. 127(10):3877-3896. (Published online Sep. 18, 2017. doi: 10.1172/JCI94668).*
Takagi H, et al. (Jan. 2003) Investigative Opthamologistl Science. 44(1):393-402. (DOI:10.1167/iovs.02-0276).*
Campochiaro PA , et al. (2015) American Academy of Opthamology 122(3):545-554 (doi: 10.1016/j.ophtha.2014.09.023).*
Brigell MG, et al. (Apr. 2014) Investigative Opthamologistal Science. 55(13). MA 1757.*
Shen J-K, et al. (Jun. 2013) Investigative Ophthalmology & Visual Science. 54(15). MA 6094.*
Attwood. Genomics. The Babel of bioinformatics. Science. Oct. 20, 2000;290(5491):471-3.

(Continued)

*Primary Examiner* — Robert S Landsman
(74) *Attorney, Agent, or Firm* — Sterne, Kessler, Goldstein & Fox P.L.L.C.

(57) ABSTRACT

The disclosure provides compositions comprising multi-specific compounds, including a compound that targets a phosphatase and a receptor tyrosine kinase agonist. Also provided are methods for the treatment of conditions associated with angiogenesis, comprising administering a multi-specific compound that targets a phosphatase and a receptor tyrosine kinase agonist.

19 Claims, 29 Drawing Sheets

Specification includes a Sequence Listing.

(56) References Cited

U.S. PATENT DOCUMENTS

| | | |
|---|---|---|
| 2003/0215899 A1 | 11/2003 | Meng et al. |
| 2004/0077065 A1 | 4/2004 | Evdokimov et al. |
| 2004/0254197 A1 | 12/2004 | Tasaka et al. |
| 2005/0059639 A1 | 3/2005 | Wei |
| 2007/0134234 A1 | 6/2007 | Smith et al. |
| 2007/0154482 A1 | 7/2007 | Sukhatme et al. |
| 2007/0299116 A1 | 12/2007 | Gray et al. |
| 2008/0004267 A1 | 1/2008 | Gray et al. |
| 2008/0108631 A1 | 5/2008 | Gray et al. |
| 2009/0022715 A1 | 1/2009 | Rotello et al. |
| 2009/0227639 A1 | 9/2009 | Gray et al. |
| 2009/0246206 A1 | 10/2009 | Nielsen et al. |
| 2010/0030487 A1 | 2/2010 | Evdokimov et al. |
| 2010/0069448 A1 | 3/2010 | Gray et al. |
| 2010/0111894 A1 | 5/2010 | Benny-Ratsaby et al. |
| 2010/0256147 A1 | 10/2010 | Hangauer |
| 2011/0212951 A1 | 9/2011 | Gray et al. |
| 2011/0268656 A1 | 11/2011 | Ho et al. |
| 2011/0268694 A1 | 11/2011 | Shalwitz et al. |
| 2011/0274699 A1 | 11/2011 | Rotello et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2012/0237442 A1 | 9/2012 | Rossi et al. |
| 2013/0023543 A1 | 1/2013 | Gray et al. |
| 2013/0095105 A1 | 4/2013 | Peters et al. |
| 2013/0096140 A1 | 4/2013 | Gray et al. |
| 2013/0324558 A1 | 12/2013 | Gray et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2015/0065781 A1 | 3/2015 | Bais et al. |
| 2015/0210656 A1 | 7/2015 | Gray et al. |
| 2015/0297675 A1 | 10/2015 | Osborne |
| 2016/0008327 A1 | 1/2016 | Shalwitz et al. |
| 2016/0030393 A1 | 2/2016 | Breslin et al. |
| 2016/0038467 A1 | 2/2016 | Peters |
| 2016/0075797 A1 | 3/2016 | Weaver et al. |
| 2016/0082129 A1 | 3/2016 | Peters |
| 2016/0130337 A1 | 5/2016 | Gekkieva et al. |
| 2016/0251421 A1 | 9/2016 | Brown et al. |
| 2016/0333090 A1 | 11/2016 | Horlick et al. |
| 2016/0340420 A1 | 11/2016 | Zhang et al. |
| 2017/0096479 A1 | 4/2017 | Koenig et al. |
| 2017/0260265 A1 | 9/2017 | Duerr et al. |
| 2017/0275353 A1 | 9/2017 | Sheng et al. |
| 2017/0298019 A1 | 10/2017 | Gardner et al. |
| 2017/0319602 A1 | 11/2017 | Peters et al. |
| 2017/0349649 A1 | 12/2017 | Rotello et al. |
| 2018/0009890 A1 | 1/2018 | Peters et al. |
| 2018/0022741 A1 | 1/2018 | Peters et al. |
| 2018/0022804 A1 | 1/2018 | Peters et al. |
| 2018/0037579 A1 | 2/2018 | Peters et al. |
| 2018/0044432 A1 | 2/2018 | Peters et al. |
| 2018/0092883 A1 | 4/2018 | Peters et al. |
| 2018/0207233 A1 | 7/2018 | Rudolf et al. |
| 2018/0221346 A1 | 8/2018 | Gray et al. |
| 2018/0237429 A1 | 8/2018 | Peters et al. |
| 2018/0237430 A1 | 8/2018 | Peters et al. |
| 2018/0251457 A1 | 9/2018 | Peters et al. |
| 2018/0353614 A1 | 12/2018 | Peters |
| 2019/0023773 A1 | 1/2019 | Rotello et al. |
| 2019/0046609 A1 | 2/2019 | Yancopoulos |
| 2019/0076405 A1 | 3/2019 | Shalwitz et al. |
| 2019/0077862 A1 | 3/2019 | Peters et al. |
| 2019/0077863 A1 | 3/2019 | Peters et al. |
| 2019/0218282 A1 | 7/2019 | Dengl et al. |
| 2019/0256889 A1 | 8/2019 | Quaggin |
| 2019/0290725 A1 | 9/2019 | Vitti et al. |
| 2019/0343918 A1 | 11/2019 | Graham et al. |
| 2019/0381008 A1 | 12/2019 | Zeitz et al. |
| 2020/0087412 A1 | 3/2020 | Fang et al. |
| 2020/0115455 A1 | 4/2020 | Bedi et al. |
| 2020/0140547 A1 | 5/2020 | Bedi et al. |
| 2021/0095017 A1 | 4/2021 | Peters et al. |
| 2021/0171618 A1 | 6/2021 | Peters |

FOREIGN PATENT DOCUMENTS

| | | |
|---|---|---|
| EP | 2592073 B1 | 8/2017 |
| EP | 2846836 B1 | 8/2019 |
| EP | 3628324 A1 | 4/2020 |
| WO | WO 9312227 A1 | 6/1993 |
| WO | WO 9631598 A1 | 10/1996 |
| WO | WO-9845331 A3 | 12/1998 |
| WO | WO 0224782 A1 | 3/2002 |
| WO | WO 2007033216 A2 | 3/2007 |
| WO | WO 2007087457 A2 | 8/2007 |
| WO | WO-2007116360 A2 | 10/2007 |
| WO | WO-2008132568 A2 | 11/2008 |
| WO | WO 2009006112 A1 | 1/2009 |
| WO | WO 2009055343 A2 | 4/2009 |
| WO | WO 2009136352 A1 | 11/2009 |
| WO | WO-2010040508 A1 | 4/2010 |
| WO | WO-2010060748 A1 | 6/2010 |
| WO | WO 2011087066 A1 | 7/2011 |
| WO | WO-2011135067 A1 | 11/2011 |
| WO | WO-2013056233 A1 | 4/2013 |
| WO | WO-2013056240 A1 | 4/2013 |
| WO | WO-2015109898 A1 | 7/2015 |
| WO | WO 2016049183 A1 | 3/2016 |
| WO | WO-2016115092 A1 | 7/2016 |
| WO | WO-2017035430 A2 | 3/2017 |
| WO | WO-2018017714 A1 | 1/2018 |
| WO | WO-2018067646 A1 | 4/2018 |
| WO | WO-2018229034 A1 | 12/2018 |
| WO | WO-2019168947 A1 | 9/2019 |
| WO | WO-2019175727 A1 | 9/2019 |
| WO | WO-2019222547 A1 | 11/2019 |
| WO | WO 2020068653 A1 | 2/2020 |

OTHER PUBLICATIONS

Campbell. Chapter 1: General properties and applications of monoclonal antibodies. Monoclonal Antibody Technology. Elsevier Science Publishers, The Netherlands, (pp. 1-32) (1984).

Clarke, JM et al., Targeted inhibition of VEGF Receptor-2: An update on Ramucirumab, Expert Opin Biol. Ther. /Aug. 2013; 13(8): 1187-1196. doi:10.1517/14712598.2013.810717.

Colman et al., Effects of amino acid sequence changes on antibody-antigen interactions, Research in Immunology, 1994; 145(1):33-36.

Crescioli, Silvia et al., IgG4 Characteristics and Functions in Cancer Immunity, Curr Allerty Asthma Rep (2016) 16:7.

Goel, et al. Effects of vascular-endothelial protein tyrosine phosphatase inhibition on breast cancer vasculature and metastatic progression. J Natl Cancer Inst. Aug. 21, 2013;105(16):1188-201. doi: 10.1093/jnci/djt164. Epub Jul. 30, 2013.

Golay, et al. Mechanism of action of therapeutic monoclonal antibodies: promises and pitfalls of in vitro and in vivo assays. Arch Biochem Biophys. Oct. 15, 2012;526(2):146-53. doi: 10.1016/j.abb.2012.02.011. Epub Feb. 25, 2012.

Houghten, et al. New Approaches to Immunization, Vaccines 86, Cold Spring Harbor Laboratory, p. 21-25, 1986.

International Search Report and Written Opinion dated Feb. 5, 2020, for PCT/US19/52405.

International Union of Basic and Clinical Pharmacology (IUPHAR) /British Pharmacological Society (BPS) Guide to Pharmacology Database: Ligand ID: 8371, International Non-proprietary Name: abicipar pegol, Synonyms: AGN-150998| MP0122; Specialist databases: IMGT/mAb-DB477, GtoPdb PubChem SID: 252166583; Link https://www.guidetopharmacology.org/GRAC/LigandDisplayForward?tab=summary&ligandId=8371, printed Jun. 15, 2020.

International Union of Basic and Clinical Pharmacology (IUPHAR) /British Pharmacological Society (BPS) Guideto Pharmacology Database: Ligand ID: 8371, International Non-proprietary Name: abicipar pegol, Biological activity: Peptide Sequence;

(56) References Cited

OTHER PUBLICATIONS https://www.guidetopharmacology.org/GRAC/LigandDisplayForward?tab=structure&ligandId=8371printed6/15/20 (MV R329387).
International Union of Basic and Clinical Pharmacology (IUPHAR)/British Pharmacological Society (BPS) Guideto Pharmacology Database: Ligand ID: 8371, International Non-proprietary Name: abiciparpegol, Target: VEGFA, printed Jun. 15, 2020:https://www.guidetopharmacology.org/GRAC/LigandDisplayForward?tab=biology&ligandId=8371.
International Union of Basic andClinical Pharmacology (IUPHAR)/British Pharmacological Society (BPS)Guideto Pharmacology Database: Ligand ID: 8371, Intl Non-proprietary Name: abicipar pegol, Clinical Data; Summary of Clinical Use, and Mechanism of Action andPharmacodynamic Effects; Link:Jun. 15, 2020:https://www.guidetopharmacology.org/GRAC/LigandDisplayForward?tab=biology&ligandId=8371, Printed Jun. 15, 2020.
IUPHAR/BPS Guide to Pharmacology database for Ligand ID: 8371, Name: abicipar pegol, available at https://www.guidetopharmacology.org/GRAC/LigandDisplayForward?tab=summary&ligandId=8371 , 5 pages, Printed Nov. 21, 2019.
Kienast, Y. et al., Ang-2-VEGF-A CrossMab, a Novel Bispecific Human IgG1 Antibody Blocking VEGF-A and Ang-2 Functions Simultaneously, Mediates Potent antitumor, Antiangiogenic, and Antimetastic Efficascy, Clinical Cancer Resarch, Oct. 4, 2013, vol. 19 No. 24, pp. 6730-6740; Abstract p. 6730, col. 2, Paragraph 2, Supplementary Figure 1; DOI 10.1158/1078-0432.CCR-13-0081.
Nguyen, et al. Vascular endothelial growth factor is a critical stimulus for diabetic macular edema. Am J Ophthalmol. Dec. 2006;142(6):961-9. Epub Aug. 2, 2006.
Owens, et al. The genetic engineering of monoclonal antibodies. J Immunol Methods. Feb. 10, 1994;168(2):149-65.
Paul. Fundamental Immunology. Chapter 8 Immunogenicty and antigen structure., 3d ed., p. 242, 1993.
Rudikoff et al. Single amino acid substitution altering antigen-binding specificity. PNAS USA 79:1979-1983 (1982).
Shen, et al. Targeting VE-PTP activates TIE2 and stabilizes the ocular vasculature. J Clin Invest. Oct. 2014;124(10):4564-76.
Silva, Raquel Lima et al., Tyrosine blocking collagen IV-derived peptide suppresses ocular neovascularization and vascular leakage, Sci Transl Med. Jan. 18, 2017; 9(373). doi:10.1126/scitranslmed.aai8030.
Simeon, Rudo et al., In vitro-engineered non-antibody protein therapeutics, Protein Cell 218, 9(1);3-14.
Skolnick, et al. From genes to protein structure and function: novel applications of computational approaches in the genomic era. Trends Biotechnol. Jan. 2000;18(1):34-9.
Tam, Susan H. et al., Functional Biophysical, and Structural Characterization of Human IgG1 and Ig4Fc Variants with Ablated Immune Functionality, Antibodies 2017, 6 12: doi:10.3390/antib6030012.
Trieu, Michelle et al., Vasculotide, an Angiopoietin-1, Mimetic, Restores Microcirculatory Perfusion and Microvascular Leakage and Decreases Fluid Resuscitation Requirements in Hemorrhagic Shock, Anesthesiology, V. 128, No. 2, p. 361, Feb. 2018.
Van Der Flier, et al. Antibody neutralization of vascular endothelial growth factor (VEGF) fails to attenuate vascular permeability and brain edema in experimental pneumococcal meningitis. J Neuroimmunol. Mar. 2005; 160(1-2):170-7.
Wang, Qin, et al., Novel VEGF Decoy Receptor Fusion Protein Conbercept Targeting Multiple VEGR Isoforms Provide Remarkable Anti-Angiogenesis Effect in Viv, Aug. 2013: PLOS ONE, vol. 8, Issue 8.
Wang, Xinhua et al, IgG engineering to modulate antibody effector functions, Genetech,Protein Cell 2018; 9(1:)63-73; DOI 10.107/sAcceptd Jun. 19, 2017.
Witte, et al. Monoclonal antibodies targeting the VEGF receptor-2 (Flk1/KDR) as an anti-angiogenic therapeutic strategy. Cancer Metastasis Rev. Jun. 1998; 17(2):155-61.

Wu et al. Humanization of a murine monoclonal antibody by simultaneous optimization of framework and CDR residues. J.Mol. Biol. 294:151-162 (1999).
Yang, Jihong et al., Comparison of Binding Characteristics and In Vitro Activities of Three Inhibitors of Vascular Endothelial Grow Factor A, Molecular Pharmaceutics, 2014, American Chemical Society, 3421-3430.
Yu et al., Interaction between Bevacizumab and Murine VEGF-A: A Reassessment, Investigative Ophthalmology & Visual Science, 2008, vol. 49 (2), pp. 522-527.
Amarasinghe,K.K.D., et al., Design and synthesis of potent, non-peptidic inhibitors of HPTPβ, Bioorganic & Medicinal Chemistry Letters, 16:4252-4256, Elsevier, Netherlands (2006).
Baumer, S., et al., "Vascular endothelial cell-specific phosphotyrosine phosphatase (VEPTP) activity is required for blood vessel development," Blood 107(12):4754-4762, The American Society of Hematology, United States (Jun. 2006).
Bosse, R. and Vestweber D., "Only simultaneous blocking of the L- and P-selectin completely inhibits neutrophil C migration into mouse peritoneum", Eur. J. Immunol. 24:3019-3024, VCH Verlagsgesellschaft mbH, Germany (1994).
Broermann, A., et al., "Dissociation of VE-PTP from VE-cadherin is required for leukocyte extravasation and for VEGF-induced vascular permeability in vivo," J Exp Med. 208(12):2393-401, The Rockefeller University Press, United States (Nov. 2011).
Campbell,A.M., "Monoclonal Antibody Technology," Chapter 1, pp. 1-32, Elsevier, Inc., Netherlands (1984).
Campochiaro, P.A., et al., "Enhanced Benefit in Diabetic Macular Edema from AKB-9778 Tie2 Activation Combined with Vascular Endothelial Growth Factor Suppression. Ophthalmology," 123(8):1-9, Elsevier, Inc., Netherlands (Aug. 2016).
Clackson, T., et al., "Making antibody fragments using phage display libraries," Nature. 352(6336):624-628, Nature Research, United Kingdom (Aug. 1991).
Co-Pending U.S. Appl. No. 17/804,396, inventors Peters, K., et al., filed May 27, 2022 (Not yet Published).
Doukas, J., et al., "Topical administration of a multi-targeted kinase inhibitor suppresses choroidal neovascularization and retinal edema," J Cell Physiol. 216(1):29-37, Author Manuscript, John Wiley & Sons, Inc., United States (Jul. 2008).
Edwards, B.M., et al., "The remarkable flexibility of the human antibody repertoire; isolation of over one thousand different antibodies to a single protein, BLyS," J Mol Biol 334(1):103-18, Elsevier, Netherlands (Nov. 2003).
Elias, L. and Hunt, W.C., "A literature analysis of prognostic factors for response and quality of response of patients with renal cell carcinoma to interleukin-2-based therapy," Oncology 61(2):91-101, S. Karger AG, Basel (2001).
Frye, M., et al., "Interfering with VE-PTP stabilizes endothelial junctions in vivo via Tie-2 in the absence ofVE-cadherin," JEM 212(13):2267-2287, The Rockefeller University Press, United States (Dec. 2015).
Fukuhara, S. and Mochizuki, N., "Vascular endothelial cells and adjoining cells for their mutual adhesion/interaction for stabilization and angiogenesis," Seikagaku. The Journal of Japanese Biochemical Society 82(4):290-301, Japanese Biochemical Society, Japan (Apr. 2010).
Fukuhara, S., et al., "Differential function of Tie2 at cell-cell contacts and cell-substratum contacts regulated by angiopoietin-1," Nat Cell Biol. 10(5):513-526, Nature Publishing Group, Germany (May 2008).
Gallagher, D.C., et al., "Angiopoietin 2 is a Potential Mediator of High-Dose Interleutkin 2-Induced Vascular Leak," Clin Cancer Res 13(7):2115-2120, American Association for Cancer Research, United States (Apr. 2007).
Gotsch, U., et al., "VE-cadherin antibody accelerates neutrophil recruitment in vivo," J Cell Sci. 110:583-588, The Company of Biologists Limited, Great Britain (Mar. 1997).
Gozes, Y., et al., "Anthrax Lethal Toxin Induces Ketotifen-Sensitive Intradermal Vascular Leakage in Certain Inbred Mice," Infect Immun. 74(2):1266-1272, The American Society for Microbiology, United States (Feb. 2006).

(56) References Cited

OTHER PUBLICATIONS

Gurnik, S., et al., "Angiopoietin-2-induced blood-brain barrier compromise and increased stroke size are rescued by VE-PTP-dependent restoration of Tie2 signaling," Acta Neuropathol 131(5):753-773, Springer, Germany (May 2016).

Hayashi, M., et al., VE-PTP regulates VEGFR2 activity in stalk cells to establish endothelial cell polarity and lumen formation. Nat Commun. 4:1672, Macmillan Publishing Limited, United Kingdom (2013).

Hudson, P.J. and Souriau, C., "Engineered antibodies," Nat Med. 9(1):129-34, Nature Publishing Group, Germany (Jan. 2003).

Imamura, T., et al., "Induction of vascular leakage through release of bradykinin and a novel kin in by cysteine proteinases from *Staphylococcus aureus*," J Exp Med. 201(10):1669-1676, The Rockefeller University Press, United States (May 2005).

International Search Report and Written Opinion for International Application No. PCT/US2012/060263, U.S. Patent and Trademark Office, Alexandria, VA, dated Dec. 6, 2012, 7 pages.

International Search Report and Written Opinion for International Application No. PCT/US2012/060273, U.S. Patent and Trademark Office, Alexandria, VA, dated Dec. 24, 2012, 9 pages.

International Search Report and Written Opinion for International Application No. PCT/US2017/042855, U.S. Patent and Trademark Office, Alexandria, VA, dated Dec. 26, 2017, 21 pages.

Jubala, C.M., et al., "CD20 expression in normal canine B cells and in canine non-Hodgkin Lymphoma," Vet Pathol. 42(4):468-476, SAGE Publications, New York (Jul. 2005).

Kipriyanov, S.M. and Le Gall, F., "Generation and production of engineered antibodies," Mol Biotechnol. 26(1):39-60, Humana Press, Inc., Springer Science+Business Media, Germany (Jan. 2004).

Lloyd, C., et al., "Modelling the human immune response: performance of a 1011 human antibody repertoire against a broad panel of therapeutically relevant antigens," Protein Engineering, Design & Selection 22:159-168, Oxford University Press, United Kingdom (Mar. 2009).

Lo, B.K.C., "Antibody humanization by CDR grafting," Ch.7 in Methods in Mol Biol., Antibody Engineering: Methods and Protocols 248:135-59, Totowa, New Jersey (2004).

Lucentis prescribing information, p. 1-28, Genentech, Inc. (2018).

Luo, G., et al., "Molecular mechanism underlying the action of a novel fusion inhibitor of influenza A virus," J Virol. 71(5):4062-4070, American Society for Microbiology, United States (May 1997).

Marneros, A., et al., "Endogenous endostatin inhibits choroidal neovascularization," FASEB J. 21(14):3809-3818, Federation of American Societies for Experimental Biology, United States (Dec. 2007).

Medicago AB phosphate-buffer saline specification sheet, p. 1-2, www.medicago.se (2010).

Mellberg, S., et al., "Transcriptional profiling reveals a critical role for tyrosine phosphatase VEPTP in regulation of VEGFR2 activity and endothelial cell morphogenesis," FASEB J. 23(5):1490-1502, Federation of American Societies for Experimental Biology, United States (May 2009).

Miles, A.A. and Miles, E.M., "Vascular reactions to histamine, histamine-liberator and leukotaxine in the skin of guinea-pigs," J Physiol. 118(2):228-257, Wiley-Blackwell on behalf of The Physiological Society, United States (Oct. 1952).

Morrissey, C., et al., "Differential expression of angiogenesis associated genes in prostate cancer bone, liver and lymph node metastases," Clin Exp Metastasis. 25(4):377-388, Springer Science+Business Media B.V., Germany (2008).

Muyldermans, S., "Single domain camel antibodies: current status," Reviews in Molecular Biotechnology 74(4):277-302, Elsevier, Netherlands (Jun. 2001).

Nishimura, E., "Current status and feature of diabetic retinopathy drug therapy," Journal of the Showa Medical Association 70(1):45-51, Showa Medical Association, Japan (Feb. 2010).

Notice of Allowance dated Jan. 15, 2020, in U.S. Appl. No. 16/180,850, Peters, K., filed Nov. 5, 2018, 9 pages.

Notice of Allowance dated Jan. 30, 2015, in U.S. Appl. No. 13/652,154, Peters, K., filed Oct. 15, 2012, 8 pages.

Notice of Allowance dated Nov. 30, 2018, in U.S. Appl. No. 15/654,289, Peters, K., filed Jul. 19, 2017, 7 pages.

Notice of Allowance dated Sep. 26, 2018, in U.S. Appl. No. 15/438,218, Peters, K., filed Feb. 21, 2017, 8 pages.

Nottebaum, A.F., et al. VE-PTP maintains the endothelial barrier via plakoglobin and becomes dissociated from VE-cadherin by leukocytes and by VEGF, J Exp Med. 205(12):2929-2945, The Rockefeller University Press, United States (Nov. 2008).

Office Action dated Apr. 17, 2015, in U.S. Appl. No. 13/652,203, Peters, K., et al., filed Oct. 15, 2012, 12 pages.

Office Action dated Apr. 7, 2014, in U.S. Appl. No. 13/652,154, Peters, K., et al., filed Oct. 15, 2012, 25 pages.

Office Action dated Aug. 22, 2016 in U.S. Appl. No. 13/652,203, Peters, K., et al., filed Oct. 15, 2012, 15 pages.

Office Action dated Aug. 3, 2018, in U.S. Appl. No. 15/438,218, Peters, K., et al., filed Feb. 21, 2017, 8 pages.

Office Action dated Aug. 30, 2019, in U.S. Appl. No. 16/180,850, Peters, K., et al., filed Nov. 5, 2018, 11 pages.

Office Action dated Aug. 30, 2019, in U.S. Appl. No. 16/180,854, Peters, K., et al., filed Nov. 5, 2018, 11 pages.

Office Action dated Jan. 4, 2016, in U.S. Appl. No. 13/652,203, Peters, K., et al., filed Oct. 15, 2012, 17 pages.

Office Action dated Jul. 6, 2018, in U.S. Appl. No. 15/654,289, Peters, K., et al., filed Jul. 19, 2017, 8 pages.

Office Action dated Jul. 9, 2018, in U.S. Appl. No. 15/463,340, Peters, K., et al., filed Mar. 20, 2017, 14 pages.

Office Action dated Mar. 1, 2018, in U.S. Appl. No. 15/438,218, Peters, K., et al., filed Feb. 21, 2017, 10 pages.

Office Action dated May 15, 2014, in U.S. Appl. No. 13/652,203, Peters, K., et al., filed Oct. 15, 2012, 12 pages.

Office Action dated Sep. 11, 2013, in U.S. Appl. No. 13/652,203, Peters, K., et al., filed Oct. 15, 2012, 10 pages.

Office Action dated Sep. 22, 2016, in U.S. Appl. No. 14/627,463, Peters, K., et al., filed Feb. 20, 2015, 24 pages.

Office Action dated Sep. 5, 2013, in U.S. Appl. No. 13/652,154, Peters, K., et al., filed Oct. 15, 2012, 23 pages.

Oliner, J., et al., "Suppression of angiogenesis and tumor growth by selective inhibition of angiopoietin-2," Cancer Cell. 6(5):507-516, Cell Press, United States (Nov. 2004).

Park, Y-H., et al., "Effect of sorafenib on experimental choroidal neovascularization in the rat," Clin Experiment Ophthalmol. 38(7):718-726, Royal Australian and New Zealand College of Ophthalmologists, Australia (Oct. 2010).

Praidou, A., et al., "Angiogenic growth factors and their inhibitors in diabetic retinopathy," Curr Diabetes Rev. 6(5):304-312, Bentham Science Publishers Ltd., United Arab Emirates (Sep. 2010).

Riemer, A.B., et al., Matching of trastuzumab (Herceptin) epitope mimics onto the surface of Her-2/neu—a new method of epitope definition. Mol Immunol. 42(9):1121-1124, Elsevier, Netherlands (May 2005).

Saharinen, P., et al., "Angiopoietins assemble distinct Tie2 signalling complexes in endothelial cell-cell and cell-matrix contacts," Nat Cell Biol. 10(5):527-537, Supplementary Information, Nature Publishing Group, Germany (May 2008).

Schindelholz, B, et al., "Regulation of CNS and motor axon guidance in *Drosophila* by the receptor tyrosine phosphatase DPTP52F," Development, 128: 4371-4382, The Company of Biologists Limited, Great Britain (2001).

Shen J, et al., "In Vivo Immunostaining Demonstrates Macrophages Associate with Growing and Regressing Vessels," Invest. Ophthalmol. Vis. Sci., 48(9):4335-4341, Association for Research in Vision and Ophthalmology, United States (2007).

Sidwell, R. W., et al. "Utilization of pulse oximetry for the study of the inhibitory effects of antiviral agents on influenza virus in mice," Antimicrob Agents Chemother. 36(2):473-476, American Society for Microbiology, United States (Feb. 1992).

Smith, L. E. H., et al., "Oxygen-induced retinopathy in the mouse," Invest Ophthalmol Vis Sci. 35(1):101-111, Association for Research in Vision and Ophthalmology (Jan. 1994).

Sone, H., et al., "Effects of intraocular or systemic administration of neutralizing antibody against vascular endothelial growth factor on

(56) References Cited

OTHER PUBLICATIONS the murine experimental model of retinopathy," Life Sci. 65(24):2573-2580, Elsevier, Netherlands (1999).
Stancovski, I., et al., "Mechanistic aspects of the opposing effects of monoclonal antibodies to the ERBB2 receptor on tumor growth," Proc Natl Acad Sci U S A. 88(19):8691-8695, United States National Academy of Sciences, United States (Oct. 1991).
Supplementary European Search Report and Search Opinion for EP Application No. EP 12840220.3, Munich, Germany, dated May 11, 2015, 7 pages.
Supplementary European Search Report and Search Opinion for EP Application No. EP 12840725.1, Munich, Germany, dated May 12, 2015.
Tobe, T., et al., "Targeted Disruption of the FGF2 Gene Does Not Prevent Choroidal Neovascularization in a Murine Model," Am. J. Pathol., 153(5):1641-1646, American Society to Investigative Pathology (1998).
Varughese, M., et al., "Internalization of a Bacillus anthracis protective antigen-c-Myc fusion protein mediated by cell surface anti-c-Myc antibodies," Mol Med. 4(2):87-95, Springer Nature, Germany (Feb. 1998).
Yacyshyn, O.K., et al., "Tyrosine phosphatase beta regulates angiopoietin-Tie2 signaling in human endothelial cells," Angiogenesis 12(1):25-33 Springer Science+Business Media B.V., Germany (2009).
Office Action dated Sep. 16, 2022, in U.S. Appl. No. 16/784,970, Rotello, R.J., et al., filed Feb. 7, 2020, 18 pages.
Office Action dated Nov. 29, 2022, in U.S. Appl. No. 16/751,824, Peters, K., et al., filed Jan. 24, 2020, 21 pages.
Office Action dated Dec. 14, 2022, in U.S. Appl. No. 17/027,034, Peters, K., et al., filed Sep. 21, 2020, 11 pages.
Saharinen, P., et al., "Therapeutic targeting of the angiopoietin-TIE pathway," Nat Rev Drug Discov 16(9):635-661, Nature Portfolio, Germany (Sep. 2017).
Souma, T., et al., "Context-dependent functions of angiopoietin 2 are determined by the endothelial phosphatase VEPTP," Proc Natl Acad Sci USA 115(6):1298-1303, National Academy of Sciences, United States (Feb. 2018).

* cited by examiner

SEQUENCE LISTING

```
<160> NUMBER OF SEQ ID NOS: 262

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ala Asn
            20                  25                  30

Ala Met Asn Trp Val Arg Gln Ala Ser Gly Lys Gly Leu Glu Trp Val
        35                  40                  45

Gly Arg Ile Arg Thr Lys Ser Asn Asn Tyr Ala Thr Tyr Tyr Ala Gly
```

```
                50                  55                  60

Ser Val Lys Asp Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Ala Tyr
                 85                  90                  95

Tyr Cys Val Arg Asp Tyr Tyr Gly Ser Ser Ala Trp Ile Thr Tyr Trp
                100                 105                 110

Gly Gln Gly Thr Leu Val Thr Val Ser Ser
            115                 120

<210> SEQ ID NO 2
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Ala Asn
             20                  25                  30

Ala Met Asn Trp Val Arg Gln Ala Pro Gly Lys Gly Leu Glu Trp Val
         35                  40                  45

Gly Arg Ile Arg Thr Lys Ser Asn Asn Tyr Ala Thr Tyr Tyr Ala Gly
     50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg Asp Tyr Tyr Gly Ser Ser Ala Trp Ile Thr Tyr Trp
                100                 105                 110

Gly Gln Gly Thr Leu Val Thr Val Ser Ser
            115                 120

<210> SEQ ID NO 3
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Arg
  1               5                  10                  15

Ser Leu Arg Leu Ser Cys Thr Ala Ser Gly Phe Thr Phe Asn Ala Asn
             20                  25                  30

Ala Met Asn Trp Val Arg Gln Ala Pro Gly Lys Gly Leu Glu Trp Val
         35                  40                  45

Gly Arg Ile Arg Thr Lys Ser Asn Asn Tyr Ala Thr Tyr Tyr Ala Gly
     50                  55                  60

Ser Val Lys Asp Arg Phe Thr Ile Ser Arg Asp Asp Ser Lys Asn Ile
 65                  70                  75                  80

Ala Tyr Leu Gln Met Asn Ser Leu Lys Thr Glu Asp Thr Ala Val Tyr
                 85                  90                  95

Tyr Cys Val Arg Asp Tyr Tyr Gly Ser Ser Ala Trp Ile Thr Tyr Trp
```

100                 105                 110

Gly Gln Gly Thr Leu Val Thr Val Ser Ser
        115                 120

<210> SEQ ID NO 4
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Ile Arg Gln Ala Pro Gly Lys Gly Leu Glu Trp Val
        35                  40                  45

Ser Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val His
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Phe
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Phe Ser Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Gly Glu Gln Pro Pro Lys Leu Leu Ile
        35                  40                  45

Tyr Trp Ala Ser Thr Arg His Thr Gly Val Pro Asp Arg Phe Ser Gly
    50                  55                  60
```

```
Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Tyr Ser Ser Tyr Pro Phe
                 85                  90                  95

Thr Phe Gly Gly Gly Thr Lys Val Glu Ile Lys
            100                 105

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
```

<210> SEQ ID NO 10
<211> LENGTH: 106
<212> TYPE: PRT
<213> ORGANISM: Homo sapiens

<400> SEQUENCE: 10

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gly Trp Thr Leu Val Phe Leu Phe Leu Leu Ser Val Thr Ala Gly
1               5                   10                  15

Val His Ser

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Val Ser Ser Ala Gln Phe Leu Gly Leu Leu Leu Leu Cys Phe Gln
1               5                   10                  15

Gly Thr Arg Cys
            20

<210> SEQ ID NO 13
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln

```
                    20                  25                  30
Pro Gly Gly Ser Leu Lys Leu Ser Cys Ala Ala Ser Gly Phe Thr Phe
                35                  40                  45
Asn Ala Asn Ala Met Asn Trp Val Arg Gln Ala Ser Gly Lys Gly Leu
            50                  55                  60
Glu Trp Val Gly Arg Ile Arg Thr Lys Ser Asn Asn Tyr Ala Thr Tyr
 65                  70                  75                  80
Tyr Ala Gly Ser Val Lys Asp Arg Phe Thr Ile Ser Arg Asp Asp Ser
                85                  90                  95
Lys Asn Thr Ala Tyr Leu Gln Met Asn Ser Leu Lys Thr Glu Asp Thr
            100                 105                 110
Ala Ala Tyr Tyr Cys Val Arg Asp Tyr Tyr Gly Ser Ser Ala Trp Ile
            115                 120                 125
Thr Tyr Trp Gly Gln Gly Thr Leu Val Thr Val Ser Ser Ala Ser Thr
            130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Lys Thr Tyr Thr Cys
            210                 215                 220
Asn Val Asp His Lys Pro Ser Asn Thr Lys Val Asp Lys Arg Val Glu
225                 230                 235                 240
Ser Lys Tyr Gly Pro Pro Cys Pro Pro Cys Pro Ala Pro Glu Phe Leu
                245                 250                 255
Gly Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
            275                 280                 285
Gln Glu Asp Pro Glu Val Gln Phe Asn Trp Tyr Val Asp Gly Val Glu
            290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
                340                 345                 350
Ile Glu Lys Thr Ile Ser Lys Ala Lys Gly Gln Pro Arg Glu Pro Gln
            355                 360                 365
Val Tyr Thr Leu Pro Pro Ser Gln Glu Glu Met Thr Lys Asn Gln Val
            370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
            420                 425                 430
Val Asp Lys Ser Arg Trp Gln Glu Gly Asn Val Phe Ser Cys Ser Val
            435                 440                 445
```

Met His Glu Ala Leu His Asn His Tyr Thr Gln Lys Ser Leu Ser Leu
    450                 455                 460

Ser Leu Gly Lys
465

<210> SEQ ID NO 14
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Asn Ala Asn Ala Met Asn Trp Val Arg Gln Ala Pro Gly Lys Gly Leu
        50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn

```
            325                 330                 335
Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
                435                 440                 445

Met His Glu Ala Leu His Asn His Tyr Thr Gln Lys Ser Leu Ser Leu
            450                 455                 460

Ser Leu Gly Lys
465

<210> SEQ ID NO 15
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Arg Ser Leu Arg Leu Ser Cys Thr Ala Ser Gly Phe Thr Phe
        35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ile Ala Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
    450                 455                 460

Ser Leu Gly Lys
465

<210> SEQ ID NO 16
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Trp Thr Leu Val Phe Leu Phe Leu Leu Ser Val Thr Ala Gly
1               5                   10                  15

Val His Ser Leu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Asn Ala Asn Ala Met Asn Trp Ile Arg Gln Ala Pro Gly Lys Gly Leu
    50                  55                  60

Glu Trp Val Ser Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asn Ala
                85                  90                  95
```

Lys Asn Ser Leu Tyr Leu Gln Met Asn Ser Leu Arg Ala Glu Asp Thr
            100                 105                 110

Ala Val His Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 17
<211> LENGTH: 234
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 17

Met Val Ser Ser Ala Gln Phe Leu Gly Leu Leu Leu Cys Phe Gln
1               5                   10                  15

Gly Thr Arg Cys Asp Val Val Met Thr Gln Ser Pro Ser Phe Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Arg Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 18
<211> LENGTH: 234
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

Met Val Ser Ser Ala Gln Phe Leu Gly Leu Leu Leu Cys Phe Gln
1               5                   10                  15

Gly Thr Arg Cys Asp Ile Val Met Thr Gln Ser Pro Asp Ser Leu Ala
            20                  25                  30

Val Ser Leu Gly Glu Arg Ala Thr Ile Asn Cys Lys Ala Ser Gln His
        35                  40                  45

Val Gly Thr Ala Val Ala Trp Tyr Gln Gln Lys Pro Gly Gln Pro Pro
    50                  55                  60

Lys Leu Leu Ile Tyr Trp Ala Ser Thr Arg His Thr Gly Val Pro Asp
65                  70                  75                  80

Arg Phe Ser Gly Ser Gly Ser Gly Thr Asp Phe Thr Leu Thr Ile Ser
                85                  90                  95

```
Ser Leu Gln Ala Glu Asp Val Ala Val Tyr Tyr Cys Gln Gln Tyr Ser
            100                 105                 110

Ser Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 19
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Phe Ser Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Lys Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

```
Val Thr Lys Ser Phe Asn Arg Gly Glu Cys
225                 230

<210> SEQ ID NO 20
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Val Ser Ser Ala Gln Phe Leu Gly Leu Leu Leu Cys Phe Gln
1               5                   10                  15

Gly Thr Arg Cys Asp Ile Val Met Thr Gln Ser Pro Asp Ser Leu Ala
                20                  25                  30

Val Ser Leu Gly Glu Arg Ala Thr Ile Asn Cys Lys Ala Ser Gln His
            35                  40                  45

Val Gly Thr Ala Val Ala Trp Tyr Gln Gln Lys Pro Glu Gln Pro Pro
    50                  55                  60

Lys Leu Leu Ile Tyr Trp Ala Ser Thr Arg His Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln Tyr Ser
            100                 105                 110

Ser Tyr Pro Phe Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 21
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45
```

```
Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430

<210> SEQ ID NO 22
<211> LENGTH: 205
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 22

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 23
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Ser Gly Gly Gly Gly Ser Gly Gly Gly Gly Ser Gly Gly
        115                 120                 125

```
Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
                180                 185                 190

Thr Trp Ala Lys Gly Arg Phe Thr Ile Ser Arg Asp Asn Ser Lys Asn
                195                 200                 205

Thr Leu Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250
```

<210> SEQ ID NO 24
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230
```

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 28
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Gln Leu Thr Gln
    130                 135                 140
```

```
Ser Pro Ser Ser Leu Ser Ala Ser Val Gly Asp Arg Val Thr Ile Thr
145                 150                 155                 160

Cys Ser Ala Ser Gln Asp Ile Ser Asn Tyr Leu Asn Trp Tyr Gln Gln
                165                 170                 175

Lys Pro Gly Lys Ala Pro Lys Val Leu Ile Tyr Phe Thr Ser Ser Leu
            180                 185                 190

His Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Ser Thr Val Pro Trp Thr Phe Gly Gln Gly Thr
225                 230                 235                 240

Lys Val Glu Ile Lys
                245

<210> SEQ ID NO 29
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
```

```
                        245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Gly Ser
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser Gly Gly Gly Gly Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser Gly Gly Gly Gly Ser Gly Gly Gly Gly Ser
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Gly Ser Gly Gly Gly Gly Ser Gly Gly Gly Gly Ser Gly
1               5                   10                  15

Gly Gly Gly Ser
            20

<210> SEQ ID NO 35
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 38
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 39
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

Gly Gly Gly Gly Ser Gly Gly Gly Ser Gly Gly Gly Ser Gly
1               5                  10                 15

Gly Gly Gly Ser Gly Gly Gly Ser Gly Gly Gly Ser Gly Gly
                20                  25                 30

Gly Gly Ser Gly Gly Gly Gly Ser Gly Gly Gly Ser
        35                  40                  45

<210> SEQ ID NO 40
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Gly Gly Gly Ser Gly Gly Gly Ser Gly Gly Gly Ser Gly
1               5                  10                 15

Gly Gly Gly Ser Gly Gly Gly Gly Ser Gly Gly Gly Ser Gly Gly
                20                  25                 30

Gly Gly Ser Gly Gly Gly Gly Ser Gly Gly Gly Ser Gly Gly Gly
        35                  40                  45

Gly Ser
    50

<210> SEQ ID NO 41
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gly Gly Gly Ser Gly Gly Gly Gly Ser Gly Gly Gly Ser Gly
1               5                  10                 15

Gly Gly Gly Ser Gly Gly Gly Ser Gly Gly Gly Ser Gly Gly
                20                  25                 30

Gly Gly Ser Gly Gly Gly Gly Ser Gly Gly Gly Ser Gly Gly Gly
        35                  40                  45

Gly Ser Gly Gly Gly Gly Ser
    50                  55

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Ser
1

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 43

Gly Gly Gly Ser Gly Gly Gly Ser
1               5

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Ser Gly Gly Gly Ser Gly Gly Gly Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Ser Gly Gly Gly Ser Gly Gly Gly Ser Gly Gly Gly Ser
1               5                   10                  15

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Ser Gly Gly Gly Ser Gly Gly Gly Ser Gly Gly Gly Ser
1               5                   10                  15

Gly Gly Gly Ser
            20

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Ser Gly Gly Gly Ser Gly Gly Gly Ser Gly Gly Gly Ser
```

```
                1               5                   10                  15
Gly Gly Gly Ser Gly Gly Gly Ser Gly Gly Gly Ser
        20                  25

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
        20                  25                  30

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
        20                  25                  30

Gly Gly Gly Ser
        35

<210> SEQ ID NO 51
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
        20                  25                  30

Gly Gly Gly Ser Gly Gly Gly Ser
        35                  40

<210> SEQ ID NO 52
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
        20                  25                  30
```

Gly Gly Gly Ser Gly Gly Gly Ser Gly Gly Gly Ser
          35                  40

<210> SEQ ID NO 53
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

<210> SEQ ID NO 54
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser
    50

<210> SEQ ID NO 55
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser
    50                  55

<210> SEQ ID NO 56
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly
1

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Gly Gly
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Gly Gly Gly Gly Gly
1               5

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Glu Ser Gly Ser Val Ser Ser Glu Gln Leu Ala Gln Phe Arg Ser
1               5                   10                  15

Leu Asp

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Gly Lys Ser Ser Gly Ser Gly Ser Glu Ser Lys Ser Thr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Ala Gly Ser Ala Ala Gly Ser Gly Glu Phe
1               5                   10

<210> SEQ ID NO 62
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Ala Ala Ala Lys
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Ala Ala Ala Lys Glu Ala Ala Ala Lys
1               5                   10

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Ala Ala Ala Lys Glu Ala Ala Ala Lys Glu Ala Ala Ala Lys Glu
1               5                   10                  15

Ala Ala Ala Lys
            20

<210> SEQ ID NO 65
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 66
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys
            20                  25                  30

<210> SEQ ID NO 67
<211> LENGTH: 5
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Ala Ala Ala Arg
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Ala Ala Ala Arg Glu Ala Ala Ala Arg
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Ala Ala Ala Arg Glu Ala Ala Ala Arg Glu Ala Ala Ala Arg
1               5                   10                  15

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Ala Ala Ala Arg Glu Ala Ala Ala Arg Glu Ala Ala Ala Arg Glu
1               5                   10                  15

Ala Ala Ala Arg
            20

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Ala Ala Ala Arg Glu Ala Ala Ala Arg Glu Ala Ala Ala Arg Glu
1               5                   10                  15

Ala Ala Ala Arg Glu Ala Ala Ala Arg
            20                  25

<210> SEQ ID NO 72
<211> LENGTH: 30
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 72

Glu Ala Ala Arg Glu Ala Ala Arg Glu Ala Ala Arg Glu
1               5                   10                  15

Ala Ala Ala Arg Glu Ala Ala Arg Glu Ala Ala Arg
            20                  25                  30

<210> SEQ ID NO 73
<211> LENGTH: 46
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 73

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 74

Pro Ala Pro Ala Pro
1               5

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 75

Ala Glu Ala Ala Ala Lys Glu Ala Ala Ala Lys Ala
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 76

Ala Asn Ala Met Asn
1               5

<210> SEQ ID NO 77
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 77

Gly Phe Thr Phe Asn Ala Asn
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Thr Phe Asn Ala Asn Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Thr Phe Asn Ala Asn Ala Met Asn
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Thr Phe Asn Ala Asn Ala Met Asn
1               5                   10

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ile Arg Thr Lys Ser Asn Asn Tyr Ala Thr Tyr Tyr Ala Gly Ser
1               5                   10                  15

Val Lys Asp

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Thr Lys Ser Asn Asn Tyr Ala
1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Arg Thr Lys Ser Asn Asn Tyr Ala Thr
1               5                   10

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Val Gly Arg Ile Arg Thr Lys Ser Asn Asn Tyr Ala Thr Tyr Tyr
1               5                   10                  15

<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Val Gly Arg Ile Arg Thr Lys Ser Asn Asn Tyr Ala Thr Tyr Tyr
1               5                   10                  15

Ala Gly Ser Val Lys Asp
            20

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Val Ser Arg Ile Arg Thr Lys Ser Asn Asn Tyr Ala Thr Tyr Tyr
1               5                   10                  15

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Val Ser Arg Ile Arg Thr Lys Ser Asn Asn Tyr Ala Thr Tyr Tyr
1               5                   10                  15

Ala Gly Ser Val Lys Asp
            20

<210> SEQ ID NO 88

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Tyr Tyr Gly Ser Ser Ala Trp Ile Thr Tyr
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Arg Asp Tyr Tyr Gly Ser Ser Ala Trp Ile Thr Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Asp Tyr Tyr Gly Ser Ser Ala Trp Ile Thr Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Ala Ser Gln His Val Gly Thr Ala Val Ala
1               5                   10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln His Val Gly Thr Ala
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93
```

```
Gln His Val Gly Thr Ala Val Ala
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Ala Ser Thr Arg His Thr
1               5

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Ala Ser
1

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Leu Ile Tyr Trp Ala Ser Thr Arg His Thr
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Tyr Ser Ser Tyr Pro Phe Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Ser Ser Tyr Pro Phe
1               5

<210> SEQ ID NO 99
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 99

Asp Tyr Tyr Tyr Met Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Ser Leu Thr Asp Tyr Tyr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Ser Leu Thr Asp Tyr Tyr Tyr
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Phe Ser Leu Thr Asp Tyr Tyr Tyr Met Thr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Phe Ser Leu Thr Asp Tyr Tyr Tyr Met Thr
1               5                   10

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

His Tyr Gly Met Asn
1               5

```
<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Tyr Asp Phe Thr His Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Tyr Asp Phe Thr His Tyr Gly
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Asp Phe Thr His Tyr Gly Met Asn
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Tyr Asp Phe Thr His Tyr Gly Met Asn
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asn Tyr Gly Met Asn
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110
```

```
Gly Tyr Thr Phe Thr Asn Tyr
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Tyr Thr Phe Thr Asn Tyr Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Tyr Thr Phe Thr Asn Tyr Gly Met Asn
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Tyr Thr Phe Thr Asn Tyr Gly Met Asn
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Ile Asp Pro Asp Asp Asp Pro Tyr Tyr Ala Thr Trp Ala Lys Gly
1               5                   10                  15

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Pro Asp Asp Asp
1               5

<210> SEQ ID NO 116
<211> LENGTH: 7
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 116

Ile Asp Pro Asp Asp Pro
1               5

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Val Gly Phe Ile Asp Pro Asp Asp Pro Tyr Tyr Ala Thr Trp
1               5                   10                  15

Ala

<210> SEQ ID NO 118
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Val Gly Phe Ile Asp Pro Asp Asp Pro Tyr Tyr Ala Thr Trp
1               5                   10                  15

Ala Lys Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Asn Thr Tyr Thr Gly Glu Pro Thr Tyr Ala Ala Asp Phe Lys
1               5                   10                  15

Arg

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Thr Tyr Thr Gly Glu
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 121

Ile Asn Thr Tyr Thr Gly Glu Pro
1               5

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Val Gly Trp Ile Asn Thr Tyr Thr Gly Glu Pro Thr Tyr
1               5                   10

<210> SEQ ID NO 123
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Val Gly Trp Ile Asn Thr Tyr Thr Gly Glu Pro Thr Tyr Ala Ala
1               5                   10                  15

Asp Phe Lys Arg
            20

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Asp His Asn Ser Gly Trp Gly Leu Asp Ile
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Gly Gly Asp His Asn Ser Gly Trp Gly Leu Asp Ile
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Pro Tyr Tyr Tyr Gly Thr Ser His Trp Tyr Phe Asp Val
1               5                   10
```

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Lys Tyr Pro Tyr Tyr Tyr Gly Thr Ser His Trp Tyr Phe Asp Val
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Tyr Pro Tyr Tyr Tyr Gly Thr Ser His Trp Tyr Phe Asp Val
1               5                   10                  15

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Pro His Tyr Tyr Gly Ser Ser His Trp Tyr Phe Asp Val
1               5                   10

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Lys Tyr Pro His Tyr Tyr Gly Ser Ser His Trp Tyr Phe Asp Val
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Tyr Pro His Tyr Tyr Gly Ser Ser His Trp Tyr Phe Asp Val
1               5                   10                  15

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 132

Gln Ala Ser Glu Ile Ile His Ser Trp Leu Ala
1               5                   10

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Ile Ile His Ser Trp
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Ile Ile His Ser Trp Leu Ala
1               5

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Ala Ser Gln Asp Ile Ser Asn Tyr Leu Asn
1               5                   10

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Asp Ile Ser Asn Tyr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Asp Ile Ser Asn Tyr Leu Asn
1               5

<210> SEQ ID NO 138
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 138

Leu Ala Ser Thr Leu Ala Ser
1               5

<210> SEQ ID NO 139
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Ala Ser
1

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Leu Leu Ile Tyr Leu Ala Ser Thr Leu Ala Ser
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Thr Ser Ser Leu His Ser
1               5

<210> SEQ ID NO 142
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Thr Ser
1

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Val Leu Ile Tyr Phe Thr Ser Ser Leu His Ser
1               5                   10
```

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Asn Val Tyr Leu Ala Ser Thr Asn Gly Ala Asn
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Gln Tyr Ser Thr Val Pro Trp Thr
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Gln Tyr Ser Thr Val Pro Trp
1               5

<210> SEQ ID NO 147
<211> LENGTH: 102
<212> TYPE: PRT
<213> ORGANISM: Homo sapiens

<400> SEQUENCE: 147

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile
            100

<210> SEQ ID NO 148
<211> LENGTH: 103
<212> TYPE: PRT
<213> ORGANISM: Homo sapiens

<400> SEQUENCE: 148

```
Asp Val Val Leu Ser Pro Ser His Gly Ile Glu Leu Ser Val Gly Glu
1               5                   10                  15

Lys Leu Val Leu Asn Cys Thr Ala Arg Thr Glu Leu Asn Val Gly Ile
            20                  25                  30

Asp Phe Asn Trp Glu Tyr Pro Ser Ser Lys His Gln His Lys Lys Leu
        35                  40                  45

Val Asn Arg Asp Leu Lys Thr Gln Ser Gly Ser Glu Met Lys Lys Phe
    50                  55                  60

Leu Ser Thr Leu Thr Ile Asp Gly Val Thr Arg Ser Asp Gln Gly Leu
65                  70                  75                  80

Tyr Thr Cys Ala Ala Ser Ser Gly Leu Met Thr Lys Lys Asn Ser Thr
                85                  90                  95

Phe Val Arg Val His Glu Lys
                100
```

<210> SEQ ID NO 149
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
                100                 105                 110

Ala Val Tyr Tyr Cys Val Arg Asp Tyr Tyr Gly Ser Ser Ala Trp Ile
            115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
```

-continued

```
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
Gln Glu Asp Pro Glu Val Gln Phe Asn Trp Tyr Val Asp Gly Val Glu
    290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Gln Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
            420                 425                 430
Val Asp Lys Ser Arg Trp Gln Glu Gly Asn Val Phe Ser Cys Ser Val
        435                 440                 445
Met His Glu Ala Leu His Asn His Tyr Thr Gln Lys Ser Leu Ser Leu
    450                 455                 460
Ser Leu Gly Lys Gly Gly Gly Ser Ser Asp Thr Gly Arg Pro Phe
465                 470                 475                 480
Val Glu Met Tyr Ser Glu Ile Pro Glu Ile Ile His Met Thr Glu Gly
                485                 490                 495
Arg Glu Leu Val Ile Pro Cys Arg Val Thr Ser Pro Asn Ile Thr Val
            500                 505                 510
Thr Leu Lys Lys Phe Pro Leu Asp Thr Leu Ile Pro Asp Gly Lys Arg
        515                 520                 525
Ile Ile Trp Asp Ser Arg Lys Gly Phe Ile Ile Ser Asn Ala Thr Tyr
    530                 535                 540
Lys Glu Ile Gly Leu Leu Thr Cys Glu Ala Thr Val Asn Gly His Leu
545                 550                 555                 560
Tyr Lys Thr Asn Tyr Leu Thr His Arg Gln Thr Asn Thr Ile Ile Asp
                565                 570                 575
Val Val Leu Ser Pro Ser His Gly Ile Glu Leu Ser Val Gly Glu Lys
            580                 585                 590
Leu Val Leu Asn Cys Thr Ala Arg Thr Glu Leu Asn Val Gly Ile Asp
        595                 600                 605
Phe Asn Trp Glu Tyr Pro Ser Ser Lys His Gln His Lys Lys Leu Val
    610                 615                 620
Asn Arg Asp Leu Lys Thr Gln Ser Gly Ser Glu Met Lys Lys Phe Leu
625                 630                 635                 640
Ser Thr Leu Thr Ile Asp Gly Val Thr Arg Ser Asp Gln Gly Leu Tyr
                645                 650                 655
Thr Cys Ala Ala Ser Ser Gly Leu Met Thr Lys Lys Asn Ser Thr Phe
            660                 665                 670
```

Val Arg Val His Glu Lys
        675

<210> SEQ ID NO 150
<211> LENGTH: 724
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser

```
                340             345             350
Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys Gly Gly Gly Ser Glu Ile Val Met Thr Gln Ser
465                 470                 475                 480

Pro Ser Thr Leu Ser Ala Ser Val Gly Asp Arg Val Ile Ile Thr Cys
                485                 490                 495

Gln Ala Ser Glu Ile Ile His Ser Trp Leu Ala Trp Tyr Gln Gln Lys
            500                 505                 510

Pro Gly Lys Ala Pro Lys Leu Leu Ile Tyr Leu Ala Ser Thr Leu Ala
        515                 520                 525

Ser Gly Val Pro Ser Arg Phe Ser Gly Ser Gly Ser Gly Ala Glu Phe
    530                 535                 540

Thr Leu Thr Ile Ser Ser Leu Gln Pro Asp Asp Phe Ala Thr Tyr Tyr
545                 550                 555                 560

Cys Gln Asn Val Tyr Leu Ala Ser Thr Asn Gly Ala Asn Phe Gly Gln
                565                 570                 575

Gly Thr Lys Leu Thr Val Leu Gly Gly Gly Gly Ser Gly Gly Gly
            580                 585                 590

Gly Ser Gly Gly Gly Gly Ser Gly Gly Gly Gly Ser Glu Val Gln Leu
        595                 600                 605

Val Glu Ser Gly Gly Gly Leu Val Gln Pro Gly Gly Ser Leu Arg Leu
    610                 615                 620

Ser Cys Thr Ala Ser Gly Phe Ser Leu Thr Asp Tyr Tyr Met Thr
625                 630                 635                 640

Trp Val Arg Gln Ala Pro Gly Lys Gly Leu Glu Trp Val Gly Phe Ile
                645                 650                 655

Asp Pro Asp Asp Asp Pro Tyr Tyr Ala Thr Trp Ala Lys Gly Arg Phe
            660                 665                 670

Thr Ile Ser Arg Asp Asn Ser Lys Asn Thr Leu Tyr Leu Gln Met Asn
        675                 680                 685

Ser Leu Arg Ala Glu Asp Thr Ala Val Tyr Tyr Cys Ala Gly Gly Asp
    690                 695                 700

His Asn Ser Gly Trp Gly Leu Asp Ile Trp Gly Gln Gly Thr Leu Val
705                 710                 715                 720

Thr Val Ser Ser

<210> SEQ ID NO 151
<211> LENGTH: 718
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 151

```
Met Gly Trp Thr Leu Val Phe Leu Phe Leu Ser Val Thr Ala Gly
1               5                   10                  15

Val His Ser Glu Val Gln Leu Val Glu Ser Gly Gly Leu Val Gln
                20                  25                  30

Pro Gly Gly Ser Leu Arg Leu Ser Cys Ala Ala Ser Gly Phe Thr Phe
            35                  40                  45

Asn Ala Asn Ala Met Asn Trp Val Arg Gln Ala Pro Gly Lys Gly Leu
        50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400
```

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Arg Leu Thr
        420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
        450                 455                 460

Ser Leu Gly Lys Gly Gly Gly Gly Ser Glu Val Gln Leu Val Glu Ser
465                 470                 475                 480

Gly Gly Gly Leu Val Gln Pro Gly Gly Ser Leu Arg Leu Ser Cys Ala
            485                 490                 495

Ala Ser Gly Tyr Asp Phe Thr His Tyr Gly Met Asn Trp Val Arg Gln
            500                 505                 510

Ala Pro Gly Lys Gly Leu Glu Trp Val Gly Trp Ile Asn Thr Tyr Thr
            515                 520                 525

Gly Glu Pro Thr Tyr Ala Ala Asp Phe Lys Arg Arg Phe Thr Phe Ser
            530                 535                 540

Leu Asp Thr Ser Lys Ser Thr Ala Tyr Leu Gln Met Asn Ser Leu Arg
545                 550                 555                 560

Ala Glu Asp Thr Ala Val Tyr Tyr Cys Ala Lys Tyr Pro Tyr Tyr Tyr
                565                 570                 575

Gly Thr Ser His Trp Tyr Phe Asp Val Trp Gly Gln Gly Thr Leu Val
            580                 585                 590

Thr Val Ser Ser Gly Gly Gly Gly Ser Gly Gly Gly Gly Ser Gly Gly
            595                 600                 605

Gly Gly Ser Asp Ile Gln Leu Thr Gln Ser Pro Ser Ser Leu Ser Ala
610                 615                 620

Ser Val Gly Asp Arg Val Thr Ile Thr Cys Ser Ala Ser Gln Asp Ile
625                 630                 635                 640

Ser Asn Tyr Leu Asn Trp Tyr Gln Gln Lys Pro Gly Lys Ala Pro Lys
                645                 650                 655

Val Leu Ile Tyr Phe Thr Ser Ser Leu His Ser Gly Val Pro Ser Arg
                660                 665                 670

Phe Ser Gly Ser Gly Ser Gly Thr Asp Phe Thr Leu Thr Ile Ser Ser
            675                 680                 685

Leu Gln Pro Glu Asp Phe Ala Thr Tyr Tyr Cys Gln Gln Tyr Ser Thr
            690                 695                 700

Val Pro Trp Thr Phe Gly Gln Gly Thr Lys Val Glu Ile Lys
705                 710                 715

<210> SEQ ID NO 152
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Arg Arg Phe Ser Thr Ala Pro Phe Ala Phe Ile Asp Ile Asn Asp
1               5                   10                  15

Val Ile Asn Phe
            20

-continued

```
<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 153

Leu Arg Arg Phe Ser Thr Xaa Pro Xaa Xaa Xaa Xaa Asn Ile Asn Asn
1               5                   10                  15

Val Xaa Asn Phe
            20

<210> SEQ ID NO 154
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
```

```
                210                 215                 220
Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
                260                 265                 270

Val Ile Leu Thr Asn Pro Ile Ser Lys Glu Lys Gln Ser His Val Val
                275                 280                 285

Ser Leu Val Val Tyr Val Pro Pro Gly Pro Gly Asp Lys Thr His Thr
                290                 295                 300

Cys Pro Leu Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
                340                 345                 350

Lys Phe Asn Trp Tyr Val Asp Gly Val Glu Val His Asn Ala Lys Thr
                355                 360                 365

Lys Pro Arg Glu Glu Gln Tyr Asn Ser Thr Tyr Arg Val Val Ser Val
                370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
                420                 425                 430

Ser Arg Asp Glu Leu Thr Lys Asn Gln Val Ser Leu Thr Cys Leu Val
                435                 440                 445

Lys Gly Phe Tyr Pro Ser Asp Ile Ala Val Glu Trp Glu Ser Asn Gly
                450                 455                 460

Gln Pro Glu Asn Asn Tyr Lys Ala Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
                500                 505                 510

Asn His Tyr Thr Gln Lys Ser Leu Ser Leu Ser Pro Gly Lys
                515                 520                 525

<210> SEQ ID NO 155
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
                20                  25                  30

Asn Ile Thr Val Thr Leu Lys Lys Phe Pro Leu Asp Thr Leu Ile Pro
                35                  40                  45
```

Asp Gly Lys Arg Ile Ile Trp Asp Ser Arg Lys Gly Phe Ile Ile Ser
            50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                 85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
            115                 120                 125

Val Gly Ile Asp Phe Asn Trp Glu Tyr Pro Ser Ser Lys His Gln His
        130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Val Val Tyr Val Pro Pro Gly Pro Gly
    290                 295

<210> SEQ ID NO 156
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 157
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
```

```
                    20                  25                  30
Leu Gly Trp Tyr Gln Gln Lys Pro Gly Lys Ala Pro Lys Leu Leu Ile
            35                  40                  45
Tyr Asp Ala Ser Asn Leu Asp Thr Gly Val Pro Ser Arg Phe Ser Gly
 50                  55                  60
Ser Gly Ser Gly Thr Tyr Phe Thr Leu Thr Ile Ser Ser Leu Gln Ala
 65                  70                  75                  80
Glu Asp Phe Ala Val Tyr Phe Cys Gln Gln Ala Lys Ala Phe Pro Pro
                85                  90                  95
Thr Phe Gly Gly Gly Thr Lys Val Asp Ile Lys Gly Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 158
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala Phe Asp
            20                  25                  30
Trp Met Gly Trp Thr Pro Leu His Leu Ala Ala His Glu Gly His Leu
        35                  40                  45
Glu Ile Val Glu Val Leu Leu Lys Asn Gly Ala Asp Val Asn Ala Thr
 50                  55                  60
Asp Val Ser Gly Tyr Thr Pro Leu His Leu Ala Ala Asp Gly His
 65                  70                  75                  80
Leu Glu Ile Val Glu Val Leu Leu Lys His Gly Ala Asp Val Asn Thr
                85                  90                  95
Lys Asp Asn Thr Gly Trp Thr Pro Leu His Leu Ser Ala Asp Leu Gly
            100                 105                 110
His Leu Glu Ile Val Glu Val Leu Leu Lys Asn Gly Ala Asp Val Asn
        115                 120                 125
Ala Gln Asp Lys Phe Gly Lys Thr Ala Phe Asp Ile Ser Ile Asp Asn
145                 150                 155
Gly Asn Glu Asp Leu Ala Glu Ile Leu Gln Lys Ala Ala
145                 150                 155
```

<210> SEQ ID NO 159
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Leu Asp Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
            20                  25                  30

Tyr Leu Gly Trp Thr Pro Leu His Leu Ala Ala His Glu Gly His Leu
        35                  40                  45

Glu Ile Val Glu Val Leu Leu Lys Ala Gly Ala Asp Val Asn Ala Lys
    50                  55                  60

Asp Val Ser Gly Tyr Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Lys Asp Asn Thr Gly Trp Thr Pro Leu His Leu Ser Ala Asp Leu Gly
            100                 105                 110

His Leu Glu Ile Val Glu Val Leu Leu Lys Ala Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Ala Ala
145                 150                 155

<210> SEQ ID NO 160
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Thr Ala Asp
            20                  25                  30

Ser Thr Gly Trp Thr Pro Leu His Leu Ala Ala Pro Trp Gly His Pro
        35                  40                  45

Glu Ile Val Glu Val Leu Leu Lys Asn Gly Ala Asp Val Asn Ala His
    50                  55                  60

Asp Tyr Gln Gly Trp Thr Pro Leu His Leu Ala Ala Thr Leu Gly His
65                  70                  75                  80

Leu Glu Ile Val Glu Val Leu Leu Lys His Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln Lys Ala Ala
        115                 120

<210> SEQ ID NO 161
<211> LENGTH: 124

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Thr Ala Asp
                20                  25                  30

Ser Thr Gly Trp Thr Pro Leu His Leu Ala Val Pro Trp Gly His Leu
            35                  40                  45

Glu Ile Val Glu Val Leu Leu Lys Tyr Gly Ala Asp Val Asn Ala Lys
    50                  55                  60

Asp Phe Gln Gly Trp Thr Pro Leu His Leu Ala Ala Ile Gly His
65                  70                  75                  80

Gln Glu Ile Val Glu Val Leu Leu Lys Asn Gly Ala Asp Val Asn Ala
                85                  90                  95

Gln Asp Lys Phe Gly Lys Thr Ala Phe Asp Ile Ser Ile Asp Asn Gly
                100                 105                 110

Asn Glu Asp Leu Ala Glu Ile Leu Gln Lys Ala Ala
            115                 120

<210> SEQ ID NO 162
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Ser Thr Gly Tyr Thr Pro Leu His Leu Ala Ala Pro Trp Gly His Leu
            35                  40                  45

Glu Ile Val Glu Val Leu Leu Lys Ala Gly Ala Asp Val Asn Ala Lys
    50                  55                  60

Asp Tyr Gln Gly Trp Thr Pro Leu His Leu Ala Ala Val Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Asp Ala Gly
                100                 105                 110

His Glu Asp Ile Ala Glu Val Leu Gln Lys Ala Ala
            115                 120

<210> SEQ ID NO 163
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Leu Gly Lys Lys Leu Leu Glu Ala Ala Arg Ala Gly Gln Asp Asp
```

```
                1               5                   10                  15
Glu Val Arg Ile Leu Met Ala Asn Gly Ala Asp Val Asn Ala Arg Asp
            20                  25                  30

Ser Thr Gly Trp Thr Pro Leu His Leu Ala Ala Pro Trp Gly His Pro
            35                  40                  45

Glu Ile Val Glu Val Leu Leu Lys Asn Gly Ala Asp Val Asn Ala Ala
            50                  55                  60

Asp Phe Gln Gly Trp Thr Pro Leu His Leu Ala Ala Val Gly His
65                  70                  75                  80

Leu Glu Ile Val Glu Val Leu Leu Lys His Gly Ala Asp Val Asn Ala
                85                  90                  95

Gln Asp Lys Phe Gly Lys Thr Ala Phe Asp Ile Ser Ile Asp Asn Gly
                100                 105                 110

Asn Glu Asp Leu Ala Glu Ile Leu Gln Lys Ala Ala
                115                 120
```

<210> SEQ ID NO 164
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Asp Leu Asp Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
                20                  25                  30

Ser Thr Gly Trp Thr Pro Leu His Leu Ala Ala Pro Trp Gly His Pro
            35                  40                  45

Glu Ile Val Glu Val Leu Leu Lys Ala Gly Ala Asp Val Asn Ala Lys
            50                  55                  60

Asp Phe Gln Gly Trp Thr Pro Leu His Leu Ala Ala Ala Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Asp Ala Gly
                100                 105                 110

His Glu Asp Ile Ala Glu Val Leu Gln Lys Ala Ala
                115                 120
```

<210> SEQ ID NO 165
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala Lys Asp
                20                  25                  30

Ser Thr Gly Trp Thr Pro Leu His Leu Ala Ala Pro Trp Gly His Pro
            35                  40                  45

Glu Ile Val Glu Val Leu Leu Lys Ala Gly Ala Asp Val Asn Ala Lys
```

```
              50                  55                  60
Asp Phe Gln Gly Trp Thr Pro Leu His Leu Ala Ala Ala Gly His
 65                  70                  75                  80

Leu Glu Ile Val Glu Val Leu Leu Lys Ala Gly Ala Asp Val Asn Ala
                 85                  90                  95

Gln Asp Lys Ser Gly Lys Thr Pro Ala Asp Leu Ala Ala Asp Ala Gly
                100                 105                 110

His Glu Asp Ile Ala Glu Val Leu Gln Lys Ala Ala
                115                 120

<210> SEQ ID NO 166
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Leu Asp Lys Lys Leu Leu Glu Ala Ala Arg Ala Gly Gln Asp Asp
 1               5                  10                  15

Glu Val Arg Ile Leu Leu Lys Ala Gly Ala Asp Val Asn Ala Lys Asp
                20                  25                  30

Ser Thr Gly Trp Thr Pro Leu His Leu Ala Ala Pro Trp Gly His Pro
             35                  40                  45

Glu Ile Val Glu Val Leu Leu Lys Ala Gly Ala Asp Val Asn Ala Lys
         50                  55                  60

Asp Phe Gln Gly Trp Thr Pro Leu His Leu Ala Ala Val Gly His
 65                  70                  75                  80

Leu Glu Ile Val Glu Val Leu Leu Lys Ala Gly Ala Asp Val Asn Ala
                 85                  90                  95

Gln Asp Lys Ser Gly Lys Thr Pro Ala Asp Leu Ala Ala Asp Ala Gly
                100                 105                 110

His Glu Asp Ile Ala Glu Val Leu Gln Lys Ala Ala
                115                 120

<210> SEQ ID NO 167
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Leu Asp Lys Lys Leu Leu Glu Ala Ala Arg Ala Gly Gln Asp Asp
 1               5                  10                  15

Glu Val Arg Ile Leu Leu Lys Ala Gly Ala Asp Val Asn Ala Lys Asp
                20                  25                  30

Ser Thr Gly Trp Thr Pro Leu His Leu Ala Ala Pro Trp Gly His Pro
             35                  40                  45

Glu Ile Val Glu Val Leu Leu Lys Ala Gly Ala Asp Val Asn Ala Lys
         50                  55                  60

Asp Tyr Gln Gly Trp Thr Pro Leu His Leu Ala Ala Val Gly His
 65                  70                  75                  80

Leu Glu Ile Val Glu Val Leu Leu Lys Ala Gly Ala Asp Val Asn Ala
                 85                  90                  95

Gln Asp Lys Ser Gly Lys Thr Pro Ala Asp Leu Ala Ala Asp Ala Gly
```

His Glu Asp Ile Ala Glu Val Leu Gln Lys Ala Ala
            115                 120

<210> SEQ ID NO 168
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Ser Thr Gly Trp Thr Pro Leu His Leu Ala Ala Pro Trp Gly His Leu
            35                  40                  45

Glu Ile Val Glu Val Leu Leu Lys Ala Gly Ala Asp Val Asn Ala Lys
        50                  55                  60

Asp Phe Gln Gly Trp Thr Pro Leu His Leu Ala Ala Val Gly His
65                  70                  75                  80

Leu Glu Ile Val Glu Val Leu Leu Lys Ala Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln Lys Ala Ala
        115                 120

<210> SEQ ID NO 169
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Pro Thr
    130                 135                 140

Pro Thr Gly Ser Asp Leu Asp Lys Lys Leu Leu Glu Ala Ala Arg Ala

```
            145                 150                 155                 160
Gly Gln Asp Asp Glu Val Arg Ile Leu Leu Lys Ala Gly Ala Asp Val
                    165                 170                 175

Asn Ala Lys Asp Ser Thr Gly Trp Thr Pro Leu His Leu Ala Ala Pro
                180                 185                 190

Trp Gly His Pro Glu Ile Val Glu Val Leu Leu Lys Ala Gly Ala Asp
                    195                 200                 205

Val Asn Ala Lys Asp Phe Gln Gly Trp Thr Pro Leu His Leu Ala Ala
            210                 215                 220

Ala Ala Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                    245                 250                 255

Ala Asp Ala Gly His Glu Asp Ile Ala Glu Val Leu Gln Lys Ala Ala
                260                 265                 270

<210> SEQ ID NO 170
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
        50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Thr Thr Pro Thr
        130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Ile Leu Leu Lys Ala Gly Ala
                165                 170                 175

Asp Val Asn Ala Lys Asp Arg Tyr Gly Asp Thr Pro Leu His Leu Ala
            180                 185                 190

Ala Asp Ile Gly His Leu Glu Ile Val Glu Val Leu Leu Lys Ala Gly
        195                 200                 205

Ala Asp Val Asn Ala Glu Asp Tyr Phe Gly Asn Thr Pro Leu His Leu
    210                 215                 220

Ala Ala Ser Tyr Gly His Leu Glu Ile Val Glu Val Leu Leu Lys Ala
225                 230                 235                 240
```

```
Gly Ala Asp Val Asn Ala Lys Asp Asp Tyr Gly Asn Thr Pro Leu His
                245                 250                 255
Leu Ala Ala Asn Thr Gly His Leu Glu Ile Val Glu Val Leu Leu Lys
        260                 265                 270
Ala Gly Ala Asp Val Asn Ala Gln Asp Lys Ser Gly Lys Thr Pro Ala
    275                 280                 285
Asp Leu Ala Ala Asp Ala Gly His Glu Asp Ile Ala Glu Val Leu Gln
290                 295                 300
Lys Ala Ala Gly Ser Pro Thr Pro Thr Pro Thr Pro Thr Pro Thr Pro
305                 310                 315                 320
Pro Thr Thr Pro Thr Pro Thr Pro Thr Gly Ser Asp Leu Asp Lys Lys
                325                 330                 335
Leu Leu Glu Ala Ala Arg Ala Gly Gln Asp Asp Glu Val Arg Ile Leu
            340                 345                 350
Leu Lys Ala Gly Ala Asp Val Asn Ala Lys Asp Ser Thr Gly Trp Thr
        355                 360                 365
Pro Leu His Leu Ala Ala Pro Trp Gly His Pro Glu Ile Val Glu Val
    370                 375                 380
Leu Leu Lys Ala Gly Ala Asp Val Asn Ala Lys Asp Phe Gln Gly Trp
385                 390                 395                 400
Thr Pro Leu His Leu Ala Ala Ala Gly His Leu Glu Ile Val Glu
                405                 410                 415
Val Leu Leu Lys Ala Gly Ala Asp Val Asn Ala Gln Asp Lys Ser Gly
            420                 425                 430
Lys Thr Pro Ala Asp Leu Ala Ala Asp Ala Gly His Glu Asp Ile Ala
        435                 440                 445
Glu Val Leu Gln Lys Ala Ala Gly Ser Pro Thr Pro Thr Pro Thr Thr
    450                 455                 460
Pro Thr Pro Thr Pro Thr Thr Pro Thr Pro Thr Pro Thr Gly Ser Asp
465                 470                 475                 480
Leu Gly Lys Lys Leu Leu Glu Ala Ala Arg Ala Gly Gln Asp Asp Glu
                485                 490                 495
Val Arg Glu Leu Leu Lys Ala Gly Ala Asp Val Asn Ala Lys Asp Tyr
            500                 505                 510
Phe Ser His Thr Pro Leu His Leu Ala Ala Arg Asn Gly His Leu Lys
        515                 520                 525
Ile Val Glu Val Leu Leu Lys Ala Gly Ala Asp Val Asn Ala Lys Asp
    530                 535                 540
Phe Ala Gly Lys Thr Pro Leu His Leu Ala Ala Asn Glu Gly His Leu
545                 550                 555                 560
Glu Ile Val Glu Val Leu Leu Lys Ala Gly Ala Asp Val Asn Ala Gln
                565                 570                 575
Asp Ile Phe Gly Lys Thr Pro Ala Asp Ile Ala Ala Asp Ala Gly His
            580                 585                 590
Glu Asp Ile Ala Glu Val Leu Gln Lys Ala Ala
        595                 600

<210> SEQ ID NO 171
<211> LENGTH: 1025
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171
```

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
                35                  40                  45

His Leu Glu Ile Val Glu Val Leu Leu Lys Asn Gly Ala Asp Val Asn
        50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly Arg Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Ser
145                 150                 155                 160

Gly Ser Pro Ala Gly Ser Pro Thr Ser Thr Glu Glu Gly Thr Ser Glu
                165                 170                 175

Ser Ala Thr Pro Glu Ser Gly Pro Gly Thr Ser Thr Glu Pro Ser Glu
                180                 185                 190

Gly Ser Ala Pro Gly Ser Pro Ala Gly Ser Pro Thr Ser Thr Glu Glu
                195                 200                 205

Gly Thr Ser Thr Glu Pro Ser Glu Gly Ser Ala Pro Gly Thr Ser Thr
                210                 215                 220

Glu Pro Ser Glu Gly Ser Ala Pro Gly Thr Ser Glu Ser Ala Thr Pro
225                 230                 235                 240

Glu Ser Gly Pro Gly Ser Glu Pro Ala Thr Ser Gly Ser Glu Thr Pro
                245                 250                 255

Gly Ser Glu Pro Ala Thr Ser Gly Ser Glu Thr Pro Gly Ser Pro Ala
                260                 265                 270

Gly Ser Pro Thr Ser Thr Glu Glu Gly Thr Ser Glu Ser Ala Thr Pro
                275                 280                 285

Glu Ser Gly Pro Gly Thr Ser Thr Glu Pro Ser Glu Gly Ser Ala Pro
                290                 295                 300

Gly Thr Ser Thr Glu Pro Ser Glu Gly Ser Ala Pro Gly Ser Pro Ala
305                 310                 315                 320

Gly Ser Pro Thr Ser Thr Glu Glu Gly Thr Ser Thr Glu Pro Ser Glu
                325                 330                 335

Gly Ser Ala Pro Gly Thr Ser Thr Glu Pro Ser Glu Gly Ser Ala Pro
                340                 345                 350

Gly Thr Ser Glu Ser Ala Thr Pro Glu Ser Gly Pro Gly Thr Ser Thr
                355                 360                 365

Glu Pro Ser Glu Gly Ser Ala Pro Gly Thr Ser Glu Ser Ala Thr Pro
                370                 375                 380

Glu Ser Gly Pro Gly Ser Glu Pro Ala Thr Ser Gly Ser Glu Thr Pro
385                 390                 395                 400

Gly Thr Ser Thr Glu Pro Ser Glu Gly Ser Ala Pro Gly Thr Ser Thr
                405                 410                 415
```

```
Glu Pro Ser Glu Gly Ser Ala Pro Gly Thr Ser Glu Ser Ala Thr Pro
                420                 425                 430

Glu Ser Gly Pro Gly Thr Ser Glu Ser Ala Thr Pro Glu Ser Gly Pro
            435                 440                 445

Gly Ser Pro Ala Gly Ser Pro Thr Ser Thr Glu Glu Gly Thr Ser Glu
        450                 455                 460

Ser Ala Thr Pro Glu Ser Gly Pro Gly Ser Glu Pro Ala Thr Ser Gly
465                 470                 475                 480

Ser Glu Thr Pro Gly Thr Ser Glu Ser Ala Thr Pro Glu Ser Gly Pro
                485                 490                 495

Gly Thr Ser Thr Glu Pro Ser Glu Gly Ser Ala Pro Gly Thr Ser Thr
            500                 505                 510

Glu Pro Ser Glu Gly Ser Ala Pro Gly Thr Thr Glu Pro Ser Glu
        515                 520                 525

Gly Ser Ala Pro Gly Thr Ser Thr Glu Pro Ser Glu Gly Ser Ala Pro
        530                 535                 540

Gly Thr Ser Thr Glu Pro Ser Glu Gly Ser Ala Pro Gly Thr Ser Thr
545                 550                 555                 560

Glu Pro Ser Glu Gly Ser Ala Pro Gly Ser Pro Ala Gly Ser Pro Thr
                565                 570                 575

Ser Thr Glu Glu Gly Thr Ser Thr Glu Pro Ser Glu Gly Ser Ala Pro
            580                 585                 590

Gly Thr Ser Glu Ser Ala Thr Pro Glu Ser Gly Pro Gly Ser Glu Pro
            595                 600                 605

Ala Thr Ser Gly Ser Glu Thr Pro Gly Thr Ser Glu Ser Ala Thr Pro
610                 615                 620

Glu Ser Gly Pro Gly Ser Glu Pro Ala Thr Ser Gly Ser Glu Thr Pro
625                 630                 635                 640

Gly Thr Ser Glu Ser Ala Thr Pro Glu Ser Gly Pro Gly Thr Ser Thr
            645                 650                 655

Glu Pro Ser Glu Gly Ser Ala Pro Gly Thr Ser Glu Ser Ala Thr Pro
                660                 665                 670

Glu Ser Gly Pro Gly Ser Pro Ala Gly Ser Pro Thr Ser Thr Glu Glu
            675                 680                 685

Gly Ser Pro Ala Gly Ser Pro Thr Ser Thr Glu Glu Gly Ser Pro Ala
        690                 695                 700

Gly Ser Pro Thr Ser Thr Glu Glu Gly Thr Ser Glu Ser Ala Thr Pro
705                 710                 715                 720

Glu Ser Gly Pro Gly Thr Ser Thr Glu Pro Ser Glu Gly Ser Ala Pro
                725                 730                 735

Gly Thr Ser Glu Ser Ala Thr Pro Glu Ser Gly Pro Gly Ser Glu Pro
            740                 745                 750

Ala Thr Ser Gly Ser Glu Thr Pro Gly Thr Ser Glu Ser Ala Thr Pro
        755                 760                 765

Glu Ser Gly Pro Gly Ser Glu Pro Ala Thr Ser Gly Ser Glu Thr Pro
        770                 775                 780

Gly Thr Ser Glu Ser Ala Thr Pro Glu Ser Gly Pro Gly Thr Ser Thr
785                 790                 795                 800

Glu Pro Ser Glu Gly Ser Ala Pro Gly Ser Pro Ala Gly Ser Pro Thr
                805                 810                 815

Ser Thr Glu Glu Gly Thr Ser Glu Ser Ala Thr Pro Glu Ser Gly Pro
            820                 825                 830

Gly Ser Glu Pro Ala Thr Ser Gly Ser Glu Thr Pro Gly Thr Ser Glu
```

```
                    835                 840                 845
Ser Ala Thr Pro Glu Ser Gly Pro Gly Ser Pro Ala Gly Ser Pro Thr
            850                 855                 860
Ser Thr Glu Glu Gly Ser Pro Ala Gly Ser Pro Thr Ser Thr Glu Glu
865                 870                 875                 880
Gly Thr Ser Thr Glu Pro Ser Glu Gly Ser Ala Pro Gly Thr Ser Glu
                885                 890                 895
Ser Ala Thr Pro Glu Ser Gly Pro Gly Thr Ser Glu Ser Ala Thr Pro
            900                 905                 910
Glu Ser Gly Pro Gly Thr Ser Glu Ser Ala Thr Pro Glu Ser Gly Pro
        915                 920                 925
Gly Ser Glu Pro Ala Thr Ser Gly Ser Glu Thr Pro Gly Ser Glu Pro
    930                 935                 940
Ala Thr Ser Gly Ser Glu Thr Pro Gly Ser Pro Ala Gly Ser Pro Thr
945                 950                 955                 960
Ser Thr Glu Glu Gly Thr Ser Thr Glu Pro Ser Glu Gly Ser Ala Pro
                965                 970                 975
Gly Thr Ser Thr Glu Pro Ser Glu Gly Ser Ala Pro Gly Ser Glu Pro
            980                 985                 990
Ala Thr Ser Gly Ser Glu Thr Pro  Gly Thr Ser Glu Ser  Ala Thr Pro
        995                 1000                1005
Glu Ser  Gly Pro Gly Thr Ser  Thr Glu Pro Ser Glu  Gly Ser Ala
    1010                1015                1020
Pro Gly
1025

<210> SEQ ID NO 172
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Gly
145                 150                 155                 160
```

```
Gly Gly Ser Gly Gly Gly Ser Cys
            165

<210> SEQ ID NO 173
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Arg Asp Ser Thr Gly Trp Thr Pro Leu His Leu Ala Ala Pro Trp Gly
            35                  40                  45

His Pro Glu Ile Val Glu Val Leu Leu Lys Asn Gly Ala Asp Val Asn
        50                  55                  60

Ala Ala Asp Phe Gln Gly Trp Thr Pro Leu His Leu Ala Ala Ala Val
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala Gly Gly
            115                 120                 125

Gly Ser Gly Gly Gly Ser Cys
        130                 135

<210> SEQ ID NO 174
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
                20                  25                  30

Ala Asp Ser Thr Gly Trp Thr Pro Leu His Leu Ala Val Pro Trp Gly
            35                  40                  45

His Leu Glu Ile Val Glu Val Leu Leu Lys Tyr Gly Ala Asp Val Asn
        50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala Gly Ser
            115                 120                 125

Gly Ser Ala Ser Pro Ala Ala Pro Ala Pro Ala Ser Pro Ala Ala Pro
        130                 135                 140
```

```
Ala Pro Ser Ala Pro Ala Ala Ser Pro Ala Ala Pro Ala Pro Ala Ser
145                 150                 155                 160
Pro Ala Ala Pro Ala Pro Ser Ala Pro Ala Ala Ser Pro Ala Ala Pro
                165                 170                 175
Ala Pro Ala Ser Pro Ala Ala Pro Ala Pro Ser Ala Pro Ala Ala Ser
                180                 185                 190
Pro Ala Ala Pro Ala Pro Ala Ser Pro Ala Ala Pro Ala Pro Ser Ala
                195                 200                 205
Pro Ala Ala Ser Pro Ala Ala Pro Ala Pro Ala Ser Pro Ala Ala Pro
        210                 215                 220
Ala Pro Ser Ala Pro Ala Ala Ser Pro Ala Ala Pro Ala Pro Ala Ser
225                 230                 235                 240
Pro Ala Ala Pro Ala Pro Ser Ala Pro Ala Ala Ser Pro Ala Ala Pro
                245                 250                 255
Ala Pro Ala Ser Pro Ala Ala Pro Ala Pro Ser Ala Pro Ala Ala Ser
                260                 265                 270
Pro Ala Ala Pro Ala Pro Ala Ser Pro Ala Ala Pro Ala Pro Ser Ala
                275                 280                 285
Pro Ala Ala Ser Pro Ala Ala Pro Ala Pro Ala Ser Pro Ala Ala Pro
        290                 295                 300
Ala Pro Ser Ala Pro Ala Ala Ser Pro Ala Ala Pro Ala Pro Ala Ser
305                 310                 315                 320
Pro Ala Ala Pro Ala Pro Ser Ala Pro Ala Ala Ser Pro Ala Ala Pro
                325                 330                 335
Ala Pro Ala Ser Pro Ala Ala Pro Ala Pro Ser Ala Pro Ala Ala Ser
                340                 345                 350
Pro Ala Ala Pro Ala Pro Ala Ser Pro Ala Ala Pro Ala Pro Ser Ala
                355                 360                 365
Pro Ala Ala Ser Pro Ala Ala Pro Ala Pro Ala Ser Pro Ala Ala Pro
        370                 375                 380
Ala Pro Ser Ala Pro Ala Ala Ser Pro Ala Ala Pro Ala Pro Ala Ser
385                 390                 395                 400
Pro Ala Ala Pro Ala Pro Ser Ala Pro Ala Ala Ser Pro Ala Ala Pro
                405                 410                 415
Ala Pro Ala Ser Pro Ala Ala Pro Ala Pro Ser Ala Pro Ala Ala Ser
                420                 425                 430
Pro Ala Ala Pro Ala Pro Ala Ser Pro Ala Ala Pro Ala Pro Ser Ala
                435                 440                 445
Pro Ala Ala Ser Pro Ala Ala Pro Ala Pro Ala Ser Pro Ala Ala Pro
        450                 455                 460
Ala Pro Ser Ala Pro Ala Ala Ser Pro Ala Ala Pro Ala Pro Ala Ser
465                 470                 475                 480
Pro Ala Ala Pro Ala Pro Ser Ala Pro Ala Ala Ser Pro Ala Ala Pro
                485                 490                 495
Ala Pro Ala Ser Pro Ala Ala Pro Ala Pro Ser Ala Pro Ala Ala Ser
                500                 505                 510
Pro Ala Ala Pro Ala Pro Ala Ser Pro Ala Ala Pro Ala Pro Ser Ala
                515                 520                 525
Pro Ala Ala Ser Pro Ala Ala Pro Ala Pro Ala Ser
        530                 535                 540

<210> SEQ ID NO 175
<211> LENGTH: 135
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 175

Gly Ser Asp Leu Gly Lys Lys Leu Leu Glu Ala Ala Arg Val Gly Gln
1               5                   10                  15

Asp Asp Glu Val Arg Ile Leu Met Ala Asp Gly Ala Asp Val Asn Ala
            20                  25                  30

Ser Asp Phe Lys Gly Asp Thr Pro Leu His Leu Ala Ala Ser Gln Gly
        35                  40                  45

His Leu Glu Ile Val Glu Val Leu Leu Lys Tyr Gly Ala Asp Val Asn
    50                  55                  60

Ala Tyr Asp Met Leu Gly Trp Thr Pro Leu His Leu Ala Ala Asp Leu
65                  70                  75                  80

Gly His Leu Glu Ile Val Glu Val Leu Leu Lys Tyr Gly Ala Asp Val
                85                  90                  95

Asn Ala Gln Asp Arg Phe Gly Lys Thr Ala Phe Asp Ile Ser Ile Asp
            100                 105                 110

Asn Gly Asn Glu Asp Leu Ala Glu Ile Leu Gln Lys Ala Ala Gly Ser
        115                 120                 125

Pro Ser Thr Ala Asp Gly Cys
    130                 135

<210> SEQ ID NO 176
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Ser Asp Leu Gly Lys Lys Leu Leu Glu Ala Val Arg Ala Gly Gln
1               5                   10                  15

Asp Asp Glu Val Arg Ile Leu Met Thr Asn Gly Ala Asp Val Asn Ala
            20                  25                  30

Lys Asp Gln Phe Gly Phe Thr Pro Leu Gln Leu Ala Ala Tyr Asn Gly
        35                  40                  45

His Leu Glu Ile Val Glu Val Leu Leu Lys Tyr Gly Ala Asp Val Asn
    50                  55                  60

Ala Phe Asp Ile Phe Gly Trp Thr Pro Leu His Leu Ala Ala Asp Leu
65                  70                  75                  80

Gly His Leu Glu Ile Val Glu Val Leu Leu Lys Asn Gly Ala Asp Val
                85                  90                  95

Asn Ala Gln Asp Lys Phe Gly Arg Thr Ala Phe Asp Ile Ser Ile Asp
            100                 105                 110

Asn Gly Asn Glu Asp Leu Ala Glu Ile Leu Gln Lys Ala Ala Ser Gly
        115                 120                 125

Ser Cys
    130

<210> SEQ ID NO 177
<211> LENGTH: 168
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Val Asp Tyr Ile Gly Trp Thr Pro Leu His Leu Ala Ala Tyr Gly
        35                  40                  45

His Leu Glu Ile Val Glu Val Leu Leu Lys Tyr Ser Ala Asp Val Asn
50                  55                  60

Ala Glu Asp Phe Ala Gly Tyr Thr Pro Leu His Leu Ala Ala Ser Asn
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Thr Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Gly
145                 150                 155                 160

Ser Pro Ser Thr Ala Asp Gly Cys
                165

<210> SEQ ID NO 178
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 178

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 179
<211> LENGTH: 33

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 179

Xaa Asp Xaa Xaa Gly Trp Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 180
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 180

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Xaa

<210> SEQ ID NO 181
<211> LENGTH: 33
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 181

Xaa Asp Xaa Xaa Gly Trp Thr Pro Leu His Leu Xaa Ala Asp Leu Gly
1               5                   10                  15

Xaa Leu Glu Ile Val Glu Val Leu Leu Lys Xaa Gly Ala Asp Val Asn
            20                  25                  30

Xaa

<210> SEQ ID NO 182
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 182

Xaa Asp Xaa Xaa Gly Xaa Thr Pro Leu His Leu Ala Ala Xaa Xaa Gly
1               5                   10                  15

His Xaa Glu Ile Val Glu Val Leu Leu Lys Xaa Gly Ala Asp Val Asn
            20                  25                  30
```

Ala

<210> SEQ ID NO 183
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 183

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 184
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 184

Xaa Asp Xaa Xaa Gly Trp Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 185

```
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 185

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Xaa

<210> SEQ ID NO 186
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 186

Xaa Asp Xaa Xaa Gly Xaa Thr Pro Leu His Leu Xaa Ala Xaa Xaa Gly
1               5                   10                  15
```

```
His Leu Glu Ile Val Glu Val Leu Leu Lys Xaa Gly Ala Asp Val Asn
            20                  25                  30

Ala

<210> SEQ ID NO 187
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 187

Xaa Asp Phe Lys Xaa Asp Thr Pro Leu His Leu Ala Ala Xaa Xaa Gly
1               5                   10                  15

His Xaa Glu Ile Val Glu Val Leu Leu Lys Xaa Gly Ala Asp Val Asn
            20                  25                  30

Ala

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 188

Xaa Asp Xaa Leu Xaa Xaa Thr Pro Leu His Leu Ala Xaa Xaa Xaa Gly
1               5                   10                  15

His Leu Glu Ile Val Glu Val Leu Leu Lys Xaa Gly Ala Asp Val Asn
```

20                  25                  30

Ala

<210> SEQ ID NO 189
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 189

Xaa Asp Xaa Xaa Gly Xaa Thr Pro Leu Xaa Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 190
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 190

Xaa Asp Xaa Xaa Gly Trp Thr Xaa Leu His Leu Ala Ala Asp Leu Gly

```
1               5                   10                  15
Xaa Leu Glu Ile Val Glu Val Leu Leu Lys Xaa Gly Ala Asp Val Asn
            20                  25                  30

Ala

<210> SEQ ID NO 191
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155

<210> SEQ ID NO 192
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gly Ser Asp Leu Gly Lys Lys Leu Leu Glu Ala Ala Arg Val Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110
```

Leu Gly His Leu Glu Ile Val Glu Val Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155

<210> SEQ ID NO 193
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly Arg Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155

<210> SEQ ID NO 194
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Thr Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

```
Asn Thr Lys Asp Asn Thr Gly Trp Thr Pro Leu His Leu Ser Ala Asp
                100                 105                 110

Leu Gly His Leu Glu Ile Val Glu Val Leu Leu Lys His Gly Ala Asp
            115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Ala Ala
145                 150                 155
```

<210> SEQ ID NO 195
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
                100                 105                 110

Leu Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Ala Ala
145                 150                 155
```

<210> SEQ ID NO 196
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80
```

```
Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Asn Gly Ala Asp
        115                 120                 125

Ile Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155
```

<210> SEQ ID NO 197
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys His Gly Ala Asp Val
                85                  90                  95

Asn Thr Thr Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155
```

<210> SEQ ID NO 198
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Tyr Met Gly Trp Thr Pro Leu His Leu Ala Ala His Asn Gly
        35                  40                  45

His Met Glu Ile Val Glu Val Leu Leu Lys Tyr Gly Ala Asp Val Asn
    50                  55                  60
```

```
Ala Ser Asp Tyr Ser Gly Tyr Thr Pro Leu His Leu Ala Ala Asp
 65                  70                  75                  80

Gly His Leu Glu Ile Val Glu Val Leu Lys Tyr Gly Ala Asp Val
             85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155
```

<210> SEQ ID NO 199
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
             20                  25                  30

Val Asp Tyr Ile Gly Trp Thr Pro Leu His Leu Ala Ala Ala Tyr Gly
         35                  40                  45

His Leu Glu Ile Val Glu Val Leu Leu Lys Tyr Ser Ala Asp Val Asn
 50                  55                  60

Ala Glu Asp Phe Ala Gly Tyr Thr Pro Leu His Leu Ala Ala Ser Asn
 65                  70                  75                  80

Gly His Leu Glu Ile Val Glu Val Leu Leu Lys Tyr Gly Ala Asp Val
             85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Thr Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155
```

<210> SEQ ID NO 200
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

```
Gly Ser Asp Leu Gly Lys Lys Leu Leu Glu Ala Ala Arg Thr Gly Gln
 1               5                  10                  15

Asp Asp Glu Val Arg Ile Leu Met Ala Asn Gly Ala Asp Val Asn Ala
             20                  25                  30

Thr Asp Tyr Met Gly Trp Thr Pro Leu His Leu Ala Ala Lys Val Gly
         35                  40                  45
```

```
His Leu Glu Ile Val Glu Val Leu Leu Lys Tyr Gly Ala Asp Val Asn
 50                  55                  60

Ala Glu Asp Tyr Asn Gly Tyr Thr Pro Leu His Leu Ala Ala Ala Met
 65                  70                  75                  80

Gly His Leu Glu Ile Ala Glu Val Leu Leu Lys Tyr Gly Ala Asp Val
                 85                  90                  95

Asn Thr Lys Asp Asn Thr Gly Trp Thr Pro Leu His Leu Ser Ala Asp
             100                 105                 110

Leu Gly His Leu Glu Ile Val Glu Val Leu Leu Lys Asn Gly Ala Asp
             115                 120                 125

Val Asn Ala Gln Asp Lys Phe Gly Lys Thr Ala Phe Asp Ile Ser Ile
         130                 135                 140

Asp Asn Gly Asn Glu Asp Leu Ala Glu Ile Leu Gln Lys Ala Ala
145                 150                 155

<210> SEQ ID NO 201
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Ser Asp Leu Gly Lys Lys Leu Leu Glu Ala Ala Arg Ala Gly Gln
 1               5                   10                  15

Asp Asp Glu Val Arg Ile Leu Met Ala Asn Gly Ala Asp Val Asn Ala
                 20                  25                  30

Arg Asp Ser Thr Gly Trp Thr Pro Leu His Leu Ala Ala Pro Trp Gly
             35                  40                  45

His Pro Glu Ile Val Glu Val Leu Leu Lys Asn Gly Ala Asp Val Asn
 50                  55                  60

Ala Ala Asp Phe Gln Gly Trp Thr Pro Leu His Leu Ala Ala Ala Val
 65                  70                  75                  80

Gly His Leu Glu Ile Val Glu Val Leu Leu Lys Tyr Gly Ala Asp Val
                 85                  90                  95

Asn Ala Gln Asp Lys Phe Gly Lys Thr Ala Phe Asp Ile Ser Ile Asp
             100                 105                 110

Asn Gly Asn Glu Asp Leu Ala Glu Ile Leu Gln Lys Ala Ala
             115                 120                 125

<210> SEQ ID NO 202
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Ser Asp Leu Gly Lys Lys Leu Leu Glu Ala Ala Arg Ala Gly Gln
 1               5                   10                  15

Asp Asp Glu Val Arg Ile Leu Met Ala Asn Gly Ala Asp Val Asn Ala
                 20                  25                  30

Arg Asp Ser Thr Gly Trp Thr Pro Leu His Leu Ala Ala Pro Trp Gly
             35                  40                  45

His Pro Glu Ile Val Glu Val Leu Leu Lys Asn Gly Ala Asp Val Asn
 50                  55                  60
```

Ala Ala Asp Phe Gln Gly Trp Thr Pro Leu His Leu Ala Ala Val
65                  70                  75                  80

Gly His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala
        115                 120                 125

<210> SEQ ID NO 203
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
                20                  25                  30

Ala Asp Ser Thr Gly Trp Thr Pro Leu His Leu Ala Ala Pro Trp Gly
            35                  40                  45

His Pro Glu Ile Val Glu Val Leu Leu Lys Asn Gly Ala Asp Val Asn
        50                  55                  60

Ala His Asp Tyr Gln Gly Trp Thr Pro Leu His Leu Ala Ala Thr Leu
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala
        115                 120                 125

<210> SEQ ID NO 204
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
                20                  25                  30

Ala Asp Ser Thr Gly Trp Thr Pro Leu His Leu Val Ala Pro Trp Gly
            35                  40                  45

His Pro Glu Ile Val Glu Val Leu Leu Lys His Gly Ala Asp Val Asn
        50                  55                  60

Thr His Asp Tyr Gln Gly Trp Thr Pro Leu His Leu Ala Ala Thr Leu
65                  70                  75                  80

Gly His Leu Glu Ile Val Glu Val Leu Leu Arg Tyr Gly Ala Asp Val
                85                  90                  95

Asn Ala Gln Asp Lys Phe Gly Lys Thr Ala Phe Asp Ile Ser Ile Asp
                100                 105                 110

-continued

```
Asn Gly Asn Glu Asp Leu Ala Glu Ile Leu Gln Lys Ala Ala
        115                 120                 125

<210> SEQ ID NO 205
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

Ala Asp Ser Thr Gly Trp Thr Pro Met His Leu Ala Ala Pro Trp Gly
        35                  40                  45

His Pro Glu Ile Val Glu Val Leu Leu Lys His Gly Ala Asp Val Asn
    50                  55                  60

Ala Gln Asp Phe Gln Gly Trp Thr Pro Leu His Leu Ala Ala Ala Ile
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 206
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

Ala Asp Ser Thr Gly Trp Thr Pro Leu His Leu Ala Val Pro Trp Gly
        35                  40                  45

His Leu Glu Ile Val Glu Val Leu Leu Lys Tyr Gly Ala Asp Val Asn
    50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 207
<211> LENGTH: 126
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 207

Gly Ser Asp Leu Gly Lys Lys Leu Leu Glu Ala Ala Arg Val Gly Gln
1               5                   10                  15

Asp Asp Glu Val Arg Ile Leu Met Ala Asp Gly Ala Asp Val Asn Ala
            20                  25                  30

Ser Asp Phe Lys Gly Asp Thr Pro Leu His Leu Ala Ala Ser Gln Gly
        35                  40                  45

His Leu Glu Ile Val Glu Val Leu Leu Lys Tyr Gly Ala Asp Val Asn
    50                  55                  60

Ala Tyr Asp Met Leu Gly Trp Thr Pro Leu His Leu Ala Ala Asp Leu
65                  70                  75                  80

Gly His Leu Glu Ile Val Glu Val Leu Leu Lys Tyr Gly Ala Asp Val
                85                  90                  95

Asn Ala Gln Asp Arg Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 208
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Ser Asp Leu Gly Lys Lys Leu Leu Glu Ala Ala Arg Val Gly Gln
1               5                   10                  15

Asp Asp Glu Val Arg Ile Leu Met Ala Asn Gly Ala Asp Val Asn Ala
            20                  25                  30

Ser Asp Phe Lys Gly Asp Thr Pro Leu His Leu Ala Ala Ser Gln Gly
        35                  40                  45

His Leu Glu Ile Val Glu Val Leu Leu Lys Asn Ser Ala Asp Val Asn
    50                  55                  60

Ala Phe Asp Leu Leu Gly Trp Thr Pro Leu His Leu Ala Ala Asp Leu
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 209
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gly Ser Asp Leu Gly Lys Lys Leu Leu Glu Ala Ala Arg Val Gly Gln
1               5                   10                  15
```

```
Asp Asp Glu Val Arg Ile Leu Met Ala Asn Gly Ala Asp Val Asn Ala
            20                  25                  30

Leu Asp Phe Lys Gly Asp Thr Pro Leu His Leu Ala Ala Ala Ser Gly
        35                  40                  45

His Leu Glu Ile Val Glu Val Leu Leu Lys Asn Gly Ala Asp Val Asn
 50                  55                  60

Ala His Asp Met Leu Ser Trp Thr Pro Leu His Leu Ala Gly Asp Leu
65                  70                  75                  80

Gly His Leu Glu Ile Val Glu Val Leu Leu Lys Tyr Gly Ala Asp Val
                85                  90                  95

Asn Ala Gln Asp Arg Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125
```

<210> SEQ ID NO 210
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

```
Gly Ser Asp Leu Gly Lys Lys Leu Leu Glu Ala Val Arg Ala Gly Gln
1               5                   10                  15

Asp Asp Glu Val Arg Ile Leu Met Thr Asn Gly Ala Asp Val Asn Ala
            20                  25                  30

Lys Asp Gln Phe Gly Phe Thr Pro Leu Gln Leu Ala Ala Tyr Asn Gly
        35                  40                  45

His Leu Glu Ile Val Glu Val Leu Leu Lys Tyr Gly Ala Asp Val Asn
 50                  55                  60

Ala Phe Asp Ile Phe Gly Trp Thr Pro Leu His Leu Ala Ala Asp Leu
65                  70                  75                  80

Gly His Leu Glu Ile Val Glu Val Leu Leu Lys Asn Gly Ala Asp Val
                85                  90                  95

Asn Ala Gln Asp Lys Phe Gly Arg Thr Ala Phe Asp Ile Ser Ile Asp
            100                 105                 110

Asn Gly Asn Glu Asp Leu Ala Glu Ile Leu Gln Lys Ala Ala
        115                 120                 125
```

<210> SEQ ID NO 211
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

```
Gly Ser Asp Leu Gly Lys Lys Leu Leu Glu Ala Val Arg Ala Gly Gln
1               5                   10                  15

Asp Asp Glu Val Arg Ile Leu Met Ala Asn Gly Ala Asp Val Asn Ala
            20                  25                  30

Ser Asp Asn Gln Gly Thr Thr Pro Leu His Leu Ala Ala Ser His Gly
        35                  40                  45

His Leu Glu Ile Val Glu Val Leu Leu Lys Tyr Gly Ala Asp Val Asn
 50                  55                  60
```

```
Asp Ala His Asp Asp Leu Gly Trp Thr Pro Leu His Leu Ser Ala Asp
 65                  70                  75                  80

Leu Gly His Leu Glu Ile Val Glu Val Leu Lys Tyr Gly Ala Asp
                 85                  90                  95

Val Asn Ala Gln Asp Lys Phe Gly Lys Thr Ala Phe Asp Ile Ser Ile
            100                 105                 110

Asp Asn Gly Asn Glu Asp Leu Ala Glu Ile Leu Gln Lys Ala Ala
            115                 120                 125

<210> SEQ ID NO 212
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gly Ser Asp Leu Gly Lys Lys Leu Leu Glu Ala Thr Arg Ala Gly Gln
 1               5                  10                  15

Asp Asp Glu Val Arg Ile Leu Met Ala Asn Gly Ala Asp Val Asn Ala
             20                  25                  30

Ser Asp Asn Gln Gly Thr Thr Pro Leu His Leu Ala Ala Ser His Gly
         35                  40                  45

His Leu Glu Ile Val Glu Val Leu Leu Lys Tyr Gly Ala Asp Val Asn
 50                  55                  60

Asp Ala His Asp Asp Leu Gly Trp Thr Pro Leu His Leu Ala Ala Asp
 65                  70                  75                  80

Leu Gly His Leu Glu Ile Val Glu Val Leu Leu Lys Tyr Gly Ala Asp
                 85                  90                  95

Val Asn Ala Gln Asp Lys Phe Gly Lys Thr Ala Phe Asp Ile Ser Ile
            100                 105                 110

Asp Asn Gly Asn Glu Asp Leu Ala Glu Ile Leu Gln Lys Ala Ala
            115                 120                 125

<210> SEQ ID NO 213
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Ser Asp Leu Gly Lys Lys Leu Leu Glu Ala Ala Arg Val Gly Gln
 1               5                  10                  15

Asp Asp Glu Val Arg Ile Leu Met Ala Asp Gly Ala Asp Val Asn Ala
             20                  25                  30

Ser Asp Phe Lys Gly Asp Thr Pro Leu His Leu Ala Ala Ser Gln Gly
         35                  40                  45

His Leu Glu Ile Val Glu Val Leu Leu Lys Tyr Gly Ala Asp Val Asn
 50                  55                  60

Ala Tyr Asp Met Leu Gly Trp Thr Pro Leu His Leu Ala Ala Asp Leu
 65                  70                  75                  80

Gly His Leu Glu Ile Val Glu Val Leu Leu Lys Tyr Gly Ala Asp Val
                 85                  90                  95

Asn Ala Gln Asp Arg Phe Gly Lys Thr Ala Phe Asp Ile Ser Ile Asp
            100                 105                 110
```

```
Asn Gly Asn Glu Asp Leu Ala Glu Ile Leu Gln Lys Ala Ala
        115                 120                 125

<210> SEQ ID NO 214
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Ser Asp Leu Gly Lys Lys Leu Leu Glu Ala Ala Arg Val Gly Gln
1               5                   10                  15

Asp Asp Glu Val Arg Ile Leu Met Ala Asn Asp Ala Asp Val Asn Ala
            20                  25                  30

Ser Asp Phe Lys Gly Asp Thr Pro Leu His Leu Ala Ala Ser Gln Gly
        35                  40                  45

His Leu Glu Ile Val Glu Val Leu Leu Lys Tyr Gly Ala Asp Val Asn
    50                  55                  60

Ala Tyr Asp Met Leu Gly Trp Thr Pro Leu His Leu Ala Ala Asp Leu
65                  70                  75                  80

Gly His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 215
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

Leu Asp Phe Lys Ser Asp Thr Pro Leu His Leu Ala Ala Ser Gly
        35                  40                  45

His Leu Glu Ile Val Glu Val Leu Leu Lys Asn Gly Ala Asp Val Asn
    50                  55                  60

Ala His Asp Met Leu Ser Trp Thr Pro Leu His Leu Ala Gly Asp Leu
65                  70                  75                  80

Gly His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 216
<211> LENGTH: 159
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 216

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Ile Tyr Gly Arg Thr Pro Leu His Leu Ala Ala Leu His Gly
        35                  40                  45

His Pro Glu Ile Val Glu Val Leu Leu Lys Tyr Gly Ala Asp Val Asn
    50                  55                  60

Ala Asn Asp Tyr Trp Gly Thr Thr Ser Leu His Leu Val Ala Ile Trp
65                  70                  75                  80

Gly His Leu Glu Ile Val Glu Val Leu Leu Lys Tyr Gly Ala Asp Val
                85                  90                  95

Asn Ala Val Asp Asp Ile Gly Gln Thr Pro Leu His Leu Ala Ala Ala
                100                 105                 110

Trp Gly His Leu Glu Ile Val Glu Val Leu Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Lys Ala Ala
145                 150                 155

<210> SEQ ID NO 217
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asn Asp Tyr Asp Gly Met Thr Pro Leu His Leu Ala Ala Met Glu Gly
        35                  40                  45

His Leu Glu Ile Val Glu Val Leu Leu Lys Tyr Gly Ala Asp Val Asn
    50                  55                  60

Ala Asn Asp His Tyr Gly Phe Thr Pro Leu His Leu Ala Trp Thr Gly
65                  70                  75                  80

Arg Leu Glu Ile Val Glu Val Leu Leu Lys Asn Gly Ala Asp Val Asn
                85                  90                  95

Ala Ala Asp Val Phe Gly Arg Thr Pro Leu His Leu Ala Ala Thr Ser
                100                 105                 110

Gly His Leu Glu Ile Val Glu Val Leu Leu Lys Tyr Gly Ala Asp Val
            115                 120                 125

Asn Ala Gln Asp Lys Phe Gly Lys Thr Ala Phe Asp Ile Ser Ile Asp
        130                 135                 140

Asn Gly Asn Glu Asp Leu Ala Glu Ile Leu Gln Lys Ala Ala
145                 150                 155

<210> SEQ ID NO 218
<211> LENGTH: 490

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Met Val Ser Ser Ala Gln Phe Leu Gly Leu Leu Leu Cys Phe Gln
1               5                   10                  15

Gly Thr Arg Cys Asp Val Val Met Thr Gln Ser Pro Ser Phe Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Arg Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Gly Gly Ser Glu
225                 230                 235                 240

Ile Val Met Thr Gln Ser Pro Ser Thr Leu Ser Ala Ser Val Gly Asp
                245                 250                 255

Arg Val Ile Ile Thr Cys Gln Ala Ser Glu Ile Ile His Ser Trp Leu
            260                 265                 270

Ala Trp Tyr Gln Gln Lys Pro Gly Lys Ala Pro Lys Leu Leu Ile Tyr
        275                 280                 285

Leu Ala Ser Thr Leu Ala Ser Gly Val Pro Ser Arg Phe Ser Gly Ser
    290                 295                 300

Gly Ser Gly Ala Glu Phe Thr Leu Thr Ile Ser Ser Leu Gln Pro Asp
305                 310                 315                 320

Asp Phe Ala Thr Tyr Tyr Cys Gln Asn Val Tyr Leu Ala Ser Thr Asn
                325                 330                 335

Gly Ala Asn Phe Gly Gln Gly Thr Lys Leu Thr Val Leu Gly Gly Gly
            340                 345                 350

Gly Gly Ser Gly Gly Gly Gly Ser Gly Gly Gly Gly Ser Gly Gly Gly
        355                 360                 365

Gly Ser Glu Val Gln Leu Val Glu Ser Gly Gly Gly Leu Val Gln Pro
    370                 375                 380
```

```
Gly Gly Ser Leu Arg Leu Ser Cys Thr Ala Ser Gly Phe Ser Leu Thr
385                 390                 395                 400

Asp Tyr Tyr Tyr Met Thr Trp Val Arg Gln Ala Pro Gly Lys Gly Leu
                405                 410                 415

Glu Trp Val Gly Phe Ile Asp Pro Asp Asp Pro Tyr Tyr Ala Thr
            420                 425                 430

Trp Ala Lys Gly Arg Phe Thr Ile Ser Arg Asp Asn Ser Lys Asn Thr
            435                 440                 445

Leu Tyr Leu Gln Met Asn Ser Leu Arg Ala Glu Asp Thr Ala Val Tyr
450                 455                 460

Tyr Cys Ala Gly Asp His Asn Ser Gly Trp Gly Leu Asp Ile Trp
465                 470                 475                 480

Gly Gln Gly Thr Leu Val Thr Val Ser Ser
                485                 490

<210> SEQ ID NO 219
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Ser Phe Leu Ser
                20                  25                  30

Ala Ser Val Gly Asp Arg Val Thr Ile Thr Cys Lys Ala Ser Gln His
            35                  40                  45

Val Gly Thr Ala Val Ala Trp Tyr Gln Gln Arg Pro Gly Lys Ala Pro
50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
                100                 105                 110

Ser Tyr Pro Phe Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys Gly Gly Gly Gly Ser Ser
225                 230                 235                 240

Asp Thr Gly Arg Pro Phe Val Glu Met Tyr Ser Glu Ile Pro Glu Ile
```

```
                    245                 250                 255

Ile His Met Thr Glu Gly Arg Glu Leu Val Ile Pro Cys Arg Val Thr
            260                 265                 270

Ser Pro Asn Ile Thr Val Thr Leu Lys Lys Phe Pro Leu Asp Thr Leu
        275                 280                 285

Ile Pro Asp Gly Lys Arg Ile Ile Trp Asp Ser Arg Lys Gly Phe Ile
    290                 295                 300

Ile Ser Asn Ala Thr Tyr Lys Glu Ile Gly Leu Leu Thr Cys Glu Ala
305                 310                 315                 320

Thr Val Asn Gly His Leu Tyr Lys Thr Asn Tyr Leu Thr His Arg Gln
                325                 330                 335

Thr Asn Thr Ile Ile Asp Val Val Leu Ser Pro Ser His Gly Ile Glu
            340                 345                 350

Leu Ser Val Gly Glu Lys Leu Val Leu Asn Cys Thr Ala Arg Thr Glu
        355                 360                 365

Leu Asn Val Gly Ile Asp Phe Asn Trp Glu Tyr Pro Ser Ser Lys His
    370                 375                 380

Gln His Lys Lys Leu Val Asn Arg Asp Leu Lys Thr Gln Ser Gly Ser
385                 390                 395                 400

Glu Met Lys Lys Phe Leu Ser Thr Leu Thr Ile Asp Gly Val Thr Arg
                405                 410                 415

Ser Asp Gln Gly Leu Tyr Thr Cys Ala Ala Ser Ser Gly Leu Met Thr
            420                 425                 430

Lys Lys Asn Ser Thr Phe Val Arg Val His Glu Lys
        435                 440

<210> SEQ ID NO 220
<211> LENGTH: 330
<212> TYPE: PRT
<213> ORGANISM: Homo sapiens

<400> SEQUENCE: 220

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 221
<211> LENGTH: 326
<212> TYPE: PRT
<213> ORGANISM: Homo sapiens

<400> SEQUENCE: 221

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 222
<211> LENGTH: 377
<212> TYPE: PRT
<213> ORGANISM: Homo sapiens

<400> SEQUENCE: 222

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
```

```
                 260                 265                 270
Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 223
<211> LENGTH: 428
<212> TYPE: PRT
<213> ORGANISM: Homo sapiens

<400> SEQUENCE: 223

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255
```

```
Arg Ala Ser Gly Lys Pro Val Asn His Ser Thr Arg Lys Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
        355                 360                 365

Ala Arg His Ser Thr Thr Gln Pro Arg Lys Thr Lys Gly Ser Gly Phe
    370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425

<210> SEQ ID NO 224
<211> LENGTH: 353
<212> TYPE: PRT
<213> ORGANISM: Homo sapiens

<400> SEQUENCE: 224

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205
```

Pro Glu Ser Lys Thr Pro Leu Thr Ala Thr Leu Ser Lys Ser Gly Asn
210 215 220

Thr Phe Arg Pro Glu Val His Leu Leu Pro Pro Ser Glu Glu Leu
225 230 235 240

Ala Leu Asn Glu Leu Val Thr Leu Thr Cys Leu Ala Arg Gly Phe Ser
245 250 255

Pro Lys Asp Val Leu Val Arg Trp Leu Gln Gly Ser Gln Glu Leu Pro
260 265 270

Arg Glu Lys Tyr Leu Thr Trp Ala Ser Arg Gln Glu Pro Ser Gln Gly
275 280 285

Thr Thr Thr Phe Ala Val Thr Ser Ile Leu Arg Val Ala Ala Glu Asp
290 295 300

Trp Lys Lys Gly Asp Thr Phe Ser Cys Met Val Gly His Glu Ala Leu
305 310 315 320

Pro Leu Ala Phe Thr Gln Lys Thr Ile Asp Arg Leu Ala Gly Lys Pro
325 330 335

Thr His Val Asn Val Ser Val Val Met Ala Glu Val Asp Gly Thr Cys
340 345 350

Tyr

<210> SEQ ID NO 225
<211> LENGTH: 340
<212> TYPE: PRT
<213> ORGANISM: Homo sapiens

<400> SEQUENCE: 225

Ala Ser Pro Thr Ser Pro Lys Val Phe Pro Leu Ser Leu Asp Ser Thr
1 5 10 15

Pro Gln Asp Gly Asn Val Val Ala Cys Leu Val Gln Gly Phe Phe
20 25 30

Pro Gln Glu Pro Leu Ser Val Thr Trp Ser Glu Ser Gly Gln Asn Val
35 40 45

Thr Ala Arg Asn Phe Pro Pro Ser Gln Asp Ala Ser Gly Asp Leu Tyr
50 55 60

Thr Thr Ser Ser Gln Leu Thr Leu Pro Ala Thr Gln Cys Pro Asp Gly
65 70 75 80

Lys Ser Val Thr Cys His Val Lys His Tyr Thr Asn Ser Ser Gln Asp
85 90 95

Val Thr Val Pro Cys Arg Val Pro Pro Pro Pro Cys Cys His Pro
100 105 110

Arg Leu Ser Leu His Arg Pro Ala Leu Glu Asp Leu Leu Leu Gly Ser
115 120 125

Glu Ala Asn Leu Thr Cys Thr Leu Thr Gly Leu Arg Asp Ala Ser Gly
130 135 140

Ala Thr Phe Thr Trp Thr Pro Ser Ser Gly Lys Ser Ala Val Gln Gly
145 150 155 160

Pro Pro Glu Arg Asp Leu Cys Gly Cys Tyr Ser Val Ser Ser Val Leu
165 170 175

Pro Gly Cys Ala Gln Pro Trp Asn His Gly Glu Thr Phe Thr Cys Thr
180 185 190

Ala Ala His Pro Glu Leu Lys Thr Pro Leu Thr Ala Asn Ile Thr Lys
195 200 205

Ser Gly Asn Thr Phe Arg Pro Glu Val His Leu Leu Pro Pro Ser
210 215 220

```
Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Glu Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340

<210> SEQ ID NO 226
<211> LENGTH: 453
<212> TYPE: PRT
<213> ORGANISM: Homo sapiens

<400> SEQUENCE: 226

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
```

```
                      245                 250                 255
    Ile Ser Trp Thr Arg Gln Asn Gly Glu Ala Val Lys Thr His Thr Asn
                      260                 265                 270

Ile Ser Glu Ser His Pro Asn Ala Thr Phe Ser Ala Val Gly Glu Ala
                  275                 280                 285

Ser Ile Cys Glu Asp Asp Trp Asn Ser Gly Glu Arg Phe Thr Cys Thr
              290                 295                 300

Val Thr His Thr Asp Leu Pro Ser Pro Leu Lys Gln Thr Ile Ser Arg
    305                 310                 315                 320

Pro Lys Gly Val Ala Leu His Arg Pro Asp Val Tyr Leu Leu Pro Pro
                    325                 330                 335

Ala Arg Glu Gln Leu Asn Leu Arg Glu Ser Ala Thr Ile Thr Cys Leu
                    340                 345                 350

Val Thr Gly Phe Ser Pro Ala Asp Val Phe Val Gln Trp Met Gln Arg
                    355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
    385                 390                 395                 400

Ser Glu Glu Glu Trp Asn Thr Gly Glu Thr Tyr Thr Cys Val Val Ala
                        405                 410                 415

His Glu Ala Leu Pro Asn Arg Val Thr Glu Arg Thr Val Asp Lys Ser
                    420                 425                 430

Thr Gly Lys Pro Thr Leu Tyr Asn Val Ser Leu Val Met Ser Asp Thr
                435                 440                 445

Ala Gly Thr Cys Tyr
                450

<210> SEQ ID NO 227
<211> LENGTH: 384
<212> TYPE: PRT
<213> ORGANISM: Homo sapiens

<400> SEQUENCE: 227

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160
```

```
Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Val Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Arg Ser Thr Thr Phe Trp Ala
                325                 330                 335

Trp Ser Val Leu Arg Val Pro Ala Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380

<210> SEQ ID NO 228
<211> LENGTH: 106
<212> TYPE: PRT
<213> ORGANISM: Homo sapiens

<400> SEQUENCE: 228

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 229

His His His Arg His Ser Phe
1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Cys His His His Arg His Ser Phe
1               5

<210> SEQ ID NO 231
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Asn Ala Asn Ala Met Asn Trp Val Arg Gln Ala Pro Gly Lys Gly Leu
        50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
        290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Gly Gly Gly Ser Asp Leu Asp Lys Lys Leu Leu Glu
465                 470                 475                 480

Ala Ala Arg Ala Gly Gln Asp Asp Glu Val Arg Ile Leu Met Ala Asn
                485                 490                 495

Gly Ala Asp Val Asn Ala Arg Asp Ser Thr Gly Trp Thr Pro Leu His
            500                 505                 510

Leu Ala Ala Pro Trp Gly His Pro Glu Ile Val Glu Val Leu Leu Lys
        515                 520                 525

Asn Gly Ala Asp Val Asn Ala Asp Phe Gln Gly Trp Thr Pro Leu
    530                 535                 540

His Leu Ala Ala Ala Val Gly His Leu Glu Ile Val Glu Val Leu Leu
545                 550                 555                 560

Lys Tyr Gly Ala Asp Val Asn Ala Gln Asp Lys Phe Gly Lys Thr Ala
                565                 570                 575

Phe Asp Ile Ser Ile Asp Asn Gly Asn Glu Asp Leu Ala Glu Ile Leu
            580                 585                 590

Gln Lys Ala Ala
        595

<210> SEQ ID NO 232
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Ser Phe Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Arg Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys Gly Gly Gly Ser Asp
225                 230                 235                 240

Leu Asp Lys Lys Leu Leu Glu Ala Ala Arg Ala Gly Gln Asp Asp Glu
                245                 250                 255

Val Arg Ile Leu Met Ala Asn Gly Ala Asp Val Asn Ala Arg Asp Ser
            260                 265                 270

Thr Gly Trp Thr Pro Leu His Leu Ala Ala Pro Trp Gly His Pro Glu
        275                 280                 285

Ile Val Glu Val Leu Leu Lys Asn Gly Ala Asp Val Asn Ala Ala Asp
290                 295                 300

Phe Gln Gly Trp Thr Pro Leu His Leu Ala Ala Val Gly His Leu
305                 310                 315                 320

Glu Ile Val Glu Val Leu Leu Lys Tyr Gly Ala Asp Val Asn Ala Gln
                325                 330                 335

Asp Lys Phe Gly Lys Thr Ala Phe Asp Ile Ser Ile Asp Asn Gly Asn
            340                 345                 350

Glu Asp Leu Ala Glu Ile Leu Gln Lys Ala Ala
        355                 360

<210> SEQ ID NO 233
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Asp Leu Asp Lys Lys Leu Leu Glu Ala Ala Arg Ala Gly Gln Asp Asp

```
                 1               5                  10                  15
Glu Val Arg Ile Leu Met Ala Asn Gly Ala Asp Val Asn Ala Arg Asp
                20                  25                  30

Ser

<210> SEQ ID NO 234
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Thr Gly Trp Thr Pro Leu His Leu Ala Ala Pro Trp Gly His Pro Glu
1               5                   10                  15
Ile Val Glu Val Leu Leu Lys Asn Gly Ala Asp Val Asn Ala Ala Asp
                20                  25                  30
Phe

<210> SEQ ID NO 235
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Gly Trp Thr Pro Leu His Leu Ala Ala Val Gly His Leu Glu
1               5                   10                  15
Ile Val Glu Val Leu Leu Lys Tyr Gly Ala Asp Val Asn Ala Gln Asp
                20                  25                  30
Lys

<210> SEQ ID NO 236
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Phe Gly Lys Thr Ala Phe Asp Ile Ser Ile Asp Asn Gly Asn Glu Asp
1               5                   10                  15
Leu Ala Glu Ile Leu Gln
                20

<210> SEQ ID NO 237
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: K, T, or Y
<220> FEATURE:
<221> NAME/KEY: MOD_RES
<222> LOCATION: (3)..(3)
<223> OTHER INFORMATION: N or M
<220> FEATURE:
```

```
<221> NAME/KEY: MOD_RES
<222> LOCATION: (4)..(4)
<223> OTHER INFORMATION: T or F
<220> FEATURE:
<221> NAME/KEY: MOD_RES
<222> LOCATION: (12)..(12)
<223> OTHER INFORMATION: S or A
<220> FEATURE:
<221> NAME/KEY: MOD_RES
<222> LOCATION: (17)..(17)
<223> OTHER INFORMATION: H or R
<220> FEATURE:
<221> NAME/KEY: MOD_RES
<222> LOCATION: (27)..(27)
<223> OTHER INFORMATION: A, Y, H, or N
<220> FEATURE:
<221> NAME/KEY: MOD_RES
<222> LOCATION: (33)..(33)
<223> OTHER INFORMATION: A or T

<400> SEQUENCE: 237

Xaa Asp Xaa Xaa Gly Trp Thr Pro Leu His Leu Xaa Ala Asp Leu Gly
1               5                   10                  15

Xaa Leu Glu Ile Val Glu Val Leu Leu Lys Xaa Gly Ala Asp Val Asn
            20                  25                  30

Xaa

<210> SEQ ID NO 238
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: K, M, N, R, or V
<220> FEATURE:
<221> NAME/KEY: MOD_RES
<222> LOCATION: (3)..(3)
<223> OTHER INFORMATION: Y, H, M, or V
<220> FEATURE:
<221> NAME/KEY: MOD_RES
<222> LOCATION: (4)..(4)
<223> OTHER INFORMATION: F, L, M, or V
<220> FEATURE:
<221> NAME/KEY: MOD_RES
<222> LOCATION: (14)..(14)
<223> OTHER INFORMATION: R, H, V, A, K, or N
<220> FEATURE:
<221> NAME/KEY: MOD_RES
<222> LOCATION: (15)..(15)
<223> OTHER INFORMATION: F, D, H, T, Y, M, or K
<220> FEATURE:
<221> NAME/KEY: MOD_RES
<222> LOCATION: (27)..(27)
<223> OTHER INFORMATION: A, H, N, or Y

<400> SEQUENCE: 238

Xaa Asp Xaa Xaa Gly Trp Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 239
<211> LENGTH: 33
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L, S, or T
<220> FEATURE:
<221> NAME/KEY: MOD_RES
<222> LOCATION: (5)..(5)
<223> OTHER INFORMATION: G, S, or C
<220> FEATURE:
<221> NAME/KEY: MOD_RES
<222> LOCATION: (14)..(14)
<223> OTHER INFORMATION: S or A
<220> FEATURE:
<221> NAME/KEY: MOD_RES
<222> LOCATION: (15)..(15)
<223> OTHER INFORMATION: Q, S, M, or N
<220> FEATURE:
<221> NAME/KEY: MOD_RES
<222> LOCATION: (18)..(18)
<223> OTHER INFORMATION: L, M, or Q
<220> FEATURE:
<221> NAME/KEY: MOD_RES
<222> LOCATION: (27)..(27)
<223> OTHER INFORMATION: A, H, N, Y, or D

<400> SEQUENCE: 239

Xaa Asp Phe Lys Xaa Asp Thr Pro Leu His Leu Ala Ala Xaa Xaa Gly
1               5                   10                  15

His Xaa Glu Ile Val Glu Val Leu Leu Lys Xaa Gly Ala Asp Val Asn
            20                  25                  30

Ala

<210> SEQ ID NO 240
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: K, S, I, N, T, or V
<220> FEATURE:
<221> NAME/KEY: MOD_RES
<222> LOCATION: (3)..(3)
<223> OTHER INFORMATION: K, N, W, A, H, M, Q, or S
<220> FEATURE:
<221> NAME/KEY: MOD_RES
<222> LOCATION: (4)..(4)
<223> OTHER INFORMATION: F, Q, L, H, or V
<220> FEATURE:
<221> NAME/KEY: MOD_RES
<222> LOCATION: (6)..(6)
<223> OTHER INFORMATION: F or T
<220> FEATURE:
<221> NAME/KEY: MOD_RES
<222> LOCATION: (10)..(10)
<223> OTHER INFORMATION: Q or H
<220> FEATURE:
<221> NAME/KEY: MOD_RES
<222> LOCATION: (14)..(14)
<223> OTHER INFORMATION: Y or S
<220> FEATURE:
<221> NAME/KEY: MOD_RES
<222> LOCATION: (15)..(15)
<223> OTHER INFORMATION: N, H, Y, or M
<220> FEATURE:
<221> NAME/KEY: MOD_RES
<222> LOCATION: (27)..(27)
<223> OTHER INFORMATION: A, H, N, or Y

<400> SEQUENCE: 240
```

```
Xaa Asp Xaa Xaa Gly Xaa Thr Pro Leu Xaa Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 241
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A, N, R, V, Y, E, H, I, K, L, Q, S, or T
<220> FEATURE:
<221> NAME/KEY: MOD_RES
<222> LOCATION: (3)..(3)
<223> OTHER INFORMATION: S, A, N, R, D, F, L, P, T, or Y
<220> FEATURE:
<221> NAME/KEY: MOD_RES
<222> LOCATION: (4)..(4)
<223> OTHER INFORMATION: T, V, S, A, L, or F
<220> FEATURE:
<221> NAME/KEY: MOD_RES
<222> LOCATION: (6)..(6)
<223> OTHER INFORMATION: W, F, or H
<220> FEATURE:
<221> NAME/KEY: MOD_RES
<222> LOCATION: (14)..(14)
<223> OTHER INFORMATION: P, I, A, L, S, T, V, or Y
<220> FEATURE:
<221> NAME/KEY: MOD_RES
<222> LOCATION: (15)..(15)
<223> OTHER INFORMATION: W, F, I, L, T, or V
<220> FEATURE:
<221> NAME/KEY: MOD_RES
<222> LOCATION: (18)..(18)
<223> OTHER INFORMATION: L or P
<220> FEATURE:
<221> NAME/KEY: MOD_RES
<222> LOCATION: (27)..(27)
<223> OTHER INFORMATION: A, H, N, or Y

<400> SEQUENCE: 241

Xaa Asp Xaa Xaa Gly Xaa Thr Pro Leu His Leu Ala Ala Xaa Xaa Gly
1               5                   10                  15

His Xaa Glu Ile Val Glu Val Leu Leu Lys Xaa Gly Ala Asp Val Asn
            20                  25                  30

Ala

<210> SEQ ID NO 242
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: H, Q, A, K, R, D, I, L, M, N, V, or Y
<220> FEATURE:
<221> NAME/KEY: MOD_RES
<222> LOCATION: (3)..(3)
<223> OTHER INFORMATION: Y, F, or H
<220> FEATURE:
<221> NAME/KEY: MOD_RES
<222> LOCATION: (4)..(4)
```

```
<223> OTHER INFORMATION: Q, F, or T
<220> FEATURE:
<221> NAME/KEY: MOD_RES
<222> LOCATION: (6)..(6)
<223> OTHER INFORMATION: W, M, G, H, N, or T
<220> FEATURE:
<221> NAME/KEY: MOD_RES
<222> LOCATION: (14)..(14)
<223> OTHER INFORMATION: T, A, M, L, or V
<220> FEATURE:
<221> NAME/KEY: MOD_RES
<222> LOCATION: (15)..(15)
<223> OTHER INFORMATION: I, L, V, D, or T
<220> FEATURE:
<221> NAME/KEY: MOD_RES
<222> LOCATION: (27)..(27)
<223> OTHER INFORMATION: A, H, N, or Y

<400> SEQUENCE: 242

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 243
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Ser Phe Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Arg Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
```

```
                210               215                 220
Val Thr Lys Ser Phe Asn Arg Gly Glu Cys Gly Gly Gly Ser Glu
225                 230                 235                 240

Val Gln Leu Val Glu Ser Gly Gly Leu Val Gln Pro Gly Gly Ser
                245                 250                 255

Leu Arg Leu Ser Cys Ala Ala Ser Gly Tyr Asp Phe Thr His Tyr Gly
                260                 265                 270

Met Asn Trp Val Arg Gln Ala Pro Gly Lys Gly Leu Glu Trp Val Gly
            275                 280                 285

Trp Ile Asn Thr Tyr Thr Gly Glu Pro Thr Tyr Ala Ala Asp Phe Lys
        290                 295                 300

Arg Arg Phe Thr Phe Ser Leu Asp Thr Ser Lys Ser Thr Ala Tyr Leu
305                 310                 315                 320

Gln Met Asn Ser Leu Arg Ala Glu Asp Thr Ala Val Tyr Tyr Cys Ala
                325                 330                 335

Lys Tyr Pro Tyr Tyr Tyr Gly Thr Ser His Trp Tyr Phe Asp Val Trp
                340                 345                 350

Gly Gln Gly Thr Leu Val Thr Val Ser Ser Gly Gly Gly Gly Ser Gly
                355                 360                 365

Gly Gly Gly Ser Gly Gly Gly Gly Ser Asp Ile Gln Leu Thr Gln Ser
            370                 375                 380

Pro Ser Ser Leu Ser Ala Ser Val Gly Asp Arg Val Thr Ile Thr Cys
385                 390                 395                 400

Ser Ala Ser Gln Asp Ile Ser Asn Tyr Leu Asn Trp Tyr Gln Gln Lys
                405                 410                 415

Pro Gly Lys Ala Pro Lys Val Leu Ile Tyr Phe Thr Ser Ser Leu His
                420                 425                 430

Ser Gly Val Pro Ser Arg Phe Ser Gly Ser Gly Ser Gly Thr Asp Phe
            435                 440                 445

Thr Leu Thr Ile Ser Ser Leu Gln Pro Glu Asp Phe Ala Thr Tyr Tyr
        450                 455                 460

Cys Gln Gln Tyr Ser Thr Val Pro Trp Thr Phe Gly Gln Gly Thr Lys
465                 470                 475                 480

Val Glu Ile Lys

<210> SEQ ID NO 244
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
            20                  25                  30

Ser Thr Gly Trp Thr Pro Leu His Leu Ala Ala Pro Trp Gly His Pro
        35                  40                  45

Glu Ile Val Glu Val Leu Leu Lys Asn Gly Ala Asp Val Asn Ala Ala
    50                  55                  60

Asp Phe Gln Gly Trp Thr Pro Leu His Leu Ala Ala Val Gly His
65                  70                  75                  80

Leu Glu Ile Val Glu Val Leu Leu Lys Tyr Gly Ala Asp Val Asn Ala
```

```
                    85                  90                  95
Gln Asp Lys Phe Gly Lys Thr Ala Phe Asp Ile Ser Ile Asp Asn Gly
                100                 105                 110

Asn Glu Asp Leu Ala Glu Ile Leu Gln Lys Ala Ala
            115                 120

<210> SEQ ID NO 245
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320
```

```
Tyr Arg Val Val Ser Val Leu Thr Val Leu His Gln Asp Trp Leu Asn
            325                 330                 335

Gly Lys Glu Tyr Lys Cys Lys Val Ser Asn Lys Gly Leu Pro Ser Ser
        340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Arg Leu Thr
        420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly
465

<210> SEQ ID NO 246
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ala Asn
            20                  25                  30

Ala Met Asn Trp Val Arg Gln Ala Ser Gly Lys Gly Leu Glu Trp Val
        35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Ala Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205
```

```
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Lys

<210> SEQ ID NO 247
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Ala Asn
            20                  25                  30
Ala Met Asn Trp Val Arg Gln Ala Pro Gly Lys Gly Leu Glu Trp Val
        35                  40                  45
Gly Arg Ile Arg Thr Lys Ser Asn Asn Tyr Ala Thr Tyr Tyr Ala Gly
    50                  55                  60
Ser Val Lys Asp Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Val Arg Asp Tyr Tyr Gly Ser Ser Ala Trp Ile Thr Tyr Trp
            100                 105                 110
```

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 248
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asn Ala Asn
                20                  25                  30

Ala Met Asn Trp Val Arg Gln Ala Pro Gly Lys Gly Leu Glu Trp Val
            35                  40                  45

Gly Arg Ile Arg Thr Lys Ser Asn Asn Tyr Ala Thr Tyr Tyr Ala Gly
50                  55                  60

Ser Val Lys Asp Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

```
Ala Leu His Asn His Tyr Thr Gln Lys Ser Leu Ser Leu Ser Leu Gly
            435                 440                 445

Lys

<210> SEQ ID NO 249
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Leu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Ile Arg Gln Ala Pro Gly Lys Gly Leu Glu Trp Val
        35                  40                  45

Ser Arg Ile Arg Thr Lys Ser Asn Asn Tyr Ala Thr Tyr Tyr Ala Gly
50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val His
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335
```

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 250
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 251
<211> LENGTH: 214

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Gly Gln Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 252
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Gln Met Thr Gln Ser Pro Phe Ser Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95
```

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 253
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Glu Gln Pro Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 254

```
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asn | Ala | Asn |
|---|---|---|---|---|---|---|---|---|---|---|---|---|---|---|---|
| | | | 20 | | | | | 25 | | | | | 30 | | |

| Ala | Met | Asn | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Arg | Thr | Lys | Ser | Asn | Asn | Tyr | Ala | Thr | Tyr | Tyr | Ala | Gly |
|---|---|---|---|---|---|---|---|---|---|---|---|---|---|---|---|
| | 50 | | | | | 55 | | | | | 60 | | | | |

| Ser | Val | Lys | Asp | Arg | Phe | Thr | Ile | Ser | Arg | Asp | Asp | Ser | Lys | Asn | Ser |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Val | Arg | Asp | Tyr | Tyr | Gly | Ser | Ser | Ala | Trp | Ile | Thr | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Leu | Val | Thr | Val | Ser | Ser | Ala | Ser | Thr | Lys | Gly | Pro |
|---|---|---|---|---|---|---|---|---|---|---|---|---|---|---|---|
| | | 115 | | | | | 120 | | | | | 125 | | | |

| Ser | Val | Phe | Pro | Leu | Ala | Pro | Cys | Ser | Arg | Ser | Thr | Ser | Glu | Ser | Thr |
|---|---|---|---|---|---|---|---|---|---|---|---|---|---|---|---|
| | 130 | | | | | 135 | | | | | 140 | | | | |

| Ala | Ala | Leu | Gly | Cys | Leu | Val | Lys | Asp | Tyr | Phe | Pro | Glu | Pro | Val | Thr |
|---|---|---|---|---|---|---|---|---|---|---|---|---|---|---|---|
| 145 | | | | | 150 | | | | | 155 | | | | | 160 |

| Val | Ser | Trp | Asn | Ser | Gly | Ala | Leu | Thr | Ser | Gly | Val | His | Thr | Phe | Pro |
|---|---|---|---|---|---|---|---|---|---|---|---|---|---|---|---|
| | | | | 165 | | | | | 170 | | | | | 175 | |

| Ala | Val | Leu | Gln | Ser | Ser | Gly | Leu | Tyr | Ser | Leu | Ser | Ser | Val | Val | Thr |
|---|---|---|---|---|---|---|---|---|---|---|---|---|---|---|---|
| | | | 180 | | | | | 185 | | | | | 190 | | |

| Val | Pro | Ser | Ser | Ser | Leu | Gly | Thr | Lys | Thr | Tyr | Thr | Cys | Asn | Val | Asp |
|---|---|---|---|---|---|---|---|---|---|---|---|---|---|---|---|
| | | 195 | | | | | 200 | | | | | 205 | | | |

| His | Lys | Pro | Ser | Asn | Thr | Lys | Val | Asp | Lys | Arg | Val | Glu | Ser | Lys | Tyr |
|---|---|---|---|---|---|---|---|---|---|---|---|---|---|---|---|
| | 210 | | | | | 215 | | | | | 220 | | | | |

| Gly | Pro | Pro | Cys | Pro | Pro | Cys | Pro | Ala | Pro | Glu | Phe | Leu | Gly | Gly | Pro |
|---|---|---|---|---|---|---|---|---|---|---|---|---|---|---|---|
| 225 | | | | | 230 | | | | | 235 | | | | | 240 |

| Ser | Val | Phe | Leu | Phe | Pro | Pro | Lys | Pro | Lys | Asp | Thr | Leu | Met | Ile | Ser |
|---|---|---|---|---|---|---|---|---|---|---|---|---|---|---|---|
| | | | | 245 | | | | | 250 | | | | | 255 | |

| Arg | Thr | Pro | Glu | Val | Thr | Cys | Val | Val | Val | Asp | Val | Ser | Gln | Glu | Asp |
|---|---|---|---|---|---|---|---|---|---|---|---|---|---|---|---|
| | | | 260 | | | | | 265 | | | | | 270 | | |

| Pro | Glu | Val | Gln | Phe | Asn | Trp | Tyr | Val | Asp | Gly | Val | Glu | Val | His | Asn |
|---|---|---|---|---|---|---|---|---|---|---|---|---|---|---|---|
| | | 275 | | | | | 280 | | | | | 285 | | | |

| Ala | Lys | Thr | Lys | Pro | Arg | Glu | Glu | Gln | Phe | Asn | Ser | Thr | Tyr | Arg | Val |
|---|---|---|---|---|---|---|---|---|---|---|---|---|---|---|---|
| | 290 | | | | | 295 | | | | | 300 | | | | |

| Val | Ser | Val | Leu | Thr | Val | Leu | His | Gln | Asp | Trp | Leu | Asn | Gly | Lys | Glu |
|---|---|---|---|---|---|---|---|---|---|---|---|---|---|---|---|
| 305 | | | | | 310 | | | | | 315 | | | | | 320 |

| Tyr | Lys | Cys | Lys | Val | Ser | Asn | Lys | Gly | Leu | Pro | Ser | Ser | Ile | Glu | Lys |
|---|---|---|---|---|---|---|---|---|---|---|---|---|---|---|---|
| | | | | 325 | | | | | 330 | | | | | 335 | |

| Thr | Ile | Ser | Lys | Ala | Lys | Gly | Gln | Pro | Arg | Glu | Pro | Gln | Val | Tyr | Thr |
|---|---|---|---|---|---|---|---|---|---|---|---|---|---|---|---|
| | | | 340 | | | | | 345 | | | | | 350 | | |

| Leu | Pro | Pro | Ser | Gln | Glu | Glu | Met | Thr | Lys | Asn | Gln | Val | Ser | Leu | Thr |
|---|---|---|---|---|---|---|---|---|---|---|---|---|---|---|---|
| | | 355 | | | | | 360 | | | | | 365 | | | |

| Cys | Leu | Val | Lys | Gly | Phe | Tyr | Pro | Ser | Asp | Ile | Ala | Val | Glu | Trp | Glu |
|---|---|---|---|---|---|---|---|---|---|---|---|---|---|---|---|

```
            370                 375                 380
Ser Asn Gly Gln Pro Glu Asn Asn Tyr Lys Thr Thr Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
                435                 440                 445

Lys Gly Gly Gly Ser Ser Asp Thr Gly Arg Pro Phe Val Glu Met
450                 455                 460

Tyr Ser Glu Ile Pro Glu Ile Ile His Met Thr Gly Arg Glu Leu
465                 470                 475                 480

Val Ile Pro Cys Arg Val Thr Ser Pro Asn Ile Thr Val Thr Leu Lys
                485                 490                 495

Lys Phe Pro Leu Asp Thr Leu Ile Pro Asp Gly Lys Arg Ile Ile Trp
                500                 505                 510

Asp Ser Arg Lys Gly Phe Ile Ile Ser Asn Ala Thr Tyr Lys Glu Ile
                515                 520                 525

Gly Leu Leu Thr Cys Glu Ala Thr Val Asn Gly His Leu Tyr Lys Thr
530                 535                 540

Asn Tyr Leu Thr His Arg Gln Thr Asn Thr Ile Ile Asp Val Val Leu
545                 550                 555                 560

Ser Pro Ser His Gly Ile Glu Leu Ser Val Gly Glu Lys Leu Val Leu
                565                 570                 575

Asn Cys Thr Ala Arg Thr Glu Leu Asn Val Gly Ile Asp Phe Asn Trp
                580                 585                 590

Glu Tyr Pro Ser Ser Lys His Gln His Lys Lys Leu Val Asn Arg Asp
                595                 600                 605

Leu Lys Thr Gln Ser Gly Ser Glu Met Lys Lys Phe Leu Ser Thr Leu
                610                 615                 620

Thr Ile Asp Gly Val Thr Arg Ser Asp Gln Gly Leu Tyr Thr Cys Ala
625                 630                 635                 640

Ala Ser Ser Gly Leu Met Thr Lys Lys Asn Ser Thr Phe Val Arg Val
                645                 650                 655

His Glu Lys

<210> SEQ ID NO 255
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ala Asn
                20                  25                  30

Ala Met Asn Trp Val Arg Gln Ala Pro Gly Lys Gly Leu Glu Trp Val
            35                  40                  45

Gly Arg Ile Arg Thr Lys Ser Asn Asn Tyr Ala Thr Tyr Tyr Ala Gly
        50                  55                  60

Ser Val Lys Asp Arg Phe Thr Ile Ser Arg Asp Asp Ser Lys Asn Ser
```

-continued

```
            65                  70                  75                  80
Leu Tyr Leu Gln Met Asn Ser Leu Lys Thr Glu Asp Thr Ala Val Tyr
                    85                  90                  95

Tyr Cys Val Arg Asp Tyr Tyr Gly Ser Ser Ala Trp Ile Thr Tyr Trp
                    100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
                    180                 185                 190

Val Pro Ser Ser Ser Leu Gly Thr Lys Thr Tyr Thr Cys Asn Val Asp
                    195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser Gln Glu Asp
                    260                 265                 270

Pro Glu Val Gln Phe Asn Trp Tyr Val Asp Gly Val Glu Val His Asn
                    275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Gln Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                    405                 410                 415

Ser Arg Trp Gln Glu Gly Asn Val Phe Ser Cys Ser Val Met His Glu
                    420                 425                 430

Ala Leu His Asn His Tyr Thr Gln Lys Ser Leu Ser Leu Ser Leu Gly
            435                 440                 445

Lys Gly Gly Gly Gly Ser Glu Ile Val Met Thr Gln Ser Pro Ser Thr
            450                 455                 460

Leu Ser Ala Ser Val Gly Asp Arg Val Ile Ile Thr Cys Gln Ala Ser
465                 470                 475                 480

Glu Ile Ile His Ser Trp Leu Ala Trp Tyr Gln Gln Lys Pro Gly Lys
                    485                 490                 495
```

Ala Pro Lys Leu Leu Ile Tyr Leu Ala Ser Thr Leu Ala Ser Gly Val
              500                 505                 510

Pro Ser Arg Phe Ser Gly Ser Gly Ser Gly Ala Glu Phe Thr Leu Thr
        515                 520                 525

Ile Ser Ser Leu Gln Pro Asp Asp Phe Ala Thr Tyr Tyr Cys Gln Asn
530                 535                 540

Val Tyr Leu Ala Ser Thr Asn Gly Ala Asn Phe Gly Gln Gly Thr Lys
545                 550                 555                 560

Leu Thr Val Leu Gly Gly Gly Gly Ser Gly Gly Gly Ser Gly
                565                 570                 575

Gly Gly Gly Ser Gly Gly Gly Ser Glu Val Gln Leu Val Glu Ser
            580                 585                 590

Gly Gly Gly Leu Val Gln Pro Gly Gly Ser Leu Arg Leu Ser Cys Thr
            595                 600                 605

Ala Ser Gly Phe Ser Leu Thr Asp Tyr Tyr Met Thr Trp Val Arg
        610                 615                 620

Gln Ala Pro Gly Lys Gly Leu Glu Trp Val Gly Phe Ile Asp Pro Asp
625                 630                 635                 640

Asp Asp Pro Tyr Tyr Ala Thr Trp Ala Lys Gly Arg Phe Thr Ile Ser
                645                 650                 655

Arg Asp Asn Ser Lys Asn Thr Leu Tyr Leu Gln Met Asn Ser Leu Arg
                660                 665                 670

Ala Glu Asp Thr Ala Val Tyr Tyr Cys Ala Gly Gly Asp His Asn Ser
            675                 680                 685

Gly Trp Gly Leu Asp Ile Trp Gly Gln Gly Thr Leu Val Thr Val Ser
        690                 695                 700

Ser
705

<210> SEQ ID NO 256
<211> LENGTH: 699
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Val Arg Gln Ala Pro Gly Lys Gly Leu Glu Trp Val
        35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr

```
              130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                    165                 170                 175
Ala Val Leu Gln Ser Ser Gly Leu Tyr Ser Leu Ser Ser Val Val Thr
                    180                 185                 190
Val Pro Ser Ser Ser Leu Gly Thr Lys Thr Tyr Thr Cys Asn Val Asp
                    195                 200                 205
His Lys Pro Ser Asn Thr Lys Val Asp Lys Arg Val Glu Ser Lys Tyr
                    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                    245                 250                 255
Arg Thr Pro Glu Val Thr Cys Val Val Val Asp Val Ser Gln Glu Asp
                    260                 265                 270
Pro Glu Val Gln Phe Asn Trp Tyr Val Asp Gly Val Glu Val His Asn
                    275                 280                 285
Ala Lys Thr Lys Pro Arg Glu Glu Gln Phe Asn Ser Thr Tyr Arg Val
                    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                    325                 330                 335
Thr Ile Ser Lys Ala Lys Gly Gln Pro Arg Glu Pro Gln Val Tyr Thr
                    340                 345                 350
Leu Pro Pro Ser Gln Glu Glu Met Thr Lys Asn Gln Val Ser Leu Thr
                    355                 360                 365
Cys Leu Val Lys Gly Phe Tyr Pro Ser Asp Ile Ala Val Glu Trp Glu
                    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                    405                 410                 415
Ser Arg Trp Gln Glu Gly Asn Val Phe Ser Cys Ser Val Met His Glu
                    420                 425                 430
Ala Leu His Asn His Tyr Thr Gln Lys Ser Leu Ser Leu Ser Leu Gly
                    435                 440                 445
Lys Gly Gly Gly Gly Ser Glu Val Gln Leu Val Glu Ser Gly Gly Gly
                    450                 455                 460
Leu Val Gln Pro Gly Gly Ser Leu Arg Leu Ser Cys Ala Ala Ser Gly
465                 470                 475                 480
Tyr Asp Phe Thr His Tyr Gly Met Asn Trp Val Arg Gln Ala Pro Gly
                    485                 490                 495
Lys Gly Leu Glu Trp Val Gly Trp Ile Asn Thr Tyr Thr Gly Glu Pro
                    500                 505                 510
Thr Tyr Ala Ala Asp Phe Lys Arg Arg Phe Thr Phe Ser Leu Asp Thr
                    515                 520                 525
Ser Lys Ser Thr Ala Tyr Leu Gln Met Asn Ser Leu Arg Ala Glu Asp
                    530                 535                 540
Thr Ala Val Tyr Tyr Cys Ala Lys Tyr Pro Tyr Tyr Tyr Gly Thr Ser
545                 550                 555                 560
```

```
His Trp Tyr Phe Asp Val Trp Gly Gln Gly Thr Leu Val Thr Val Ser
            565                 570                 575

Ser Gly Gly Gly Gly Ser Gly Gly Gly Gly Ser Gly Gly Gly Gly Ser
            580                 585                 590

Asp Ile Gln Leu Thr Gln Ser Pro Ser Ser Leu Ser Ala Ser Val Gly
            595                 600                 605

Asp Arg Val Thr Ile Thr Cys Ser Ala Ser Gln Asp Ile Ser Asn Tyr
            610                 615                 620

Leu Asn Trp Tyr Gln Gln Lys Pro Gly Lys Ala Pro Lys Val Leu Ile
625                 630                 635                 640

Tyr Phe Thr Ser Ser Leu His Ser Gly Val Pro Ser Arg Phe Ser Gly
            645                 650                 655

Ser Gly Ser Gly Thr Asp Phe Thr Leu Thr Ile Ser Ser Leu Gln Pro
            660                 665                 670

Glu Asp Phe Ala Thr Tyr Tyr Cys Gln Gln Tyr Ser Thr Val Pro Trp
            675                 680                 685

Thr Phe Gly Gln Gly Thr Lys Val Glu Ile Lys
            690                 695

<210> SEQ ID NO 257
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Val Arg Gln Ala Pro Gly Lys Gly Leu Glu Trp Val
            35                  40                  45

Gly Arg Ile Arg Thr Lys Ser Asn Asn Tyr Ala Thr Tyr Tyr Ala Gly
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
```

```
                210                 215                 220
Gly Pro Pro Cys Pro Pro Cys Pro Ala Pro Glu Phe Leu Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Gly Gly Gly Gly Ser Asp Leu Asp Lys Lys Leu Leu Glu Ala Ala Arg
    450                 455                 460

Ala Gly Gln Asp Asp Glu Val Arg Ile Leu Met Ala Asn Gly Ala Asp
465                 470                 475                 480

Val Asn Ala Arg Asp Ser Thr Gly Trp Thr Pro Leu His Leu Ala Ala
                485                 490                 495

Pro Trp Gly His Pro Glu Ile Val Glu Val Leu Leu Lys Asn Gly Ala
            500                 505                 510

Asp Val Asn Ala Ala Asp Phe Gln Gly Trp Thr Pro Leu His Leu Ala
        515                 520                 525

Ala Ala Val Gly His Leu Glu Ile Val Glu Val Leu Leu Lys Tyr Gly
    530                 535                 540

Ala Asp Val Asn Ala Gln Asp Lys Phe Gly Lys Thr Ala Phe Asp Ile
545                 550                 555                 560

Ser Ile Asp Asn Gly Asn Glu Asp Leu Ala Glu Ile Leu Gln Lys Ala
                565                 570                 575

Ala
```

<210> SEQ ID NO 258
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 258

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Ile Val Met Thr
    210                 215                 220

Gln Ser Pro Ser Thr Leu Ser Ala Ser Val Gly Asp Arg Val Ile Ile
225                 230                 235                 240

Thr Cys Gln Ala Ser Glu Ile Ile His Ser Trp Leu Ala Trp Tyr Gln
                245                 250                 255

Gln Lys Pro Gly Lys Ala Pro Lys Leu Leu Ile Tyr Leu Ala Ser Thr
            260                 265                 270

Leu Ala Ser Gly Val Pro Ser Arg Phe Ser Gly Ser Gly Ser Gly Ala
        275                 280                 285

Glu Phe Thr Leu Thr Ile Ser Ser Leu Gln Pro Asp Asp Phe Ala Thr
    290                 295                 300

Tyr Tyr Cys Gln Asn Val Tyr Leu Ala Ser Thr Asn Gly Ala Asn Phe
305                 310                 315                 320

Gly Gln Gly Thr Lys Leu Thr Val Leu Gly Gly Gly Gly Ser Gly
                325                 330                 335

Gly Gly Gly Ser Gly Gly Gly Ser Gly Gly Gly Ser Glu Val
            340                 345                 350

Gln Leu Val Glu Ser Gly Gly Gly Leu Val Gln Pro Gly Gly Ser Leu
        355                 360                 365

Arg Leu Ser Cys Thr Ala Ser Gly Phe Ser Leu Thr Asp Tyr Tyr Tyr
    370                 375                 380

Met Thr Trp Val Arg Gln Ala Pro Gly Lys Gly Leu Glu Trp Val Gly
385                 390                 395                 400

Phe Ile Asp Pro Asp Asp Pro Tyr Tyr Ala Thr Trp Ala Lys Gly
                405                 410                 415
```

```
Arg Phe Thr Ile Ser Arg Asp Asn Ser Lys Asn Thr Leu Tyr Leu Gln
            420                 425                 430

Met Asn Ser Leu Arg Ala Glu Asp Thr Ala Val Tyr Tyr Cys Ala Gly
            435                 440                 445

Gly Asp His Asn Ser Gly Trp Gly Leu Asp Ile Trp Gly Gln Gly Thr
            450                 455                 460

Leu Val Thr Val Ser Ser
465                 470

<210> SEQ ID NO 259
<211> LENGTH: 424
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Ser Asp Thr Gly Arg
        210                 215                 220

Pro Phe Val Glu Met Tyr Ser Glu Ile Pro Glu Ile Ile His Met Thr
225                 230                 235                 240

Glu Gly Arg Glu Leu Val Ile Pro Cys Arg Val Thr Ser Pro Asn Ile
                245                 250                 255

Thr Val Thr Leu Lys Lys Phe Pro Leu Asp Thr Leu Ile Pro Asp Gly
            260                 265                 270

Lys Arg Ile Ile Trp Asp Ser Arg Lys Gly Phe Ile Ile Ser Asn Ala
            275                 280                 285

Thr Tyr Lys Glu Ile Gly Leu Leu Thr Cys Glu Ala Thr Val Asn Gly
```

```
                290                 295                 300
His Leu Tyr Lys Thr Asn Tyr Leu Thr His Arg Gln Thr Asn Thr Ile
305                 310                 315                 320

Ile Asp Val Val Leu Ser Pro Ser His Gly Ile Glu Leu Ser Val Gly
            325                 330                 335

Glu Lys Leu Val Leu Asn Cys Thr Ala Arg Thr Glu Leu Asn Val Gly
            340                 345                 350

Ile Asp Phe Asn Trp Glu Tyr Pro Ser Ser Lys His Gln His Lys Lys
            355                 360                 365

Leu Val Asn Arg Asp Leu Lys Thr Gln Ser Gly Ser Glu Met Lys Lys
            370                 375                 380

Phe Leu Ser Thr Leu Thr Ile Asp Gly Val Thr Arg Ser Asp Gln Gly
385                 390                 395                 400

Leu Tyr Thr Cys Ala Ala Ser Ser Gly Leu Met Thr Lys Lys Asn Ser
            405                 410                 415

Thr Phe Val Arg Val His Glu Lys
            420

<210> SEQ ID NO 260
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Val Gln Leu Val
    210                 215                 220
```

```
Glu Ser Gly Gly Gly Leu Val Gln Pro Gly Gly Ser Leu Arg Leu Ser
225                 230                 235                 240

Cys Ala Ala Ser Gly Tyr Asp Phe Thr His Tyr Gly Met Asn Trp Val
            245                 250                 255

Arg Gln Ala Pro Gly Lys Gly Leu Glu Trp Val Gly Trp Ile Asn Thr
        260                 265                 270

Tyr Thr Gly Glu Pro Thr Tyr Ala Ala Asp Phe Lys Arg Arg Phe Thr
    275                 280                 285

Phe Ser Leu Asp Thr Ser Lys Ser Thr Ala Tyr Leu Gln Met Asn Ser
290                 295                 300

Leu Arg Ala Glu Asp Thr Ala Val Tyr Tyr Cys Ala Lys Tyr Pro Tyr
305                 310                 315                 320

Tyr Tyr Gly Thr Ser His Trp Tyr Phe Asp Val Trp Gly Gln Gly Thr
            325                 330                 335

Leu Val Thr Val Ser Ser Gly Gly Gly Ser Gly Gly Gly Gly Ser
                340                 345                 350

Gly Gly Gly Gly Ser Asp Ile Gln Leu Thr Gln Ser Pro Ser Ser Leu
            355                 360                 365

Ser Ala Ser Val Gly Asp Arg Val Thr Ile Thr Cys Ser Ala Ser Gln
370                 375                 380

Asp Ile Ser Asn Tyr Leu Asn Trp Tyr Gln Gln Lys Pro Gly Lys Ala
385                 390                 395                 400

Pro Lys Val Leu Ile Tyr Phe Thr Ser Ser Leu His Ser Gly Val Pro
            405                 410                 415

Ser Arg Phe Ser Gly Ser Gly Ser Gly Thr Asp Phe Thr Leu Thr Ile
        420                 425                 430

Ser Ser Leu Gln Pro Glu Asp Phe Ala Thr Tyr Tyr Cys Gln Gln Tyr
    435                 440                 445

Ser Thr Val Pro Trp Thr Phe Gly Gln Gly Thr Lys Val Glu Ile Lys
450                 455                 460

<210> SEQ ID NO 261
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
            85                  90                  95

Thr Phe Gly Gly Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
    115                 120                 125
```

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Asp Leu Asp Lys Lys
210                 215                 220

Leu Leu Glu Ala Ala Arg Ala Gly Gln Asp Asp Glu Val Arg Ile Leu
225                 230                 235                 240

Met Ala Asn Gly Ala Asp Val Asn Ala Arg Asp Ser Thr Gly Trp Thr
                245                 250                 255

Pro Leu His Leu Ala Ala Pro Trp Gly His Pro Glu Ile Val Glu Val
            260                 265                 270

Leu Leu Lys Asn Gly Ala Asp Val Asn Ala Ala Asp Phe Gln Gly Trp
        275                 280                 285

Thr Pro Leu His Leu Ala Ala Val Gly His Leu Glu Ile Val Glu
290                 295                 300

Val Leu Leu Lys Tyr Gly Ala Asp Val Asn Ala Gln Asp Lys Phe Gly
305                 310                 315                 320

Lys Thr Ala Phe Asp Ile Ser Ile Asp Asn Gly Asn Glu Asp Leu Ala
                325                 330                 335

Glu Ile Leu Gln Lys Ala Ala
            340

<210> SEQ ID NO 262
<211> LENGTH: 448
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Asn Ala Asn
            20                  25                  30

Ala Met Asn Trp Val Arg Gln Ala Pro Gly Lys Gly Leu Glu Trp Val
        35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Asp Tyr Gly Ser Ser Ala Trp Ile Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr

```
                130              135              140
Ala Ala Leu Gly Cys Leu Val Lys Asp Tyr Phe Pro Glu Pro Val Thr
145              150              155              160

Val Ser Trp Asn Ser Gly Ala Leu Thr Ser Gly Val His Thr Phe Pro
            165              170              175

Ala Val Leu Gln Ser Ser Gly Leu Tyr Ser Leu Ser Ser Val Val Thr
            180              185              190

Val Pro Ser Ser Ser Leu Gly Thr Lys Thr Tyr Thr Cys Asn Val Asp
            195              200              205

His Lys Pro Ser Asn Thr Lys Val Asp Lys Arg Val Glu Ser Lys Tyr
            210              215              220

Gly Pro Pro Cys Pro Pro Cys Pro Ala Pro Glu Phe Leu Gly Gly Pro
225              230              235              240

Ser Val Phe Leu Phe Pro Pro Lys Pro Lys Asp Thr Leu Met Ile Ser
            245              250              255

Arg Thr Pro Glu Val Thr Cys Val Val Val Asp Val Ser Gln Glu Asp
            260              265              270

Pro Glu Val Gln Phe Asn Trp Tyr Val Asp Gly Val Glu Val His Asn
            275              280              285

Ala Lys Thr Lys Pro Arg Glu Glu Gln Phe Asn Ser Thr Tyr Arg Val
            290              295              300

Val Ser Val Leu Thr Val Leu His Gln Asp Trp Leu Asn Gly Lys Glu
305              310              315              320

Tyr Lys Cys Lys Val Ser Asn Lys Gly Leu Pro Ser Ser Ile Glu Lys
            325              330              335

Thr Ile Ser Lys Ala Lys Gly Gln Pro Arg Glu Pro Gln Val Tyr Thr
            340              345              350

Leu Pro Pro Ser Gln Glu Glu Met Thr Lys Asn Gln Val Ser Leu Thr
            355              360              365

Cys Leu Val Lys Gly Phe Tyr Pro Ser Asp Ile Ala Val Glu Trp Glu
370              375              380

Ser Asn Gly Gln Pro Glu Asn Asn Tyr Lys Thr Thr Pro Pro Val Leu
385              390              395              400

Asp Ser Asp Gly Ser Phe Phe Leu Tyr Ser Arg Leu Thr Val Asp Lys
            405              410              415

Ser Arg Trp Gln Glu Gly Asn Val Phe Ser Cys Ser Val Met His Glu
            420              425              430

Ala Leu His Asn His Tyr Thr Gln Lys Ser Leu Ser Leu Ser Leu Gly
            435              440              445
```

METHOD OF TREATING OCULAR CONDITIONS BY ADMINISTERING AN ANTIBODY THAT ACTIVATES TIE2 AND BINDS VEGF

CROSS-REFERENCE

This application is a continuation of U.S. application Ser. No. 16/579,078, filed Sep. 23, 2019, now U.S. Pat. No. 10,894,824, which claims the benefit of U.S. Provisional Application No. 62/735,331, filed Sep. 24, 2018, and U.S. Provisional Application No. 62/832,461, filed Apr. 11, 2019, each of which is incorporated herein by reference in its entirety.

SEQUENCE LISTING

The instant application contains a Sequence Listing which has been submitted electronically in ASCII format via EFS-Web and is hereby incorporated by reference in its entirety. Said ASCII copy, created Dec. 7, 2020, is named 45725729301_SL.TXT and is 344,503 bytes in size.

BACKGROUND

Individual compounds with the ability to modulate distinct targets can be combined to generate multispecific compounds. Such multispecific compounds can have advantages over the parent compounds administered individually. These advantages can include, for example, a simpler dosing regimen, longer half-life within a subject, or the ability to bind targets in close proximity.

INCORPORATION BY REFERENCE

Each patent, publication, and non-patent literature cited in the application is hereby incorporated by reference in its entirety as if each was incorporated by reference individually.

SUMMARY

In some embodiments, the disclosure provides a compound comprising: (a) a first domain, wherein the first domain modulates a phosphatase, wherein the phosphatase modulates Tie2; and (b) a second domain that specifically binds a receptor tyrosine kinase agonist.

In some embodiments, the disclosure provides a method of treating a condition in a subject in need thereof, the method comprising administering to the subject a therapeutically-effective amount of a compound disclosed herein.

BRIEF DESCRIPTION OF THE FIGURES

FIG. 21A provides a western blot. FIG. 21B provides quantification of Tie2 activation. FIG. 21C provides quantification of VEGFR2 phosphorylation.

FIG. 22A provides a western blot. FIG. 22B provides quantification of Tie2 activation. FIG. 22C provides quantification of VEGFR2 phosphorylation.

FIG. 23A provides quantification of Tie2 activation. FIG. 23B provides quantification of VEGFR2 phosphorylation.

FIG. 24A provides quantification of Tie2 activation. FIG. 24B provides quantification of VEGFR2 phosphorylation.

FIG. 25A provides quantification of Tie2 activation. FIG. 25B provides quantification of VEGFR2 phosphorylation.

FIG. 26A provides quantification of Tie2 activation. FIG. 26B provides quantification of VEGFR2 phosphorylation.

FIG. 27A provides quantification of Tie2 activation. FIG. 27B provides quantification of VEGFR2 phosphorylation.

DETAILED DESCRIPTION

Figure 1:
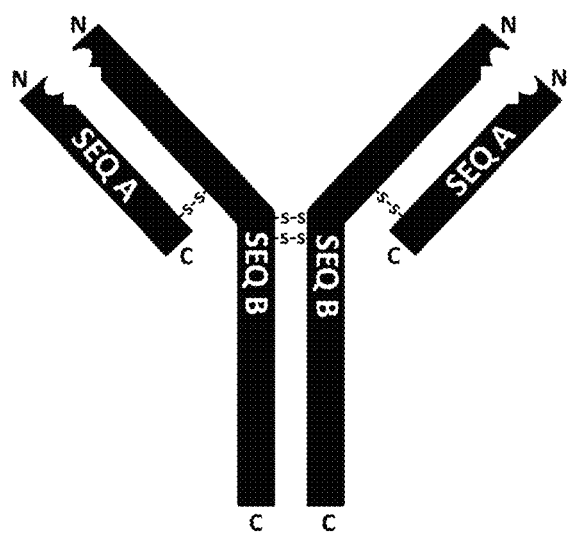
FIG. 1: Schematic of the basic four chain antibody unit. Light chain sequences are represented by "SEQ A". Heavy chain sequences are represented by "SEQ B". N and C denote N- and C-termini, respectively. —S—S— denotes disulfide bonds.

The present disclosure provides compositions and methods for modulating phosphatases and kinases, for example, receptor tyrosine kinases. Compositions and methods are provided for modulating Tie2, for example, to promote Tie2 phosphorylation, signaling, and/or activation. In some embodiments, the disclosure provides compositions and methods for targeting a phosphatase that modulates Tie2 signaling. In some embodiments, the phosphatase that modulates Tie2 signaling is human protein tyrosine phosphatase-beta (HPTP-β).

Compositions and methods are provided for modulating receptor tyrosine kinases, for example, to reduce receptor tyrosine kinase phosphorylation, signaling, and/or activation. In some embodiments, the disclosure provides compositions and methods for targeting a receptor tyrosine kinase agonist, e.g. vascular endothelial growth factor (VEGF). In some embodiments, the disclosure provides compositions and methods for targeting a receptor tyrosine kinase, e.g. a VEGF receptor.

In some embodiments, the present disclosure provides compositions and methods for targeting human protein tyrosine phosphatase-beta (HPTP-β) or vascular endothelial protein tyrosine phosphatase (VE-PTP or VEPTP), and vascular endothelial growth factor (VEGF). In some embodiments, the present disclosure provides multispecific compounds, agents, antibodies, fragments, or derivatives thereof that target HPTP-β (VE-PTP) and VEGF.

The agents disclosed herein can be used for the treatment of disorders that are characterized by, for example, vascular instability, angiogenesis, neovascularization, vascular leakage, and/or edema. The agents disclosed herein can be used for the treatment of, for example, vascular disorders, ocular disorders, cancers, renal disorders, and complications of diabetes.

HPTP-β/VE-PTP, Tie2, and Vascular Stability

HPTP-β is a member of the receptor-like family of the protein tyrosine phosphatases (PTPases). HPTP-β is a transmembrane protein found primarily in vascular endothelial cells that displays structural and functional similarity to cell adhesion molecules. Orthologues of HPTP-β are found in various species including, for example, zebrafish, chicken, dog, mouse, marmoset, and monkey. The orthologues are generally referred to as vascular endothelial protein tyrosine phosphatase (VE-PTP). HPTP-β (VE-PTP) can influence vascular stability through effects on Tie2-mediated signaling.

Tie2 (tyrosine kinase with immunoglobulin and epidermal growth factor homology domains 2) is a membrane receptor tyrosine kinase expressed primarily in vascular endothelial cells. Upstream factors can regulate Tie2 phosphorylation, influencing downstream signaling and vascular stabilization. Non-limiting examples of such factors include angiopoietin 1 (Ang1/Angpt1), angiopoietin 2 (Ang2/Angpt2), and HPTP-β (VE-PTP).

Ang1 is an agonist of Tie2. Binding of Ang1 to Tie2 promotes receptor phosphorylation and downstream signaling to induce vascular stabilization through highly organized angiogenesis, tightening of endothelial cell junctions, enhancement of endothelial viability, reduction of endothelial inflammation, and improvement of endothelial function.

Ang2 acts in a context-dependent antagonist or agonist of Tie2. During angiogenesis, Ang2 acts as a negative regulator of Ang1-Tie2 signaling.

HPTP-β (VE-PTP) is a phosphatase that can modulate Tie2 signaling. HPTP-β (VE-PTP) can dephosphorylate the Tie2 receptor. Under physiological conditions, HPTP-β (VE-PTP) regulates the duration of Tie2 phosphorylation. Inhibition of HPTP-β (VE-PTP), therefore, can result in increased Tie2 phosphorylation, increased Tie2-mediated signaling, and enhanced vascular stability. Inhibitors of HPTP-β (VE-PTP) are Tie2 activators. For example, a compound, inhibitor, antibody, antibody fragment, variant, or derivative thereof that binds HPTP-β (VE-PTP) can promote Tie2 phosphorylation, thereby activating Tie2 downstream signaling, and promoting vascular stability.

By the process described above, HPTP-β (VE-PTP) activity can contribute to, for example, disorders that are characterized by vascular instability, angiogenesis, neovascularization, vascular leakage, and/or edema. For example, HPTP-β (VE-PTP) activity can contribute to vascular disorders, ocular disorders, cancers, renal disorders, complications of diabetes, and other disorders. Inhibition of HPTP-β (VE-PTP) activity can reduce such disorders.

VEGF and Vascular Stability

Vascular endothelial growth factors (VEGFs) are primarily found in endothelial cells, and are implicated in pathological neovascularization in a number of diseases. The VEGFs are members of the cystine-knot growth factor superfamily, the PDGF family, and the VEGF family. The VEGFs can act as pro-angiogenic factors. The VEGF family consists of VEGF-A, VEGF-B, VEGF-C, VEGF-D and placental growth factor (PGF). Nine VEGF-A isoforms exist: $VEGF_{121}$, $VEGF_{145}$, $VEGF_{148}$, $VEGF_{162}$, $VEGF_{165}$, $VEGF_{165b}$, $VEGF_{13}$, $VEGF_{189}$, and $VEGF_{206}$.

VEGF is a hypoxia-regulated gene, and VEGF levels are increased in hypoxic or ischemic conditions. VEGF is an agonist of VEGF receptors (VEGFRs). VEGFRs are receptor tyrosine kinases; binding of VEGF to a VEGFR can result in phosphorylation of the receptor, and subsequently of downstream signal transducers. VEGFR-mediated signaling can result in aberrant vasculogenesis, angiogenesis, and permeabilization of blood vessels, contributing to pathologic vascular instability. Thus, inhibition of VEGF can result in decreased VEGFR-mediated signaling and enhanced vascular stability. For example, an inhibitor, antibody, antibody fragment, variant, or derivative thereof that binds VEGF can reduce VEGFR ligation, thereby reducing VEGFR-mediated signaling, and promoting vascular stability. Non-limiting examples of agents that bind VEGF include aflibercept (Eylea®), a recombinant protein comprising the VEGF-binding portions of human VEGF receptors 1 and 2 fused to the Fc portion of human IgG1; brolucizumab, a humanized single-chain antibody fragment (scFv); RTH258, a humanized single-chain antibody fragment (scFv); ranibizumab (Lucentis®), a humanized monoclonal antibody fragment (Fab); bevacizumab (Avastin®), a humanized monoclonal antibody; conbercept, a recombinant fusion protein comprising extracellular domains from VEGF receptors 1 and 2 fused to the Fc portion of human IgG1; Abicipar, a designed ankyrin repeat protein (DARPin); MP0112, a DARPin; MP0250, a DARPin; CT-322, an adnectin; and PRS-050, an anticalin.

By the process described above, VEGF can contribute to, for example, disorders that are characterized by vascular instability, angiogenesis, neovascularization, vascular leakage, and/or edema. For example, VEGF can contribute to vascular disorders, ocular disorders, cancers, renal disorders, complications of diabetes, and other disorders. For example, ischemia in the eye can lead to increased VEGF production, resulting in vascular leakage and pathological neovascularization in the retina. Inhibition of VEGFR-mediated signaling can reduce such disorders.

Receptor Tyrosine Kinases (RTKs) and Receptor Tyrosine Kinase Agonists

Receptor tyrosine kinases (RTKs) are cell surface receptors that participate in the regulation of cell growth, differentiation, and survival. Binding of an agonist to a RTK can cause neighboring RTKs to associate with each other, forming dimers. Dimerization can cause cross-phosphorylation—each RTK in the dimer phosphorylates multiple tyrosine residues on the other RTK. Once cross-phosphorylated, the cytoplasmic tails of the RTKs can initiate signal transduction pathways, for example, by serving as docking platforms for various intracellular proteins. RTK signaling can lead to changes of gene transcription and expression in a cell.

Non-limiting examples of RTKs include AATK, AATYK, AATYK1, AATYK2, ACH, ALK, ARK, AXL, BDB, BDB1, BEK, BFGFR, BREK, Brt, CAK, CCK4, CD115, CD117, CD135, CD136, CD140a, CD140b, CD167, CD202b, CD220, CD221, CD246, CD309, CD331, CD332, CD333, CD334, CDHF12, CDHR16, CDw136, CEK, CEK2, CEK3, c-Eyk, CFD1, C-FMS, C-Kit, cprk, c-ros-1, CSF1R, CSFR, D3S3195, DDR1, DDR2, DFNB97, DKFZp761P1010, Dtk, ECT1, EDDR1, EGFR, EphA10, EphA1-8. EphB1, EphB2, EphB3, EphB4, EphB6, ErbB2, ErbB3, ErbB4, Etk-2, FGFR1, FGFR2. FGFR3. FGFR4, FLG, FLK1, FLK2, FLT, FLT1, FLT2, FLT3, FLT4, FMS, GAS9, H2, H3, H4, H5, HGFR, HSCR1, IGF1R, IGFIR, IGFR, INSR, INSRR, IRR, JKT5A, JTK11, JTK12, JTK13, JTK14, JTK2, JTK4, JTK5, JWS, KAL2, KDR, KGFR, KIAA0641, KIAA1079, KIAA1883, KIT, KPI2, K-SAM, LMR1, LMR2, LMR3, LMTK1, LMTK2, LMTK3, LTK, MCF3, MEN2A, MEN2B, Mer, MERTK, MET, MGC18216, MST1R, MTC, MTC1, MTRK1, MuSK, NEP, NOK, N-SAM, NTRK2, NTRK3, NTRK4, NTRKR1, NTRKR2, PBT, PCL, PDGFR, PDGFR1, PDGFR2, PDGFRA, PDGFR-alpha, PDGFRB, PDGFR-beta, PPP1R100, PPP1R101, PPP1R77, PTC, PTK3A, PTK7, PTK8, RCCP2, Rek, RET, RET51, RON, ROR1, ROR2, ROS, ROS1, RP38, RSE, RTK6, RYK, Ryk, RYK1, SCFR, Sky, STK, STYK1, SuRTK106, TEK, TIE1, TIE2, Tif, TK14, TK25, TKT, TRK, TrkA, TrkB, TrkC, TYK1, TYKLM3, TYRO10, Tyro12, Tyro3, Tyro7, UFO, VEGFR, VEGFR1, VEGFR2, VEGFR3, VMCM, and VMCM1.

Non-limiting examples of RTK agonists include VEGF, Ang1, Ang2, BDNF, EGF, FGF, HGF, IGF, insulin, MSP, NGF, NT-3, and PDGF.

Antibodies and Antigen-Binding Compounds.

The basic four chain antibody unit comprises two identical heavy chain (H) polypeptide sequences and two identical light chain (L) polypeptide sequences. Each of the heavy chains can comprise one N-terminal variable ($V_H$) region and three or four C-terminal constant ($C_H1$, $C_H2$, $C_H3$, and $C_H4$) regions. Each of the light chains can comprise one N-terminal variable ($V_L$) region and one C-terminal constant ($C_L$) region. The light chain variable region is aligned with the heavy chain variable region and the light chain constant region is aligned with heavy chain constant region $C_{H1}$. The pairing of a heavy chain variable region and light chain variable region together forms a single antigen-binding site. Each light chain is linked to a heavy chain by one covalent disulfide bond. The two heavy chains are linked to each other by one or more disulfide bonds depending on the heavy chain isotype. Each heavy and light chain also comprises regularly-spaced intrachain disulfide bridges. The C-terminal constant regions of the heavy chains comprise the Fc region of the antibody, which mediate effector functions, for example, through interactions with Fc receptors or complement proteins. FIG. 1 provides a simple representative schematic basic four chain antibody unit; light chain sequences are represented by "SEQ A". Heavy chain sequences are represented by "SEQ B", —S—S— denotes disulfide bonds, N and C denote N- and C-termini, respectively.

The light chain can be designated kappa or lambda based on the amino acid sequence of the constant region. The heavy chain can be designated alpha, delta, epsilon, gamma, or mu based on the amino acid sequence of the constant region. Antibodies are categorized into five immunoglobulin classes, or isotypes, based on the heavy chain. IgA comprises alpha heavy chains, IgD comprises delta heavy chains, IgE comprises epsilon heavy chains, IgG comprises gamma heavy chains, and IgM comprises mu heavy chains. Antibodies of the IgG, IgD, and IgE classes comprise monomers of the four chain unit described above (two heavy and two light chains), while the IgM and IgA classes can comprise multimers of the four chain unit. The alpha and gamma classes are further divided into subclasses on the basis of differences in the sequence and function of the heavy chain constant region. Subclasses of IgA and IgG expressed by humans include IgG1, IgG2, IgG3, IgG4, IgA1 and IgA2.

The constant regions are minimally involved in antigen binding. Rather, the constant regions can mediate various effector functions. Different IgG isotypes or subclasses can be associated with different effector functions or therapeutic characteristics, for example, because of interactions with different Fc receptors and/or complement proteins. Antibodies comprising Fc regions that engage activating Fc receptors can, for example, participate in antibody-dependent cell-mediated cytotoxicity (ADCC), antibody-dependent cellular phagocytosis (ADCP), complement-dependent cytotoxicity (CDC), induction of signaling through immunoreceptor tyrosine-based activation motifs (ITAMs), and induction of cytokine secretion. Antibodies comprising Fc regions that engage inhibitory Fc receptors can, for example, induce signaling through immunoreceptor tyrosine-based inhibitory motifs (ITIMs).

Different antibody subclasses comprise different abilities to elicit immune effector functions. For example, IgG1 and IgG3 can effectively recruit complement to activate CDC, IgG2 elicits minimal ADCC. IgG4 has a lesser ability to trigger immune effector functions. Modifications to the constant regions can also affect antibody characteristics, for example, enhancement or reduction of Fc receptor ligation, enhancement or reduction of ADCC, enhancement or reduction of ADCP, enhancement or reduction of CDC, enhancement or reduction of signaling through ITAMs, enhancement or reduction of cytokine induction, enhancement or reduction of signaling through ITIMs, enhancement or reduction of half-life, or enhancement or reduction of coengagement of antigen with Fc receptors. Modifications can include, for example, amino acid mutations, altering post-translational modifications (e.g., glycosylation), combining domains from different isotypes or subclasses, or a combination thereof.

A compound or antibody of the disclosure can comprise constant regions or Fc regions that are selected or modified to provide suitable antibody characteristics, for example, suitable characteristics for treating a disease or condition as disclosed herein. In some embodiments, IgG1 can be used, for example, to promote immune activation effector functions (e.g., ADCC, ADCP, CDC, ITAM signaling, cytokine induction, or a combination thereof for the treatment of a cancer). In some embodiments, IgG4 can be used, for example, in cases where antagonistic properties of the antibody in the absence of immune effector functions are desirable (e.g., for treatment of ocular disorders).

Non-limiting examples of antibody modifications and their effects are provided in TABLE 1.

TABLE 1

| Effect | Isotype | Mutation(s)/modification(s) |
|---|---|---|
| Enhanced ADCC | IgG1 | F243L/R292P/Y300L/V305I/P396L |
| Enhanced ADCC | IgG1 | S239D/I332E |
| Enhanced ADCC | IgG1 | S239D/I332E/A330L |
| Enhanced ADCC | IgG1 | S298A/E333A/K334A |
| Enhanced ADCC | IgG1 | In one heavy chain: L234Y/L235Q/G236W/S239M/H268D/D270E/S298A In the opposing heavy chain: D270E/K326D/A330M/K334E |
| Enhanced ADCP | IgG1 | G236A/S239D/I332E |
| Enhanced CDC | IgG1 | K326W/E333S |
| Enhanced CDC | IgG1 | S267E/H268F/S324T |
| Enhanced CDC | IgG1, IgG3 | Combination of domains from IgG1/IgG3 |
| Enhanced CDC | IgG1 | E345R/E430G/S440Y |
| Loss of glycosylation, reduced effector functions | IgG1 | N297A or N297Q or N297G |
| Reduced effector functions | IgG1, IgG4 | L235E |
| Reduced effector functions | IgG1 | L234A/L235A |
| Reduced effector functions | IgG4 | F234A/L235A |
| Reduced effector functions | IgG4 | F234A/L235A/G237A/P238S |
| Reduced effector functions | IgG4 | F234A/L235A/ΔG236/G237A/P238S |
| Reduced effector functions | IgG2, IgG4 | Combination of domains from IgG2/IgG4 |
| Reduced effector functions | IgG2 | H268Q/V309L/A330S/P331S |
| Reduced effector functions | IgG2 | V234A/G237A/P238S/H268A/V309L/A330S/P331S |
| Reduced effector functions | IgG1 | L234A/L235A/G237A/P238S/H268A/A330S/P331S |
| Increased half-life | IgG1 | M252Y/S254T/T256E |
| Increased half-life | IgG1 | M428L/N434S |
| Increased antigen/Fc receptor coengagement | IgG1 | S267E/L328F |
| Altered antigen/Fc receptor coengagement | IgG1 | N325S/L328F |
| Reduced Fab arm exchange | IgG4 | S228P |

The variable (V) regions mediate antigen binding and define the specificity of a particular antibody for an antigen. The variable region comprises relatively invariant sequences called framework regions, and hypervariable regions, which differ considerably in sequence among antibodies of different binding specificities. The variable region of each antibody heavy or light chain comprises four framework regions separated by three hypervariable regions. The variable regions of heavy and light chains fold in a manner that brings the hypervariable regions together in close proximity to create an antigen binding site. The four framework regions largely adopt an f3-sheet configuration, while the three hypervariable regions form loops connecting, and in some cases forming part of, the f3-sheet structure.

Within hypervariable regions are amino acid residues that primarily determine the binding specificity of the antibody. Sequences comprising these residues are known as complementarity determining regions (CDRs). One antigen binding site of an antibody comprises six CDRs, three in the hypervariable regions of the light chain, and three in the hypervariable regions of the heavy chain. The CDRs in the light chain are designated L1, L2, and L3, while the CDRs in the heavy chain are designated H1, H2, and H3. CDRs can also be designated LCDR1, LCDR2, LCDR3, HCDR1, HCDR2, and HCDR3, respectively. The contribution of each CDR to antigen binding varies among antibodies. CDRs can vary in length. For example, CDRs are often 5 to 14 residues in length, but CDRs as short as 0 residues or as long as 25 residues or longer exist.

Several methods are used to predict or designate CDR sequences. These methods can use different numbering systems, for example, because sequence insertions and deletions are numbered differently.

The Kabat method was developed by aligning a limited number of antibody sequences and determining the positions of the most variable residues. Based on the alignment, a numbering scheme was introduced for residues in the variable regions. This numbering scheme can be used to determine the positions marking the beginning and the end of each CDR. One iteration of the Kabat numbering system identifies CDRs in the light chain variable region using the following residue positions: LCDR1 around residues 24-34; LCDR2 around residues 50-56; and LCDR3 around residues 89-97. One iteration of the Kabat numbering system identifies CDRs in the heavy chain variable region using the following residue positions: HCDR1 around residues 31-35; HCDR2 around residues 50-65; and HCDR3 around residues 95-102.

The Chothia method was developed based on analysis of three dimensional antibody structures. The analysis determined that hypervariable loops adopt a restricted set of conformations based on the presence of certain residues at key positions in CDRs and flanking framework regions. This method uses a similar numbering scheme as the Kabat method, but numbers insertions and deletions differently. One iteration of the Chothia numbering system identifies CDRs in the light chain variable region using the following residue positions: LCDR1 around residues 24-34; LCDR2 around residues 50-56; and LCDR3 around residues 89-97. One iteration of the Chothia numbering system identifies CDRs in the heavy chain variable region using the following residue positions: HCDR1 around residues 26-34; HCDR2 around residues 52-56; and HCDR3 around residues 95-102.

The IMGT method (International ImMunoGeneTics database) was developed by integrating existing definitions of framework regions and CDRs, structural data, and data from alignment of antibody variable region sequences. This integration led to the identification of conserved residues in the framework regions that can be used as reference points for identifying CDRs. Examples of conserved residues in variable regions include cysteine at approximately residue 23 (in framework region 1), tryptophan at approximately residue 41 (in framework region 2), a hydrophobic amino acid at approximately residue 89 (in framework region 3), cysteine at approximately residue 104 (in framework region 3), and phenylalanine or tryptophan at approximately residue 118 (in framework region 4). CDRs can be identified in a sequence encoding an antibody variable region of interest by using a computational alignment-based algorithm.

The IMGT method of numbering consistently assigns the same numbers to the conserved amino acids, but the lengths of CDRs and framework regions are permitted to vary. Therefore, IMGT numbering of residues is not necessarily sequential. The length of CDRs identified by the IMGT method can vary. For example, LCDR1 or HCDR1 can be about 5 to about 12 amino acids, LCDR2 or HCDR2 can be about 0 to about 10 amino acids, and LCDR3 or HCDR3 can be about 5 to about 91 amino acids.

The Paratome method was developed based on multiple structural alignments of available antibody-antigen complexes. The structural positions that bind antigen were found to be similar among the examined antibodies, and antibody sequences from the data set were annotated with Antigen Binding Regions (ABRs, similar to CDRs). ABRs in a query sequence can be identified using a computational tool, which first aligns the query sequence against antibodies with solved antibody-antigen structures, then infers the positions of ABRs based on the alignment. Antibodies with solved structures can also have ABRs identified using a structural, rather than sequence-based, alignment method.

A subset of residues within CDRs contacts an antigen. These residues that contact antigen can be referred to as specificity-determining residues (SDRs). However, residues other than SDRs can contribute to binding activity by helping to maintain the conformation of the binding site. The number of SDRs in an antibody can vary based on the size and type of antigen that is recognized, for example, between 0-14 SDRs can be found within a CDR. SDRs can be enriched in some residues, such as tyrosine, serine, tryptophan, and asparagine.

A monoclonal antibody can be obtained from a population of substantially-homogeneous antibodies, i.e., the individual antibodies comprising the population are identical except for possible naturally-occurring mutations that can be present in minor amounts. In contrast to polyclonal antibody preparations, which include different antibodies directed against different epitopes, each monoclonal antibody is directed against a single epitope.

A compound herein can be a monoclonal antibody, for example, a chimeric antibody wherein a portion of the heavy and/or light chain is identical to or homologous to a corresponding sequence in an antibody derived from a particular species or belonging to a particular antibody class or subclass, while the remainder of the chain(s) is identical or homologous to a corresponding sequence in an antibody derived from another species or belonging to another antibody class or subclass, or an antigen-binding fragment of such an antibody.

An antibody fragment or antigen-binding fragment can comprise a portion of an antibody, for example, the antigen-binding or variable region of the intact antibody. Non-limiting examples of antibody fragments include Fab, Fab', $F(ab')_2$, dimers and trimers of Fab conjugates, Fv, scFv, minibodies, dia-, tria-, and tetrabodies, and linear antibodies. Fab and Fab' are antigen-binding fragments that can comprise the $V_H$ and $C_H1$ domains of the heavy chain linked to the $V_L$ and $C_L$ domains of the light chain via a disulfide bond. A $F(ab')_2$ can comprise two Fab or Fab' that are joined by disulfide bonds. A Fv can comprise the $V_H$ and $V_L$ domains held together by non-covalent interactions. A scFv (single-chain variable fragment) is a fusion protein that can comprise the $V_H$ and $V_L$ domains connected by a peptide linker. Manipulation of the orientation of the $V_H$ and $V_L$ domains and the linker length can be used to create different forms of molecules that can be monomeric, dimeric (diabody), trimeric (triabody), or tetrameric (tetrabody). Minibodies are scFv-$C_H3$ fusion proteins that assemble into bivalent dimers.

Non-limiting examples of epitopes include amino acids, sugars, lipids, phosphoryl, and sulfonyl groups. An epitope can have specific three-dimensional structural characteristics, and/or specific charge characteristics. Epitopes can be conformational or linear.

For human administration, monoclonal antibodies generated from non-human species can be further optimized by a humanization process to reduce the likelihood of immunogenicity while preserving target specificity. Humanization processes involve the incorporation of human DNA to the genetic sequence of the genes that produce the isolated antibodies. The recombinant DNA is cloned and expressed in cells for large-scale production of the newly humanized antibodies.

An example of a humanized antibody is a modified chimeric antibody. A chimeric antibody can be generated as described above. The chimeric antibody is further mutated outside of the CDRs to substitute non-human sequences in the variable regions with the homologous human sequences. Another example of a humanized antibody is a CDR-grafted antibody, in which non-human CDR sequences are introduced into the human heavy and light chain variable sequences of a human antibody scaffold to replace the corresponding human CDR sequences.

A humanized antibody can be produced in mammalian cells, bioreactors, or transgenic animals, such as mouse, chicken, sheep, goat, pig, or marmoset. The transgenic animal can have a substantial portion of the human antibody-producing genome inserted into the genome of the animal.

In addition to antibodies and antibody fragments, other antigen-binding compounds can also bind target molecules. Non-limiting examples of non-antibody-derived antigen-binding compounds include ankyrin proteins, ankyrin repeat proteins, designed ankyrin repeat proteins (DARPins), affibodies, avimers, adnectins, anticalins, Fynomers, Kunitz domains, knottins, β-hairpin mimetics, and receptors and derivatives thereof, e.g. VEGF receptors, or the VEGF-binding portions of human VEGF receptors 1 and 2.

Designed ankyrin repeat proteins (DARPins) can be protein scaffolds based on ankyrin repeat proteins. A DARPin can comprise one or more ankyrin repeats that comprise a shared sequence and/or structural motif. The individual ankyrin repeats can comprise a shared sequence and/or structural motif despite comprising mutations, substitutions, additions and/or deletions when compared to one other. A DARPin can comprise, for example, about 1, 2, 3, 4, 5, 6, 7, 8, 9, or 10 ankyrin repeats, or more. A DARPin can comprise an N-terminal capping repeat, one or more internal ankyrin repeats, and a C-terminal capping repeat. Each ankyrin repeat can comprise framework residues and protein-interaction residues. The framework residues can contribute to structure or folding topology, for example, the structure of an ankyrin repeat or interaction with a neighboring ankyrin repeat. Protein-interaction residues can contribute to binding of a target molecule, for example, via direct interaction with the target molecule, or by stabilizing directly-interacting residues in a conformation that allows binding.

Compounds, antibodies, fragments or derivatives thereof, or other compounds that bind target molecules in this disclosure can bind to targets with a $K_D$ of, for example, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 9 pM, less than about 8 pM, less than about 7 pM, less than about 6 pM, less than about 5 pM, less than about 4 pM, less than about 3 pM, less than about 2 pM, less than about 1 pM, less than about 900 fM, less than about 800 fM, less than about 700 fM, less than about 600 fM, less than about 500 fM, less than about 400 fM, less than about 300 fM, less than about 200 fM, less than about 100 fM, less than about 90 fM, less than about 80 fM, less than about 70 fM, less than about 60 fM, less than about 50 fM, less than about 40 fM, less than about 30 fM, less than about 20 fM, or less than about 10 fM.

In some embodiments, a compound, antibody, fragment or derivatives thereof, or other compound that a bind target molecule in this disclosure can bind to the target with a $K_D$ of, for example, about 10 fM to about 500 nM, about 30 fM to about 500 nM, about 30 fM to about 400 nM, about 30 fM to about 300 nM, about 30 fM to about 200 nM, about 30 fM to about 100 nM, about 30 fM to about 90 nM, about 30 fM to about 80 nM, about 30 fM to about 70 nM, about 30 fM to about 60 nM, about 30 fM to about 50 nM, about 30 fM to about 40 nM, about 30 fM to about 30 nM, about 30 fM to about 20 nM, about 30 fM to about 10 nM, about 30 fM to about 9 nM, about 30 fM to about 8 nM, about 30 fM to about 7 nM, about 30 fM to about 6 nM, about 30 fM to about 5 nM, about 30 fM to about 4 nM, about 30 fM to about 3 nM, about 30 fM to about 2 nM, about 30 fM to about 1 nM, about 30 fM to about 900 pM, about 30 fM to about 800 pM, about 30 fM to about 700 pM, about 30 fM to about 600 pM, about 30 fM to about 500 pM, about 30 fM to about 400 pM, about 30 fM to about 300 pM, about 30 fM to about 200 pM, about 30 fM to about 100 pM, about 30 fM to about 90 pM, about 30 fM to about 80 pM, about 30 fM to about 70 pM, about 30 fM to about 60 pM, about 30 fM to about 50 pM, about 30 fM to about 40 pM, about 30 fM to about 30 pM, about 30 fM to about 20 pM, about 30 fM to about 10 pM, about 30 fM to about 1 pM, about 30 fM to about 900 fM, about 30 fM to about 800 fM, about 30 fM to about 700 fM, about 30 fM to about 600 fM, about 30 fM to about 500 fM, about 30 fM to about 400 fM, about 30 fM to about 300 fM, about 30 fM to about 200 fM, about 30 fM to about 100 fM, about 30 fM to about 500 nM, about 30 fM to about 400 nM, about 30 fM to about 300 nM, about 30 fM to about 200 nM, about 30 fM to about 100 nM, about 30 fM to about 90 nM, about 30 fM to about 80 nM, about 30 fM to about 70 nM, about 30 fM to about 60 nM, about 30 fM to about 50 nM, about 30 fM to about 40 nM, about 30 fM to about 30 nM, about 30 fM to about 20 nM, about 30 fM to about 10 nM, about 30 fM to about 9 nM, about 30 fM to about 8 nM, about 30 fM to about 7 nM, about 30 fM to about 6 nM, about 30 fM to about 5 nM, about 30 fM to about 4 nM, about 30 fM to about 3 nM, about 30 fM to about 2 nM, about 30 fM to about 1 nM, about 30 fM to about 900 pM, about 30 fM to about 800 pM, about 30 fM to about 700 pM, about 30 fM to about 600 pM, about 30 fM to about 500 pM, about 30 fM to about 400 pM, about 30 fM to about 300 pM, about 30 fM to about 200 pM, about 30 fM to about 100 pM, about 30 fM to about 90 pM, about 30 fM to about 80 pM, about 30 fM to about 70 pM, about 30 fM to about 60 pM, about 30 fM to about 50 pM, about 30 fM to about 40 pM, about 30 fM to about 30 pM, about 30 fM to about 20 pM, about 30 fM to about 10 pM, about 1 pM to about 500 nM, about 1 pM to about 400 nM, about 1 pM to about 300 nM, about 1 pM to about 200 nM, about 1 pM to about 100 nM, about 1 pM to about 90 nM, about 1 pM to about 80 nM, about 1 pM to about 70 nM, about 1 pM to about 60 nM, about 1 pM to about 50 nM, about 1 pM to about 40 nM, about 1 pM to about 30 nM, about 1 pM to about 20 nM, about 1 pM to about 10 nM, about 1 pM to about 9 nM, about 1 pM to about 8 nM, about 1 pM to about 7 nM, about 1 pM to about 6 nM, about 1 pM to about 5 nM, about 1 pM to about 4 nM, about 1 pM to about 3 nM, about 1 pM to about 2 nM, about 1 pM to about 1 nM, about 1 pM to about 900 pM, about 1 pM to about 800 pM, about 1 pM to about 700 pM, about 1 pM to about 600 pM, about 1 pM to about 500 pM, about 1 pM to about 400 pM, about 1 pM to about 300 pM, about 1 pM to about 200 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 100 pM to about 500 nM, about 100 pM to about 400 nM, about 100 pM to about 300 nM, about 100 pM to about 200 nM, about 100 pM to about 100 nM, about 100 pM to about 90 nM, about 100 pM to about 80 nM, about 100 pM to about 70 nM, about 100 pM to about 60 nM, about 100 pM to about 50 nM, about 100 pM to about 40 nM, about 100 pM to about 30 nM, about 100 pM to about 20 nM, about 100 pM to about 10 nM, about 100 pM to about 9 nM, about 100 pM to about 8 nM, about 100 pM to about 7 nM, about 100 pM to about 6 nM, about 100 pM to about 5 nM, about 100 pM to about 4 nM, about 100 pM to about 3 nM, about 100 pM to about 2 nM, about 100 pM to about 1 nM, about 100 pM to about 900 pM, about 100 pM to about 800 pM, about 100 pM to about 700 pM, about 100 pM to about 600 pM, about 100 pM to about 500 pM, about 100 pM to about 400 pM, about 100 pM to about 300 pM, or about 100 pM to about 200 pM.

In some embodiments, a compound, antibody, fragment or derivatives thereof, or other compound of the disclosure can bind HPTP-β (VE-PTP) with a $K_D$ of about 500 fM to about 500 pM. In some embodiments, a compound, antibody, fragment or derivatives thereof, or other compound of the disclosure can bind HPTP-β (VE-PTP) with a $K_D$ of about 1 pM to about 500 pM. In some embodiments, a compound, antibody, fragment or derivatives thereof, or other compound of the disclosure can bind HPTP-β (VE-PTP) with a $K_D$ of about 60 pM to about 500 pM. In some embodiments, a compound, antibody, fragment or derivatives thereof, or other compound of the disclosure can bind HPTP-β (VE-PTP) with a $K_D$ of about 100 pM to about 500 pM. In some embodiments, a compound, antibody, fragment or derivatives thereof, or other compound of the disclosure can bind HPTP-β (VE-PTP) with a $K_D$ of about 1 pM to about 300 pM. In some embodiments, a compound, antibody, fragment or derivatives thereof, or other compound of the disclosure can bind HPTP-β (VE-PTP) with a $K_D$ of about 1 pM to about 200 pM. In some embodiments, a compound, antibody, fragment or derivatives thereof, or other compound of the disclosure can bind HPTP-β (VE-PTP) with a $K_D$ of about 1 pM to about 120 pM. In some embodiments, a compound, antibody, fragment or derivatives thereof, or other compound of the disclosure can bind HPTP-β (VE-PTP) with a $K_D$ of about 1 pM to about 70 pM.

In some embodiments, a compound, antibody, fragment or derivatives thereof, or other compound of the disclosure can bind VEGF with a $K_D$ of about 30 fM to about 900 pM. In some embodiments, a compound, antibody, fragment or derivatives thereof, or other compound of the disclosure can bind VEGF with a $K_D$ of about 30 fM to about 600 pM. In some embodiments, a compound, antibody, fragment or derivatives thereof, or other compound of the disclosure can bind VEGF with a $K_D$ of about 30 fM to about 200 pM. In some embodiments, a compound, antibody, fragment or derivatives thereof, or other compound of the disclosure can bind VEGF with a $K_D$ of about 30 fM to about 30 pM. In some embodiments, a compound, antibody, fragment or derivatives thereof, or other compound of the disclosure can bind VEGF with a $K_D$ of about 30 fM to about 40 pM. In some embodiments, a compound, antibody, fragment or derivatives thereof, or other compound of the disclosure can bind VEGF with a $K_D$ of about 30 fM to about 1 pM. In some embodiments, a compound, antibody, fragment or derivatives thereof, or other compound of the disclosure can bind VEGF with a $K_D$ of about 30 fM to about 200 fM. In some embodiments, a compound, antibody, fragment or derivatives thereof, or other compound of the disclosure can bind VEGF with a $K_D$ of about 1 pM to about 900 pM. In some embodiments, a compound, antibody, fragment or derivatives thereof, or other compound of the disclosure can bind VEGF with a $K_D$ of about 1 pM to about 600 pM. In some embodiments, a compound, antibody, fragment or derivatives thereof, or other compound of the disclosure can bind VEGF with a $K_D$ of about 1 pM to about 200 pM. In some embodiments, a compound, antibody, fragment or derivatives thereof, or other compound of the disclosure can bind VEGF with a $K_D$ of about 1 pM to about 30 pM. In some embodiments, a compound, antibody, fragment or derivatives thereof, or other compound of the disclosure can bind VEGF with a $K_D$ of about 1 pM to about 40 pM.

In some embodiments, a compound, antibody, fragment or derivatives thereof, or other compound of the disclosure can bind VEGF with a $K_D$ of about 30 fM to about 2 pM. In some embodiments, a compound, antibody, fragment or derivatives thereof, or other compound of the disclosure can bind VEGF with a $K_D$ of about 35 fM to about 200 fM. In some embodiments, a compound, antibody, fragment or derivatives thereof, or other compound of the disclosure can bind VEGF with a $K_D$ of about 100 fM to about 2 pM.

In some embodiments, a compound, antibody, fragment or derivatives thereof, or other compound of the disclosure can bind VEGF with a $K_D$ of about 20 pM to about 1 nM. In some embodiments, a compound, antibody, fragment or derivatives thereof, or other compound of the disclosure can bind VEGF with a $K_D$ of about 20 pM to about 800 pM. In some embodiments, a compound, antibody, fragment or derivatives thereof, or other compound of the disclosure can bind VEGF with a $K_D$ of about 20 pM to about 350 pM.

In some embodiments, a compound, antibody, fragment or derivatives thereof, or other compound of the disclosure can bind VEGF with a $K_D$ of about 30 fM to about 700 pM.

In some embodiments, a compound, antibody, fragment or derivatives thereof, or other compound of the disclosure can bind VEGF with a $K_D$ of about 40 fM to about 520 pM. In some embodiments, a compound, antibody, fragment or derivatives thereof, or other compound of the disclosure can bind VEGF with a $K_D$ of about 40 fM to about 110 pM.

Polyvalent, Multispecific Compounds

Antigen-binding compounds can be combined to generate polyvalent and/or multispecific compounds. Such polyvalent and/or multispecific compounds can have advantages over the parent compounds administered individually. These advantages can include, for example, a simpler dosing regimen, longer half-life within a subject, and the ability to bind target antigens in close proximity.

Multispecific antibodies can be produced by a number of methods. In one method, monospecific antibodies or derivatives thereof can be chemically coupled, for example, via chemical coupling of two IgG antibody units into a conjugate.

In another method, cloning techniques can be used to append additional antigen binding domain(s) to a conventional IgG antibody or derivative thereof. An additional antigen-binding domain can be, for example, a single variable domain (sVD), a single-chain variable fragment (scFv), a single-chain Fab, a peptide, an ankyrin protein, an ankyrin repeat protein, a designed ankyrin repeat protein (DARPin), an affibody, an avimer, an adnectin, an anticalin, a Fynomer, a Kunitz domain, a knottin, a β-hairpin mimetic, a tetrameric polyethylene oxide clustered peptide, a peptide derived from one or more receptors (e.g. VEGF receptors, or the VEGF-binding portions of human VEGF receptors 1 and 2), or a derivative thereof.

The additional antigen-binding domain (e.g., sVD, scFv, single-chain Fab, peptide, ankyrin protein, ankyrin repeat protein, DARPin, affibody, avimer, adnectin, anticalin, Fynomer, Kunitz domain, knottin, β-hairpin mimetic, tetrameric polyethylene oxide clustered peptide, or peptide derived from one or more receptors) can be appended to the N or C-terminus of the light chain and/or heavy chain of the IgG or Fab, for example, via a peptide linker. In some embodiments, a scFv can be appended to the C-termini of the heavy chains of an IgG to provide a tetravalent bispecific antibody. A scFv can be appended to the C-termini of the light chains of an IgG to provide a tetravalent bispecific antibody. A scFv can be appended to the C-termini of the light chains and the C-termini of the heavy chains of an IgG, to provide a hexavalent bispecific antibody. In some embodiments, a DARPin can be appended to the C-termini of the heavy chains of an IgG to provide a tetravalent bispecific antibody. A DARPin can be appended to the C-termini of the light chains of an IgG to provide a tetravalent bispecific antibody. A DARPin can be appended to the C-termini of the light chains and the C-termini of the heavy chains of an IgG, to provide a hexavalent bispecific antibody. Additional examples of multispecific antibodies produced by cloning techniques include: (i) DVD-Ig™ (dual variable domain immunoglobulin, tandem linkage of the second $V_H$ and $V_L$ to the N-termini of HC and LC, respectively), (ii) Tandemab (tandem linkage of 2 $V_H$-$C_H$1 in combination of common LC), (iii) DNL (natural association of 2 antibodies or antibody fragments anchored with DDD (dimerization and docking domain) from PKA (protein kinase A) and AD (anchoring domain) from A-kinase anchor protein (AKAP), respectively), (iv) LUZ-Y (leucine zipper tethered at the C-termini of HC and later proteolytically removed), (v) 2-in-1-IgG (same LC and HC capable of dual recognition), and (vi) mAb$^2$ (engineered loops in $C_H3$ domain of IgG to obtain second specificity).

Another class of multispecific antibodies can be characterized by structures with variable domains or scFvs as the building blocks. Non-limiting examples of such multispecific antibodies include two $V_H$ domains joined in tandem, diabodies (heterodimers containing 2 polypeptide chains encoding $V_L$A-$V_H$B and $V_H$A-$V_L$B in the order of $V_H$-$V_L$ or $V_L$—$V_H$ with a linker of 5 amino acids), dsDbs (interchain disulfide bond between $V_L$ and $V_H$ of the same antibody), DARTs (dual-affinity re-targeting, interchain disulfide bond between 2 $V_L$), scDbs (single chain Diabody), tandAbs (Diabody dimer via flexible linkers in between), and 2 scFvs connected in tandem by an adjustable linker.

Another class of multispecific antibodies can contain different antigen binding fragments, while retaining the basic IgG structure. Such antibodies can comprise, for example, two distinct heavy chains and/or two distinct light chains. Various techniques can be used to promote pairing of desirable light and heavy chain combinations, rather than random chain associations. Non-limiting examples of such techniques include use of a common light chain, orthogonal Fab interface (complementary mutations introduced at LC and HC interface in one Fab and no change to the other Fab), CrossMab (wherein one Fab $V_H$ or $C_H1$ domain(s) can be switched with the partner $V_L$ or $C_L$ domain(s), with the other Fab untouched), and replacing the Fab with a single chain antigen-binding domain. Further examples include engineering strategies that can introduce mutations into the $C_H3$ domains to promote heterodimerization based on steric or electrostatic complementarity. The "knobs in holes" approach can involve creating a "knob" by replacing threonine at position 366 with a bulky tryptophan residue on one heavy chain, and making a corresponding "hole" by triple mutations (T366S, L368A and Y407V) on the partner heavy chain. Another approach can involve creating alternating human IgG and IgA fragments in $C_H3$ to provide the so-called SEEDbody (Strand-Exchange Engineered Domain) to guide heavy chain heterodimerization.

Non-limiting schematics of multispecific antibodies are provided in FIGS. 2-15.

Figure 2:
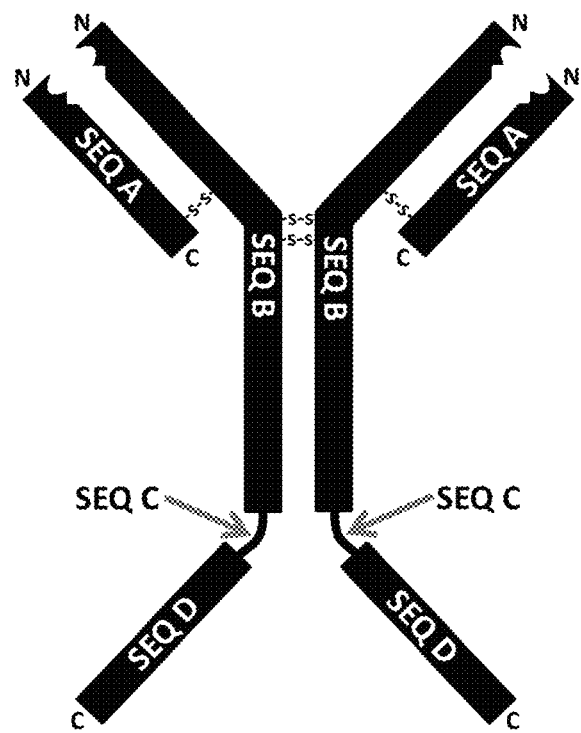
FIG. 2: Schematic of a tetravalent, bispecific antibody with sequences appended to the heavy chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

FIG. 2 provides a schematic of a tetravalent, bispecific antibody with sequences appended to the heavy chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

Figure 3:
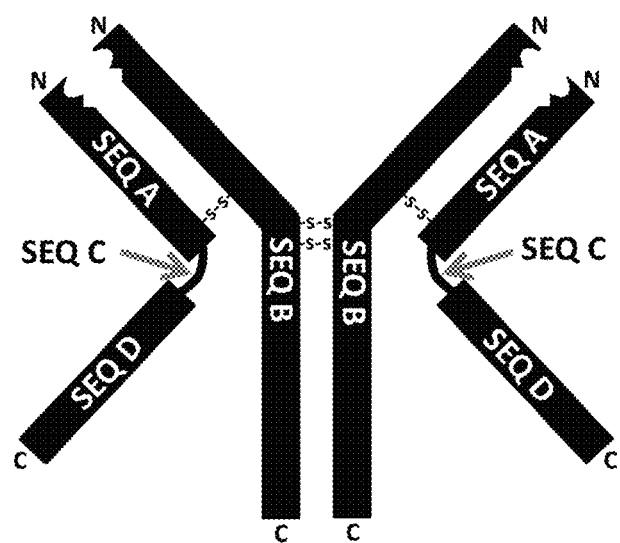
FIG. 3: Schematic of a tetravalent, bispecific antibody with sequences appended to the light chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

FIG. 3 provides a schematic of a tetravalent, bispecific antibody with sequences appended to the light chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

Figure 4:
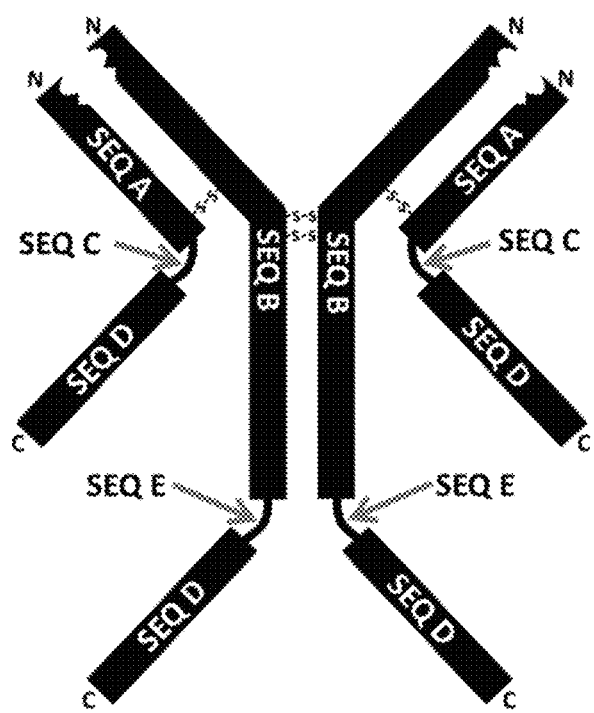
FIG. 4: Schematic of a hexavalent, bispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D". N and C denote N- and C-termini, respectively. —S—S— denotes disulfide bonds.

FIG. 4 provides a schematic of a hexavalent, bispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D". N and C denote N- and C-termini, respectively. —S—S— denotes disulfide bonds.

Figure 5:
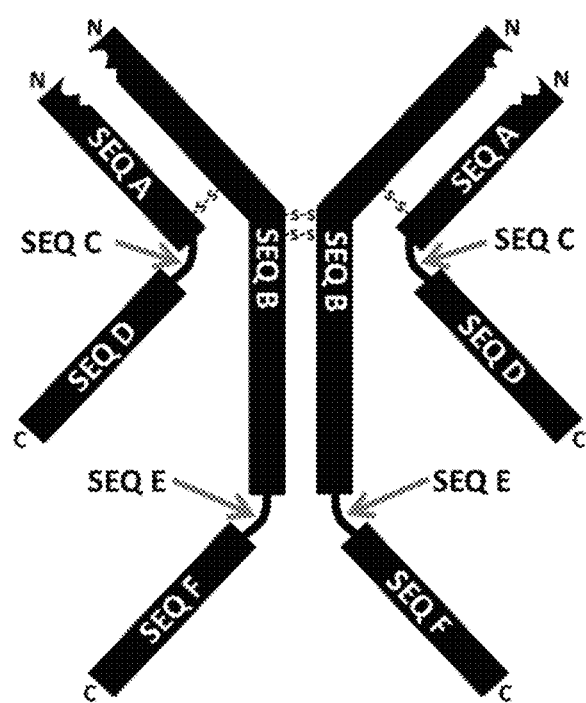
FIG. 5: Schematic of a hexavalent, trispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D" and "SEQ F". N and C denote N- and C-termini, respectively. —S—S— denotes disulfide bonds.

FIG. 5 provides a schematic of a hexavalent, trispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D" and "SEQ F". N and C denote N- and C-termini, respectively. —S—S— denotes disulfide bonds.

Figure 6:
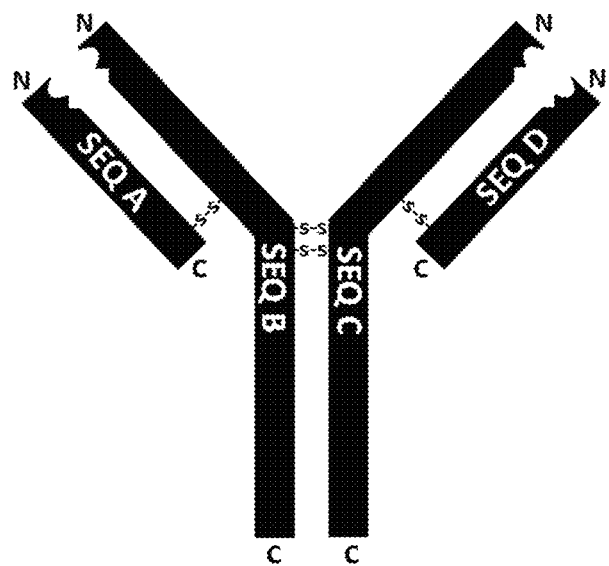
FIG. 6: Schematic of a bivalent, bispecific antibody with two different heavy chain sequences and two different light chain sequences. Light chain sequences are represented by "SEQ A" and "SEQ D". Heavy chain sequences are represented by "SEQ B" and "SEQ C". N and C denote N- and C-termini, respectively. —S—S— denotes disulfide bonds.

FIG. 6 provides a schematic of a bivalent, bispecific antibody with two different heavy chain sequences and two different light chain sequences. Light chain sequences are represented by "SEQ A" and "SEQ D". Heavy chain sequences are represented by "SEQ B" and "SEQ C". N and C denote N- and C-termini, respectively. —S—S— denotes disulfide bonds.

Figure 7:
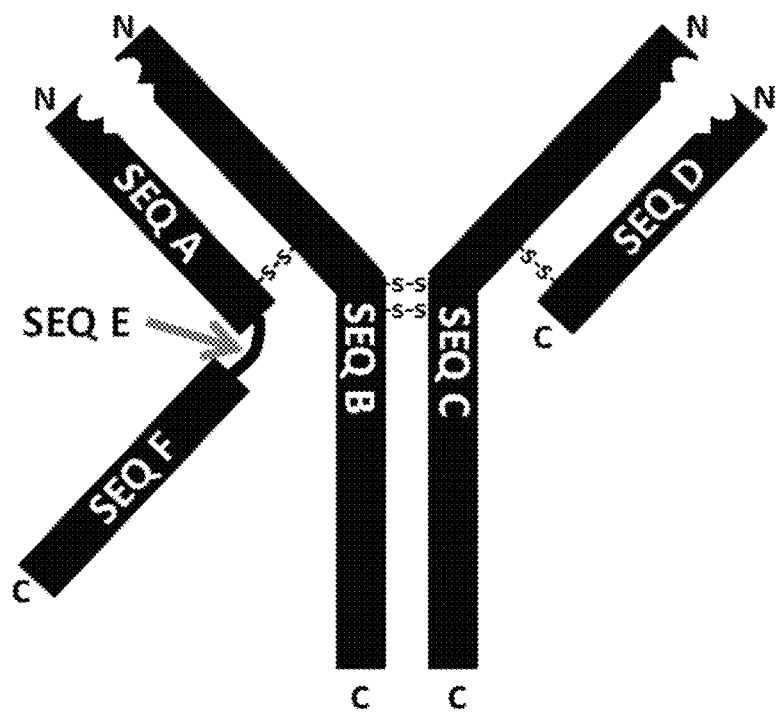
FIG. 7: Schematic of a trivalent, trispecific antibody with two different heavy chain sequences, two different light chain sequences, and a sequence appended to the C-terminus of one light chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

FIG. 7 provides a schematic of a trivalent, trispecific antibody with two different heavy chain sequences, two different light chain sequences, and a sequence appended to the C-terminus of one light chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

Figure 8:
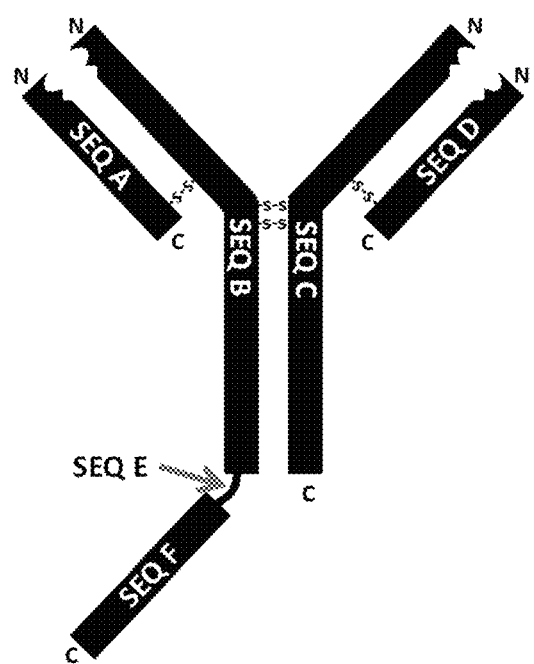
FIG. 8: Schematic of a trivalent, trispecific antibody with two different heavy chain sequences, two different light chain sequences, and a sequence appended to the C-terminus of one heavy chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

FIG. 8 provides a schematic of a trivalent, trispecific antibody with two different heavy chain sequences, two different light chain sequences, and a sequence appended to the C-terminus of one heavy chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

Figure 9:
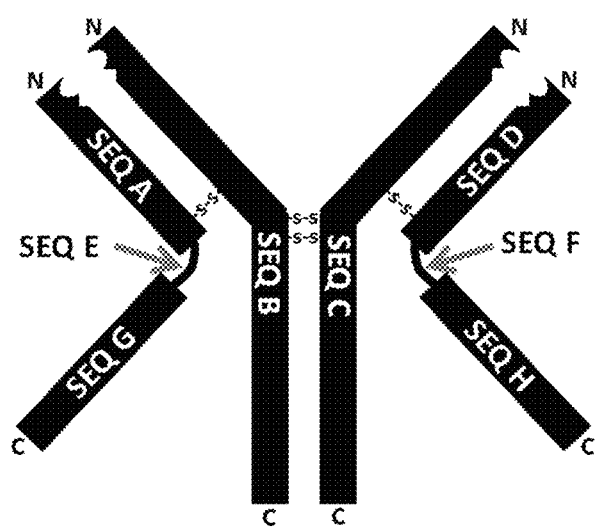
FIG. 9: Schematic of a tetravalent antibody with two different heavy chain sequences, two different light chain sequences, and sequences appended to both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 9 provides a schematic of a tetravalent antibody with two different heavy chain sequences, two different light chain sequences, and sequences appended to both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 10:
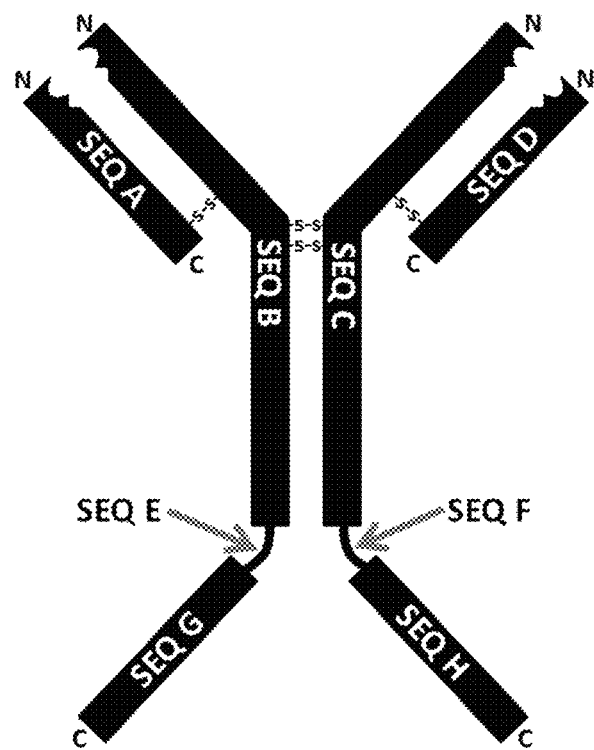
FIG. 10: Schematic of a tetravalent antibody with two different heavy chain sequences, two different light chain sequences, and sequences appended to both heavy chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 10 provides a schematic of a tetravalent antibody with two different heavy chain sequences, two different light chain sequences, and sequences appended to both heavy chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 11:
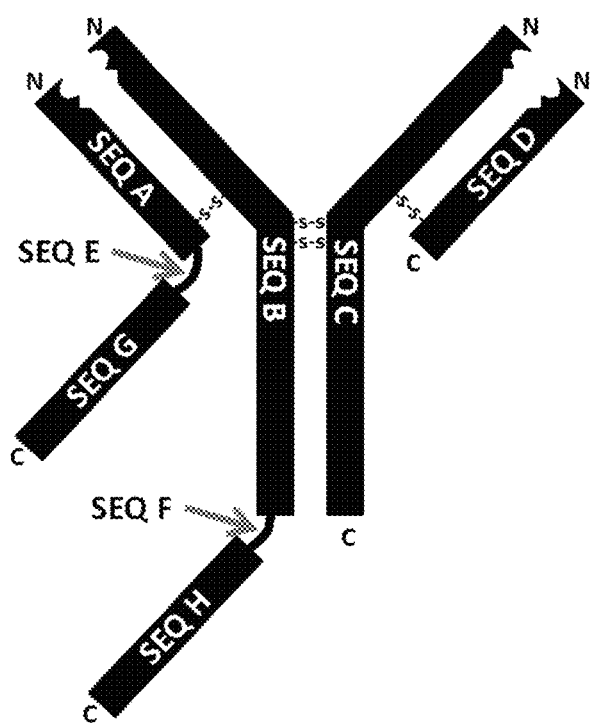
FIG. 11: Schematic of a tetravalent antibody with two different heavy chain sequences, two different light chain sequences, and sequences appended to one heavy chain C-terminus and one light chain C-terminus in cis. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 11 provides a schematic of a tetravalent antibody with two different heavy chain sequences, two different light chain sequences, and sequences appended to one heavy chain C-terminus and one light chain C-terminus in cis. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 12:
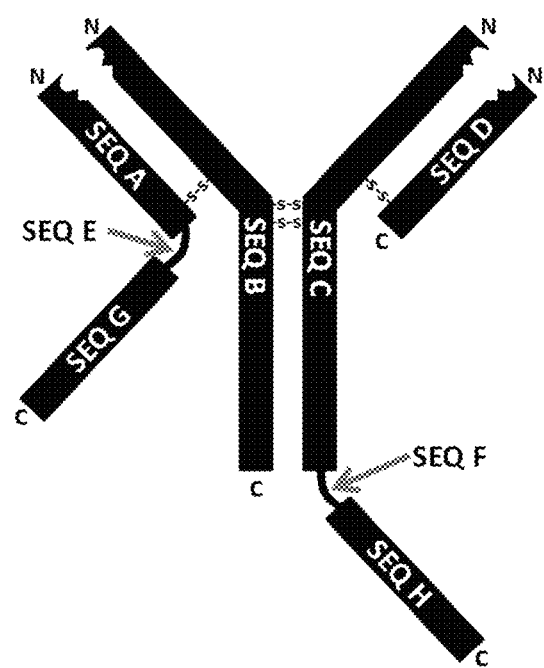
FIG. 12: Schematic of a tetravalent antibody with two different heavy chain sequences, two different light chain sequences, and sequences appended to one heavy chain C-terminus and one light chain C-terminus in trans. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 12 provides a schematic of a tetravalent antibody with two different heavy chain sequences, two different light chain sequences, and sequences appended to one heavy chain C-terminus and one light chain C-terminus in trans. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 13:
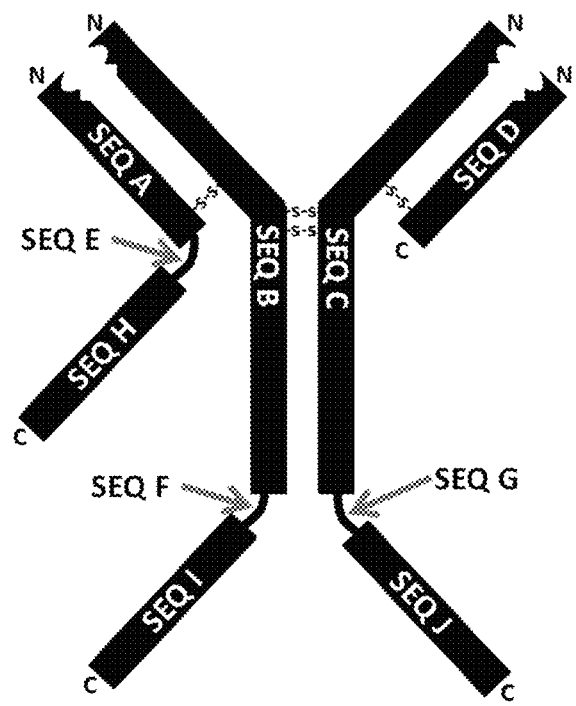
FIG. 13: Schematic of a pentavalent antibody with two different heavy chain sequences, two different light chain sequences, and sequences appended to both heavy chain C-termini and one light chain C-terminus. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

FIG. 13 provides a schematic of a pentavalent antibody with two different heavy chain sequences, two different light chain sequences, and sequences appended to both heavy chain C-termini and one light chain C-terminus. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

Figure 14:
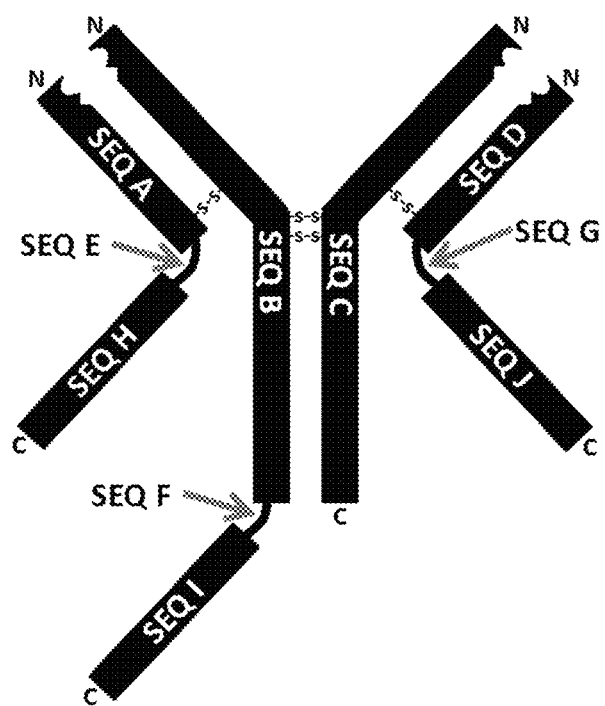
FIG. 14: Schematic of a pentavalent antibody with two different heavy chain sequences, two different light chain sequences, and sequences appended to one heavy chain C-terminus and both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

FIG. 14 provides a schematic of a pentavalent antibody with two different heavy chain sequences, two different light chain sequences, and sequences appended to one heavy chain C-terminus and both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

Figure 15:
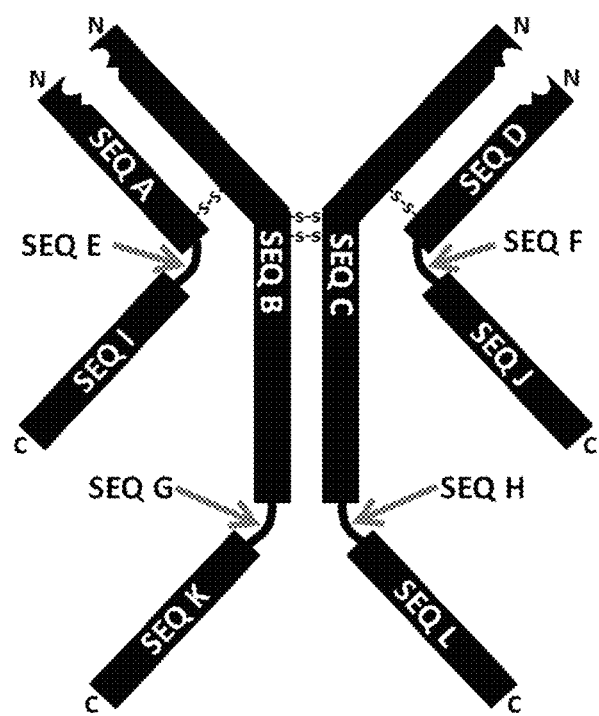
FIG. 15: Schematic of a hexavalent antibody with two different heavy chain sequences, two different light chain sequences, and sequences appended to the heavy chain and light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", "SEQ G", and "SEQ H". Appended antigen binding domain sequences are represented by "SEQ I", "SEQ J", "SEQ K" and "SEQ L". N and C denote N- and C-termini, respectively. —S—S— denotes disulfide bonds.

FIG. 15 provides a schematic of a hexavalent antibody with two different heavy chain sequences, two different light chain sequences, and sequences appended to the heavy chain and light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", "SEQ G", and "SEQ H". Appended antigen binding domain sequences are represented by "SEQ I", "SEQ J", "SEQ K", and "SEQ L". N and C denote N- and C-termini, respectively. —S—S— denotes disulfide bonds.

Antigen-binding compounds specific for, for example, HPTP-β (VE-PTP), can be combined with antigen-binding compounds specific for, for example, a RTK agonist, to provide a polyvalent multispecific compound that can bind both HPTP-β (VE-PTP) and the RTK agonist. For example, an antigen binding compound specific for HPTP-β (VE-PTP) can be combined with an antigen-binding compound specific for VEGF, Ang1, Ang2, BDNF, EGF, FGF, HGF, IGF, insulin, MSP, NGF, NT-3, PDGF, or any combination thereof, to provide a polyvalent multispecific compound that can bind both HPTP-β (VE-PTP) and a RTK agonist.

Antigen-binding compounds specific for, for example, HPTP-β (VE-PTP), can be combined with antigen-binding compounds specific for, for example, VEGF, to provide a polyvalent multispecific compound that can bind both HPTP-β (VE-PTP) and VEGF. Compounds that bind both HPTP-β (VE-PTP) and VEGF can inhibit HPTP-β (VE-PTP), activate Tie2, inhibit VEGF binding to VEGFRs, and inhibit VEGFR signaling.

Sequences derived from aflibercept, a recombinant protein comprising the VEGF-binding portions of human VEGF receptors 1 and 2, can be combined with antigen-binding compounds specific for HPTP-β (VE-PTP). For example, sequences derived from aflibercept can be fused to the C-termini of the heavy chains of a HPTP-β (VE-PTP)-specific antibody, to provide a tetravalent, bispecific antibody (FIG. 2). Sequences derived from aflibercept can be fused to the C-termini of the light chains of a HPTP-β (VE-PTP)-specific antibody, to provide a tetravalent, bispecific antibody (FIG. 3). Sequences derived from aflibercept can be fused to the C-termini of the light chains and heavy chains of a HPTP-β (VE-PTP)-specific antibody, to provide a hexavalent, bispecific antibody (FIG. 4).

Sequences derived from brolucizumab, a humanized single-chain antibody fragment (scFv) inhibitor of VEGF that binds to the receptor binding site of VEGF, can be combined with antigen-binding compounds specific for HPTP-β (VE-PTP). For example, sequences from brolucizumab can be fused to the C-termini of the heavy chains of a HPTP-β (VE-PTP)-specific antibody, to provide a tetravalent, bispecific antibody (FIG. 2). Sequences derived from brolucizumab can be fused to the C-termini of the light chains of a HPTP-β (VE-PTP)-specific antibody, to provide a tetravalent, bispecific antibody (FIG. 3). Sequences derived from brolucizumab can be fused to the C-termini of the light chains and heavy chains of a HPTP-β (VE-PTP)-specific antibody, to provide a hexavalent, bispecific antibody (FIG. 4).

Sequences derived from ranibizumab, a humanized monoclonal antibody fragment (Fab) that binds to and inhibits the activity of VEGF, can be combined with antigen-binding compounds specific for HPTP-β (VE-PTP). For example, the sequences from ranibizumab can be cloned into an scFv, and the ranibizumab-derived scFv can be fused to can be fused to the C-termini of the heavy chains of a HPTP-β (VE-PTP)-specific antibody, to provide a tetravalent, bispecific antibody (FIG. 2). The ranibizumab-derived scFv can be fused to the C-termini of the light chains of a HPTP-β (VE-PTP)-specific antibody, to provide a tetravalent, bispecific antibody (FIG. 3). The ranibizumab-derived scFv can be fused to the C-termini of the light chains and heavy chains of a HPTP-β (VE-PTP)-specific antibody, to provide a hexavalent, bispecific antibody (FIG. 4).

Sequences derived from bevacizumab, a humanized monoclonal antibody that that binds to and inhibits activity of VEGF, can be combined with antigen-binding compounds specific for HPTP-β (VE-PTP). For example, the sequences from bevacizumab can be cloned into an scFv, and the bevacizumab-derived scFv can be fused to can be fused to the C-termini of the heavy chains of a HPTP-β (VE-PTP)-specific antibody, to provide a tetravalent, bispecific antibody (FIG. 2). The bevacizumab-derived scFv can be fused to the C-termini of the light chains of a HPTP-β (VE-PTP)-specific antibody, to provide a tetravalent, bispecific antibody (FIG. 3). The bevacizumab-derived scFv can be fused to the C-termini of the light chains and heavy chains of a HPTP-β (VE-PTP)-specific antibody, to provide a hexavalent, bispecific antibody (FIG. 4).

Sequences derived from conbercept, a recombinant protein comprising the VEGF-binding portions of VEGF receptors 1 and 2, can be combined with antigen-binding compounds specific for HPTP-β (VE-PTP). For example, sequences derived from conbercept can be fused to the C-termini of the heavy chains of a HPTP-β (VE-PTP)-specific antibody, to provide a tetravalent, bispecific antibody (FIG. 2). Sequences derived from conbercept can be fused to the C-termini of the light chains of a HPTP-β (VE-PTP)-specific antibody, to provide a tetravalent, bispecific antibody (FIG. 3). Sequences derived from conbercept can be fused to the C-termini of the light chains and heavy chains of a HPTP-β (VE-PTP)-specific antibody, to provide a hexavalent, bispecific antibody (FIG. 4).

Sequences derived from abicipar, a VEGF-binding DARPin, can be combined with antigen-binding compounds specific for HPTP-β (VE-PTP). For example, sequences derived from abicipar can be fused to the C-termini of the heavy chains of a HPTP-β (VE-PTP)-specific antibody, to provide a tetravalent, bispecific antibody (FIG. 2). Sequences derived from abicipar can be fused to the C-termini of the light chains of a HPTP-β (VE-PTP)-specific antibody, to provide a tetravalent, bispecific antibody (FIG. 3). Sequences derived from abicipar can be fused to the C-termini of the light chains and heavy chains of a HPTP-β (VE-PTP)-specific antibody, to provide a hexavalent, bispecific antibody (FIG. 4).

Antigen-binding compounds specific for HPTP-β (VE-PTP) can be combined with DARPins or amino acid sequences therefrom, for example, amino acid sequences comprising any one of SEQ ID NOS: 158-217. Amino acid sequences comprising any one of SEQ ID NOS: 158-217 can be fused to the C-termini of the heavy chains of a HPTP-β (VE-PTP)-specific antibody, to provide a tetravalent, bispecific antibody (FIG. 2). Amino acid sequences comprising any one of SEQ ID NOS: 158-217 can be fused to the C-termini of the light chains of a HPTP-β (VE-PTP)-specific antibody, to provide a tetravalent, bispecific antibody (FIG. 3). Amino acid sequences comprising any one of SEQ ID NOS: 158-217 can be fused to the C-termini of the light chains and heavy chains of a HPTP-β (VE-PTP)-specific antibody, to provide a hexavalent, bispecific antibody (FIG. 4).

Multiple VEGF-specific compounds can be combined with an antigen-binding compound specific for HPTP-β (VE-PTP). For example, one binding domain, (e.g. aflibercept-derived sequences) can be fused to the C-termini of the heavy chains of an anti-HPTP-β (VE-PTP) antibody, and another binding domain (e.g. brolucizumab-derived sequences) be fused to the C-termini of the light chains of the HPTP-β (VE-PTP)-specific antibody, to provide a hexavalent, trispecific antibody (FIG. 5).

If different heavy chains are used in the basic four chain IgG antibody unit (e.g., using the "knobs in holes" approach), antibodies can be generated that are bivalent, trivalent, tetravalent, pentavalent, or hexavalent, and that are monospecific, bispecific, trispecific, tetraspecific, pentaspecific, or hexaspecific.

In one non-limiting example, one arm of the antibody unit can contain CDRs specific for HPTP-β (VE-PTP), while the other arm of the antibody unit can contain CDRs specific for VEGF (FIG. 6).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one light chain, to provide a trivalent bispecific antibody (FIG. 7).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one heavy chain, to provide a trivalent bispecific antibody (FIG. 8).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one light chain, and a second, different binding domain specific for VEGF can be fused to the other light chain, to provide a tetravalent trispecific antibody (FIG. 9).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to the other heavy chain, to provide a tetravalent trispecific antibody (FIG. 10).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to one light chain in cis, to provide a tetravalent trispecific antibody (FIG. 11).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to one light chain in trans, to provide a tetravalent trispecific antibody (FIG. 12).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to a second heavy chain, and a third, different binding domain specific for VEGF can be fused to one light chain, to provide a pentavalent tetraspecific antibody (FIG. 13).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to a one light chain, and a third, different binding domain specific for VEGF can be fused to the other light chain, to provide a pentavalent tetraspecific antibody (FIG. 14).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to the other heavy chain, a third, different binding domain specific for VEGF can be fused to one light chain, and a fourth binding domain specific for VEGF can be fused to the other light chain, to provide a hexavalent pentaspecific antibody (FIG. 15).

In one non-limiting example, both antigen binding fragments of the basic antibody unit can be HPTP-β (VE-PTP)-specific, one binding domain, (e.g. an aflibercept-derived sequence) can be fused to the C-terminus of one heavy chain, and second binding domain (e.g. a brolucizumab-derived sequence) be fused to the C-terminus of the other heavy chain, to provide a tetravalent, trispecific antibody (FIG. 10). In one non-limiting example, both antigen binding fragments of the basic antibody unit can be HPTP-β (VE-PTP)-specific, an aflibercept-derived sequence can be fused to the C-terminus of one light chain, and a brolucizumab-derived sequence be fused to the C-terminus of another light chain, to provide a tetravalent, trispecific antibody (FIG. 9). In one non-limiting example, both antigen binding fragments of the basic antibody unit can be HPTP-β (VE-PTP)-specific, an aflibercept-derived sequence can be fused to the C-terminus of one heavy chain, and a brolucizumab-derived sequence be fused to the C-terminus of one light chain, to provide a tetravalent, trispecific antibody (FIG. 11, FIG. 12). In one non-limiting example, both antigen binding fragments of the basic antibody unit can be HPTP-β (VE-PTP)-specific, an aflibercept-derived sequence can be fused to the C-terminus of one heavy chain, a brolucizumab-derived sequence can be fused to the C-terminus of another heavy chain, and ranibizumab-derived sequences can be fused to the C-termini of both light chains, to provide a hexavalent, tetraspecific antibody (FIG. 15). In one non-limiting example, both antigen binding fragments of the basic antibody unit can be HPTP-β (VE-PTP)-specific, an aflibercept-derived sequence can be fused to the C-terminus of one heavy chain, a brolucizumab-derived sequence can be fused to the C-terminus of another heavy chain, a ranibizumab-derived sequence can be fused to the C-terminus of one light chain, and a bevacizumab-derived sequence can be fused to the C-terminus of another light chain, to provide a hexavalent, pentaspecific antibody (FIG. 15).

Antigen-binding compounds specific for, for example, HPTP-β (VE-PTP), can be combined with other amino acid sequences to provide polyvalent multispecific compounds that, for example, enhance Tie2 activation, enhance Tie2 phosphorylation, enhance Tie2 signaling, reduce VEGFR activation, reduce VEGFR phosphorylation, reduce VEGFR signaling, or a combination thereof.

Antigen-binding compounds specific for HPTP-β (VE-PTP) can be combined with collagen IV-derived biomimetic peptides, for example, amino acid sequences comprising SEQ ID NO: 152 or SEQ ID NO: 153. Amino acid sequences comprising SEQ ID NO: 152 or SEQ ID NO: 153 can be fused to the C-termini of the heavy chains of a HPTP-β (VE-PTP)-specific antibody, to provide a tetravalent, bispecific antibody (FIG. 2). Amino acid sequences comprising SEQ ID NO: 152 or SEQ ID NO: 153 can be fused to the C-termini of the light chains of a HPTP-β (VE-PTP)-specific antibody, to provide a tetravalent, bispecific antibody (FIG. 3). Amino acid sequences comprising SEQ ID NO: 152 or SEQ ID NO: 153 the C-termini of the light chains and heavy chains of a HPTP-β (VE-PTP)-specific antibody, to provide a hexavalent, bispecific antibody (FIG. 4).

Antigen-binding compounds specific for HPTP-β (VE-PTP) can be combined with Ang1 mimetics, for example, vasculotide. Sequences derived from vasculotide can be fused to the C-termini of the heavy chains of a HPTP-β (VE-PTP)-specific antibody, to provide a tetravalent, bispecific antibody (FIG. 2). Sequences derived from vasculotide can be fused to the C-termini of the light chains of a HPTP-β (VE-PTP)-specific antibody, to provide a tetravalent, bispecific antibody (FIG. 3). Sequences derived from vasculotide can be fused to the C-termini of the light chains and heavy chains of a HPTP-β (VE-PTP)-specific antibody, to provide a hexavalent, bispecific antibody (FIG. 4).

Antigen-binding compounds specific for, for example, HPTP-β (VE-PTP), can be combined with antigen-binding compounds specific for, for example, a RTK, to provide a polyvalent multispecific compound that can bind both HPTP-β (VE-PTP) and the RTK. For example, an antigen binding compound specific for HPTP-β (VE-PTP) can be combined with an antigen-binding compound specific for VEGFR (e.g. VEGFR2), to provide a polyvalent multispecific compound that can bind both HPTP-β (VE-PTP) and VEGFR.

Compounds that bind both HPTP-β (VE-PTP) and VEGFR can inhibit HPTP-β (VE-PTP), activate Tie2, inhibit VEGF binding to VEGFR, and inhibit VEGFR signaling.

Sequences derived from ramucirumab, a humanized monoclonal antibody that binds an extracellular domain of VEGFR2 and inhibits VEGFR2 signaling, can be combined with antigen-binding compounds specific for HPTP-β (VE-PTP). For example, the sequences from ramucirumab can be cloned into an scFv, and the ramucirumab-derived scFv can be fused to can be fused to the C-termini of the heavy chains of a HPTP-β (VE-PTP)-specific antibody, to provide a tetravalent, bispecific antibody (FIG. 2). The ramucirumab-derived scFv can be fused to the C-termini of the light chains of a HPTP-β (VE-PTP)-specific antibody, to provide a tetravalent, bispecific antibody (FIG. 3). The ramucirumab-derived scFv can be fused to the C-termini of the light chains and heavy chains of a HPTP-β (VE-PTP)-specific antibody, to provide a hexavalent, bispecific antibody (FIG. 4).

Multiple compounds that enhance Tie2 activation, enhance Tie2 phosphorylation, enhance Tie2 signaling, reduce VEGFR activation, reduce VEGFR phosphorylation, reduce VEGFR signaling, or a combination thereof, can be combined with an antigen-binding compound specific for HPTP-β (VE-PTP). For example, one binding domain, (e.g. brolucizumab-derived sequences) can be fused to the C-termini of the heavy chains of an anti-HPTP-β (VE-PTP) antibody, and another binding domain (e.g. vasculotide-derived sequences) be fused to the C-termini of the light chains of the HPTP-β (VE-PTP)-specific antibody, to provide a hexavalent, trispecific antibody (FIG. 5).

Compounds, antibodies, or derivatives thereof disclosed herein can have 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 domains or more. Each domain can modulate, bind, antagonize, inhibit or activate any targets disclosed herein, for example, a phosphatase, a phosphatase that modulates Tie2 signaling, a protein tyrosine phosphatase, a receptor-like protein tyrosine phosphatase, a Tie2 modulator, HPTP-β (VE-PTP), an extracellular domain of HPTP-β (VE-PTP), the first FN3 repeat of an extracellular domain of HPTP-β (VE-PTP), a kinase, a tyrosine kinase, a receptor tyrosine kinase, a receptor tyrosine kinase activator, a receptor tyrosine kinase agonist, a growth factor, a growth factor receptor activator, a growth factor receptor agonist, a cysteine-knot growth factor superfamily member, a pro-angiogenic factor, a PDGF family member, a VEGF receptor, a VEGF receptor agonist, a VEGF family member, a VEGF, VEGF-A, VEGF-B, VEGF-C, VEGF-D, PGF, $VEGF_{121}$, $VEGF_{145}$, $VEGF_{148}$, $VEGF_{162}$, $VEGF_{165}$, $VEGF_{165b}$, $VEGF_{183}$, $VEGF_{189}$ or $VEGF_{206}$.

Inhibitors, Activators, Modulators, and Binding Agents

A HPTP-β (VE-PTP) inhibitor, modulator, or binding agent of the disclosure can include a compound, a recombinant protein, an antibody, antigen-binding fragment, variant, or derivative thereof, a Tie2-peptomimetic, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The inhibitor, modulator, or binding agent can undergo modifications, for example, enzymatic cleavage or posttranslational modifications.

In some embodiments, a HPTP-β (VE-PTP) inhibitor, modulator, or binding agent of the disclosure can inhibit HPTP-β (VE-PTP) by interfering with the interaction of HPTP-β (VE-PTP) and Tie2. In some embodiments, a HPTP-β (VE-PTP) inhibitor, modulator, or binding agent of the disclosure can inhibit HPTP-β (VE-PTP) by stabilizing HPTP-β (VE-PTP) in an inactive conformation. In some embodiments, a HPTP-β (VE-PTP) inhibitor, modulator, or binding agent of the disclosure can inhibit HPTP-β (VE-PTP) by promoting internalization of HPTP-β (VE-PTP) (e.g., promoting endocytosis and degradation of HPTP-β (VE-PTP)). In some embodiments, a HPTP-β (VE-PTP) inhibitor, modulator, or binding agent of the disclosure can inhibit HPTP-β (VE-PTP) by blocking binding of a ligand that activates HPTP-β (VE-PTP). In some embodiments, a HPTP-β (VE-PTP) inhibitor, modulator, or binding agent of the disclosure can inhibit HPTP-β (VE-PTP) by modulating oligomerization of HPTP-β (VE-PTP).

In some embodiments, a HPTP-β (VE-PTP) inhibitor, modulator, or binding agent of the disclosure can bind to a dominant-negative isoform of HPTP-β (VE-PTP). A dominant-negative isoform can correspond to a form of HPTP-β (VE-PTP) deficient in phosphatase activity that can compete with endogenous HPTP-β (VE-PTP).

A HPTP-β (VE-PTP) inhibitor, modulator, or binding agent of the disclosure can comprise a plurality of HPTP-β (VE-PTP) binding sites. In some embodiments, a HPTP-β (VE-PTP) inhibitor, modulator, or binding agent can bind to two HPTP-β (VE-PTP) molecules simultaneously, thereby bringing the two HPTP-β (VE-PTP) molecules into close proximity. In some embodiments, a HPTP-β (VE-PTP) inhibitor, modulator, or binding agent can bind to three HPTP-β (VE-PTP) molecules simultaneously, thereby bringing the three HPTP-β (VE-PTP) molecules into close proximity. In some embodiments, a HPTP-β (VE-PTP) inhibitor, modulator, or binding agent can bind to four HPTP-β (VE-PTP) molecules simultaneously, thereby bringing the four HPTP-β (VE-PTP) molecules into close proximity.

A HPTP-β (VE-PTP) inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

A compound of the present disclosure can be used for targeting HPTP-β (VE-PTP) to restore Tie2 activity. A HPTP-β (VE-PTP) inhibitor, modulator, or binding agent can thus be a Tie2 activator. In some embodiments, a compound of the present disclosure can initiate or inhibit a signaling cascade downstream of HPTP-β (VE-PTP) or Tie2, for example, Akt/PI3-K signaling, Rac1 signaling, MAPK/Ras signaling, or NF-κB signaling.

Inhibition of HPTP-β (VE-PTP) can lead to vascular stabilization, which can be beneficial for the treatment of, for example, disorders that are characterized by vascular instability, angiogenesis, neovascularization, vascular leakage, and/or edema. For example, inhibition of HPTP-β (VE-PTP) can be beneficial for the treatment of vascular disorders, ocular disorders, cancers, renal disorders, complications of diabetes, and other disorders. In some embodiments, a HPTP-β (VE-PTP) inhibitor, modulator, or binding agent of the disclosure can be used to treat, for example, diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy.

A Tie2 activator, modulator, or binding agent of the disclosure can include, for example, a compound, a recombinant protein, a peptide, an antibody, an antigen-binding fragment, variant, or derivative thereof, an angiopoietin 1 recombinant protein, an Ang1 mimetic, a Tie2 agonist, a HPTP-β (VE-PTP) phosphatase inhibitor, a Tie2-peptomimetic, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The activator, modulator, or binding agent can undergo modifications, for example, enzymatic cleavage or posttranslational modifications.

A Tie2 activator, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the activator, modulator, or binding agent. Non-limiting examples of the moiety to which the activator, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

In some embodiments, a compound of the present disclosure can initiate or inhibit a signaling cascade downstream of Tie2, for example, Akt/PI3-K signaling, Rac1 signaling, MAPK/Ras signaling, or NF-κB signaling.

The activation of Tie2 can lead to vascular stabilization, which can be beneficial for the treatment of, for example, disorders that are characterized by vascular instability, angiogenesis, neovascularization, vascular leakage, and/or edema. For example, activation of Tie2 can be beneficial for the treatment of ocular disorders, cancers, renal disorders, complications of diabetes, and other disorders. In some embodiments, a Tie2 activator, modulator, or binding agent of the disclosure can be used to treat diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy.

A VEGF inhibitor, modulator, or binding agent of the disclosure can include a compound, a recombinant protein, a peptide, an antibody, antigen-binding fragment, variant, or derivative thereof, a DARPin or derivative thereof, an affinibody, an avimer, an adnectin, an anticalin, a Fynomer, a Kunitz domain, a knottin, a β-hairpin mimetic, a tetrameric polyethylene oxide clustered peptide, a collagen IV-biomimetic peptide, or a peptide derived from one or more receptors (e.g. VEGF receptors, or the VEGF-binding portions of human VEGF receptors 1 and 2), either alone or in combination with another amino acid sequence or multiple other amino acid sequences. The inhibitor, modulator, or binding agent can undergo modifications, for example, enzymatic cleavage or posttranslational modifications.

A VEGF inhibitor, modulator, or binding agent of the disclosure can comprise a plurality of VEGF binding sites. In some embodiments, a VEGF inhibitor, modulator, or binding agent can bind to two VEGF molecules simultaneously, thereby bringing the two VEGF molecules into close proximity. In some embodiments, a VEGF inhibitor, modulator, or binding agent can bind to three VEGF molecules simultaneously, thereby bringing the three VEGF molecules into close proximity. In some embodiments, a VEGF inhibitor, modulator, or binding agent can bind to four VEGF molecules simultaneously, thereby bringing the four VEGF molecules into close proximity.

A VEGF inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

A VEGFR inhibitor, modulator, or binding agent of the disclosure can include a compound, a recombinant protein, an antibody, an antigen-binding fragment, variant, or derivative thereof, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The inhibitor, modulator, or binding agent can undergo modifications, for example, enzymatic cleavage or posttranslational modifications.

A VEGFR inhibitor, modulator, or binding agent of the disclosure can comprise a plurality of VEGFR binding sites. In some embodiments, a VEGFR inhibitor, modulator, or binding agent can bind to two VEGFR molecules simultaneously, thereby bringing the two VEGFR molecules into close proximity. In some embodiments, a VEGFR inhibitor, modulator, or binding agent can bind to three VEGFR molecules simultaneously, thereby bringing the three VEGFR molecules into close proximity. In some embodiments, a VEGFR inhibitor, modulator, or binding agent can bind to four VEGFR molecules simultaneously, thereby bringing the four VEGFR molecules into close proximity.

A VEGFR inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

In some embodiments, a VEGFR inhibitor, modulator, or binding agent of the disclosure can inhibit VEGFR by stabilizing VEGFR in an inactive conformation. In some embodiments, a VEGFR inhibitor, modulator, or binding agent of the disclosure can inhibit VEGFR by promoting internalization of VEGFR (e.g., promoting endocytosis and degradation of VEGFR). In some embodiments, a VEGFR inhibitor, modulator, or binding agent of the disclosure can inhibit VEGFR by blocking binding of a ligand that activates VEGFR (e.g., blocking VEGF ligation of VEGFR). In some embodiments, a VEGFR inhibitor, modulator, or binding agent of the disclosure can inhibit VEGFR by modulating oligomerization of VEGFR (e.g., preventing or reducing the likelihood of dimerization or oligomerization of VEGFR).

A compound of the present disclosure can be used for interfering with the interaction of VEGF and VEGFR, thereby reducing VEGFR phosphorylation and downstream signaling. In some embodiments, inhibition of VEGF can reduce aberrant vasculogenesis, angiogenesis, or blood vessel permeabilization, thereby reducing pathologic vascular instability. In some embodiments, inhibition of VEGF can be beneficial for the treatment of disorders that are characterized by vascular instability, angiogenesis, neovascularization, vascular leakage, and/or edema. For example, inhibition of VEGF can be beneficial for the treatment of vascular disorders, ocular disorders, cancers, renal disorders, complications of diabetes, and other disorders. In some embodiments, a VEGF inhibitor, modulator, or binding agent of the disclosure can be used to treat diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy. In some embodiments, inhibition of VEGF can reduce cancer.

Methods

The promotion of Tie2-signaling and inhibition of VEGFR signaling can lead to vascular stabilization, which can be beneficial for the treatment of a condition with a vascular component. A compound disclosed herein can be used to treat, for example, a disease characterized by changes in the vasculature, a disease characterized by decreased Tie2 activation, or a disease characterized by involvement of VEGF in pathogenesis, whether progressive or non-progressive, acute or chronic.

In some embodiments, a compound disclosed herein can be used to treat an ocular disorder. A compound disclosed herein can be used to treat, for example, age-related macular degeneration (dry form), age-related macular degeneration (wet form), atopic keratitis, Bests disease, blepharitis, blurry vision, choroidal neovascularization, chronic retinal detachment, chronic uveitis/vitritis, choroiditis, conjunctivitis, contact lens overwear, corneal graft neovascularization, corneal graft rejection, corneal neovascularization, cystoid macular edema, diabetic macular edema, double vision, diabetic retinopathy, diseases associated with rubeosis (neovascularization of the angle), diseases caused by abnormal proliferation of fibrovascular or fibrous tissue including all forms of proliferative vitreoretinopathy, Eales disease, elevated intraocular pressure, epidemic keratoconjunctivitis, floaters, glaucoma, hard yellow exudates within 500 m of the center of the fovea with adjacent retinal thickening, hyperviscosity syndromes, infections causing choroiditis, infections causing retinitis, iris neovascularization, ischemic retinopathy, loss of contrast, macular telangectasia, mariginal keratolysis, multifocal choroiditis, myopia, neovascular glaucoma, non-proliferative diabetic retinopathy (NPDR), ocular edema, ocular hemorrhage, ocular histoplasmosis, ocular hypertension, ocular inflammation, ocular ischemia, ocular neovascularization, ocular trauma, ocular vascular leak, optic pits, papilloedema, pars planitis, phylectenulosis, polypoidal choroidal vasculopathy, post-laser complications, proliferative diabetic retinopathy, pterygium keratitis sicca, radial keratotomy, retinal angiomatous proliferation, retinal degeneration, retinal edema (including macular edema), retinal neovascularization, retinal perfusion, retinal thickening within 1 disc diameter of the center of the fovea, retinal thickening within 500 m of the center of the fovea, retinal vein occlusion (central or branch), retinitis, retinitis pigmentosa, retinopathy, retinopathy of prematurity, scleritis, Stargarts disease, superior limbic keratitis, surgery induced edema, surgery induced neovascularization, Terrien's marginal degeneration, trachoma, trauma, uveitis, vasculitis (e.g. central retinal vein occlusion), or other ophthalmic diseases wherein the eye disease or disorder is associated with ocular neovascularization, vascular leakage, or retinal edema, or a combination thereof.

In some embodiments, a compound disclosed herein can be used to treat a complication of diabetes (e.g., a comorbidity of diabetes). A compound disclosed herein can be used to treat, for example, Acute glomerulonephritis, Acute myocardial infarction, Amputation, Amyotrophy, Aneurysm, Angina pectoris, Aortic aneurysm, Aortic dissection, Atherosclerosis, Atherosclerotic cardiovascular disease, Atrial fibrillation, Autonomic neuropathy, Blindness, Cardiovascular complications of diabetes, Cerebrovascular complications of diabetes, Charcot's arthropathy, Chronic glomerulonephritis, Chronic renal failure, Claudication, Clinically significant macular edema, Coronary artery disease, Cranial nerve palsy, Cystoid macular degeneration, Cystoid macular edema, Diabetic cardiomyopathy, Diabetic cheiroarthropathy, Diabetic coma, Diabetic encephalopathy, Diabetic foot wound, Diabetic hyperglycemia, Diabetic hyperlipidemia, Diabetic hyperosmolar syndrome, Diabetic hypoglycemia, Diabetic ketoacidosis, Diabetic myonecrosis, Diabetic nephropathy, Diabetic neuropathy, Diabetic ophthalmologic disease, Diabetic peripheral vascular disease, Diabetic retinopathy, Diffuse idiopathic skeletal hyperostosis, Dupuytren's contracture, Embolism, End-stage renal disease, Erectile dysfunction, Forestier disease, Gangrene, Gas gangrene, Gastroparesis/diarrhea, Heart failure, Hyperglycemic crisis, Hypertension, Ischemic heart disease, Ketoacidosis, Lipohypertrophy, Metabolic complications of diabetes, Mononeuropathy, Myocardial infarction, Nephritis, Nephropathy, Nephrosis, Nephrotic syndrome, Neurogenic bladder, Neuropathic arthropathy, Neuropathy, Orthostatic hypotension, Osteoarthritis, Osteoporosis, Periodontal disease, Peripheral vascular disease, Polyneuropathy, Proliferative retinopathy, Renal failure, Renal insufficiency, Restrictive lung disease, Retinal detachment, Retinal edema, Retinopathy, Stroke, Thrombosis, Transient ischemic attack, Ulceration, Ventricular fibrillation, Vitreous hemorrhage, or a combination thereof.

In some embodiments, a compound disclosed herein can be used to treat a renal disorder. A compound disclosed herein can be used to treat, for example, Acute kidney injury, Acute proliferative glomerulonephritis, Adenine phosphoribosyltransferase deficiency, Alport syndrome, Analgesic nephropathy, Autosomal dominant polycystic kidney disease, Autosomal recessive polycystic kidney disease, Balkan endemic nephropathy, Benign nephrosclerosis, Bright's disease, Cardiorenal syndrome, CFHR5 nephropathy, Chronic kidney disease, Chronic kidney disease-mineral and bone disorder, Congenital nephrotic syndrome, Conorenal syndrome, Contrast-induced nephropathy, Cystic kidney disease, Dents disease, Diabetic nephropathy, Diffuse proliferative nephritis, Distal renal tubular acidosis, Diuresis, EAST syndrome, End Stage Renal Disease, Epithelial-mesenchymal transition, Epstein syndrome, Fanconi syndrome, Fechtner syndrome, Focal proliferative nephritis, Focal segmental glomerulosclerosis, Fraley syndrome, Galloway Mowat syndrome, Gitelman syndrome, Glomerulocystic kidney disease, Glomerulopathy, Goodpasture syndrome, High anion gap metabolic acidosis, HIV-associated nephropathy, Horseshoe kidney, Hydronephrosis, Hypertensive kidney disease, IgA nephropathy, Interstitial nephritis, Juvenile nephronophthisis, Kidney cancer, Kidney disease, Kidney stone disease, Lightwood-Albright syndrome, Lupus nephritis, Malarial nephropathy, Medullary cystic kidney disease, Medullary sponge kidney, Membranous glomerulonephritis, Mesoamerican nephropathy, Milk-alkali syndrome, Minimal mesangial glomerulonephritis, Multicystic dysplastic kidney, Nephritis, Nephrocalcinosis, Nephrogenic diabetes insipidus, Nephromegaly, Nephroptosis, Nephrosis, Nephrotic syndrome, Nutcracker syndrome, Papillorenal syndrome, Phosphate nephropathy, Polycystic kidney disease, Primary hyperoxaluria, Proximal renal tubular acidosis, Pyelonephritis, Pyonephrosis, Rapidly progressive glomerulonephritis, Renal agenesis, Renal angina, Renal artery stenosis, Renal cyst, Renal ischemia, Renal osteodystrophy, Renal papillary necrosis, Renal tubular acidosis, Renal vein thrombosis, Secondary hypertension, Serpentine fibula-polycystic kidney syndrome, Shunt nephritis, Sickle cell nephropathy, Thin basement membrane disease, Transplant glomerulopathy, Tubulointerstitial nephritis and uveitis, Tubulopathy, Uremia, Uremic frost, Wunderlich syndrome, or a combination thereof.

In some embodiments, a compound disclosed herein can be used to treat a cancer. A compound disclosed herein can be used to treat, for example, acute leukemia, astrocytomas, biliary cancer (cholangiocarcinoma), bone cancer, breast cancer, brain stem glioma, bronchioloalveolar cell lung cancer, cancer of the adrenal gland, cancer of the anal region, cancer of the bladder, cancer of the endocrine system, cancer of the esophagus, cancer of the head or neck, cancer of the kidney, cancer of the parathyroid gland, cancer of the penis, cancer of the pleural/peritoneal membranes, cancer of the salivary gland, cancer of the small intestine, cancer of the thyroid gland, cancer of the ureter, cancer of the urethra, carcinoma of the cervix, carcinoma of the endometrium, carcinoma of the fallopian tubes, carcinoma of the renal pelvis, carcinoma of the vagina, carcinoma of the vulva, cervical cancer, chronic leukemia, colon cancer, colorectal cancer, cutaneous melanoma, ependymoma, epidermoid tumors, Ewings sarcoma, gastric cancer, glioblastoma, glioblastoma multiforme, glioma, hematologic malignancies, hepatocellular (liver) carcinoma, hepatoma, Hodgkin's Disease, intraocular melanoma, Kaposi sarcoma, lung cancer, lymphomas, medulloblastoma, melanoma, meningioma, mesothelioma, multiple myeloma, muscle cancer, neoplasms of the central nervous system (CNS), neuronal cancer, non-small cell lung cancer, osteosarcoma, ovarian cancer, pancreatic cancer, pediatric malignancies, pituitary adenoma, prostate cancer, rectal cancer, renal cell carcinoma, sarcoma of soft tissue, schwanoma, skin cancer, spinal axis tumors, squamous cell carcinomas, stomach cancer, synovial sarcoma, testicular cancer, uterine cancer, or tumors and their metastases, including refractory versions of any of the above cancers, or a combination thereof.

In some embodiments, a compound disclosed herein can be used to treat a disease characterized by changes in the vasculature, a disease characterized by decreased Tie2 activation, or a disease characterized by involvement of VEGF in pathogenesis. A compound disclosed herein can be used to treat, for example, acne rosacea, acute lung injury, acute respiratory distress syndrome (ARDS), adhesion formation from abdominal surgery, adipositas, albuminuria, allergic edema, allergy, angina, angiofibroma, arteriosclerosis, artery occlusion, ascites, atheroma, atherosclerosis, asthma, avascular necrosis, bacterial ulcers, *Bartonella bacilliformis* infection, Behcet's disease, Buerger's disease (thromboangiitis obliterans), cardiac fibrosis, cardiac hypertrophy, cardiomyopathy, carotid obstructive disease, cerebral infarction, chemical burns, COPD, Crohn's disease, cytokine-induced vascular leak, destabilized blood flow, diabetes (including non-insulin dependent diabetes mellitus), dysfunctional uterine bleeding, endometriosis, Epstein-Barr virus infection, erectile dysfunction, excessive hair growth, follicular cysts, foot ulcer (e.g., diabetic foot ulcer), fungal ulcers, giant cell arteritis, glomerulosclerosis, Graves' disease, Hashimoto's autoimmune thyroiditis, hemangioma, hemangioendothelioma, hemophilic joints, hemorrhage, hepatitis C, hereditary hemorrhagic telangiectasia (HHT), Herpes simplex infections, Herpes zoster infections, hypertension, idiopathic thrombocytopenic purpura, impaired wound healing, inflammatory and infectious processes (e.g. hepatitis, pneumonia, glomerulonephritis), interstitial fibrosis, ischemia, kidney disease, leishmaniasis, leukomalacia, lipid degeneration, liver regeneration, Lupus nephritis, Lyme disease, lymphoproliferative disorders, malaria (*Plasmodium* infection), Mooren ulcer, multiple sclerosis, mycobacterial infections, myocardial infarction, nasal polyps, nephropathy, neuronal inflammation, neuropathy, obesity, osteomyelitis, osteophyte, ovarian hyperstimulation, Paget's disease, pannus growth, peripheral artery disease, peritoneal sclerosis, pemphigoid, polyarteritis, protozoan infections, pseudoxanthoma elasticum, psoriasis, pulmonary hypertension, pyogenic granulomas, renal fibrosis, respiratory distress, rheumatoid arthritis, rickettsial infection, scar keloids, sepsis, sickle cell anemia, Stevens-Johnson disease, stroke, synovitis, systemic lupus erythematosus, syphilis, thyroid enlargement, thyroiditis, toxic shock syndrome, toxoplasmosis, trauma, ulcerative colitis, vascular leak, vascular leak syndrome, vascular malformations (e.g. Osler-Weber syndrome), vein occlusion, viral hemorrhagic fevers (e.g., dengue fever), vitamin A deficiency, warts, or Wegener's sarcoidosis, or a combination thereof.

Sequences

As used herein, the abbreviations for the L-enantiomeric and D-enantiomeric amino acids are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). In some embodiments, the amino acid is a L-enantiomer. In some embodiments, the amino acid is a D-enantiomer.

TABLE 2 shows the amino acid sequences of humanized $V_H$ antibody regions that bind HPTP-β (VE-PTP). SEQ ID NO: 1 is $V_H1$, SEQ ID NO: 2 is $V_H2$, SEQ ID NO: 3 is $V_H3$, and SE ID NO: 4 is $V_{H4}$.

TABLE 2

| SEQ ID NO: | Name | Amino acid sequence |
|---|---|---|
| 1 | $V_{H1}$ | EVQLVESGGGLVQPGGSLKLSCAASGFTFNA NAMNWVRQASGKGLEWVGRIRTKSNNYATYY AGSVKDRFTISRDDSKNTAYLQMNSLKTEDT AAYYCVRDYYGSSAWITYWGQGTLVTVSS |
| 2 | $V_{H2}$ | EVQLVESGGGLVQPGGSLRLSCAASGFTFNA NAMNWVRQAPGKGLEWVGRIRTKSNNYATYY AGSVKDRFTISRDDSKNSLYLQMNSLKTEDT AVYYCVRDYYGSSAWITYWGQGTLVTVSS |
| 3 | $V_{H3}$ | EVQLVESGGGLVQPGRSLRLSCTASGFTFNA NAMNWVRQAPGKGLEWVGRIRTKSNNYATYY AGSVKDRFTISRDDSKNIAYLQMNSLKTEDT AVYYCVRDYYGSSAWITYWGQGTLVTVSS |
| 4 | $V_{H4}$ | LVQLVESGGGLVKPGGSLRLSCAASGFTFNA NAMNWIRQAPGKGLEWVSRIRTKSNNYATYY AGSVKDRFTISRDNAKNSLYLQMNSLRAEDT AVHYCVRDYYGSSAWITYWGQGTLVTVSS |

TABLE 3 shows the amino acid sequences of humanized $V_L$ antibody regions that bind HPTP-β (VE-PTP). SEQ ID NO: 5 is $V_{L1}$, SEQ ID NO: 6 is $V_{L2}$, SEQ ID NO: 7 is $V_{L3}$, and SEQ ID NO: 8 is $V_{L4}$.

TABLE 3

| SEQ ID NO: | Name | Amino acid sequence |
|---|---|---|
| 5 | $V_{L1}$ | DVVMTQSPSFLSASVGDRVTITCKASQHVGTAVAWYQ QRPGKAPKLLIYWASTRHTGVPSRFSGSGSGTEFTLT ISSLQPEDFATYFCQQYSSYPFTFGGGTKLEIK |
| 6 | $V_{L2}$ | DIVMTQSPDSLAVSLGERATINCKASQHVGTAVAWYQ QKPGQPPKLLIYWASTRHTGVPDRFSGSGSGTDFTLT ISSLQAEDVAVYYCQQYSSYPFTFGQGTKLEIK |
| 7 | $V_{L3}$ | DIQMTQSPFLSASVGDRVTITCKASQHVGTAVAWYQ QKPGKAPKLLIYWASTRHTGVPSRFSGSGSGTDFTLT ISSLQPEDFATYFCQQYSSYPFTFGGGTKLEIK |
| 8 | $V_{L4}$ | DIVMTQSPDSLAVSLGERATINCKASQHVGTAVAWYQ QKPEQPPKLLIYWASTRHTGVPDRFSGSGSGTDFTLT ISSLQAEDVAVYYCQQYSSYPFTFGGGTKVEIK |

Each of the $V_H$ domains can be synthesized in-frame with a constant domain sequence, for example, a human IgG1, IgG2, IgG3, IgG4, IgE, IgA1, IgA2, IgM, or IgD sequence.

A DNA sequence encoding the entire heavy chain sequence can be codon optimized and verified.

Illustrative amino acid sequences of constant domain sequences are provided in TABLE 4. In some embodiments, a $V_H$ domain disclosed herein is synthesized in-frame with a human IgG1 constant domain sequence. A human IgG1 constant domain sequence can comprise SEQ ID NO: 220. In some embodiments, a $V_H$ domain disclosed herein is synthesized in-frame with a human IgG2 constant domain sequence. A human IgG2 constant domain sequence can comprise SEQ ID NO: 221. In some embodiments, a $V_H$ domain disclosed herein is synthesized in-frame with a human IgG3 constant domain sequence. A human IgG3 constant domain sequence can comprise SEQ ID NO: 222. In some embodiments, a $V_H$ domain disclosed herein is synthesized in-frame with a human IgG4 constant domain sequence. The human IgG4 isotype constant domain sequence can be mutated to a proline rather than a serine at position 228 to reduce Fab-arm exchange (stabilizing S228P mutation). An amino acid sequence of the IgG4 constant domain with S228P mutation can comprise SEQ ID NO: 9. In some embodiments, a $V_H$ domain disclosed herein is synthesized in-frame with a human IgE constant domain sequence. A human IgE constant domain sequence can comprise SEQ ID NO: 223. In some embodiments, a $V_H$ domain disclosed herein is synthesized in-frame with a human IgA1 constant domain sequence. A human IgA1 constant domain sequence can comprise SEQ ID NO: 224. In some embodiments, a $V_H$ domain disclosed herein is synthesized in-frame with a human IgA2 constant domain sequence. A human IgA2 constant domain sequence can comprise SEQ ID NO: 225. In some embodiments, a $V_H$ domain disclosed herein is synthesized in-frame with a human IgM constant domain sequence. A human IgM constant domain sequence can comprise SEQ ID NO: 226. In some embodiments, a $V_H$ domain disclosed herein is synthesized in-frame with a human IgD constant domain sequence. A human IgD constant domain sequence can comprise SEQ ID NO: 227.

TABLE 4

| SEQ ID NO: | Name | Amino acid sequence |
| --- | --- | --- |
| 220 | IgG1 constant | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 221 | IgG2 constant | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD ISVEWESNGQPENNYKTTPPMLDSDGSFFLYSKLTVDKSRWQ QGNVFSCSVMHEALHNHYTQKSLSLSPGK |
| 222 | IgG3 constant | ASTKGPSVFPLAPCSRSTSGGTAALGCLVKDYFPEPVTVSWNS GALTSGVHTFPAVLQSSGLYSLSSVVTVPSSSLGTQTYTCNVN HKPSNTKVDKRVELKTPLGDTTHTCPRCPEPKSCDTPPPCPRC PEPKSCDTPPPCPRCPEPKSCDTPPPCPRCPAPELLGGPSVFLFP PKPKDTLMISRTPEVTCVVVDVSHEDPEVQFKWYVDGVEVH NAKTKPREEQYNSTFRVVSVLTVLHQDWLNGKEYKCKVSNK ALPAPIEKTISKTKGQPREPQVYTLPPSREEMTKNQVSLTCLV KGFYPSDIAVEWESSGQPENNYNTTPPMLDSDGSFFLYSKLTV DKSRWQQGNIFSCSVMHEALHNRFTQKSLSLSPGK |
| 9 | IgG4 constant | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| 223 | IgE constant | ASTQSPSVFPLTRCCKNIPSNATSVTLGCLATGYFPEPVMVTW DTGSLNGTTMTLPATTLTLSGHYATISLLTVSGAWAKQMFTC RVAHTPSSTDWVDNKTFSVCSRDFTPPTVKILQSSCDGGGHFP PTIQLLCLVSGYTPGTINITWLEDGQVMDVDLSTASTTQEGEL ASTQSELTLSQKHWLSDRTYTCQVTYQGHTFEDSTKKCADSN PRGVSAYLSRPSPFDLFIRKSPTITCLVVDLAPSKGTVNLTWSR ASGKPVNHSTRKEEKQRNGTLTVTSTLPVGTRDWIEGETYQC RVTHPHLPRALMRSTTKTSGPRAAPEVYAFATPEWPGSRDKR TLACLIQNFMPEDISVQWLHNEVQLPDARHSTTQPRKTKGSG FFVFSRLEVTRAEWEQKDEFICRAVHEAASPSQTVQRAVSVN PGK |

TABLE 4-continued

| SEQ ID NO: | Name | Amino acid sequence |
|---|---|---|
| 224 | IgA1 constant | ASPTSPKVFPLSLCSTQPDGNVVIACLVQGFFPQEPLSVTWSES GQGVTARNFPPSQDASGDLYTTSSQLTLPATQCLAGKSVTCH VKHYTNPSQDVTVPCPVPSTPPTPSPSTPPTPSPSCCHPRLSLH RPALEDLLLGSEANLTCTLTGLRDASGVTFTWTPSSGKSAVQ GPPERDLCGCYSVSSVLPGCAEPWNHGKTFTCTAAYPESKTP LTATLSKSGNTFRPEVHLLPPPSEELALNELVTLTCLARGFSPK DVLVRWLQGSQELPREKYLTWASRQEPSQGTTTFAVTSILRV AAEDWKKGDTFSCMVGHEALPLAFTQKTIDRLAGKPTHVNV SVVMAEVDGTCY |
| 225 | IgGA2 constant | ASPTSPKVFPLSLDSTPQDGNVVVACLVQGFFPQEPLSVTWSE SGQNVTARNFPPSQDASGDLYTTSSQLTLPATQCPDGKSVTC HVKHYTNSSQDVTVPCRVPPPPPCCHPRLSLHRPALEDLLLGS EANLTCTLTGLRDASGATFTWTPSSGKSAVQGPPERDLCGCY SVSSVLPGCAQPWNHGETFTCTAAHPELKTPLTANITKSGNTF RPEVHLLPPPSEELALNELVTLTCLARGFSPKDVLVRWLQGSQ ELPREKYLTWASRQEPSQGTTTYAVTSILRVAAEDWKKGETF SCMVGHEALPLAFTQKTIDRMAGKPTHINVSVVMAEADGTC Y |
| 226 | IgM constant | GSASAPTLFPLVSCENSPSDTSSVAVGCLAQDFLPDSITFSWKY KNNSDISSTRGFPSVLRGGKYAATSQVLLPSKDVMQGTDEHV VCKVQHPNGNKEKNVPLPVIAELPPKVSVFVPPRDGFFGNPR KSKLICQATGFSPRQIQVSWLREGKQVGSGVTTDQVQAEAKE SGPTTYKVTSTLTIKESDWLGQSMFTCRVDHRGLTFQQNASS MCVPDQDTAIRVFAIPPSFASIFLTKSTKLTCLVTDLTTYDSVTI SWTRQNGEAVKTHTNISESHPNATFSAVGEASICEDDWNSGE RFTCTVTHTDLPSPLKQTISRPKGVALHRPDVYLLPPAREQLN LRESATITCLVTGFSPADVFVQWMQRGQPLSPEKYVTSAPMP EPQAPGRYFAHSILTVSEEEWNTGETYTCVVAHEALPNRVTE RTVDKSTGKPTLYNVSLVMSDTAGTCY |
| 227 | IgD constant | APTKAPDVFPIISGCRHPKDNSPVVLACLITGYHPTSVTVTWY MGTQSQPQRTFPEIQRRDSYYMTSSQLSTPLQQWRQGEYKCV VQHTASKSKKEIFRWPESPKAQASSVPTAQPQAEGSLAKATT APATTRNTGRGGEEKKKEKEKEEQEERETKTPECPSHTQPLG VYLLTPAVQDLWLRDKATFTCFVVGSDLKDAHLTWEVAGK VPTGGVEEGLLERHSNGSQSQHSRLTLPRSLWNAGTSVTCTL NHPSLPPQRLMALREPAAQAPVKLSLNLLASSDPPEAASWLL CEVSGFSPPNILLMWLEDQREVNTSGFAPARPPPQPRSTTFWA WSVLRVPAPPSPQPATYTCVVSHEDSRTLLNASRSLEVSYVTD HGPMK |

Each of the $V_L$ domains can be synthesized in-frame with a human light chain constant domain sequence, e.g. a kappa (IgK) or lambda (IgL) chain. The entire light chain sequence can then be codon optimized, and the DNA sequence can be verified. TABLE 5 provides example light chain constant domain sequences.

In some embodiments, a $V_L$ domain disclosed herein is synthesized in-frame with a human IgK constant domain sequence. A human IgK constant domain sequence can comprise SEQ ID NO: 10. In some embodiments, a $V_L$ domain disclosed herein is synthesized in-frame with a human IgL constant domain sequence. A human IgL constant domain sequence can comprise SEQ ID NO: 228.

TABLE 5

| SEQ ID NO: | Name | Amino acid sequence |
|---|---|---|
| 10 | IgK constant | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| 228 | IgL constant | GQPKANPTVTLFPPSSEELQANKATLVCLISD FYPGAVTVAWKADGSPVKAGVETTKPSKQSNN KYAASSYLSLTPEQWKSHRSYSCQVTHEGSTV EKTVAPTECS |

Signal peptides can result in higher protein expression and/or secretion by a cell. The following signal peptides can be appended to all the constructs disclosed herein.

Heavy chain signal peptide (SEQ ID NO: 11):
MGWTLVFLFLLSVTAGVHS

Light chain signal peptide (SEQ ID NO: 12):
MVSSAQFLGLLLLCFQGTRC

Signal peptidases can cleave a signal peptide off a protein, for example, during a secretion process, generating a mature protein that does not comprise the signal peptide sequence. In some embodiments, a signal peptide is cleaved off a compound or antibody of the disclosure. In some embodiments, a mature compound or antibody of the disclosure does not comprise a signal peptide.

TABLE 6 and TABLE 7 list the full amino acid sequences of humanized heavy and light chains that bind HPTP-β (VE-PTP), respectively. HC1, HC2, HC3 and HC4 are the human IgG4 isotype constant domain with stabilizing S228P mutation joined to $V_{H1}$, $V_{H2}$, $V_{H3}$ and $V_{H4}$, respectively, and with signal peptide appended. Amino acids 1-19 of SEQ ID NOs: 13, 14, 15, and 16 are the heavy chain signal peptide (SEQ ID NO: 11). Also shown are HC1, HC2, HC3, and HC4 without the signal peptide appended (SEQ ID NOs:

246, 247, 248, and 249). In some embodiments, a mature compound or antibody of the disclosure does not comprise the signal peptide(s).

LC1, LC2, LC3 and LC4 are the human IgK isotype constant domain joined to $V_{L1}$, $V_{L2}$, $V_{L3}$, and $V_{L4}$, respectively, and with signal peptide appended. Amino acids 1-20 of SEQ ID NOs: 17, 18, 19, and 20 are the light chain signal peptide (SEQ ID NO: 12). Also shown are LC1, LC2, LC3, and LC4 without the signal peptide appended (SEQ ID NOs: 250, 251, 252, and 253). In some embodiments, a mature compound or antibody of the disclosure does not comprise the signal peptide(s).

TABLE 6

| SEQ ID NO: | Name | Amino acid sequence |
|---|---|---|
| 13 | signal peptide - HC1 | MGWTLVFLFLLSVTAGVHSEVQLVESGGGLVQPGGSLKLSCA ASGFTFNANAMNWVRQASGKGLEWVGRIRTKSNNYATYYAG SVKDRFTISRDDSKNTAYLQMNSLKTEDTAAYYCVRDYYGSS AWITYWGQGTLVTVSSASTKGPSVFPLAPCSRSTSESTAALGCL VKDYFPEPVTVSWNSGALTSGVHTFPAVLQSSGLYSLSSVVTV PSSSLGTKTYTCNVDHKPSNTKVDKRVESKYGPPCPPCPAPEFL GGPSVFLFPPKPKDTLMISRTPEVTCVVVDVSQEDPEVQFNWY VDGVEVHNAKTKPREEQFNSTYRVVSVLTVLHQDWLNGKEY KCKVSNKGLPSSIEKTISKAKGQPREPQVYTLPPSQEEMTKNQV SLTCLVKGFYPSDIAVEWESNGQPENNYKTTPPVLDSDGSFFLY SRLTVDKSRWQEGNVFSCSVMHEALHNHYTQKSLSLSLGK |
| 246 | HC1 | EVQLVESGGGLVQPGGSLKLSCAASGFTFNANAMNWVRQAS GKGLEWVGRIRTKSNNYATYYAGSVKDRFTISRDDSKNTAYL QMNSLKTEDTAAYYCVRDYYGSSAWITYWGQGTLVTVSSAST KGPSVFPLAPCSRSTSESTAALGCLVKDYFPEPVTVSWNSGALT SGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFN STYRVVSVLTVLHQDWLNGKEYKCKVSNKGLPSSIEKTISKAK GQPREPQVYTLPPSQEEMTKNQVSLTCLVKGFYPSDIAVEWES NGQPENNYKTTPPVLDSDGSFFLYSRLTVDKSRWQEGNVFSCS VMHEALHNHYTQKSLSLSLGK |
| 14 | signal peptide - HC2 | MGWTLVFLFLLSVTAGVHSEVQLVESGGGLVQPGGSLRLSCA ASGFTFNANAMNWVRQAPGKGLEWVGRIRTKSNNYATYYAG SVKDRFTISRDDSKNSLYLQMNSLKTEDTAVYYCVRDYYGSS AWITYWGQGTLVTVSSASTKGPSVFPLAPCSRSTSESTAALGCL VKDYFPEPVTVSWNSGALTSGVHTFPAVLQSSGLYSLSSVVTV PSSSLGTKTYTCNVDHKPSNTKVDKRVESKYGPPCPPCPAPEFL GGPSVFLFPPKPKDTLMISRTPEVTCVVVDVSQEDPEVQFNWY VDGVEVHNAKTKPREEQFNSTYRVVSVLTVLHQDWLNGKEY KCKVSNKGLPSSIEKTISKAKGQPREPQVYTLPPSQEEMTKNQV SLTCLVKGFYPSDIAVEWESNGQPENNYKTTPPVLDSDGSFFLY SRLTVDKSRWQEGNVFSCSVMHEALHNHYTQKSLSLSLGK |
| 247 | HC2 | EVQLVESGGGLVQPGGSLRLSCAASGFTFNANAMNWVRQAPG KGLEWVGRIRTKSNNYATYYAGSVKDRFTISRDDSKNSLYLQ MNSLKTEDTAVYYCVRDYYGSSAWITYWGQGTLVTVSSASTK GPSVFPLAPCSRSTSESTAALGCLVKDYFPEPVTVSWNSGALTS GVHTFPAVLQSSGLYSLSSVVTVPSSSLGTKTYTCNVDHKPSNT KVDKRVESKYGPPCPPCPAPEFLGGPSVFLFPPKPKDTLMISRTP EVTCVVVDVSQEDPEVQFNWYVDGVEVHNAKTKPREEQFNST YRVVSVLTVLHQDWLNGKEYKCKVSNKGLPSSIEKTISKAKGQ PREPQVYTLPPSQEEMTKNQVSLTCLVKGFYPSDIAVEWESNG QPENNYKTTPPVLDSDGSFFLYSRLTVDKSRWQEGNVFSCSVM HEALHNHYTQKSLSLSLGK |
| 15 | signal peptide - HC3 | MGWTLVFLFLLSVTAGVHSEVQLVESGGGLVQPGRSLRLSCT ASGFTFNANAMNWVRQAPGKGLEWVGRIRTKSNNYATYYAG SVKDRFTISRDDSKNIAYLQMNSLKTEDTAVYYCVRDYYGSSA WITYWGQGTLVTVSSASTKGPSVFPLAPCSRSTSESTAALGCLV KDYFPEPVTVSWNSGALTSGVHTFPAVLQSSGLYSLSSVVTVP SSSLGTKTYTCNVDHKPSNTKVDKRVESKYGPPCPPCPAPEFL GGPSVFLFPPKPKDTLMISRTPEVTCVVVDVSQEDPEVQFNWY VDGVEVHNAKTKPREEQFNSTYRVVSVLTVLHQDWLNGKEY KCKVSNKGLPSSIEKTISKAKGQPREPQVYTLPPSQEEMTKNQV SLTCLVKGFYPSDIAVEWESNGQPENNYKTTPPVLDSDGSFFLY SRLTVDKSRWQEGNVFSCSVMHEALHNHYTQKSLSLSLGK |
| 248 | HC3 | EVQLVESGGGLVQPGRSLRLSCTASGFTFNANAMNWVRQAPG KGLEWVGRIRTKSNNYATYYAGSVKDRFTISRDDSKNIAYLQ MNSLKTEDTAVYYCVRDYYGSSAWITYWGQGTLVTVSSASTK GPSVFPLAPCSRSTSESTAALGCLVKDYFPEPVTVSWNSGALTS GVHTFPAVLQSSGLYSLSSVVTVPSSSLGTKTYTCNVDHKPSNT KVDKRVESKYGPPCPPCPAPEFLGGPSVFLFPPKPKDTLMISRTP |

TABLE 6-continued

| SEQ ID NO: | Name | Amino acid sequence |
|---|---|---|
| | | EVTCVVVDVSQEDPEVQFNWYVDGVEVHNAKTKPREEQFNST YRVVSVLTVLHQDWLNGKEYKCKVSNKGLPSSIEKTISKAKGQ PREPQVYTLPPSQEEMTKNQVSLTCLVKGFYPSDIAVEWESNG QPENNYKTTPPVLDSDGSFFLYSRLTVDKSRWQEGNVFSCSVM HEALHNHYTQKSLSLSLGK |
| 16 | signal peptide - HC4 | MGWTLVFLFLLSVTAGVHSLVQLVESGGGLVKPGGSLRLSCA ASGFTFNANAMNWIRQAPGKGLEWVSRIRTKSNNYATYYAGS VKDRFTISRDNAKNSLYLQMNSLRAEDTAVHYCVRDYYGSSA WITYWGQGTLVTVSSASTKGPSVFPLAPCSRSTSESTAALGCLV KDYFPEPVTVSWNSGALTSGVHTFPAVLQSSGLYSLSSVVTVP SSSLGTKTYTCNVDHKPSNTKVDKRVESKYGPPCPPCPAPEFL GGPSVFLEPPKPKDTLMISRTPEVTCVVVDVSQEDPEVQFNWY VDGVEVHNAKTKPREEQFNSTYRVVSVLTVLHQDWLNGKEY KCKVSNKGLPSSIEKTISKAKGQPREPQVYTLPPSQEEMTKNQV SLTCLVKGFYPSDIAVEWESNGQPENNYKTTPPVLDSDGSFFLY SRLTVDKSRWQEGNVFSCSVMHEALHNHYTQKSLSLSLGK |
| 249 | HC4 | LVQLVESGGGLVKPGGSLRLSCAASGFTENANAMNWIRQAPG KGLEWVSRIRTKSNNYATYYAGSVKDRFTISRDNAKNSLYLQ MNSLRAEDTAVHYCVRDYYGSSAWITYWGQGTLVTVSSASTK GPSVFPLAPCSRSTSESTAALGCLVKDYFPEPVTVSWNSGALTS GVHTFPAVLQSSGLYSLSSVVTVPSSSLGTKTYTCNVDHKPSNT KVDKRVESKYGPPCPPCPAPEFLGGPSVFLEPPKPKDTLMISRTP EVTCVVVDVSQEDPEVQFNWYVDGVEVHNAKTKPREEQFNST YRVVSVLTVLHQDWLNGKEYKCKVSNKGLPSSIEKTISKAKGQ PREPQVYTLPPSQEEMTKNQVSLTCLVKGFYPSDIAVEWESNG QPENNYKTTPPVLDSDGSFFLYSRLTVDKSRWQEGNVFSCSVM HEALHNHYTQKSLSLSLGK |

TABLE 7

| SEQ ID NO: | Name | Amino acid sequence |
|---|---|---|
| 17 | signal peptide-LC1 | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| 250 | LC1 | DVVMTQSPSFLSASVGDRVTITCKASQHVGTAVAWYQQRP GKAPKLLIYWASTRHTGVPSRFSGSGSGTEFTLTISSLQPEDF ATYFCQQYSSYPFTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC |
| 18 | signal peptide-LC2 | MVSSAQFLGLLLLCFQGTRCDIVMTQSPDSLAVSLGERATIN CKASQHVGTAVAWYQQKPGQPPKLLIYWASTRHTGVPDRF SGSGSGTDFTLTISSLQAEDVAVYYCQQYSSYPFTFGQGTKL EIKRTVAAPSVFIFPPSDEQLKSGTASVVCLLNNFYPREAKV QWKVDNALQSGNSQESVTEQDSKDSTYSLSSTLTLSKADYE KHKVYACEVTHQGLSSPVTKSFNRGEC |
| 251 | LC2 | DIVMTQSPDSLAVSLGERATINCKASQHVGTAVAWYQQKP GQPPKLLIYWASTRHTGVPDRFSGSGSGTDFTLTISSLQAED VAVYYCQQYSSYPFTFGQGTKLEIKRTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPV TKSFNRGEC |
| 19 | signal peptide-LC3 | MVSSAQFLGLLLLCFQGTRCDIQMTQSPFSLSASVGDRVTIT CKASQHVGTAVAWYQQKPGKAPKLLIYWASTRHTGVPSRF SGSGSGTDFTLTISSLQPEDFATYFCQQYSSYPFTFGGGTKLE IKRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| 252 | LC3 | DIQMTQSPFSLSASVGDRVTITCKASQHVGTAVAWYQQKPG KAPKLLIYWASTRHTGVPSRFSGSGSGTDFTLTISSLQPEDFA TYFCQQYSSYPFTFGGGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |

TABLE 7-continued

| SEQ ID NO:Name | | Amino acid sequence |
|---|---|---|
| 20 | signal peptide-LC4 | MVSSAQFLGLLLLCFQGTRCDIVMTQSPDSLAVSLGERATIN CKASQHVGTAVAWYQQKPEQPPKLLIYWASTRHTGVPDRF SGSGSGTDFTLTISSLQAEDVAVYYCQQYSSYPFTFGGGTKV EIKRTVAAPSVFIFPPSDEQLKSGTASVVCLLNNFYPREAKV QWKVDNALQSGNSQESVTEQDSKDSTYSLSSTLTLSKADYE KHKVYACEVTHQGLSSPVTKSFNRGEC |
| 253 | LC4 | DIVMTQSPDSLAVSLGERATINCKASQHVGTAVAWYQQKP EQPPKLLIYWASTRHTGVPDRFSGSGSGTDFTLTISSLQAED VAVYYCQQYSSYPFTFGGGTKVEIKRTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPV TKSFNRGEC |

Any of the $V_H$ regions disclosed herein can be combined with any of the $V_L$ regions disclosed herein, with or without additional sequences appended, to produce compounds that bind anti-HPTP-β (VE-PTP). For example, signal peptides and constant region sequences can be appended to $V_H$ and $V_L$ regions as shown in TABLE 6 and TABLE 7 respectively, and the resulting heavy and light chains can be paired in any combination to form antibodies. TABLE 8 shows 16 possible pairings of HC1-4 and LC1-4 that bind HPTP-β (VE-PTP). Transfection and expression of each of the anti-HPTP-β (VE-PTP) antibodies in TABLE 8 can be pursued.

TABLE 8

| | | | |
|---|---|---|---|
| HC1:LC1 | HC1:LC2 | HC1:LC3 | HC1:LC4 |
| HC2:LC1 | HC2:LC2 | HC2:LC3 | HC2:LC4 |
| HC3:LC1 | HC3:LC2 | HC3:LC3 | HC3:LC4 |
| HC4:LC1 | HC4:LC2 | HC4:LC3 | HC4:LC4 |

Antibodies or antigen-binding compounds specific for HPTP-β (VE-PTP) can be combined with antibodies or compounds that activate Tie2, inhibit VEGF, or inhibit VEGFR, to form multispecific compounds.

TABLE 9 provides sequences of collagen IV-derived biomimetic peptides. SEQ ID NO: 152 is AXT-107, an integrin-targeting collagen IV-derived biomimetic peptide that can inhibit VEGFR phosphorylation/activation/signaling and promote Tie2 phosphorylation/activation/signaling. SEQ ID NO: 153 provides a consensus sequence, wherein X is any standard amino acid or non-genetically encoded amino acid. In some embodiments, X at position 7 is M, A, or G; X at position 9 is F, A, Y, or G; X at position 0 is M, A, G, D-Alanine (dA), or norleucine (Nle); X at position 11 is F, A, Y, G, or 4-chlorophenylalanine (4-CiPhe); X at position 12 and position 18 are independently selected from 2-Aminobutyric acid (Abu), G, S, A, V, T, I, L, or Allylglycine (AllylGly).

TABLE 9

| SEQ ID NO: | Amino acid sequence |
|---|---|
| 152 | LRRFSTAPFAFIDINDVINF |
| 153 | LRRFSTXPXXXXNINNVXNF |

TABLE 10 provides sequences related to vasculotide, a synthetic Ang1 mimetic peptide that can act as a Tie2 agonist and activate Tie2 signaling. SEQ ID NO: 229 provides the sequence of a synthetic 7-mer that binds the Tie2 receptor. SEQ ID NO: 230 provides an 8-mer with a cysteine residue added at the N-terminus, allowing covalent tethering to a polyethylene glycol backbone to generate a tetrameric polyethylene oxide clustered version of the peptide.

TABLE 10

| SEQ ID NO: | Amino acid sequence |
|---|---|
| 229 | HHHRHSF |
| 230 | CHHHRHSF |

Antibodies or antigen-binding compounds specific for HPTP-β (VE-PTP) can be combined with antibodies or compounds specific to VEGF or VEGFR to form multispecific compounds that bind HPTP-β (VE-PTP) and VEGF or VEGFR. TABLE 11, TABLE 12, TABLE 13, TABLE 14, TABLE 15, and TABLE 17 provide example sequences of compounds specific for VEGF. TABLE 16 provides sequences of an antibody that binds VEGFR.

TABLE 11 provides sequences related to aflibercept, a recombinant protein comprising VEGF-binding portions of human VEGF receptors 1 and 2 fused to the Fc portion of human IgG1. SEQ ID NO: 21 is the full amino acid sequence of aflibercept. SEQ ID NO: 22 is a shortened sequence containing the VEGF-binding portions of human VEGF receptors 1 and 2 without the Fc portion of IgG.

TABLE 11

| SEQ ID NO: | Name | Amino acid sequence |
|---|---|---|
| 21 | AFL$_1$ | SDTGRPFVEMYSEIPEIIHMTEGRELVIPCRVTSPNITVT LKKFPLDTLIPDGKRIIWDSRKGFIISNATYKEIGLLTCE ATVNGHLYKTNYLTHRQTNTIIDVVLSPSHGIELSVGE KLVLNCTARTELNVGIDFNWEYPSSKHQHKKLVNRDL KTQSGSEMKKFLSTLTIDGVTRSDQGLYTCAASSGLMT KKNSTFVRVHEKDKTHTCPPCPAPELLGGPSVFLFPPKP KDTLMISRTPEVTCVVVDVSHEDPEVKFNWYVDGVEV HNAKTKPREEQYNSTYRVVSVLTVLHQDWLNGKEYK CKVSNKALPAPIEKTISKAKGQPREPQVYTLPPSRDELT KNQVSLTCLVKGFYPSDIAVEWESNGQPENNYKTTPPV LDSDGSFFLYSKLTVDKSRWQQGNVFSCSVMHEALHN HYTQKSLSLSPG |
| 22 | AFL$_2$ | SDTGRPFVEMYSEIPEIIHMTEGRELVIPCRVTSPNITVT LKKFPLDTLIPDGKRIIWDSRKGFIISNATYKEIGLLTCE ATVNGHLYKTNYLTHRQTNTIIDVVLSPSHGIELSVGE KLVLNCTARTELNVGIDFNWEYPSSKHQHKKLVNRDL KTQSGSEMKKFLSTLTIDGVTRSDQGLYTCAASSGLMT KKNSTFVRVHEK |

TABLE 12 provides the sequence of brolucizumab (SEQ ID NO: 23), a humanized single-chain antibody fragment (scFv) inhibitor of VEGF that binds to the receptor binding site of VEGF and thereby interferes with the interaction of VEGF with VEGFR1 and VEGFR2.

TABLE 12

| SEQ ID NO: | Name | Amino acid sequence |
|---|---|---|
| 23 | BRO$_{scFv1}$ | EIVMTQSPSTLSASVGDRVIITCQASEIIHSWLAWYQQKPGKAPKLLIYLASTLASGVPSRFSGSGSGAEFTLTISSLQPDDFATYYCQNVYLASTNGANFGQGTKLTVLGGGGGSGGGGSGGGGSGGGGSEVQLVESGGGLVQPGGSLRLSCTASGFSLTDYYYMTWVRQAPGKGLEWVGFIDPDDDPYYATWAKGRFTISRDNSKNTLYLQMNSLRAEDTAVYYCAGGDHNSGWGLDIWGQGTLVTVSS |

TABLE 13 provides sequences related to ranibizumab, a humanized monoclonal antibody fragment (Fab) that binds to and inhibits activity of VEGF. SEQ ID NO: 24 is the heavy chain sequence of ranibizumab. SEQ ID NO: 25 is the light chain sequence of ranibizumab. SEQ ID NO: 26 is a shortened sequence of the ranibizumab heavy chain that can be used in cloning a single-chain antibody fragment (scFv). SEQ ID NO: 27 is a shortened sequence of the ranibizumab light chain that can be used in cloning a single-chain antibody fragment (scFv). SEQ ID NO: 28 is a single-chain antibody fragment (scFv) comprising SEQ ID NO: 26, SEQ ID NO: 27, and SEQ ID NO: 33 (linker peptide, underlined).

TABLE 13

| SEQ ID NO: | Name | Amino acid sequence |
|---|---|---|
| 24 | RAN$_{H1}$ | EVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHL |
| 25 | RAN$_{L1}$ | DIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 26 | RAN$_{H2}$ | EVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSS |
| 27 | RAN$_{L2}$ | DIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK |
| 28 | RAN$_{scFv1}$ | EVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSSGGGGSGGGGSGGGGSDIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK |

TABLE 14 provides sequences related to bevacizumab, a humanized monoclonal antibody that that binds to and inhibits activity of VEGF. SEQ ID NO: 29 is the heavy chain sequence of bevacizumab. SEQ ID NO: 30 is the light chain sequence of bevacizumab.

TABLE 14

| SEQ ID NO: | Name | Amino acid sequence |
|---|---|---|
| 29 | BEV$_{H1}$ | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 30 | BEV$_{L1}$ | DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 15 provides sequences related to conbercept, a recombinant protein comprising extracellular domains from VEGF receptors 1 and 2 fused to the Fc portion of human IgG1. SEQ ID NO: 154 is the full amino acid sequence of conbercept. SEQ ID NO: 155 is a shortened sequence containing sequences from VEGF receptors 1 and 2 without the Fc portion of IgG.

TABLE 15

| SEQ ID NO: | Name | Amino acid sequence |
|---|---|---|
| 154 | CON$_1$ | GRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEKPFVAFGSGMESLVEATVGERVRIPAKYLGYPPPEIKWYKNGIPLESNHTIKAGHVLTIMEVSERDTGNYTVILTNPISKEKQSHVVSLVVYVPPGPGDKTHTCPLCPAPELLGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKATPPVLDSDGSFFLYSKLTVDKSRWQQGNVFSCSVMHEALHNHYTQKSLSLSPGK |
| 155 | CON$_2$ | GRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEKPFVAFGSGMESLVEATVGERVRIPAKYLGYPPPEIKWYKNGIPLESNHTIKAGHVLTIMEVSERDTGNYTVILTNPISKEKQSHVVSLVVYVPPGPG |

TABLE 16 provides sequences related to ramucirumab, a humanized monoclonal antibody that binds to an extracellular domain of VEGFR2 and inhibits VEGFR2 signaling. SEQ ID NO: 156 is the heavy chain sequence of ramucirumab. SEQ ID NO: 157 is the light chain sequence of ramucirumab.

TABLE 16

| SEQ ID NO: | Name | Amino acid sequence |
|---|---|---|
| 156 | RAM$_{H1}$ | EVQLVQSGGGLVKPGGSLRLSCAASGFTFSSYSMNWVRQA PGKGLEWVSSISSSSSYIYYADSVKGRFTISRDNAKNSLY LQMNSLRAEDTAVYYCARVTDAFDIWGQGTMVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPGK |
| 157 | RAM$_{L1}$ | DIQMTQSPSSVSASIGDRVTITCRASQGIDNWLGWYQQKP GKAPKLLIYDASNLDTGVPSRFSGSGSGTYFTLTISSLQA EDFAVYFCQQAKAFPPTFGGGTKVDIKGTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |

TABLE 17 provides DARPin and DAR-Pin-derived amino acid sequences that bind VEGF and inhibit VEGFR signaling. SEQ ID NOS: 158-168 comprise designed ankyrin repeats with binding specificity for VEGF. SEQ ID NO: 169 comprises designed ankyrin repeats with a binding specificity for VEGF and designed ankyrin repeats with a binding specificity for serum albumin. SEQ ID NO: 170 comprises designed ankyrin repeats with a binding specificity for VEGF, designed ankyrin repeats with a binding specificity for hepatocyte growth factor, and designed ankyrin repeats with a binding specificity for serum albumin. SEQ ID NOS: 171-177 comprise designed ankyrin repeats with a binding specificity for VEGF. SEQ ID NO: 173 provides the sequence of abicipar, which comprises designed ankyrin repeats with a binding specificity for VEGF. SEQ ID NOS: 178-190 provide individual designed ankyrin repeat sequence motifs with binding specificity for VEGF, wherein X represents any amino acid. SEQ ID NOS: 191-217 comprise designed ankyrin repeats with binding specificity for VEGF.

TABLE 17

| SEQ ID NO: | Amino acid sequence |
|---|---|
| 158 | DLGKKLLEAARAGQDDEVRILMANGADVNAFDWMGWTPLHLAAHE GHLEIVEVLLKNGADVNATDVSGYTPLHLAAADGHLEIVEVLLKHGA DVNTKDNTGWTPLHLSADLGHLEIVEVLLKNGADVNAQDKFGKTAF DISIDNGNEDLAEILQKAA |
| 159 | DLDKKLLEAARAGQDDEVRILLKAGADVNAKDYLGWTPLHLAAHEG HLEIVEVLLKAGADVNAKDVSGYTPLHLAAADGHLEIVEVLLKAGAD VNAKDNTGWTPLHLSADLGHLEIVEVLLKAGADVNAQDKFGKTAFDI SIDNGNEDLAEILQKAA |
| 160 | DLGKKLLEAARAGQDDEVRILMANGADVNTADSTGWTPLHLAAPWG HPEIVEVLLKNGADVNAHDYQGWTPLHLAATLGHLEIVEVLLKHGAD VNAQDKFGKTAFDISIDNGNEDLAEILQKAA |
| 161 | DLGKKLLEAARAGQDDEVRILMANGADVNTADSTGWTPLHLAVPWG HLEIVEVLLKYGADVNAKDFQGWTPLHLAAAIGHQEIVEVLLKNGAD VNAQDKFGKTAFDISIDNGNEDLAEILQKAA |
| 162 | DLDKKLLEAARAGQDDEVRILMANGADVNAKDSTGYTPLHLAAPWG HLEIVEVLLKAGADVNAKDYQGWTPLHLAAAVGHLEIVEVLLKAGA DVNAQDKSGKTPADLAADAGHEDIAEVLQKAA |
| 163 | DLGKKLLEAARAGQDDEVRILMANGADVNARDSTGWTPLHLAAPWG HPEIVEVLLKNGADVNAADFQGWTPLHLAAAVGHLEIVEVLLKHGAD VNAQDKFGKTAFDISIDNGNEDLAEILQKAA |
| 164 | DLDKKLLEAARAGQDDEVRILLKAGADVNAKDSTGWTPLHLAAPWG HPEIVEVLLKAGADVNAKDFQGWTPLHLAAAAGHLEIVEVLLKAGAD VNAQDKSGKTPADLAADAGHEDIAEVLQKAA |
| 165 | DLGKKLLEAARAGQDDEVRILLKAGADVNAKDSTGWTPLHLAAPWG HPEIVEVLLKAGADVNAKDFQGWTPLHLAAAAGHLEIVEVLLKAGAD VNAQDKSGKTPADLAADAGHEDIAEVLQKAA |
| 166 | DLDKKLLEAARAGQDDEVRILLKAGADVNAKDSTGWTPLHLAAPWG HPEIVEVLLKAGADVNAKDFQGWTPLHLAAAVGHLEIVEVLLKAGAD VNAQDKSGKTPADLAADAGHEDIAEVLQKAA |
| 167 | DLDKKLLEAARAGQDDEVRILLKAGADVNAKDSTGWTPLHLAAPWG HPEIVEVLLKAGADVNAKDYQGWTPLHLAAAVGHLEIVEVLLKAGA DVNAQDKSGKTPADLAADAGHEDIAEVLQKAA |
| 168 | DLDKKLLEAARAGQDDEVRILMANGADVNAKDSTGWTPLHLAAPW GHLEIVEVLLKAGADVNAKDFQGWTPLHLAAAVGHLEIVEVLLKAGA DVNAQDKFGKTAFDISIDNGNEDLAEILQKAA |
| 169 | DLGKKLLEAARAGQDDEVRELLKAGADVNAKDYFSHTPLHLAARNG HLKIVEVLLKAGADVNAKDFAGKTPLHLAANEGHLEIVEVLLKAGAD VNAQDIFGKTPADIAADAGHEDIAEVLQKAAGSPTPTPTTPTPTTPTP |

TABLE 17-continued

| SEQ ID NO: | Amino acid sequence |
|---|---|
|  | TPTGSDLDKKLLEAARAGQDDEVRILLKAGADVNAKDSTGWTPLHLA<br>APWGHPEIVEVLLKAGADVNAKDFQGWTPLHLAAAAGHLEIVEVLLK<br>AGADVNAQDKSGKTPADLAADAGHEDIAEVLQKAA |
| 170 | GSDLGKKLLEAARAGQDDEVRELLKAGADVNAKDYFSHTPLHLAAR<br>NGHLKIVEVLLKAGADVNAKDFAGKTPLHLAANEGHLEIVEVLLKAG<br>ADVNAQDIFGKTPADIAADAGHEDIAEVLQKAAGSPTPTPTTPTPTT<br>PTPTPTGSDLGKKLLEAARAGQDDEVRILLKAGADVNAKDRYGDTPL<br>HLAADIGHLEIVEVLLKAGADVNAEDYFGNTPLHLAASYGHLEIVEVL<br>LKAGADVNAKDDYGNTPLHLAANTGHLEIVEVLLKAGADVNAQDKS<br>GKTPADLAADAGHEDIAEVLQKAAGSPTPTPTTPTPTPTTPTPTGSD<br>LDKKLLEAARAGQDDEVRILLKAGADVNAKDSTGWTPLHLAAPWGH<br>PEIVEVLLKAGADVNAKDFQGWTPLHLAAAAGHLEIVEVLLKAGADV<br>NAQDKSGKTPADLAADAGHEDIAEVLQKAAGSPTPTPTTPTPTTPTP<br>TPTGSDLGKKLLEAARAGQDDEVRELLKAGADVNAKDYFSHTPLHLA<br>ARNGHLKIVEVLLKAGADVNAKDFAGKTPLHLAANEGHLEIVEVLLK<br>AGADVNAQDIFGKTPADIAADAGHEDIAEVLQKAA |
| 171 | GSDLGKKLLEAARAGQDDEVRILMANGADVNAFDWMGWTPLHLAA<br>HEGHLEIVEVLLKNGADVNATDVSGYTPLHLAAADGHLEIVEVLLKY<br>GADVNTKDNTGWTPLHLSADLGRLEIVEVLLKYGADVNAQDKFGKT<br>AFDISIDNGNEDLAEILQKAASGSPAGSPTSEEGTSESATPESGPGTSTE<br>PSEGSAPGSPAGSPTSEEGTSTEPSEGSAPGTSTEPSEGSAPGTSESATP<br>ESGPGSEPATSGSETPGSEPATSGSETPGSPAGSPTSEEGTSESATPESG<br>PGTSTEPSEGSAPGTSTEPSEGSAPGSPAGSPTSEEGTSTEPSEGSAPGT<br>STEPSEGSAPGTSESATPESGPGTSTEPSEGSAPGTSESATPESGPGSEPA<br>TSGSETPGTSTEPSEGSAPGTSTEPSEGSAPGTSESATPESGPGTSESATP<br>ESGPGSPAGSPTSEEGTSESATPESGPGSEPATSGSETPGTSESATPESG<br>PGTSTEPSEGSAPGTSTEPSEGSAPGTSTEPSEGSAPGTSTEPSEGSAPGT<br>STEPSEGSAPGTSTEPSEGSAPGSPAGSPTSEEGTSTEPSEGSAPGTSES<br>ATPESGPGSEPATSGSETPGTSESATPESGPGSEPATSGSETPGTSESATP<br>ESGPGTSTEPSEGSAPGTSESATPESGPGSPAGSPTSEEGSPAGSPTSTE<br>EGSPAGSPTSEEGTSESATPESGPGTSTEPSEGSAPGTSESATPESGPGS<br>EPATSGSETPGTSESATPESGPGSEPATSGSETPGTSESATP<br>ESGPGSPAGSPTSEEGSPAGSPTSEEGTSTEPSEGSAPGTSESATPESG<br>PGTSESATPESGPGTSESATPESGPGSEPATSGSETPGSEPATSGSETPGS<br>PAGSPTSEEGTSTEPSEGSAPGTSTEPSEGSAPGSEPATSGSETPGTSES<br>ATPESGPGTSTEPSEGSAPG |
| 172 | GSDLGKKLLEAARAGQDDEVRILMANGADVNAFDWMGWTPLHLAA<br>HEGHLEIVEVLLKNGADVNATDVSGYTPLHLAAADGHLEIVEVLLKH<br>GADVNTKDNTGWTPLHLSADLGHLEIVEVLLKNGADVNAQDKFGKT<br>AFDISIDNGNEDLAEILQKAAGGGSGGGSC |
| 173 | GSDLDKKLLEAARAGQDDEVRILMANGADVNARDSTGWTPLHLAAP<br>WGHPEIVEVLLKNGADVNAADFQGWTPLHLAAAVGHLEIVEVLLKY<br>GADVNAQDKFGKTAFDISIDNGNEDLAEILQKAAGGGSGGGSC |
| 174 | GSDLGKKLLEAARAGQDDEVRILMANGADVNTADSTGWTPLHLAVP<br>WGHLEIVEVLLKYGADVNAKDFQGWTPLHLAAAIGHQEIVEVLLKNG<br>ADVNAQDKFGKTAFDISIDNGNEDLAEILQKAAGSGSASPAAPAPASP<br>AAPAPSAPAASPAAPAPASPAAPAPSAPAASPAAPAPASPAAPAPSAPA<br>ASPAAPAPASPAAPAPSAPAASPAAPAPASPAAPAPSAPAASPAAPAPA<br>SPAAPAPSAPAASPAAPAPASPAAPAPSAPAASPAAPAPASPAAPAPSA<br>PAASPAAPAPASPAAPAPSAPAASPAAPAPASPAAPAPSAPAASPAAPA<br>PASPAAPAPSAPAASPAAPAPASPAAPAPSAPAASPAAPAPASPAAPAP<br>SAPAASPAAPAPASPAAPAPSAPAASPAAPAPASPAAPAPSAPAASPAA<br>PAPASPAAPAPSAPAASPAAPAPASPAAPAPSAPAASPAAPAPASPAAP<br>APSAPAASPAAPAPASPAAPAPSAPAASPAAPAPASPAAPAPSAPAASP<br>AAPAPAS |
| 175 | GSDLGKKLLEAARVGQDDEVRILMADGADVNASDFKGDTPLHLAAS<br>QGHLEIVEVLLKYGADVNAYDMLGWTPLHLAADLGHLEIVEVLLKY<br>GADVNAQDRFGKTAFDISIDNGNEDLAEILQKAAGSPSTADGC |
| 176 | GSDLGKKLLEAVRAGQDDEVRILMTNGADVNAKDQFGFTPLQLAAY<br>NGHLEIVEVLLKYGADVNAFDIFGWTPLHLAADLGHLEIVEVLLKNGA<br>DVNAQDKFGRTAFDISIDNGNEDLAEILQKAASGSC |
| 177 | GSDLGKKLLEAARAGQDDEVRILMANGADVNAVDYIGWTPLHLAAA<br>YGHLEIVEVLLKYSADVNAEDFAGYTPLHLAASNGHLEIVEVLLKYGA<br>DVNTKDNTGWTPLHLSADLGHLEIVEVLLKYGADVNTQDKFGKTAFD<br>ISIDNGNEDLAEILQKAAGSPSTADGC |
| 178 | XDXXGXTPLHLAAXXGHLEIVEVLLKXGADVNA |
| 179 | XDXXGWTPLHLAAXXGHLEIVEVLLKXGADVNA |

TABLE 17-continued

| SEQ ID NO: | Amino acid sequence |
|---|---|
| 180 | XDXXGXTPLHLAAXXGHLEIVEVLLKXGADVNX |
| 181 | XDXXGWTPLHLXADLGXLEIVEVLLKXGADVNX |
| 182 | XDXXGXTPLHLAAXXGHXEIVEVLLKXGADVNA |
| 183 | XDXXGXTPLHLAAXXGHLEIVEVLLKXGADVNA |
| 184 | XDXXGWTPLHLAAXXGHLEIVEVLLKXGADVNA |
| 185 | XDXXGXTPLHLAAXXGHLEIVEVLLKXGADVNX |
| 186 | XDXXGXTPLHLXAXXGHLEIVEVLLKXGADVNA |
| 187 | XDFKXDTPLHLAAXXGHXEIVEVLLKXGADVNA |
| 188 | XDXLXXTPLHLAXXXGHLEIVEVLLKXGADVNA |
| 189 | XDXXGXTPLXLAAXXGHLEIVEVLLKXGADVNA |
| 190 | XDXXGWTXLHLAADLGXLEIVEVLLKXGADVNA |
| 191 | GSDLGKKLLEAARAGQDDEVRILMANGADVNAFDWMGWTPLHLAAHEGHLEIVEVLLKNGADVNATDVSGYTPLHLAAADGHLEIVEVLLKYGADVNTKDNTGWTPLHLSADLGHLEIVEVLLKYGADVNAQDKFGKTAFDISIDNGNEDLAEILQKAA |
| 192 | GSDLGKKLLEAARVGQDDEVRILMANGADVNAFDWMGWTPLHLAAHEGHLEIVEVLLKNGADVNATDVSGYTPLHLAAADGHLEIVEVLLKYGADVNTKDNTGWTPLHLSADLGHLEIVEVLLKYGADVNAQDKFGKTAFDISIDNGNEDLAEILQKAA |
| 193 | GSDLGKKLLEAARAGQDDEVRILMANGADVNAFDWMGWTPLHLAAHEGHLEIVEVLLKNGADVNATDVSGYTPLHLAAADGHLEIVEVLLKYGADVNTKDNTGWTPLHLSADLGRLEIVEVLLKYGADVNAQDKFGKTAFDISIDNGNEDLAEILQKAA |
| 194 | GSDLGKKLLEAARAGQDDEVRILMANGADVNAFDWMGWTPLHLAAHEGHLEIVEVLLKNGTDVNATDVSGYTPLHLAAADGHLEIVEVLLKYGADVNTKDNTGWTPLHLSADLGHLEIVEVLLKHGADVNAQDKFGKTAFDISIDNGNEDLAEILQKAA |
| 195 | GSDLGKKLLEAARAGQDDEVRILMANGADVNAFDWMGWTPLHLAAHEGHLEIVEVLLKNGADVNATDVSGYTPLHLAAADGHLEIVEVLLKHGADVNTKDNTGWTPLHLSADLGHLEIVEVLLKNGADVNAQDKFGKTAFDISIDNGNEDLAEILQKAA |
| 196 | GSDLGKKLLEAARAGQDDEVRILMANGADVNAFDWMGWTPLHLAAHEGHLEIVEVLLKNGADVNATDVSGYTPLHLAAADGHLEIVEVLLKHGADVNTKDNTGWTPLHLSADLGHLEIVEVLLKNGADINAQDKFGKTAFDISIDNGNEDLAEILQKAA |
| 197 | GSDLGKKLLEAARAGQDDEVRILMANGADVNAFDWMGWTPLHLAAHEGHLEIVEVLLKNGADVNATDVSGYTPLHLAAADGHLEIVEVLLKHGADVNTTDNTGWTPLHLSADLGHLEIVEVLLKYGADVNAQDKFGKTAFDISIDNGNEDLAEILQKAA |
| 198 | GSDLGKKLLEAARAGQDDEVRILMANGADVNAFDYMGWTPLHLAAHNGHMEIVEVLLKYGADVNASDYSGYTPLHLAAADGHLEIVEVLLKYGADVNTKDNTGWTPLHLSADLGHLEIVEVLLKYGADVNAQDKFGKTAFDISIDNGNEDLAEILQKAA |
| 199 | GSDLGKKLLEAARAGQDDEVRILMANGADVNAVDYIGWTPLHLAAAYGHLEIVEVLLKYSADVNAEDFAGYTPLHLAASNGHLEIVEVLLKYGADVNTKDNTGWTPLHLSADLGHLEIVEVLLKYGADVNTQDKFGKTAFDISIDNGNEDLAEILQKAA |
| 200 | GSDLGKKLLEAARTGQDDEVRILMANGADVNATDYMGWTPLHLAAKVGHLEIVEVLLKYGADVNAEDYNGYTPLHLAAAMGHLEIAEVLLKYGADVNTKDNTGWTPLHLSADLGHLEIVEVLLKNGADVNAQDKFGKTAFDISIDNGNEDLAEILQKAA |
| 201 | GSDLGKKLLEAARAGQDDEVRILMANGADVNARDSTGWTPLHLAAPWGHPEIVEVLLKNGADVNAADFQGWTPLHLAAAVGHLEIVEVLLKYGADVNAQDKFGKTAFDISIDNGNEDLAEILQKAA |
| 202 | GSDLGKKLLEAARAGQDDEVRILMANGADVNARDSTGWTPLHLAAPWGHPEIVEVLLKNGADVNAADFQGWTPLHLAAAVGHLEIVEVLLKHGADVNAQDKFGKTAFDISIDNGNEDLAEILQKAA |

TABLE 17-continued

| SEQ ID NO: | Amino acid sequence |
|---|---|
| 203 | GSDLGKKLLEAARAGQDDEVRILMANGADVNTADSTGWTPLHLAAP<br>WGHPEIVEVLLKNGADVNAHDYQGWTPLHLAATLGHLEIVEVLLKY<br>GADVNAQDKFGKTAFDISIDNGNEDLAEILQKAA |
| 204 | GSDLGKKLLEAARAGQDDEVRILMANGADVNTADSTGWTPLHLVAP<br>WGHPEIVEVLLKHGADVNTHDYQGWTPLHLAATLGHLEIVEVLLRYG<br>ADVNAQDKFGKTAFDISIDNGNEDLAEILQKAA |
| 205 | GSDLGKKLLEAARAGQDDEVRILMANGADVNTADSTGWTPMHLAAP<br>WGHPEIVEVLLKHGADVNAQDFQGWTPLHLAAAIGHLEIVEVLLKYG<br>ADVNAQDKFGKTAFDISIDNGNEDLAEILQKAA |
| 206 | GSDLGKKLLEAARAGQDDEVRILMANGADVNTADSTGWTPLHLAVP<br>WGHLEIVEVLLKYGADVNAKDFQGWTPLHLAAAIGHQEIVEVLLKNG<br>ADVNAQDKFGKTAFDISIDNGNEDLAEILQKAA |
| 207 | GSDLGKKLLEAARVGQDDEVRILMADGADVNASDFKGDTPLHLAAS<br>QGHLEIVEVLLKYGADVNAYDMLGWTPLHLAADLGHLEIVEVLLKY<br>GADVNAQDRFGKTAFDISIDNGNEDLAEILQKAA |
| 208 | GSDLGKKLLEAARVGQDDEVRILMANGADVNASDFKGDTPLHLAAS<br>QGHLEIVEVLLKNSADVNAFDLLGWTPLHLAADLGHLEIVEVLLKYG<br>ADVNAQDKFGKTAFDISIDNGNEDLAEILQKAA |
| 209 | GSDLGKKLLEAARVGQDDEVRILMANGADVNALDFKGDTPLHLAAA<br>SGHLEIVEVLLKNGADVNAHDMLSWTPLHLAGDLGHLEIVEVLLKYG<br>ADVNAQDRFGKTAFDISIDNGNEDLAEILQKAA |
| 210 | GSDLGKKLLEAVRAGQDDEVRILMTNGADVNAKDQFGFTPLQLAAY<br>NGHLEIVEVLLKYGADVNAFDIFGWTPLHLAADLGHLEIVEVLLKNGA<br>DVNAQDKFGRTAFDISIDNGNEDLAEILQKAA |
| 211 | GSDLGKKLLEAVRAGQDDEVRILMANGADVNASDNQGTTPLHLAAS<br>HGHLEIVEVLLKYGADVNDAHDDLGWTPLHLSADLGHLEIVEVLLKY<br>GADVNAQDKFGKTAFDISIDNGNEDLAEILQKAA |
| 212 | GSDLGKKLLEATRAGQDDEVRILMANGADVNASDNQGTTPLHLAAS<br>HGHLEIVEVLLKYGADVNDAHDDLGWTPLHLAADLGHLEIVEVLLKY<br>GADVNAQDKFGKTAFDISIDNGNEDLAEILQKAA |
| 213 | GSDLGKKLLEAARVGQDDEVRILMADGADVNASDFKGDTPLHLAAS<br>QGHLEIVEVLLKYGADVNAYDMLGWTPLHLAADLGHLEIVEVLLKY<br>GADVNAQDRFGKTAFDISIDNGNEDLAEILQKAA |
| 214 | GSDLGKKLLEAARVGQDDEVRILMANDADVNASDFKGDTPLHLAAS<br>QGHLEIVEVLLKYGADVNAYDMLGWTPLHLAADLGHLEIVEVLLKH<br>GADVNAQDKFGKTAFDISIDNGNEDLAEILQKAA |
| 215 | GSDLGKKLLEAARAGQDDEVRILMANGADVNTLDFKSDTPLHLAAAS<br>GHLEIVEVLLKNGADVNAHDMLSWTPLHLAGDLGHLEIVEVLLKHGA<br>DVNAQDKFGKTAFDISIDNGNEDLAEILQKAA |
| 216 | GSDLGKKLLEAARAGQDDEVRILMANGADVNAKDIYGRTPLHLAAL<br>HGHPEIVEVLLKYGADVNANDYWGTTSLHLVAIWGHLEIVEVLLKYG<br>ADVNAVDDIGQTPLHLAAAWGHLEIVEVLLKHGADVNAQDKFGKTA<br>FDISIDNGNEDLAEILQKAA |
| 217 | GSDLGKKLLEAARAGQDDEVRILMANGADVNANDYDGMTPLHLAA<br>MEGHLEIVEVLLKYGADVNANDHYGFTPLHLAWTGRLEIVEVLLKNG<br>ADVNAADVFGRTPLHLAATSGHLEIVEVLLKYGADVNAQDKFGKTAF<br>DISIDNGNEDLAEILQKAA |

Antibodies or antigen-binding compounds specific for VEGF can be combined with antibodies or antigen-binding compounds specific to HPTP-β (VE-PTP) to form multi-specific compounds, such as bispecific compounds that bind VEGF and HPTP-β (VE-PTP). Any compounds in this disclosure specific for VEGF can be combined with any compounds in this disclosure specific to HPTP-β (VE-PTP). Any of the compounds in this disclosure specific for VEGF or HPTP-β (VE-PTP) can be modified as necessary for the generation of a multispecific compound. Non-limiting examples of modifications necessary for the generation of a multispecific compound include the addition of amino acid residues, the removal of amino acid residues, the replacement of amino acid residues, and the use of linkers. In some embodiments, 1, 2, 3, 4, 5, 6, 7, 8, 9, 10, 11, 12, 13, 14, 15, 16, 17, 18, 19, 20, 21, 22, 23, 24, 25, or more residues can be added to an N-terminus and/or a C-terminus of a sequence disclosed herein, and the resulting sequence can be used in the generation of a multi-specific construct. In some embodiments, 1, 2, 3, 4, 5, 6, 7, 8, 9, 10, 11, 12, 13, 14, 15, 16, 17, 18, 19, 20, 21, 22, 23, 24, 25, or more residues can be removed from an N-terminus and/or a C-terminus of a sequence disclosed herein, and the remaining sequence can be used in the generation of a multi-specific construct. For example, N- and/or C-terminal residues can be removed from SEQ ID NO: 173 (e.g., to generate SEQ ID NO: 244), and the truncated sequence can be used in a multi-specific construct. In some embodiments, the sequences in any of SEQ ID NOS: 13-20 or 246-253 can be modified. For example, one or more C-terminal residues can be removed (e.g., the C-terminal lysine can be removed from any of SEQ ID NOS: 13-16 or 246-249, and the remaining residues (residues 1-467) can be used in a multi-specific construct).

A compound described herein can include a linker between different domains of the compound. A linker can be a chemical bond, for example, a covalent bond or a non-covalent bond. A linker as described herein can include a flexible or rigid linker.

A linker of the disclosure can include a chemical linker. For example, two amino acid sequences of the disclosure can be connected together by a chemical linker. Each chemical linker of the disclosure can be alkylene, alkenylene, alkynylene, heteroalkylene, cycloalkylene, heterocycloalkylene, arylene, or heteroarylene, any of which is optionally substituted. In some embodiments, a chemical linker of the disclosure can be an ester, ether, amide, thioether, or polyethyleneglycol (PEG). In some embodiments, a linker can reverse the order of the amino acids sequence in a compound, for example, so that the amino acid sequences linked by the linked are head-to-head, rather than head-to-tail. Non-limiting examples of such linkers include diesters of dicarboxylic acids, such as oxalyl diester, malonyl diester, succinyl diester, glutaryl diester, adipyl diester, pimetyl diester, fumaryl diester, maleyl diester, phthalyl diester, isophthalyl diester, and terephthalyl diester. Non-limiting examples of such linkers include diamides of dicarboxylic acids, such as oxalyl diamide, malonyl diamide, succinyl diamide, glutaryl diamide, adipyl diamide, pimetyl diamide, fumaryl diamide, maleyl diamide, phthalyl diamide, isophthalyl diamide, and terephthalyl diamide. Non-limiting examples of such linkers include diamides of diamino linkers, such as ethylene diamine, 1,2-di(methylamino)ethane, 1,3-diaminopropane, 1,3-di(methylamino) propane, 1,4-di(methylamino)butane, 1,5-di(methylamino) pentane, 1,6-di(methylamino)hexane, and pipyrizine.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

A linker can be a peptide. A linker can comprise a linker sequence, for example, a linker peptide sequence. A linker sequence can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 51, 53, 54, 55, 56, 57, 58, 59, 60, 61, 62, 63, 64, 65, 66, 67, 68, 69, or 70 amino acid residues in length.

A flexible linker can have a sequence containing stretches of glycine and serine residues. The small size of the glycine and serine residues provides flexibility, and allows for mobility of the connected functional domains. The incorporation of serine or threonine can maintain the stability of the linker in aqueous solutions by forming hydrogen bonds with the water molecules, thereby reducing unfavorable interactions between the linker and protein moieties.

Flexible linkers can also contain additional amino acids such as threonine and alanine to maintain flexibility, as well as polar amino acids such as lysine and glutamine to improve solubility.

A flexible linker can comprise repeats of SEQ ID NO: 42 (GGGS), for example, SEQ ID NOS: 42-55. A flexible linker can comprise repeats of SEQ ID NO: 31 (GGGGS), for example, SEQ ID NOS: 31-41. Several other types of flexible linkers, including SEQ ID NO: 59 (KESGSVSSE-QLAQFRSLD) and SEQ ID NO: 60 (EGKSSGSGS-ESKST), can also be used. The SEQ ID NO: 61 (GSAGSAAGSEF) linker can also be used, in which large hydrophobic residues are minimized to maintain good solubility in aqueous solutions. The length of the flexible linkers can be adjusted to allow for proper folding or to achieve optimal biological activity of the fused proteins.

A rigid linker can have, for example, an alpha helix-structure. An alpha-helical rigid linker can act as a spacer between protein domains. A rigid linker can comprise repeats of SEQ ID NO: 62 (EAAAK), for example, SEQ ID NOS: 62-66. A rigid linker can comprise repeats of SEQ ID NO: 67 (EAAAR), for example, SEQ ID NOS: 67-72. A rigid linker can have a proline-rich sequence, (XP)n, with X designating alanine, lysine, glutamine, or any amino acid. The presence of proline in non-helical linkers can increase stiffness, and allow for effective separation of protein domains.

A linker can comprise any of the sequences disclosed in TABLE 18, which can be used to link any portion of a compound disclosed herein to any portion of another compound disclosed herein:

TABLE 18

| SEQ ID NO: | Sequence |
|---|---|
| 31 | GGGGS |
| 32 | GGGGSGGGGS |
| 33 | GGGGSGGGGSGGGGS |
| 34 | GGGGSGGGGSGGGGSGGGGS |
| 35 | GGGGSGGGGSGGGGSGGGGSGGGGS |
| 36 | GGGGSGGGGSGGGGSGGGGSGGGGSGGGGS |
| 37 | GGGGSGGGGSGGGGSGGGGSGGGGSGGGGSGGGGS |

TABLE 18-continued

| SEQ ID NO: | Sequence |
|---|---|
| 38 | GGGGSGGGGSGGGGSGGGGSGGGGSGGGGSGGGGSGGGGS |
| 39 | GGGGSGGGGSGGGGSGGGGSGGGGSGGGGSGGGGSGGGGSGGGGS |
| 40 | GGGGSGGGGSGGGGSGGGGSGGGGSGGGGSGGGGSGGGGSGGGGSGGGGS |
| 41 | GGGGSGGGGSGGGGSGGGGSGGGGSGGGGSGGGGSGGGGSGGGGSGGGGSGGGGS |
| 42 | GGGS |
| 43 | GGGSGGGS |
| 44 | GGGSGGGSGGGS |
| 45 | GGGSGGGSGGGSGGGS |
| 46 | GGGSGGGSGGGSGGGSGGGS |
| 47 | GGGSGGGSGGGSGGGSGGGSGGGS |
| 48 | GGGSGGGSGGGSGGGSGGGSGGGSGGGS |
| 49 | GGGSGGGSGGGSGGGSGGGSGGGSGGGSGGGS |
| 50 | GGGSGGGSGGGSGGGSGGGSGGGSGGGSGGGSGGGS |
| 51 | GGGSGGGSGGGSGGGSGGGSGGGSGGGSGGGSGGGSGGGS |
| 52 | GGGSGGGSGGGSGGGSGGGSGGGSGGGSGGGSGGGSGGGSGGGS |
| 53 | GGGSGGGSGGGSGGGSGGGSGGGSGGGSGGGSGGGSGGGSGGGSGGGS |
| 54 | GGGSGGGSGGGSGGGSGGGSGGGSGGGSGGGSGGGSGGGSGGGSGGGSGGGS |
| 55 | GGGSGGGSGGGSGGGSGGGSGGGSGGGSGGGSGGGSGGGSGGGSGGGSGGGSGGGS |
| 56 | GG |
| 57 | GGGGGG |
| 58 | GGGGGGGG |
| 59 | KESGSVSSEQLAQFRSLD |
| 60 | EGKSSGSGSESKST |
| 61 | GSAGSAAGSGEF |
| 62 | EAAAK |
| 63 | EAAAKEAAAK |
| 64 | EAAAKEAAAKEAAAKEAAAK |
| 65 | EAAAKEAAAKEAAAKEAAAKEAAAK |
| 66 | EAAAKEAAAKEAAAKEAAAKEAAAKEAAAK |
| 67 | EAAAR |
| 68 | EAAAREAAAR |
| 69 | EAAAREAAAREAAAR |
| 70 | EAAAREAAAREAAAREAAAR |
| 71 | EAAAREAAAREAAAREAAAREAAAR |
| 72 | EAAAREAAAREAAAREAAAREAAAREAAAR |
| 73 | AEAAAKEAAAKEAAAKEAAAKALEAEAAAKEAAAKEAAAKEAAAKA |
| 74 | PAPAP |
| 75 | AEAAAKEAAAKA |

The VEGF-binding and VEGFR-binding compounds described in TABLE 11, TABLE 12, TABLE 13, TABLE 14, TABLE 15, TABLE 16, and TABLE 17 can be combined with the HPTP-β (VE-PTP)-binding compounds described in TABLE 2, TABLE 3, TABLE 6, TABLE 7, and TABLE 8.

Any of the 16 antibodies described in TABLE 8 can be combined with aflibercept or aflibercept-related sequences to generate a bispecific antibody. Non-limiting schematic examples are presented in FIG. 2, FIG. 3, and FIG. 4. For example, SEQ ID NO: 22 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 22 (FIG. 2). SEQ ID NO: 22 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 22 (FIG. 3). SEQ ID NO: 22 can be appended onto SEQ ID NO: 14 or SEQ ID NO: 247, and SEQ ID NO: 22 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 22 (FIG. 4).

Any of the 16 antibodies described in TABLE 8 can be combined with brolucizumab or brolucizumab-related sequences to generate a bispecific antibody. Non-limiting schematic examples are presented in FIG. 2, FIG. 3, and FIG. 4. For example, SEQ ID NO: 23 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 23 (FIG. 2). SEQ ID NO: 23 can be appended onto SEQ ID NO: 17 or SEQ ID NO: 250 of antibody HC2:LC1 to generate a tetravalent bispecific antibody wherein the light chain of HC2:LC1 is appended with SEQ ID NO: 23 (FIG. 3). SEQ ID NO: 23 can be appended onto SEQ ID NO: 14 or SEQ ID NO: 247, and SEQ ID NO: 23 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 23 (FIG. 4).

Any of the 16 antibodies described in TABLE 8 can be combined with ranibizumab or ranibizumab-related sequences to generate a bispecific antibody. Non-limiting schematic examples are presented in FIG. 2, FIG. 3, and FIG. 4. For example, SEQ ID NO: 28 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 28 (FIG. 2). SEQ ID NO: 28 can be appended onto SEQ ID NO: 17 or SEQ ID NO: 250 of antibody HC2:LC1 to generate a tetravalent bispecific antibody wherein the light chain of HC2:LC1 is appended with SEQ ID NO: 28 (FIG. 3). SEQ ID NO: 28 can be appended onto SEQ ID NO: 14 or SEQ ID NO: 247, and SEQ ID NO: 28 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 28 (FIG. 4).

Any of the 16 antibodies described in TABLE 8 can be combined with bevacizumab or bevacizumab-related sequences to generate a bispecific antibody. Non-limiting schematic examples are presented in FIG. 2, FIG. 3, and FIG. 4. For example, an antigen-binding scFv of bevacizumab could be generated as demonstrated for ranibizumab in TABLE 13. The bevacizumab-derived antigen-binding scFv can be appended onto SEQ ID NO: 14 or SEQ ID NO: 247 of antibody HC2:LC1 to generate a tetravalent bispecific antibody wherein the heavy chain of HC2:LC1 is appended with the bevacizumab-derived antigen-binding scFv (FIG. 2). The bevacizumab-derived antigen-binding scFv can be appended onto SEQ ID NO: 17 or SEQ ID NO: 250 of antibody HC2:LC1 to generate a tetravalent bispecific antibody, in which the light chain of HC2:LC1 is appended with the bevacizumab-derived antigen-binding scFv (FIG. 3). The bevacizumab-derived antigen-binding scFv can be appended onto SEQ ID NO: 14 or SEQ ID NO: 247, and the bevacizumab-derived antigen-binding scFv can be appended onto SEQ ID NO: 17 or SEQ ID NO: 250 of antibody HC2:LC1 to generate a hexavalent bispecific antibody, in which the heavy and light chains of HC2:LC1 are appended with the bevacizumab-derived antigen-binding scFv (FIG. 4).

Any of the 16 antibodies described in TABLE 8 can be combined with abicipar or abicipar-related sequences to generate a bispecific antibody. Non-limiting schematic examples are presented in FIG. 2, FIG. 3, and FIG. 4. For example, SEQ ID NO: 173 or SEQ ID NO: 244 can be appended onto SEQ ID NO: 14, SEQ ID NO: 247, residues 1-467 SEQ ID NO: 14, or residues 1-467 SEQ ID NO: 247 of antibody HC2:LC1 to generate a tetravalent bispecific antibody wherein the heavy chain of HC2:LC1 is appended with SEQ ID NO: 173 or SEQ ID NO: 244 (FIG. 2). SEQ ID NO: 173 or SEQ ID NO: 244 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 173 or SEQ ID NO: 244 (FIG. 3). SEQ ID NO: 173 or SEQ ID NO: 244 can be appended onto SEQ ID NO: 14, SEQ ID NO: 247, residues 1-467 SEQ ID NO: 14, or residues 1-467 SEQ ID NO: 247, and SEQ ID NO: 173 or SEQ ID NO: 244 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 173 or SEQ ID NO: 244 (FIG. 4).

Any of the 16 antibodies described in TABLE 8 can be combined with conbercept or conbercept-related sequences to generate a bispecific antibody. Non-limiting schematic examples are presented in FIG. 2, FIG. 3, and FIG. 4. For example, SEQ ID NO: 155 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 155 (FIG. 2). SEQ ID NO: 155 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 155 (FIG. 3). SEQ ID NO: 155 can be appended onto SEQ ID NO: 14 or SEQ ID NO: 247, and SEQ ID NO: 155 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 155 (FIG. 4).

Any of the 16 antibodies described in TABLE 8 can be combined with ramucirumab or ramucirumab-related sequences to generate a bispecific antibody. Non-limiting schematic examples are presented in FIG. 2, FIG. 3, and FIG. 4. For example, an antigen-binding scFv of ramucirumab could be generated as demonstrated for ranibizumab in TABLE 13. The ramucirumab-derived antigen-binding scFv can be appended onto SEQ ID NO: 14 or SEQ ID NO: 247 of antibody HC2:LC1 to generate a tetravalent bispecific antibody wherein the heavy chain of HC2:LC1 is appended with the ramucirumab-derived antigen-binding scFv (FIG. 2). The ramucirumab-derived antigen-binding scFv can be appended onto SEQ ID NO: 17 or SEQ ID NO: 250 of antibody HC2:LC1 to generate a tetravalent bispecific antibody, in which the light chain of HC2:LC1 is appended with the ramucirumab-derived antigen-binding scFv (FIG. 3). The ramucirumab-derived antigen-binding scFv can be appended onto SEQ ID NO: 14 or SEQ ID NO: 247, and the ramucirumab-derived antigen-binding scFv can be appended onto SEQ ID NO: 17 or SEQ ID NO: 250 of antibody HC2:LC1 to generate a hexavalent bispecific antibody, in which the heavy and light chains of HC2:LC1 are appended with the ramucirumab-derived antigen-binding scFv (FIG. 4).

Any of the 16 antibodies described in TABLE 8 can be combined with DARPins, DARPin repeats, or sequences therefrom, to generate a multispecific antibody. Non-limiting schematic examples are presented in FIG. 2, FIG. 3, and FIG. 4. For example, an amino acid sequence comprising any of SEQ ID NOS: 158-217 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising any of SEQ ID NOS: 158-217 (FIG. 2). An amino acid sequence comprising any of SEQ ID NOS: 158-217 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising any of SEQ ID NOS: 158-217 (FIG. 3). An amino acid sequence comprising any of SEQ ID NOS: 158-217 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising any of SEQ ID NOS: 158-217 (FIG. 4).

The Tie2 activating compounds described in TABLE 9 and TABLE 10 can be combined with the HPTP-β (VE-PTP)-binding compounds described in TABLE 2, TABLE 3, TABLE 6, TABLE 7, and TABLE 8.

Any of the 16 antibodies described in TABLE 8 can be combined with collagen IV-derived biomimetic peptide sequences to generate a multispecific antibody. Non-limiting schematic examples are presented in FIG. 2, FIG. 3, and FIG. 4. For example, an amino acid sequence comprising SEQ ID NO: 152 or SEQ ID NO: 153 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising SEQ ID NO: 152 or SEQ ID NO: 153 (FIG. 2). An amino acid sequence comprising SEQ ID NO: 152 or SEQ ID NO: 153 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising SEQ ID NO: 152 or SEQ ID NO: 153 (FIG. 3). An amino acid sequence comprising SEQ ID NO: 152 or SEQ ID NO: 153 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising SEQ ID NO: 152 or SEQ ID NO: 153 (FIG. 4).

Any of the 16 antibodies described in TABLE 8 can be combined with Ang2 mimetics, or sequences therefrom, to generate a multispecific antibody. Non-limiting schematic examples are presented in FIG. 2, FIG. 3, and FIG. 4. For example, an amino acid sequence comprising any of SEQ ID NOS: 229-230 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising any of SEQ ID NOS: 229-230 (FIG. 2). An amino acid sequence comprising any of SEQ ID NOS: 229-230 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising any of SEQ ID NOS: 229-230 (FIG. 3). An amino acid sequence comprising any of SEQ ID NOS: 229-230 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising any of SEQ ID NOS: 229-230 (FIG. 4).

The Tie2 activating compounds described in TABLE 9 and TABLE 10 can be combined with the VEGF-binding and VEGFR-binding compounds described in TABLE 11, TABLE 12, TABLE 13, TABLE 14, TABLE 15, TABLE 16, and TABLE 17 to generate multi-specific compounds.

Any of the compounds in this disclosure, e.g., the multi-specific fusion constructs described above, can be modified as necessary to promote desirable protein folding or biological activity.

CDRs

Sequences in this disclosure can comprise complementarity determining regions (CDRs). CDRs can be identified by the Kabat method, the Chothia method, the IMGT method, or the Paratome method. A CDR of a sequence herein can be, for example, between 0 and 91 residues in length, between 0 and 25 residues in length, between 5 and 14 residues in length, about 0 residues in length, about 1 residue in length, about 2 residues in length, about 3 residues in length, about 4 residues in length, about 5 residues in length, about 6 residues in length, about 7 residues in length, about 8 residues in length, about 9 residues in length, about 10 residues in length, about 11 residues in length, about 12 residues in length, about 13 residues in length, about 14 residues in length, about 15 residues in length, about 16 residues in length, about 17 residues in length, about 18 residues in length, about 19 residues in length, about 20 residues in length, about 21 residues in length, about 22 residues in length, about 23 residues in length, about 24 residues in length, or about 25 residues in length.

A compound of this disclosure with a binding specificity for or an ability to modulate HPTP-β (VE-PTP) can comprise, for example, any of the CDRs in TABLE 19, TABLE 20, TABLE 21, TABLE 22, TABLE 23, or TABLE 24.

TABLE 19 provides non-limiting examples of HCDR1 sequences specific for HPTP-β (VE-PTP).

TABLE 19

| SEQ ID NO: | Amino acid sequence |
| --- | --- |
| 76 | ANAMN |
| 77 | GFTFNAN |
| 78 | GFTFNANA |

TABLE 19-continued

| SEQ ID NO: | Amino acid sequence |
|---|---|
| 79 | FTFNANAMN |
| 80 | GFTFNANAMN |

TABLE 20 provides non-limiting examples of HCDR2 sequences specific for HPTP-β (VE-PTP).

TABLE 20

| SEQ ID NO: | Amino acid sequence |
|---|---|
| 81 | RIRTKSNNYATYYAGSVKD |
| 82 | RTKSNNYA |
| 83 | IRTKSNNYAT |
| 84 | WVGRIRTKSNNYATYY |
| 85 | WVGRIRTKSNNYATYYAGSVKD |
| 86 | WVSRIRTKSNNYATYY |
| 87 | WVSRIRTKSNNYATYYAGSVKD |

TABLE 21 provides non-limiting examples of HCDR3 sequences specific for HPTP-β (VE-PTP).

TABLE 21

| SEQ ID NO: | Amino acid sequence |
|---|---|
| 88 | DYYGSSAWITY |
| 89 | VRDYYGSSAWITY |
| 90 | RDYYGSSAWITY |

TABLE 22 provides non-limiting examples of LCDR1 sequences specific for HPTP-β (VE-PTP).

TABLE 22

| SEQ ID NO: | Amino acid sequence |
|---|---|
| 91 | KASQHVGTAVA |
| 92 | QHVGTA |
| 93 | QHVGTAVA |

TABLE 23 provides non-limiting examples of LCDR2 sequences specific for HPTP-β (VE-PTP).

TABLE 23

| SEQ ID NO: | Amino acid sequence |
|---|---|
| 94 | WASTRHT |
| 95 | WAS |
| 96 | LLIYWASTRHT |

TABLE 24 provides non-limiting examples of LCDR3 sequences specific for HPTP-β (VE-PTP).

TABLE 24

| SEQ ID NO: | Amino acid sequence |
|---|---|
| 97 | QQYSSYPFT |
| 98 | QQYSSYPF |

Compounds of this disclosure with a binding specificity for or an ability to modulate VEGF can comprise any of the CDRs in TABLE 25, TABLE 26, TABLE 27, TABLE 28, TABLE 29, or TABLE 30.

TABLE 25 provides non-limiting examples of HCDR1 sequences specific for VEGF.

TABLE 25

| SEQ ID NO: | Amino acid sequence |
|---|---|
| 99 | DYYMT |
| 100 | GFSLTDYY |
| 101 | GFSLTDYYY |
| 102 | FSLTDYYMT |
| 103 | GFSLTDYYYMT |
| 104 | HYGMN |
| 105 | GYDFTHY |
| 106 | GYDFTHYG |
| 107 | YDFTHYGMN |
| 108 | GYDFTHYGMN |
| 109 | NYGMN |
| 110 | GYTFTNY |
| 111 | GYTFTNYG |
| 112 | YTFTNYGMN |
| 113 | GYTFTNYGMN |

TABLE 26 provides non-limiting examples of HCDR2 sequences specific for VEGF.

TABLE 26

| SEQ ID NO: | Amino acid sequence |
|---|---|
| 114 | FIDPDDDPYYATWAKG |
| 115 | DPDDD |
| 116 | IDPDDDP |
| 117 | WVGFIDPDDDPYYATWA |
| 118 | WVGFIDPDDDPYYATWAKG |
| 119 | WINTYTGEPTYAADFKR |
| 120 | NTYTGE |
| 121 | INTYTGEP |
| 122 | WVGWINTYTGEPTY |
| 123 | WVGWINTYTGEPTYAADFKR |

TABLE 27 provides non-limiting examples of HCDR3 sequences specific for VEGF.

TABLE 27

| SEQ ID NO: | Amino acid sequence |
|---|---|
| 124 | GDHNSGWGLDI |
| 125 | AGGDHNSGWGLDI |
| 126 | YPYYYGTSHWYFDV |
| 127 | AKYPYYYGTSHWYFDV |
| 128 | KYPYYYGTSHWYFDV |
| 129 | YPHYYGSSHWYFDV |
| 130 | AKYPHYYGSSHWYFDV |
| 131 | KYPHYYGSSHWYFDV |

TABLE 28 provides non-limiting examples of LCDR1 sequences specific for VEGF.

TABLE 28

| SEQ ID NO: | Amino acid sequence |
|---|---|
| 132 | QASEIIHSWLA |
| 133 | EIIHSW |
| 134 | EIIHSWLA |
| 135 | SASQDISNYLN |
| 136 | QDISNY |
| 137 | QDISNYLN |

TABLE 29 provides non-limiting examples of LCDR2 sequences specific for VEGF.

TABLE 29

| SEQ ID NO: | Amino acid sequence |
|---|---|
| 138 | LASTLAS |
| 139 | LAS |
| 140 | LLIYLASTLAS |
| 141 | FTSSLHS |
| 142 | FTS |
| 143 | VLIYFTSSLHS |

TABLE 30 provides non-limiting examples of LCDR3 sequences specific for VEGF.

TABLE 30

| SEQ ID NO: | Amino acid sequence |
|---|---|
| 144 | QNVYLASTNGAN |
| 145 | QQYSTVPWT |
| 146 | QQYSTVPW |

TABLE 31 provides aflibercept-derived sequences corresponding to the D2 domain of human VEGF receptor 1 (SEQ ID NO: 147) and the D3 domain of human VEGF receptor 2 (SEQ ID NO: 148).

TABLE 31

| SEQ ID NO: | Amino acid sequence |
|---|---|
| 147 | SDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTII |
| 148 | DVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK |

TABLE 32 provides abicipar-derived sequences. SEQ ID NOS: 233-236 correspond to ankyrin repeats within abicipar. SEQ ID NOS: 237-242 provide consensus sequences for VEGF binding ankyrin repeats. In SEQ ID NO: 237, X1 is K, T, or Y; X2 is N or M; X3 is T or F; X4 is S or A; X5 is H or R; X6 is A, Y, H, or N; and X7 is A or T. In SEQ ID NO: 238, X1 is K, M, N, R, or V; X2 is Y, H, M, or V; X3 is F, L, M, or V; X4 is R, H, V, A, K, or N; X5 is F, D, H, T, Y, M, or K; and X6 is A, H, N, or Y. In SEQ ID NO: 239, X1 is L, S, or T; X2 is G, S, or C; X3 is S or A; X4 is Q, S, M, or N; X5 is L, M, or Q; and X6 is A, H, N, Y, or D. In SEQ ID NO: 240, X1 is K, S, N, T, or V; X2 is K, N, W, A, H, M, Q, or S; X3 is F, Q, L, H, or V; X4 is F or T; X5 is Q or H; X6 is Y or S; X7 is N, H, Y, or M; and X8 is A, H, N, or Y. In SEQ ID NO: 241, X1 is A, N, R, V, Y, E, H, I, K, L, Q, S, or T; X2 is S, A, N, R, D, F, L, P, T, or Y; X3 is T, V, S, A, L, or F; X4 is W, F, or H; X5 is P, I, A, L, S, T, V, or Y; X6 is W, F, I, L, T, or V; X7 is L or P; and X8 is A, H, N, or Y. In SEQ ID NO: 242, X1 is H, Q, A, K, R, D, I, L, M, N, V, or Y; X2 is Y, F, or H; X3 is Q, F, or T; X4 is W, M, G, H, N, or T; X5 is T, A, M, L, or V; X6 is I, L, V, D, or T; and X7 is A, H, N, or Y. SEQ ID NO: 244 provides a truncated sequence derived from abicipar that comprises designed ankyrin repeats with a binding specificity for VEGF.

TABLE 32

| SEQ ID NO: | Amino acid sequence |
|---|---|
| 233 | DLDKKLLEAARAGQDDEVRILMANGADVNARDS |
| 234 | TGWTPLHLAAPWGHPEIVEVLLKNGADVNAADF |
| 235 | QGWTPLHLAAAVGHLEIVEVLLKYGADVNAQDK |
| 236 | FGKTAFDISIDNGNEDLAEILQ |
| 237 | X1DX2X3GWTPLHLX4ADLGX5LEIVEVLLKX6GADVNX7 |
| 238 | X1DX2X3GWTPLHLAAX4X5GHLEIVEVLLKX6GADVNA |
| 239 | X1DFKX2DTPLHLAAX3X4GHX5EIVEVLLKX6GADVNA |
| 240 | X1DX2X3GX4TPLX5LAAX6X7GHLEIVEVLLKX8GADVNA |
| 241 | X1DX2X3GX4TPLHLAAX5X6GHX7EIVEVLLKX8GADVNA |
| 242 | X1DX2X3GX4TPLHLAAX5X6GHLEIVEVLLKX7GADVNADLDKKLLEAARAGQDDEVRILMANGADVNARDSTGWTPLHLAAPWGHPEIVE |
| 244 | VLLKNGADVNAADFQGWTPLHLAAAVGHLEIVEVLLKYGADVNAQDKFGKTAFDISIDNGNEDLAEILQKAA |

Homology

A sequence of a compound herein can have at least about 70% homology, at least about 71% homology, at least about 72% homology, at least about 73% homology, at least about 74% homology, at least about 75% homology, at least about 76% homology, at least about 77% homology, at least about 78% homology, at least about 79% homology, at least about 80% homology, at least about 81% homology, at least about 82% homology, at least about 83% homology, at least about 84% homology, at least about 85% homology, at least about 86% homology, at least about 87% homology, at least about 88% homology, at least about 89% homology, at least about 90% homology, at least about 91% homology, at least about 92% homology, at least about 93% homology, at least about 94% homology, at least about 95% homology, at least about 96% homology, at least about 97% homology, at least about 98% homology, at least about 99% homology, at least about 99.1% homology, at least about 99.2% homology, at least about 99.3% homology, at least about 99.4% homology, at least about 99.5% homology, at least about 99.6% homology, at least about 99.7% homology, at least about 99.8% homology, at least about 99.9% homology, at least about 99.91% homology, at least about 99.92% homology, at least about 99.93% homology, at least about 99.94% homology, at least about 99.95% homology, at least about 99.96% homology, at least about 99.97% homology, at least about 99.98% homology, or at least about 99.99% homology to an amino acid sequence provided herein.

Various methods and software programs can be used to determine the homology between two or sequences, such as NCBI BLAST, Clustal W, MAFFT, Clustal Omega, AlignMe, Praline, or another suitable method or algorithm.

Pharmaceutical Compositions

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism.

Pharmaceutical formulations for administration can include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. The active ingredient can be in powder form for constitution with a suitable vehicle, for example, sterile pyrogen-free water, before use.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising compounds described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers, and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements, or has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16, or about 24 hours.

The disclosed compositions can optionally comprise pharmaceutically-acceptable preservatives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

A compound described herein can be conveniently formulated into pharmaceutical compositions composed of one or more pharmaceutically-acceptable carriers. See e.g., Remington's Pharmaceutical Sciences, latest edition, by E.W. Martin Mack Pub. Co., Easton, PA, incorporated by reference in its entirety, which discloses typical carriers and conventional methods of preparing pharmaceutical compositions. Such carriers can be carriers for administration of compositions to humans and non-humans, including solutions such as sterile water, saline, and buffered solutions at physiological pH. Pharmaceutical compositions can also include one or more additional active ingredients such as antimicrobial agents, anti-inflammatory agents, and anesthetics.

Non-limiting examples of pharmaceutically-acceptable carriers include saline, Ringer's solution, and dextrose solution. In some embodiments, the pH of the solution can be from about 5 to about 8, and can be from about 7 to about 7.5. Further carriers include sustained release preparations such as semipermeable matrices of solid hydrophobic polymers containing the compound. The matrices can be in the form of shaped articles, for example, films, liposomes, microparticles, or microcapsules.

Compositions suitable for topical administration can be used. In some embodiments, compositions of the disclosure can comprise a liquid comprising an active agent in solution, in suspension, or both. Liquid compositions can include gels. A liquid composition can be, for example, aqueous. A composition is an in situ gellable aqueous composition. In iteration, the composition is an in situ gellable aqueous solution. Such a composition can comprise a gelling agent in a concentration effective to promote gelling upon contact with the eye or lacrimal fluid in the exterior of the eye. Aqueous compositions can have ophthalmic ally-compatible pH and osmolality. The composition can comprise an ophthalmic depot formulation comprising an active agent for subconjunctival administration. Microparticles comprising an active agent can be embedded in a biocompatible, pharmaceutically-acceptable polymer or a lipid encapsulating agent. The depot formulations can be adapted to release all or substantially all the active material over an extended period of time. The polymer or lipid matrix, if present, can be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, for example, by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion can comprise polymers and can be bioerodible or non-bioerodible.

Pharmaceutical formulations can include additional carriers, as well as thickeners, diluents, buffers, preservatives, and surface active agents in addition to the agents disclosed herein.

The pH of the disclosed composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, at least 9, at least 10, at least 11 or at least 12 pH units. The pH of the composition can be, for example, at most 3, at most 4, at most 5, at most 6, at most 7, at most 8, at most 9, at most 10, at most 11, or at most 12 pH units. A pharmaceutical formulation disclosed herein can have a pH of from about 5.5 to about 6.5. For example, a formulation of the present disclosure can have a pH of about 5.5, about 5.6, about 5.7, about 5.8, about 5.9, about 6.0, about 6.1, about 6.2, about 6.3, about 6.4, or about 6.5. In some embodiments, the pH is 6.2±0.3, 6.2±0.2, 6.2±0.1, about 6.2, or 6.2.

If the pH is outside the range desired by the formulator, the pH can be adjusted by using sufficient pharmaceutically-acceptable acids and bases.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anti-cholinergics/anti-spasmotics, antidiabetic agents, antihypertensive agents, anti-neoplastics, cardiovascular agents, central nervous system agents, coagulation modifiers, hormones, immunologic agents, immunosuppressive agents, and ophthalmic preparations.

In some embodiments, the pharmaceutical composition provided herein comprises a therapeutically effective amount of a compound in admixture with a pharmaceutically-acceptable carrier and/or excipient, for example, saline, phosphate buffered saline, phosphate and amino acids, polymers, polyols, sugar, buffers, preservatives, and other proteins. Illustrative agents include octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene, and glycol.

In some embodiments, a pharmaceutical formulation disclosed herein can comprise: (i) a compound or antibody disclosed herein; (ii) a buffer; (iii) a non-ionic detergent; (iv) a tonicity agent; and (v) a stabilizer. In some embodiments, the pharmaceutical formulation disclosed herein is a stable liquid pharmaceutical formulation.

In some embodiments, an ophthalmic formulation disclosed herein can comprise: (i) a compound or antibody disclosed herein; (ii) a buffer; (iii) a non-ionic detergent; (iv) a tonicity agent; and (v) a stabilizer. In some embodiments, the ophthalmic formulation disclosed herein is a stable liquid pharmaceutical formulation or a stable liquid ophthalmic formulation.

In some embodiments, a pharmaceutical formulation or ophthalmic formulation disclosed herein is a liquid formulation that can comprise about 5 mg/mL to about 150 mg/mL of antibody or compound, about 7.5 mg/mL to about 140 mg/mL of antibody or compound, about 10 mg/mL to about 130 mg/mL of antibody or compound, about 10 mg/mL to about 100 mg/mL of antibody or compound, about 20 mg/mL to about 80 mg/mL of antibody or compound, or about 30 mg/mL to about 70 mg/mL of antibody or compound. For example, a formulation of the present disclosure can comprise about 5 mg/mL, about 10 mg/mL, about 15 mg/mL, about 20 mg/mL, about 25 mg/mL, about 30 mg/mL, about 35 mg/mL, about 40 mg/mL, about 50 mg/mL, about 60 mg/mL, about 70 mg/mL, about 80 mg/mL, about 90 mg/mL, about 100 mg/mL, about 120 mg/mL, about 140 mg/mL, or about 150 mg/mL of a compound, antibody, or antigen-binding fragment thereof described herein.

In some embodiments, a pharmaceutical formulation or ophthalmic formulation disclosed herein can comprise a buffer. In some embodiments, the buffer serves to maintain a stable pH and to help stabilize a compound or antibody disclosed herein. In some embodiments, the buffer or buffer system comprises at least one buffer that has a buffering range that overlaps fully or in part the range of pH 5.5-7.4. In some embodiments, the buffer has a pKa of about 6.2±0.5. In some embodiments, the buffer comprises a sodium phosphate buffer. In some embodiments, the sodium phosphate is present at a concentration of about 5 mM to about 15 mM, about 6 mM to about 14 mM, about 7 mM to about 13 mM, about 8 mM to about 12 mM, about 9 mM to about 11 mM, or about 10 mM. In certain embodiments, the buffer system comprises sodium phosphate at 10 mM, at a pH of 6.20.3 or 6.10.3.

In some embodiments, a pharmaceutical formulation or ophthalmic formulation disclosed herein can comprise a non-ionic detergent. In some embodiments, the non-ionic detergent is a nonionic polymer containing a polyoxyethylene moiety. In some embodiments, the non-ionic detergent is any one or more of polysorbate 20, poloxamer 188 or polyethylene glycol 3350. In some embodiments, the non-ionic detergent is polysorbate 20. In some embodiments, the non-ionic detergent is polysorbate 80. In some embodiments, a pharmaceutical formulation or ophthalmic formulation disclosed herein can contain about 0.01% to about 1% non-ionic detergent. For example, a formulation of the present disclosure can comprise about 0.0085%, about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.3%, about 0.4%, about 0.5%, about 0.6%, about 0.7%, about 0.8%, about 0.9%, about 1%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, or about 2% polysorbate 20, polysorbate 80 or poloxamer 188.

In some embodiments, a pharmaceutical formulation or ophthalmic formulation disclosed herein can comprise a tonicity agent. In some embodiments, the tonicity agent is sodium chloride or potassium chloride. In some embodiments, the tonicity agent is sodium chloride. In some embodiments, the sodium chloride is present at a concentration of about 5 mM to about 100 mM, about 10 mM to about 50 mM, or about 40 mM.

In some embodiments, a pharmaceutical formulation or ophthalmic formulation disclosed herein can comprise a stabilizer. In some embodiments, the stabilizer is a thermal stabilizer that can stabilize an antibody or compound disclosed herein under conditions of thermal stress. In some embodiments, the stabilizer maintains greater than about 93% of the compound or antibody in a native conformation when the solution containing the compound or antibody and the thermal stabilizer is kept at about 45° C. for up to about 28 days. In some embodiments, the stabilizer prevents aggregation of the compound or antibody and less than 4% of the compound or antibody is aggregated when the solution containing the compound or antibody and the thermal stabilizer is kept at about 45° C. for up to about 28 days. In some embodiments, the stabilizer maintains greater than about 96% of the compound or antibody in a native conformation when the solution containing the compound or antibody and the thermal stabilizer is kept at about 37° C. for up to about 28 days. In some embodiments, the stabilizer prevents aggregation of the compound or antibody and less than about 2% of the compound or antibody is aggregated when the solution containing the compound or antibody and the thermal stabilizer is kept at about 37° C. for up to about 28 days.

In some embodiments, the thermal stabilizer is a sugar or sugar alcohol, for example, sucrose, sorbitol, glycerol, trehalose, or mannitol, or any combination thereof. In some embodiments, the stabilizer is a sugar. In some embodiments, the sugar is sucrose, mannitol or trehalose. In some embodiments, the stabilizer is sucrose. In some embodiments, a pharmaceutical formulation or ophthalmic formulation disclosed herein can comprise about 1% to about 20% sugar or sugar alcohol, about 2% to about 18% sugar or sugar alcohol, about 3% to about 15% sugar or sugar alcohol, about 4% to about 10% sugar or sugar alcohol, or about 5% sugar or sugar alcohol. For example, a pharmaceutical formulation or ophthalmic formulation of the present disclosure can comprise about 4%, about 5%, about 6%, about 7%, about 8%, about 9%, about 10%, about 11%, about 12%, about 13%, or about 14% sugar or sugar alcohol (e.g., sucrose, trehalose or mannitol). In some embodiments, the stabilizer is at a concentration of from about 1% w/v to about 20% w/v. In some embodiments, the stabilizer is sucrose at a concentration of from about 1% w/v to about 15% w/v, or from about 1% w/v to about 10% w/v. In some embodiments, the stabilizer is sucrose at a concentration of 5% w/v or about 5% w/v. In some embodiments, the stabilizer is sucrose at a concentration of 7.5% w/v or about 7.5% w/v. In some embodiments, the stabilizer is sucrose at a concentration of 10% w/v or about 10% w/v. In some embodiments, the stabilizer is sucrose at a concentration of 12.5% w/v or about 12.5% w/v. In some embodiments, the stabilizer is sucrose at a concentration of 15% w/v or about 15% w/v. In some embodiments, the stabilizer is sucrose at a concentration of 20% w/v or about 20% w/v.

Administration of Pharmaceutical Compositions

A pharmaceutical composition disclosed herein can be administered in a therapeutically-effective amount by various forms and routes including, for example, oral, topical, parenteral, intravenous injection, intravenous infusion, subcutaneous injection, subcutaneous infusion, intramuscular injection, intramuscular infusion, intradermal injection, intradermal infusion, intraperitoneal injection, intraperitoneal infusion, intracerebral injection, intracerebral infusion, subarachnoid injection, subarachnoid infusion, intraocular injection, intraspinal injection, intrasternal injection, ophthalmic administration, endothelial administration, local administration, intranasal administration, intrapulmonary administration, rectal administration, intraarterial administration, intrathecal administration, inhalation, intralesional administration, intradermal administration, epidural administration, absorption through epithelial or mucocutaneous linings (e.g., oral mucosa, rectal and intestinal mucosa), intracapsular administration, subcapsular administration, intracardiac administration, transtracheal administration, subcuticular administration, subarachnoid administration, subcapsular administration, intraspinal administration, or intrasternal administration.

A pharmaceutical composition can be administered in a local manner, for example, via injection of the compound directly into an organ, optionally in a depot or sustained release formulation or implant. A pharmaceutical composition can be provided in the form of a rapid release formulation, in the form of an extended release formulation, or in the form of an intermediate release formulation. A rapid release form can provide an immediate release. An extended release formulation can provide a controlled release or a sustained delayed release.

In some embodiments, a pump can be used for delivery of the pharmaceutical composition. In some embodiments, a pen delivery device can be used, for example, for subcutaneous delivery of a composition of the disclosure. Such a pen delivery device can be reusable or disposable. A reusable pen delivery device can use a replaceable cartridge that contains a pharmaceutical composition disclosed herein. Once all of the pharmaceutical composition within the cartridge has been administered and the cartridge is empty, the empty cartridge can readily be discarded and replaced with a new cartridge that contains the pharmaceutical composition. The pen delivery device can then be reused. A disposable pen has no replaceable cartridge. Rather, the disposable pen delivery device comes prefilled with the pharmaceutical composition held in a reservoir within the device. Once the reservoir is emptied of the pharmaceutical composition, the entire device is discarded.

A pharmaceutical composition disclosed herein can be administered, for example, to the eye via any suitable form or route including, for example, topical, oral, systemic, intravitreal, intracameral, intracanieral, subconjunctival, subtenon, retrobulbar, intraocular, intrastromal, intracorneal, posterior juxtascleral, periocular, subretinal, or suprachoroidal administration. The delivery method can include an invasive method for direct delivery of the composition to ocular cells. In some embodiments, a liquid pharmaceutical composition comprising an antibody or compound can be delivered via a subretinal injection, intravitreal injection (e.g., front, mid or back vitreal injection), intravitreal implant, intraorbital injection, intraorbital administration, subcutaneous injection, intracameral injection, intracanieral injection, subconjunctival injection, subconjunctival implant, injection into the anterior chamber via the temporal limbus, intrastromal injection, intracorneal injection, aqueous humor injection, subtenon injection, or subtenon implant. The compositions can be administered by injecting the formulation in any part of the eye including anterior chamber, posterior chamber, vitreous chamber (intravitreal), retina proper, and/or subretinal space.

A pharmaceutical composition disclosed herein can be delivered via a non-invasive method. Examples of non-invasive modes of administering the formulation can include using a needleless injection device, and topical administration, for example, eye drops to the cornea. Multiple administration routes can be employed for efficient delivery of the pharmaceutical composition. In some embodiments, the composition is delivered via multiple administration routes, for example, subretinal and intravitreous, to increase the efficiency of antibody delivery. In some embodiments, the subretinal and/or intravitreal injection is preceded by a vitrectomy.

In some embodiments, a liquid formulation comprising from 10 mg/mL to 120 mg/mL of antibody or compound is in a prefilled syringe and is administered intravitreally in a volume of up to about 500 µL. In some embodiments, a liquid formulation comprising from 10 mg/mL to 120 mg/mL of antibody or compound is in a prefilled syringe and is administered intravitreally in a volume of up to about 100 µL. In some embodiments, a liquid formulation comprising from 10 mg/mL to 120 mg/mL of antibody or compound is in a prefilled syringe and is administered intravitreally in a volume of about 50 µL.

A pharmaceutical composition disclosed herein can be targeted to any suitable ocular cell including, for example, endothelial cells such as vascular endothelial cells, cells of the retina such as retinal pigment epilthelium (RPE), corneal cells, fibroblasts, astrocytes, glial cells, pericytes, iris epithelial cells, cells of neural origin, ciliary epithelial cells, Müller cells, muscle cells surrounding and attached to the eye such as cells of the lateral rectus muscle, orbital fat cells, cells of the sclera and episclera, cells of the trabecular meshwork, or connective tissue cells.

Dosing

A compound, antibody, or therapeutic agent described herein can be administered before, during, or after the occurrence of a disease or condition, and the timing of administering a composition containing the compound, antibody, or therapeutic agent can vary. For example, the composition can be used as a prophylactic and can be administered continuously to subjects with a propensity to conditions or diseases in order to lessen a likelihood of the occurrence of the disease or condition. The composition can be administered to a subject already suffering from a disease or condition, in an amount sufficient to cure or at least partially arrest the symptoms of the disease or condition, or to cure, heal, improve, or ameliorate the condition. The composition can be administered to a subject during or as soon as possible after the onset of the symptoms. The administration of the compound, antibody, or therapeutic agent can be initiated within the first 48 hours of the onset of the symptoms, within the first 24 hours of the onset of the symptoms, within the first 6 hours of the onset of the symptoms, or within 3 hours of the onset of the symptoms. The initial administration can be via any practical route, such as by any route described herein using any formulation described herein. The compound, antibody, or therapeutic agent can be administered as soon as is practicable after the onset of a disease or condition is detected or suspected, and for a length of time necessary for the treatment of the disease, such as, for example, from about 1 month to about 3 months. The length of treatment can vary for each subject. Amounts effective for this use can vary based on the severity and course of the disease or condition, previous therapy, the subject's health status, weight, and response to the drugs, and the judgment of the treating physician. Improvement of clinical symptoms can be monitored, for example, by indirect ophthalmoscopy, fundus photography, fluorescein angiography, electroretinography, external eye examination, slit lamp biomicroscopy, applanation tonometry, pachymetry, optical coherence tomography, or autorefraction.

A pharmaceutical composition described herein can be in a unit dosage form suitable for a single administration of a precise dosage. In unit dosage form, the formulation can be divided into unit doses containing appropriate quantities of one or more compounds, antibodies or therapeutic agents. The unit dosage can be in the form of a package containing discrete quantities of the formulation. Non-limiting examples are packaged injectables, vials, and ampoules. An aqueous suspension composition disclosed herein can be packaged in a single-dose non-reclosable container. Multiple-dose reclosable containers can be used, for example, in combination with or without a preservative. A formulation for injection disclosed herein can be present in a unit dosage form, for example, in ampoules, or in multi-dose containers with a preservative.

Multiple compounds, antibodies or therapeutic agents disclosed herein can be administered in any order or simultaneously. If simultaneously, the multiple compounds, antibodies or therapeutic agents can be provided in a single, unified form, or in multiple forms, for example, as multiple separate injections or infusions. The compounds, antibodies or therapeutic agents can be packed together or separately, in a single package or in a plurality of packages. One or all of the compounds, antibodies or therapeutic agents can be given in multiple doses. If not simultaneous, the timing between the multiple doses can vary to as much as about a month.

An intraocular injection can be performed between any interval of time to improve efficiency of delivery and/or to minimize or avoid damage to surrounding tissue. The interval of time between two or more intraocular injections can be from, for example, about 1 minute to about 60 minutes, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, or about 55 minutes to about 60 minutes.

An intraocular injection can be performed at any rate. The rate of intraocular injection can be from, for example, about 1 µL/sec to about 500 µL/sec, about 1 µL/sec to about 10 µL/sec, about 10 µL/sec to about 20 µL/sec, about 20 µL/sec to about 30 µL/sec, about 30 µL/sec to about 40 µL/sec, about 40 µL/sec to about 50 µL/sec, about 50 µL/sec to about 60 µL/sec, about 60 µL/sec to about 70 µL/sec, about 70 µL/sec to about 80 µL/sec, about 80 µL/sec to about 90 L/sec, about 90 µL/sec to about 100 µL/sec, about 100 µL/sec to about 110 µL/sec, about 110 L/sec to about 120 µL/sec, about 120 µL/sec to about 130 µL/sec, about 130 µL/sec to about 140 µL/sec, about 140 µL/sec to about 150 µL/sec, about 150 µL/sec to about 160 µL/sec, about 160 µL/sec to about 170 µL/sec, about 170 µL/sec to about 180 µL/sec, about 180 µL/sec to about 190 µL/sec, about 190 µL/sec to about 200 µL/sec, about 200 µL/sec to about 300 µL/sec, about 300 µL/sec to about 400 µL/sec, or about 400 µL/sec to about 500 µL/sec.

A compound, antibody, or therapeutic agent disclosed herein can be administered at a dosage of about 0.0001 mg/kg to about 1000 mg/kg, about 0.001 mg/kg to about 100 mg/kg, about 0.01 mg/kg to about 100 mg/kg, about 0.01 mg/kg to about 20 mg/kg, about 0.02 mg/kg to about 7 mg/kg, about 0.03 mg/kg to about 5 mg/kg, about 0.05 mg/kg to about 3 mg/kg, about 0.1 mg/kg to about 50 mg/kg, about 0.1 mg/kg to about 0.5 mg/kg, about 0.2 mg/kg to about 0.6 mg/kg, about 0.3 mg/kg to about 0.7 mg/kg, about 0.4 mg/kg to about 0.8 mg/kg, about 0.1 mg/kg to about 0.9 mg/kg, about 0.01 mg/kg to about 50 mg/kg, about 0.1 mg/kg to about 10 mg/kg, about 1 mg/kg to about 10 mg/kg, about 5 mg/kg to about 10 mg/kg, about 1 mg/kg to about 5 mg/kg, or about 3 mg/kg to about 7 mg/kg by mass of the subject.

A compound, antibody, or therapeutic agent described herein can be administered at any interval desired. The administration of the compound, antibody, or therapeutic agent can have regular or irregular dosing schedules to accommodate either the person administering the compound, antibody, or therapeutic agent or the subject receiving the compound, antibody, or therapeutic agent. For example, the compound, antibody, or therapeutic agent can be administered twice a day, once a day, five times a week, four times a week, three times a week, two times a week, once a week, once every two weeks, once every three weeks, once every four weeks, once a month, once every five weeks, once every six weeks, once every eight weeks, once every two months, once every twelve weeks, once every three months, once every four months, once every six months, once a year, or less frequently. In some embodiments, administration is every other week.

The amount administered can be of the same amount in each dose or the dosage can vary between doses. For example, a first amount can be administered in the morning and a second amount can be administered in the evening.

A compound, antibody, or therapeutic agent described herein can be administered in any amount necessary or convenient. For example, a compound described herein can be administered in an amount from about 0.05 mg to about 300 mg, about 0.1 mg to about 300 mg, about 0.1 mg to about 200 mg, about 0.1 mg to about 100 mg, about 0.05 mg to about 1.5 mg, about 0.1 mg to about 1.5 mg, about 0.05 mg to about 1 mg, about 1 mg to about 1.5 mg, about 0.5 mg to about 6 mg, about 1 mg to about 4 mg, about 2 mg to about 10 mg, about 10 mg to about 30 mg, about 30 mg to about 50 mg, about 50 mg to about 70 mg, about 70 mg to about 100 mg, or about 0.1 mg to about 1 mg, about 0.05 mg, about 0.06 mg, about 0.07 mg, about 0.08 mg, about 0.09 mg, about 0.1 mg, about 0.11 mg, about 0.12 mg, about 0.13 mg, about 0.14 mg, about 0.15 mg, about 0.16 mg, about 0.17, mg, about 0.18 mg, about 0.19 mg, about 0.2 mg, about 0.21 mg, about 0.22 mg, about 0.23 mg, about 0.24 mg, about 0.25 mg, about 0.26 mg, about 0.27, mg, about 0.28 mg, about 0.29 mg, about 0.3 mg, about 0.31 mg, about 0.32 mg, about 0.33 mg, about 0.34 mg, about 0.35 mg, about 0.36 mg, about 0.37, mg, about 0.38 mg, about 0.39 mg, about 0.4 mg, about 0.41 mg, about 0.42 mg, about 0.43 mg, about 0.44 mg, about 0.45 mg, about 0.46 mg, about 0.47, mg, about 0.48 mg, about 0.49 mg, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg about 200 mg, about 210 mg, about 220 mg, about 230 mg, about 240 mg, about 250 mg, about 260 mg, about 270 mg, about 280 mg, about 290 mg, or about 300 mg per dose for a subject by any route of administration.

Combination Therapies

A pharmaceutical composition provided herein can be administered in conjunction with other therapies, for example, chemotherapy, radiation, surgery, anti-inflammatory agents, or vitamins. The other agents can be administered prior to, after, or concomitantly with the pharmaceutical composition.

In some embodiments, a compound or antibody described herein can be used singly or in combination with one or more therapeutic agents as a component of mixtures.

In some embodiments, the disclosure provides co-administration of a multispecific compound or antibody targeting, for example, HPTP-β (VE-PTP) and VEGF, with one or more additional anti-VEGF agents, which can stabilize the vasculature against neovascularization. In some embodiments, co-administration of the multispecific compound or antibody with one or more additional anti-VEGF agents can stabilize the vasculature against leakage. An anti-VEGF agent can be a compound, a recombinant protein, an antibody, an antigen-binding fragment, variant, or derivative thereof (e.g., a scFv), a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors, e.g. VEGF receptors, or the VEGF-binding portions of human VEGF receptors 1 and 2.

Non-limiting examples of anti-VEGF agents include bevacizumab (Avastin®), ranibizumab (Lucentis®), aflibercept (Eylea®), conbercept, brolucizumab, RTH258, VEGF receptor tyrosine kinase inhibitors such as sorafenib, sunitinib, axitinib, pazopanib, vandetinib, cabozantinib, regorafenib, and 4-(4-bromo-2-fluoroanilino)-6-methoxy-7-(1-methylpiperidin-4-ylmethoxy)quinazoline (ZD6474), VEGF variants, soluble VEGF receptor fragments or traps, aptamers capable of blocking VEGF or VEGFR (e.g. Pegaptanib), neutralizing anti-VEGFR antibodies or fragments thereof (e.g., ramucirumab, p1C11, 1121, 1121B), anti-KDR antibodies, anti-flt1 antibodies, low molecular weight inhibitors of VEGFR tyrosine kinases, DARPins that bind VEGF (e.g., abicipar, MP0112, MP0250), proteins comprising one or more designed ankyrin repeats that bind VEGF, adnectins (e.g., CT-322), anticalins (e.g., PRS-050), collagen IV-derived biomimetic peptides (e.g., AXT-107)

Further non-limiting examples of VEGF-modulating agents include anti-inflammatory agents, for example, dexamethasone, fluocinolone, and triamcinolone. The multispecific compound or antibody targeting, for example, HPTP-β (VE-PTP) and VEGF, can be administered in combination with any additional anti-VEGF agent in any combination, for example, at the beginning of treatment, at any time during treatment, or at any time after treatment with the additional anti-VEGF agent has concluded. In addition, the dosage of the multispecific compound or antibody can be adjusted during treatment. Also, the dosage of the additional anti-VEGF agent can be adjusted during treatment. The multispecific compound or antibody can be administered, for example, monthly, once every 3 months, once every 6 months, or yearly, wherein the additional anti-VEGF agent is administered at any frequency between treatments. Also disclosed herein are methods for treating a disease or condition as disclosed herein. The method comprises administering to a subject:

a) a therapeutically-effective amount of a multispecific compound or antibody targeting, for example, HPTP-β (VE-PTP) and VEGF; and b) a therapeutically-effective amount of an additional anti-VEGF agent;

wherein the administration of the multispecific compound or antibody and the additional anti-VEGF agent can be conducted as described herein.

In some embodiments, the disclosure provides co-administration of a multispecific compound or antibody targeting, for example, HPTP-β (VE-PTP) and VEGF, with one or more additional anti-HPTP-β (VE-PTP) agents, which can stabilize the vasculature against neovascularization. In some embodiments, co-administration of the multispecific compound or antibody with one or more additional anti-HPTP-β (VE-PTP) agents can stabilize the vasculature against leakage. An anti-HPTP-β (VE-PTP) agent can be a compound, a recombinant protein, an antibody, an antigen-binding fragment, variant, or derivative thereof (e.g., a scFv), a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors. In some embodiments, the additional anti-HPTP-β (VE-PTP) agent(s) can activate Tie2 signaling by promoting protein phosphorylation, such as phosphorylation of the Tie2 protein. In some embodiments, the additional anti-HPTP-β (VE-PTP) agent(s) can bind to HPTP-β (VE-PTP).

The multispecific compound or antibody targeting, for example, HPTP-β (VE-PTP) and VEGF, can be administered in combination with any additional anti-HPTP-β (VE-PTP) agent in any combination, for example, at the beginning of treatment, at any time during treatment, or at any time after treatment with the additional anti-HPTP-β (VE-PTP) agent has concluded. The dosage of the multispecific compound or antibody can be adjusted during treatment. The dosage of the additional anti-HPTP-β (VE-PTP) agent can be adjusted during treatment. The multispecific compound or antibody can be administered, for example, monthly, once every 3 months, once every 6 months, or yearly, wherein the additional anti-HPTP-β (VE-PTP) agent is administered at any frequency between treatments. Also disclosed herein are methods for treating a disease or condition as disclosed herein. The method comprises administering to a subject:
- a) a therapeutically-effective amount of a multispecific compound or antibody targeting, for example, HPTP-β (VE-PTP) and VEGF; and
- b) a therapeutically-effective amount of an additional anti-HPTP-β (VE-PTP) agent;

wherein the administration of the multispecific compound or antibody and the additional anti-HPTP-β (VE-PTP) agent can be conducted as described herein.

In some embodiments, the disclosure provides co-administration of a multispecific compound or antibody targeting, for example, HPTP-β (VE-PTP) and VEGF, with one or more additional Tie2 receptor activating compounds. An additional Tie2 receptor activating compound can be, for example, an angiopoietin 1 recombinant protein, an Ang1 mimetic, a Tie2 agonist, a peptide, a HPTP-β (VE-PTP) phosphatase inhibitor, a Tie2-peptomimetic, a tetrameric polyethylene oxide clustered peptide, a collagen IV-biomimetic peptide, a compound, a recombinant protein, an antibody, an antigen-binding fragment, variant, or derivative thereof (e.g., an scFv), an affinibody, an avimer, an adnectin, a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors. In some embodiments, the one or more additional Tie2 receptor activating compounds are small molecules. In some embodiments, the one or more additional Tie2 receptor activating compounds improve drainage through ocular lymphatics, Schlemm's canal, or corneal limbal lymphatics. In some embodiments, the one or more additional Tie2 receptor activating compounds are administered as eye drops. In some embodiments, the one or more additional Tie2 receptor activating compounds are administered to treat primary open angle glaucoma, age-related macular degeneration, cardiovascular disease, or cystic kidney disease. In some embodiments, the one or more additional Tie2 receptor activating compounds can be, for example, MAN-01, AXT-107, or vasculotide. In some embodiments, a compound disclosed herein can be co-administered with, for example, MAN-01, AXT-107, or vasculotide.

The multispecific compound or antibody targeting, for example, HPTP-β (VE-PTP) and VEGF, can be administered in combination with any additional Tie2 receptor activating compound in any combination, for example, at the beginning of treatment, at any time during treatment, or at any time after treatment with the additional Tie2 receptor activating compound has concluded. The dosage of the multispecific compound or antibody can be adjusted during treatment. The dosage of the additional Tie2 receptor activating compound can be adjusted during treatment. The multispecific compound or antibody can be administered, for example, monthly, once every 3 months, once every 6 months, or yearly, wherein the additional Tie2 receptor activating compound is administered at any frequency between treatments with the multispecific compound or antibody. Also disclosed herein are methods for treating a disease or condition as disclosed herein. The method comprises administering to a subject:
- a) a therapeutically-effective amount of a multispecific compound or antibody targeting, for example, HPTP-β (VE-PTP) and VEGF; and
- b) a therapeutically-effective amount of a Tie2 activator;

wherein the administration of the multispecific compound or antibody and the additional Tie2 receptor activating compound can be conducted as described herein.

Mouse Models
Oxygen-Induced Ischemic Retinopathy Model

The oxygen-induced ischemic retinopathy model can be considered to mimic aspects of proliferative retinal neovascularization and proliferative diabetic retinopathy. One week old mice can be placed in an airtight chamber and exposed to hyperoxia (75±3% oxygen) for five days, resulting in hyperoxia-induced neovascularization, for example, at the junction between the vascularized and avascular retina between postnatal day 17 and 21. Mice can be dosed with a compound of interest, for example, an antibody or compound of the disclosure, to determine the effect on neovascularization and/or vascular leakage. Neovascularization and/or vascular leakage can be assessed as described below.

Rho/VEGF Mouse Model

The Rho/VEGF mouse model can mimic aspects of neovascular age-related macular degeneration. Transgenic mice with vascular endothelial growth factor (VEGF) expression driven by the rhodopsin promoter (rho/VEGF mice) can develop retinal neovascularization, retinal angiomatous proliferation, and retinal vascular leakage. In rho/VEGF mice, VEGF expression in photoreceptors can begin between postnatal days 5 and 10, the period when the deep capillary bed is developing. Neovascularization can originate from the deep capillary bed of the retina and grow into the subretinal space. Mice can be dosed with a compound of interest, for example, an antibody or compound of the disclosure, to determine the effect on neovascularization and/or vascular leakage. Neovascularization and/or vascular leakage can be assessed as described below.

Tet/Opsin/VEGF Mouse Model

Mice with a VEGF under the control of a reverse tetracycline transactivator (rtTA) inducible promoter coupled to the rhodopsin promoter (Tet/opsin/VEGF mice) can be used as an inducible model of neovascularization, retinal vascular leakage, and retinal detachment. In these mice, VEGF transgene expression in the retina can be induced by administering doxycycline. Neovascularization can be evident by three to four days after VEGF induction. Neovascularization can be more extensive, and can cause outer retinal folds followed by total retinal detachment within about five days. Mice can be dosed with a compound of interest, for example, an antibody or compound of the disclosure, to determine the effect on neovascularization, vascular leakage, and/or retinal detachment. Neovascularization and/or vascular leakage can be assessed as described below. To assess retinal detachment, eyes can be frozen in cutting temperature embedding solution, ten micron sections cut through the entire eye, and sections stained with Hoechst. Sections can be examined by light microscopy, the mean length of the retinal detachment per section measured by image analysis, and the detached percentage of the retina calculated.

Tet/Opsin/Ang2 Mouse Model

Tet/opsin/Ang2 mice have inducible expression of Ang2 in the retina. These mice can be used to study the impact of Ang2 expression in various experimental conditions. For example, Tet/opsin/Ang2 mice can be used to determine the effect of Ang2 expression on neovascularization when VEGF levels are high versus low, or the effect of Ang2 expression in the oxygen induced ischemic retinopathy model. Mice can be dosed with a compound of interest, for example, an antibody or compound of the disclosure, to determine the impact of Ang2 expression on therapeutic efficacy.

Laser-Induced Choroidal Neovascularization Model

The laser-induced choroidal neovascularization model can be considered to mimic aspects of neovascular age-related macular degeneration. Anesthetized mice can have their pupils dilated, and burns can be delivered, for example, to the retina by a krypton laser using a slit lamp system and a cover glass as a contact lens. Multiple burns can be produced in a single eye, for example, burns in three locations per eye. Burns can cause rupture of Bruch's membrane. Choroidal neovascularization can be assessed at various time points after laser treatment, for example, one week, two weeks, or four weeks after laser treatment. Mice can be dosed with a compound of interest, for example, an antibody or compound of the disclosure, to determine the effect on neovascularization. Eyecups can be stained with FITC-labeled GSA, choroids flat mounted, and the area of choroidal neovascularization at each Bruch's membrane rupture site measured with fluorescence microscopy and image analysis. Neovascularization and/or vascular leakage can also be assessed as described below.

Assessment of Neovascularization

Neovascularization can be assessed using a range of techniques.

Fluorescein angiograms can be done by taking serial fundus photographs after injection of a dye to reveal blood vessels, allowing identification of the presence, location, and size of a neovascular complex. For example, an intraperitoneal injection of 0.3 mL of 1% fluorescein sodium can be given, serial fundus photographs taken, and the choroidal neovascularization area, total lesion area, and leakage area can be measured.

Eyes can be processed for evaluation by fluorescent, light, or electron microscopy. For example, mice can be perfused with fluorescently labelled dextran, or eyes can be injected with GSA or antibodies targeting PECAM. Eyes can be processed for observation under a fluorescent microscope, and the extent of neovascularization can be quantified, for example, by quantifying the area of neovascularization per retina, by quantifying the area of neovascularization at each Bruch's membrane rupture site, or by quantifying the number of nuclei of new vessels extending from the retina into the vitreous.

The area of retinal neovascularization can be determined, for example, using FITC-labeled GSA lectin and fluorescence microscopy. Eyes can be fixed in 10% formalin, dissected intact, washed with PBS, blocked in 8% swine serum, and stained with FITC-labeled GSA lectin for a time appropriate to stain retinal neovascularization and hyaloid vessels, but not normal retinal vessels (e.g., 40-50 minutes). Retinas can be flat mounted, digital images can be obtained with a fluorescent microscope and merged into a single image of the entire retina. Software can be used to measure the area of neovascularization per retina.

The area of subretinal neovascularization can be determined, for example, using FITC-labeled GSA lectin and fluorescence microscopy. Eyes can be fixed in 10% formalin, and retinas can be dissected, blocked with 5% swine serum, stained with FITC-conjugated GSA for two hours to stain vascular cells, and flat mounted with the photoreceptor side up. The area of subretinal neovascularization can be measured with fluorescence microscopy and image analysis.

Assessment of Retinal Vascular Leakage

Retinal vascular leakage can be assessed by measuring extravasated serum albumin using an immunofluorescent technique. For example, eyes can be fixed in 10% formalin, retinas can be dissected, washed, blocked, and stained using an anti-albumin antibody and a fluorescently-conjugated secondary antibody. The vessels can be labeled by counterstaining with GSA lectin, and retinas flat mounted. Retinas can be examined by fluorescence microscopy, and the area of albumin staining determined by image analysis. Retinal vascular leakage is relevant to, for example, diabetic macular edema and macular edema due to retinal vein occlusion.

Miles Assay for Vascular Leakage

The Miles assay can be used to assess vascular leakage in dermal subcutaneous blood vessels. Evans blue is a dye that binds albumin. Under physiologic conditions the endothelium is impermeable to albumin, so Evans blue bound albumin remains restricted within blood vessels. In pathologic conditions that promote increased vascular permeability, endothelial cells partially lose close contacts. The endothelium becomes permeable to small proteins such as albumin. Mice can be injected intravenously with 1% Evans blue dye in PBS, and injected intradermally with VEGF. Thirty minutes after intradermal injections, tissue at the intradermal injection sites can be excised and extracted in formamide to assess Evans blue dye extravasation. Vascular leakage can be quantified by measurement of the dye incorporated per milligram of tissue, for example, using optical density measurements and a standard curve. Mice can be dosed with a compound of interest, for example, an antibody or compound of the disclosure, to determine the effect on vascular leakage.

Cancer Models

The efficacy of a compound or antibody of the disclosure as a treatment for cancer can be tested in a range of cancer models. In some cancer models, cancer cells from a cell line can be implanted in a recipient animal, for example, a mouse. Non-limiting examples of suitable mouse strains include C57BL6, BALB/C, C3H, FVB/N, and FVB/N-Tg (IMTV-PyVT)634Mul. Non-limiting examples of suitable cancer cell lines include 4T1, E0771, and P0008. Cells of the 4T1 or E0771 cell lines can, for example, be implanted into a mammary pad as a model of breast cancer. 4T1 or E0771 cells can be implanted, for example, into the third mammary fat pad of female nude mice.

The size of solid tumors can be measured with calipers and tumor volume calculated. Tumors can be processed for histopathological evaluation or fluorescence microscopy, to assess, for example, tumor area, tumor grade, metastases count, metastases area, the number of cell nuclei per tumor focus, intratumoral vessel diameter, intratumoral vessel density, tumor vascular maturity, perivascular cell coverage, proximity between perivascular cells and endothelial cells, or to grade tumors foci as intravascular or extravascular.

Spontaneous metastasis models can be used to study the effects of a compound or antibody of the disclosure on metastasis. After tumor implant, a primary tumor can be resected (e.g., upon reaching 5 mm in size), and the animal later evaluated macroscopically or histopathologically for metastases, for example, to determine the number and size of metastases in the lungs, liver, lymph nodes, and bones.

To evaluate the impact of vessel stability on metastasis, a model can be used wherein tumor cells can be injected intravenously, and the animal subsequently evaluated for intravascular versus extravasated metastases. For example, 4T-1 cells can be injected intravenously, and the lungs processed for histopathologic evaluation to quantify intravascular versus extravascular metastases.

Metastases can be counted and measured macroscopically, for example, by immersing lungs in Bouin's solution, then examining them with a stereomicroscope.

To measure tumor vessel permeability in vivo, intravital multiphoton microscopy can be used. Animals can be injected with fluorescently labeled bovine serum albumin, for example, pre-treatment and post-treatment time points. At each time point, two distinct regions within the tumor can be selected and a 200 micron image stack recording BSA fluorescence taken through each region every ten minutes for an hour, using a multiphoton laser scanning microscope. The analysis approach can involve three-dimensional vessel tracing to create vessel metrics and a three-dimensional map of voxel intensity versus distance to the nearest vessel over time. Images can be corrected for sample movement over time with three-dimensional image registration. The normalized transvascular flux can be calculated.

Illustrative CDR Combinations

In some embodiments, an antibody or compound of this disclosure comprises a HCDR1. In some embodiments, an antibody or compound of this disclosure comprises a HCDR2. In some embodiments, an antibody or compound of this disclosure comprises a HCDR3. In some embodiments, an antibody or compound of this disclosure comprises a LCDR1. In some embodiments, an antibody or compound of this disclosure comprises a LCDR2. In some embodiments, an antibody or compound of this disclosure comprises a LCDR3.

In some embodiments, an antibody or compound of this disclosure comprises a HCDR1 and a HCDR2. In some embodiments, an antibody or compound of this disclosure comprises a HCDR1 and a HCDR3. In some embodiments, an antibody or compound of this disclosure comprises a HCDR1 and a LCDR1. In some embodiments, an antibody or compound of this disclosure comprises a HCDR1 and a LCDR2. In some embodiments, an antibody or compound of this disclosure comprises a HCDR1 and a LCDR3. In some embodiments, an antibody or compound of this disclosure comprises a HCDR2 and a HCDR3. In some embodiments, an antibody or compound of this disclosure comprises a HCDR2 and a LCDR1. In some embodiments, an antibody or compound of this disclosure comprises a HCDR2 and a LCDR2. In some embodiments, an antibody or compound of this disclosure comprises a HCDR2 and a LCDR3. In some embodiments, an antibody or compound of this disclosure comprises a HCDR3 and a LCDR1. In some embodiments, an antibody or compound of this disclosure comprises a HCDR3 and a LCDR2. In some embodiments, an antibody or compound of this disclosure comprises a HCDR3 and a LCDR3. In some embodiments, an antibody or compound of this disclosure comprises a LCDR1 and a LCDR2. In some embodiments, an antibody or compound of this disclosure comprises a LCDR1 and a LCDR3. In some embodiments, an antibody or compound of this disclosure comprises a LCDR2 and a LCDR3.

In some embodiments, an antibody or compound of this disclosure comprises a HCDR1, a HCDR2, and a HCDR3. In some embodiments, an antibody or compound of this disclosure comprises a HCDR1, a HCDR2, and a LCDR1. In some embodiments, an antibody or compound of this disclosure comprises a HCDR1, a HCDR2, and a LCDR2. In some embodiments, an antibody or compound of this disclosure comprises a HCDR1, a HCDR2, and a LCDR3. In some embodiments, an antibody or compound of this disclosure comprises a HCDR1, a HCDR3, and a LCDR1. In some embodiments, an antibody or compound of this disclosure comprises a HCDR1, a HCDR3, and a LCDR2. In some embodiments, an antibody or compound of this disclosure comprises a HCDR1, a HCDR3, and a LCDR3. In some embodiments, an antibody or compound of this disclosure comprises a HCDR1, a LCDR1, and a LCDR2. In some embodiments, an antibody or compound of this disclosure comprises a HCDR1, a LCDR1, and a LCDR3. In some embodiments, an antibody or compound of this disclosure comprises a HCDR1, a LCDR2, and a LCDR3. In some embodiments, an antibody or compound of this disclosure comprises a HCDR2, a HCDR3, and a LCDR1. In some embodiments, an antibody or compound of this disclosure comprises a HCDR2, a HCDR3, and a LCDR2. In some embodiments, an antibody or compound of this disclosure comprises a HCDR2, a HCDR3, and a LCDR3. In some embodiments, an antibody or compound of this disclosure comprises a HCDR2, a LCDR1, and a LCDR2. In some embodiments, an antibody or compound of this disclosure comprises a HCDR2, a LCDR1, and a LCDR3. In some embodiments, an antibody or compound of this disclosure comprises a HCDR2, a LCDR2, and a LCDR3. In some embodiments, an antibody or compound of this disclosure comprises a HCDR3, a LCDR1, and a LCDR2. In some embodiments, an antibody or compound of this disclosure comprises a HCDR3, a LCDR1, and a LCDR3. In some embodiments, an antibody or compound of this disclosure comprises a HCDR3, a LCDR2, and a LCDR3. In some embodiments, an antibody or compound of this disclosure comprises a LCDR1, a LCDR2, and a LCDR3.

In some embodiments, an antibody or compound of this disclosure comprises a HCDR1, a HCDR2, a HCDR3, and a LCDR1. In some embodiments, an antibody or compound of this disclosure comprises a HCDR1, a HCDR2, a HCDR3, and a LCDR2. In some embodiments, an antibody or compound of this disclosure comprises a HCDR1, a HCDR2, a HCDR3, and a LCDR3. In some embodiments, an antibody or compound of this disclosure comprises a HCDR1, a HCDR2, a LCDR1, and a LCDR2. In some embodiments, an antibody or compound of this disclosure comprises a HCDR1, a HCDR2, a LCDR1, and a LCDR3. In some embodiments, an antibody or compound of this disclosure comprises a HCDR1, a HCDR2, a LCDR2, and a LCDR3. In some embodiments, an antibody or compound of this disclosure comprises a HCDR1, a HCDR3, a LCDR1, and a LCDR2. In some embodiments, an antibody or compound of this disclosure comprises a HCDR1, a HCDR3, a LCDR1, and a LCDR3. In some embodiments, an antibody or compound of this disclosure comprises a HCDR1, a HCDR3, a LCDR2, and a LCDR3. In some embodiments, an antibody or compound of this disclosure comprises a HCDR1, a LCDR1, a LCDR2, and a LCDR3. In some embodiments, an antibody or compound of this disclosure comprises a HCDR2, a HCDR3, a LCDR1, and a LCDR2. In some embodiments, an antibody or compound of this disclosure comprises a HCDR2, a HCDR3, a LCDR1, and a LCDR3. In some embodiments, an antibody or compound of this disclosure comprises a HCDR2, a HCDR3, a LCDR2, and a LCDR3. In some embodiments, an antibody or compound of this disclosure comprises a HCDR2, a LCDR1, a LCDR2, and a LCDR3. In some embodiments, an antibody or compound of this disclosure comprises a HCDR3, a LCDR1, a LCDR2, and a LCDR3.

In some embodiments, an antibody or compound of this disclosure comprises a HCDR1, a HCDR2, a HCDR3, a LCDR1, and a LCDR2. In some embodiments, an antibody or compound of this disclosure comprises a HCDR1, a HCDR2, a HCDR3, a LCDR1, and a LCDR3. In some embodiments, an antibody or compound of this disclosure comprises a HCDR1, a HCDR2, a HCDR3, a LCDR2, and a LCDR3. In some embodiments, an antibody or compound of this disclosure comprises a HCDR1, a HCDR2, a LCDR1, a LCDR2, and a LCDR3. In some embodiments, an antibody or compound of this disclosure comprises a HCDR1, a HCDR3, a LCDR1, a LCDR2, and a LCDR3. In some embodiments, an antibody or compound of this disclosure comprises a HCDR2, a HCDR3, a LCDR1, a LCDR2, and a LCDR3.

In some embodiments, an antibody or compound of this disclosure comprises a HCDR1, a HCDR2, a HCDR3, a LCDR1, a LCDR2, and a LCDR3.

In some embodiments, an antibody or compound of this disclosure comprises any one of SEQ ID NOS: 76-80. In some embodiments, an antibody or compound of this disclosure comprises any one of SEQ ID NOS: 81-87. In some embodiments, an antibody or compound of this disclosure comprises any one of SEQ ID NOS: 88-90. In some embodiments, an antibody or compound of this disclosure comprises any one of SEQ ID NOS: 91-93. In some embodiments, an antibody or compound of this disclosure comprises any one of SEQ ID NOS: 94-96. In some embodiments, an antibody or compound of this disclosure comprises any one of SEQ ID NOS: 97-98.

In some embodiments, an antibody or compound of this disclosure comprises any one of SEQ ID NOS: 76-80 and any one of SEQ ID NOS: 81-87. In some embodiments, an antibody or compound of this disclosure comprises any one of SEQ ID NOS: 76-80 and any one of SEQ ID NOS: 88-90. In some embodiments, an antibody or compound of this disclosure comprises any one of SEQ ID NOS: 76-80 and any one of SEQ ID NOS: 91-93. In some embodiments, an antibody or compound of this disclosure comprises any one of SEQ ID NOS: 76-80 and any one of SEQ ID NOS: 94-96. In some embodiments, an antibody or compound of this disclosure comprises any one of SEQ ID NOS: 76-80 and any one of SEQ ID NOS: 97-98. In some embodiments, an antibody or compound of this disclosure comprises any one of SEQ ID NOS: 81-87 and any one of SEQ ID NOS: 88-90. In some embodiments, an antibody or compound of this disclosure comprises any one of SEQ ID NOS: 81-87 and any one of SEQ ID NOS: 91-93. In some embodiments, an antibody or compound of this disclosure comprises any one of SEQ ID NOS: 81-87 and any one of SEQ ID NOS: 94-96. In some embodiments, an antibody or compound of this disclosure comprises any one of SEQ ID NOS: 81-87 and any one of SEQ ID NOS: 97-98. In some embodiments, an antibody or compound of this disclosure comprises any one of SEQ ID NOS: 88-90 and any one of SEQ ID NOS: 91-93. In some embodiments, an antibody or compound of this disclosure comprises any one of SEQ ID NOS: 88-90 and any one of SEQ ID NOS: 94-96. In some embodiments, an antibody or compound of this disclosure comprises any one of SEQ ID NOS: 88-90 and any one of SEQ ID NOS: 97-98. In some embodiments, an antibody or compound of this disclosure comprises any one of SEQ ID NOS: 91-93 and any one of SEQ ID NOS: 94-96. In some embodiments, an antibody or compound of this disclosure comprises any one of SEQ ID NOS: 91-93 and any one of SEQ ID NOS: 97-98. In some embodiments, an antibody or compound of this disclosure comprises any one of SEQ ID NOS: 94-96 and any one of SEQ ID NOS: 97-98.

In some embodiments, an antibody or compound of this disclosure comprises any one of SEQ ID NOS: 76-80, any one of SEQ ID NOS: 81-87, and any one of SEQ ID NOS: 88-90. In some embodiments, an antibody or compound of this disclosure comprises any one of SEQ ID NOS: 76-80, any one of SEQ ID NOS: 81-87, and any one of SEQ ID NOS: 91-93. In some embodiments, an antibody or compound of this disclosure comprises any one of SEQ ID NOS: 76-80, any one of SEQ ID NOS: 81-87, and any one of SEQ ID NOS: 94-96. In some embodiments, an antibody or compound of this disclosure comprises any one of SEQ ID NOS: 76-80, any one of SEQ ID NOS: 81-87, and any one of SEQ ID NOS: 97-98. In some embodiments, an antibody or compound of this disclosure comprises any one of SEQ ID NOS: 76-80, any one of SEQ ID NOS: 88-90, and any one of SEQ ID NOS: 91-93. In some embodiments, an antibody or compound of this disclosure comprises any one of SEQ ID NOS: 76-80, any one of SEQ ID NOS: 88-90, and any one of SEQ ID NOS: 94-96. In some embodiments, an antibody or compound of this disclosure comprises any one of SEQ ID NOS: 76-80, any one of SEQ ID NOS: 88-90, and any one of SEQ ID NOS: 97-98. In some embodiments, an antibody or compound of this disclosure comprises any one of SEQ ID NOS: 76-80, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, and any one of SEQ ID NOS: 91-93. In some embodiments, an antibody or compound of this disclosure comprises any one of SEQ ID NOS: 81-87, any one of SEQ ID NOS: 88-90, and any one of SEQ ID NOS: 94-96. In some embodiments, an antibody or compound of this disclosure comprises any one of SEQ ID NOS: 81-87, any one of SEQ ID NOS: 88-90, and any one of SEQ ID NOS: 97-98. In some embodiments, an antibody or compound of this disclosure comprises any one of SEQ ID NOS: 81-87, any one of SEQ ID NOS: 91-93, and any one of SEQ ID NOS: 94-96. In some embodiments, an antibody or compound of this disclosure comprises any one of SEQ ID NOS: 81-87, any one of SEQ ID NOS: 91-93, and any one of SEQ ID NOS: 97-98. In some embodiments, an antibody or compound of this disclosure comprises any one of SEQ ID NOS: 81-87, any one of SEQ ID NOS: 94-96, and any one of SEQ ID NOS: 97-98. In some embodiments, an antibody or compound of this disclosure comprises any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 91-93. In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 81-87, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises SEQ ID NO: 76. In some embodiments, an antibody or compound of this disclosure comprises SEQ ID NO: 81. In some embodiments, an antibody or compound of this disclosure comprises SEQ ID NO: 88. In some embodiments, an antibody or compound of this disclosure comprises SEQ ID NO: 91. In some embodiments, an antibody or compound of this disclosure comprises SEQ ID NO: 94. In some embodiments, an antibody or compound of this disclosure comprises SEQ ID NO: 97. In some embodiments, an antibody or compound of this disclosure comprises SEQ ID NO: 77. In some embodiments, an antibody or compound of this disclosure comprises SEQ ID NO: 82.

In some embodiments, an antibody or compound of this disclosure comprises SEQ ID NO: 76 and SEQ ID NO: 81. In some embodiments, an antibody or compound of this disclosure comprises SEQ ID NO: 76 and SEQ ID NO: 88. In some embodiments, an antibody or compound of this disclosure comprises SEQ ID NO: 76 and SEQ ID NO: 91. In some embodiments, an antibody or compound of this disclosure comprises SEQ ID NO: 76 and SEQ ID NO: 94. In some embodiments, an antibody or compound of this disclosure comprises SEQ ID NO: 76 and SEQ ID NO: 97. In some embodiments, an antibody or compound of this disclosure comprises SEQ ID NO: 81 and SEQ ID NO: 88. In some embodiments, an antibody or compound of this disclosure comprises SEQ ID NO: 81 and SEQ ID NO: 91. In some embodiments, an antibody or compound of this disclosure comprises SEQ ID NO: 81 and SEQ ID NO: 94. In some embodiments, an antibody or compound of this disclosure comprises SEQ ID NO: 81 and SEQ ID NO: 97. In some embodiments, an antibody or compound of this disclosure comprises SEQ ID NO: 88 and SEQ ID NO: 91. In some embodiments, an antibody or compound of this disclosure comprises SEQ ID NO: 88 and SEQ ID NO: 94. In some embodiments, an antibody or compound of this disclosure comprises SEQ ID NO: 88 and SEQ ID NO: 97. In some embodiments, an antibody or compound of this disclosure comprises SEQ ID NO: 91 and SEQ ID NO: 94. In some embodiments, an antibody or compound of this disclosure comprises SEQ ID NO: 91 and SEQ ID NO: 97. In some embodiments, an antibody or compound of this disclosure comprises SEQ ID NO: 94 and SEQ ID NO: 97. In some embodiments, an antibody or compound of this disclosure comprises SEQ ID NO: 77 and SEQ ID NO: 82. In some embodiments, an antibody or compound of this disclosure comprises SEQ ID NO: 77 and SEQ ID NO: 88. In some embodiments, an antibody or compound of this disclosure comprises SEQ ID NO: 77 and SEQ ID NO: 91. In some embodiments, an antibody or compound of this disclosure comprises SEQ ID NO: 77 and SEQ ID NO: 94. In some embodiments, an antibody or compound of this disclosure comprises SEQ ID NO: 77 and SEQ ID NO: 97. In some embodiments, an antibody or compound of this disclosure comprises SEQ ID NO: 82 and SEQ ID NO: 88. In some embodiments, an antibody or compound of this disclosure comprises SEQ ID NO: 82 and SEQ ID NO: 91. In some embodiments, an antibody or compound of this disclosure comprises SEQ ID NO: 82 and SEQ ID NO: 94. In some embodiments, an antibody or compound of this disclosure comprises SEQ ID NO: 82 and SEQ ID NO: 97.

In some embodiments, an antibody or compound of this disclosure comprises SEQ ID NO: 76, SEQ ID NO: 81, and SEQ ID NO: 88. In some embodiments, an antibody or compound of this disclosure comprises SEQ ID NO: 76, SEQ ID NO: 81, and SEQ ID NO: 91. In some embodiments, an antibody or compound of this disclosure comprises SEQ ID NO: 76, SEQ ID NO: 81, and SEQ ID NO: 94. In some embodiments, an antibody or compound of this disclosure comprises SEQ ID NO: 76, SEQ ID NO: 81, and SEQ ID NO: 97. In some embodiments, an antibody or compound of this disclosure comprises SEQ ID NO: 76, SEQ ID NO: 88, and SEQ ID NO: 91. In some embodiments, an antibody or compound of this disclosure comprises SEQ ID NO: 76, SEQ ID NO: 88, and SEQ ID NO: 94. In some embodiments, an antibody or compound of this disclosure comprises SEQ ID NO: 76, SEQ ID NO: 88, and SEQ ID NO: 97. In some embodiments, an antibody or compound of this disclosure comprises SEQ ID NO: 76, SEQ ID NO: 91, and SEQ ID NO: 94. In some embodiments, an antibody or compound of this disclosure comprises SEQ ID NO: 76, SEQ ID NO: 91, and SEQ ID NO: 97. In some embodiments, an antibody or compound of this disclosure comprises SEQ ID NO: 76, SEQ ID NO: 94, and SEQ ID NO: 97. In some embodiments, an antibody or compound of this disclosure comprises SEQ ID NO: 81, SEQ ID NO: 88, and SEQ ID NO: 91. In some embodiments, an antibody or compound of this disclosure comprises SEQ ID NO: 81, SEQ ID NO: 88, and SEQ ID NO: 94. In some embodiments, an antibody or compound of this disclosure comprises SEQ ID NO: 81, SEQ ID NO: 88, and SEQ ID NO: 97. In some embodiments, an antibody or compound of this disclosure comprises SEQ ID NO: 81, SEQ ID NO: 91, and SEQ ID NO: 94. In some embodiments, an antibody or compound of this disclosure comprises SEQ ID NO: 81, SEQ ID NO: 91, and SEQ ID NO: 97. In some embodiments, an antibody or compound of this disclosure comprises SEQ ID NO: 81, SEQ ID NO: 94, and SEQ ID NO: 97. In some embodiments, an antibody or compound of this disclosure comprises SEQ ID NO: 88, SEQ ID NO: 91, and SEQ ID NO: 94. In some embodiments, an antibody or compound of this disclosure comprises SEQ ID NO: 88, SEQ ID NO: 91, and SEQ ID NO: 97. In some embodiments, an antibody or compound of this disclosure comprises SEQ ID NO: 88, SEQ ID NO: 94, and SEQ ID NO: 97. In some embodiments, an antibody or compound of this disclosure comprises SEQ ID NO: 91, SEQ ID NO: 94, and SEQ ID NO: 97. In some embodiments, an antibody or compound of this disclosure comprises SEQ ID NO: 77, SEQ ID NO: 82, and SEQ ID NO: 88. In some embodiments, an antibody or compound of this disclosure comprises SEQ ID NO: 77, SEQ ID NO: 82, and SEQ ID NO: 91. In some embodiments, an antibody or compound of this disclosure comprises SEQ ID NO: 77, SEQ ID NO: 82, and SEQ ID NO: 94. In some embodiments, an antibody or compound of this disclosure comprises SEQ ID NO: 77, SEQ ID NO: 82, and SEQ ID NO: 97. In some embodiments, an antibody or compound of this disclosure comprises SEQ ID NO: 77, SEQ ID NO: 88, and SEQ ID NO: 91. In some embodiments, an antibody or compound of this disclosure comprises SEQ ID NO: 77, SEQ ID NO: 88, and SEQ ID NO: 94. In some embodiments, an antibody or compound of this disclosure comprises SEQ ID NO: 77, SEQ ID NO: 88, and SEQ ID NO: 97. In some embodiments, an antibody or compound of this disclosure comprises SEQ ID NO: 77, SEQ ID NO: 91, and SEQ ID NO: 94. In some embodiments, an antibody or compound of this disclosure comprises SEQ ID NO: 77, SEQ ID NO: 91, and SEQ ID NO: 97. In some embodiments, an antibody or compound of this disclosure comprises SEQ ID NO: 77, SEQ ID NO: 94, and SEQ ID NO: 97. In some embodiments, an antibody or compound of this disclosure comprises SEQ ID NO: 82, SEQ ID NO: 88, and SEQ ID NO: 91. In some embodiments, an antibody or compound of this disclosure comprises SEQ ID NO: 82, SEQ ID NO: 88, and SEQ ID NO: 94. In some embodiments, an antibody or compound of this disclosure comprises SEQ ID NO: 82, SEQ ID NO: 88, and SEQ ID NO: 97. In some embodiments, an antibody or compound of this disclosure comprises SEQ ID NO: 82, SEQ ID NO: 91, and SEQ ID NO: 94. In some embodiments, an antibody or compound of this disclosure comprises SEQ ID NO: 82, SEQ ID NO: 91, and SEQ ID NO: 97. In some embodiments, an antibody or compound of this disclosure comprises SEQ ID NO: 82, SEQ ID NO: 94, and SEQ ID NO: 97.

In some embodiments, an antibody or compound of this disclosure comprises SEQ ID NO: 76, SEQ ID NO: 81, SEQ ID NO: 88, and SEQ ID NO: 91. In some embodiments, an antibody or compound of this disclosure comprises SEQ ID NO: 76, SEQ ID NO: 81, SEQ ID NO: 88, and SEQ ID NO: 94. In some embodiments, an antibody or compound of this disclosure comprises SEQ ID NO: 76, SEQ ID NO: 81, SEQ ID NO: 88, and SEQ ID NO: 97. In some embodiments, an antibody or compound of this disclosure comprises SEQ ID NO: 76, SEQ ID NO: 81, SEQ ID NO: 91, and SEQ ID NO: 94. In some embodiments, an antibody or compound of this disclosure comprises SEQ ID NO: 76, SEQ ID NO: 81, SEQ ID NO: 91, and SEQ ID NO: 97. In some embodiments, an antibody or compound of this disclosure comprises SEQ ID NO: 76, SEQ ID NO: 81, SEQ ID NO: 94, and SEQ ID NO: 97. In some embodiments, an antibody or compound of this disclosure comprises SEQ ID NO: 76, SEQ ID NO: 88, SEQ ID NO: 91, and SEQ ID NO: 94. In some embodiments, an antibody or compound of this disclosure comprises SEQ ID NO: 76, SEQ ID NO: 88, SEQ ID NO: 91, and SEQ ID NO: 97. In some embodiments, an antibody or compound of this disclosure comprises SEQ ID NO: 76, SEQ ID NO: 88, SEQ ID NO: 94, and SEQ ID NO: 97. In some embodiments, an antibody or compound of this disclosure comprises SEQ ID NO: 76, SEQ ID NO: 91, SEQ ID NO: 94, and SEQ ID NO: 97. In some embodiments, an antibody or compound of this disclosure comprises SEQ ID NO: 81, SEQ ID NO: 88, SEQ ID NO: 91, and SEQ ID NO: 94. In some embodiments, an antibody or compound of this disclosure comprises SEQ ID NO: 81, SEQ ID NO: 88, SEQ ID NO: 91, and SEQ ID NO: 97. In some embodiments, an antibody or compound of this disclosure comprises SEQ ID NO: 81, SEQ ID NO: 88, SEQ ID NO: 94, and SEQ ID NO: 97. In some embodiments, an antibody or compound of this disclosure comprises SEQ ID NO: 81, SEQ ID NO: 91, SEQ ID NO: 94, and SEQ ID NO: 97. In some embodiments, an antibody or compound of this disclosure comprises SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, and SEQ ID NO: 91. In some embodiments, an antibody or compound of this disclosure comprises SEQ ID NO: 77, SEQ ID NO: 82, SEQ ID NO: 88, and SEQ ID NO: 94. In some embodiments, an antibody or compound of this disclosure comprises SEQ ID NO: 77, SEQ ID NO: 82, SEQ ID NO: 88, and SEQ ID NO: 97. In some embodiments, an antibody or compound of this disclosure comprises SEQ ID NO: 77, SEQ ID NO: 82, SEQ ID NO: 91, and SEQ ID NO: 94. In some embodiments, an antibody or compound of this disclosure comprises SEQ ID NO: 77, SEQ ID NO: 82, SEQ ID NO: 91, and SEQ ID NO: 97. In some embodiments, an antibody or compound of this disclosure comprises SEQ ID NO: 77, SEQ ID NO: 82, SEQ ID NO: 94, and SEQ ID NO: 97. In some embodiments, an antibody or compound of this disclosure comprises SEQ ID NO: 77, SEQ ID NO: 88, SEQ ID NO: 91, and SEQ ID NO: 94. In some embodiments, an antibody or compound of this disclosure comprises SEQ ID NO: 77, SEQ ID NO: 88, SEQ ID NO: 91, and SEQ ID NO: 97. In some embodiments, an antibody or compound of this disclosure comprises SEQ ID NO: 77, SEQ ID NO: 88, SEQ ID NO: 94, and SEQ ID NO: 97. In some embodiments, an antibody or compound of this disclosure comprises SEQ ID NO: 77, SEQ ID NO: 91, SEQ ID NO: 94, and SEQ ID NO: 97. In some embodiments, an antibody or compound of this disclosure comprises SEQ ID NO: 82, SEQ ID NO: 88, SEQ ID NO: 91, and SEQ ID NO: 94. In some embodiments, an antibody or compound of this disclosure comprises SEQ ID NO: 82, SEQ ID NO: 88, SEQ ID NO: 91, and SEQ ID NO: 97. In some embodiments, an antibody or compound of this disclosure comprises SEQ ID NO: 82, SEQ ID NO: 88, SEQ ID NO: 94, and SEQ ID NO: 97. In some embodiments, an antibody or compound of this disclosure comprises SEQ ID NO: 82, SEQ ID NO: 91, SEQ ID NO: 94, and SEQ ID NO: 97. In some embodiments, an antibody or compound of this disclosure comprises SEQ ID NO: 88, SEQ ID NO: 91, SEQ ID NO: 94, and SEQ ID NO: 97.

In some embodiments, an antibody or compound of this disclosure comprises SEQ ID NO: 76, SEQ ID NO: 81, SEQ ID NO: 88, SEQ ID NO: 91, and SEQ ID NO: 94. In some embodiments, an antibody or compound of this disclosure comprises SEQ ID NO: 76, SEQ ID NO: 81, SEQ ID NO: 88, SEQ ID NO: 91, and SEQ ID NO: 97. In some embodiments, an antibody or compound of this disclosure comprises SEQ ID NO: 76, SEQ ID NO: 81, SEQ ID NO: 88, SEQ ID NO: 94, and SEQ ID NO: 97. In some embodiments, an antibody or compound of this disclosure comprises SEQ ID NO: 76, SEQ ID NO: 81, SEQ ID NO: 91, SEQ ID NO: 94, and SEQ ID NO: 97. In some embodiments, an antibody or compound of this disclosure comprises SEQ ID NO: 76, SEQ ID NO: 88, SEQ ID NO: 91, SEQ ID NO: 94, and SEQ ID NO: 97. In some embodiments, an antibody or compound of this disclosure comprises SEQ ID NO: 81, SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, SEQ ID NO: 91, and SEQ ID NO: 94. In some embodiments, an antibody or compound of this disclosure comprises SEQ ID NO: 77, SEQ ID NO: 82, SEQ ID NO: 88, SEQ ID NO: 91, and SEQ ID NO: 97. In some embodiments, an antibody or compound of this disclosure comprises SEQ ID NO: 77, SEQ ID NO: 82, SEQ ID NO: 88, SEQ ID NO: 94, and SEQ ID NO: 97. In some embodiments, an antibody or compound of this disclosure comprises SEQ ID NO: 77, SEQ ID NO: 82, SEQ ID NO: 91, SEQ ID NO: 94, and SEQ ID NO: 97. In some embodiments, an antibody or compound of this disclosure comprises SEQ ID NO: 82, SEQ ID NO: 88, SEQ ID NO: 91, SEQ ID NO: 94, and SEQ ID NO: 97.

In some embodiments, an antibody or compound of this disclosure comprises SEQ ID NO: 76, SEQ ID NO: 81, SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, SEQ ID NO: 91, SEQ ID NO: 94, and SEQ ID NO: 97.

In some embodiments, an antibody or compound of this disclosure comprises SEQ ID NO: 78. In some embodiments, an antibody or compound of this disclosure comprises SEQ ID NO: 83. In some embodiments, an antibody or compound of this disclosure comprises SEQ ID NO: 89. In some embodiments, an antibody or compound of this disclosure comprises SEQ ID NO: 92. In some embodiments, an antibody or compound of this disclosure comprises SEQ ID NO: 95. In some embodiments, an antibody or compound of this disclosure comprises SEQ ID NO: 97.

In some embodiments, an antibody or compound of this disclosure comprises SEQ ID NO: 78 and SEQ ID NO: 83. In some embodiments, an antibody or compound of this disclosure comprises SEQ ID NO: 78 and SEQ ID NO: 89. In some embodiments, an antibody or compound of this disclosure comprises SEQ ID NO: 78 and SEQ ID NO: 92. In some embodiments, an antibody or compound of this disclosure comprises SEQ ID NO: 78 and SEQ ID NO: 95. In some embodiments, an antibody or compound of this disclosure comprises SEQ ID NO: 78 and SEQ ID NO: 97. In some embodiments, an antibody or compound of this disclosure comprises SEQ ID NO: 83 and SEQ ID NO: 89. In some embodiments, an antibody or compound of this disclosure comprises SEQ ID NO: 83 and SEQ ID NO: 92. In some embodiments, an antibody or compound of this disclosure comprises SEQ ID NO: 83 and SEQ ID NO: 95. In some embodiments, an antibody or compound of this disclosure comprises SEQ ID NO: 83 and SEQ ID NO: 97. In some embodiments, an antibody or compound of this disclosure comprises SEQ ID NO: 89 and SEQ ID NO: 92. In some embodiments, an antibody or compound of this disclosure comprises SEQ ID NO: 89 and SEQ ID NO: 95. In some embodiments, an antibody or compound of this disclosure comprises SEQ ID NO: 89 and SEQ ID NO: 97. In some embodiments, an antibody or compound of this disclosure comprises SEQ ID NO: 92 and SEQ ID NO: 95. In some embodiments, an antibody or compound of this disclosure comprises SEQ ID NO: 92 and SEQ ID NO: 97. In some embodiments, an antibody or compound of this disclosure comprises SEQ ID NO: 95 and SEQ ID NO: 97.

In some embodiments, an antibody or compound of this disclosure comprises SEQ ID NO: 78, SEQ ID NO: 83, and SEQ ID NO: 89. In some embodiments, an antibody or compound of this disclosure comprises SEQ ID NO: 78, SEQ ID NO: 83, and SEQ ID NO: 92. In some embodiments, an antibody or compound of this disclosure comprises SEQ ID NO: 78, SEQ ID NO: 83, and SEQ ID NO: 95. In some embodiments, an antibody or compound of this disclosure comprises SEQ ID NO: 78, SEQ ID NO: 83, and SEQ ID NO: 97. In some embodiments, an antibody or compound of this disclosure comprises SEQ ID NO: 78, SEQ ID NO: 89, and SEQ ID NO: 92. In some embodiments, an antibody or compound of this disclosure comprises SEQ ID NO: 78, SEQ ID NO: 89, and SEQ ID NO: 95. In some embodiments, an antibody or compound of this disclosure comprises SEQ ID NO: 78, SEQ ID NO: 89, and SEQ ID NO: 97. In some embodiments, an antibody or compound of this disclosure comprises SEQ ID NO: 78, SEQ ID NO: 92, and SEQ ID NO: 95. In some embodiments, an antibody or compound of this disclosure comprises SEQ ID NO: 78, SEQ ID NO: 92, and SEQ ID NO: 97. In some embodiments, an antibody or compound of this disclosure comprises SEQ ID NO: 78, SEQ ID NO: 95, and SEQ ID NO: 97. In some embodiments, an antibody or compound of this disclosure comprises SEQ ID NO: 83, SEQ ID NO: 89, and SEQ ID NO: 92. In some embodiments, an antibody or compound of this disclosure comprises SEQ ID NO: 83, SEQ ID NO: 89, and SEQ ID NO: 95. In some embodiments, an antibody or compound of this disclosure comprises SEQ ID NO: 83, SEQ ID NO: 89, and SEQ ID NO: 97. In some embodiments, an antibody or compound of this disclosure comprises SEQ ID NO: 83, SEQ ID NO: 92, and SEQ ID NO: 95. In some embodiments, an antibody or compound of this disclosure comprises SEQ ID NO: 83, SEQ ID NO: 92, and SEQ ID NO: 97. In some embodiments, an antibody or compound of this disclosure comprises SEQ ID NO: 83, SEQ ID NO: 95, and SEQ ID NO: 97. In some embodiments, an antibody or compound of this disclosure comprises SEQ ID NO: 89, SEQ ID NO: 92, and SEQ ID NO: 95. In some embodiments, an antibody or compound of this disclosure comprises SEQ ID NO: 89, SEQ ID NO: 92, and SEQ ID NO: 97. In some embodiments, an antibody or compound of this disclosure comprises SEQ ID NO: 89, SEQ ID NO: 95, and SEQ ID NO: 97. In some embodiments, an antibody or compound of this disclosure comprises SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, and SEQ ID NO: 92. In some embodiments, an antibody or compound of this disclosure comprises SEQ ID NO: 78, SEQ ID NO: 83, SEQ ID NO: 89, and SEQ ID NO: 95. In some embodiments, an antibody or compound of this disclosure comprises SEQ ID NO: 78, SEQ ID NO: 83, SEQ ID NO: 89, and SEQ ID NO: 97. In some embodiments, an antibody or compound of this disclosure comprises SEQ ID NO: 78, SEQ ID NO: 83, SEQ ID NO: 92, and SEQ ID NO: 95. In some embodiments, an antibody or compound of this disclosure comprises SEQ ID NO: 78, SEQ ID NO: 83, SEQ ID NO: 92, and SEQ ID NO: 97. In some embodiments, an antibody or compound of this disclosure comprises SEQ ID NO: 78, SEQ ID NO: 83, SEQ ID NO: 95, and SEQ ID NO: 97. In some embodiments, an antibody or compound of this disclosure comprises SEQ ID NO: 78, SEQ ID NO: 89, SEQ ID NO: 92, and SEQ ID NO: 95. In some embodiments, an antibody or compound of this disclosure comprises SEQ ID NO: 78, SEQ ID NO: 89, SEQ ID NO: 92, and SEQ ID NO: 97. In some embodiments, an antibody or compound of this disclosure comprises SEQ ID NO: 78, SEQ ID NO: 89, SEQ ID NO: 95, and SEQ ID NO: 97. In some embodiments, an antibody or compound of this disclosure comprises SEQ ID NO: 78, SEQ ID NO: 92, SEQ ID NO: 95, and SEQ ID NO: 97. In some embodiments, an antibody or compound of this disclosure comprises SEQ ID NO: 83, SEQ ID NO: 89, SEQ ID NO: 92, and SEQ ID NO: 95. In some embodiments, an antibody or compound of this disclosure comprises SEQ ID NO: 83, SEQ ID NO: 89, SEQ ID NO: 92, and SEQ ID NO: 97. In some embodiments, an antibody or compound of this disclosure comprises SEQ ID NO: 83, SEQ ID NO: 89, SEQ ID NO: 95, and SEQ ID NO: 97. In some embodiments, an antibody or compound of this disclosure comprises SEQ ID NO: 83, SEQ ID NO: 92, SEQ ID NO: 95, and SEQ ID NO: 97. In some embodiments, an antibody or compound of this disclosure comprises SEQ ID NO: 89, SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, SEQ ID NO: 92, and SEQ ID NO: 95. In some embodiments, an antibody or compound of this disclosure comprises SEQ ID NO: 78, SEQ ID NO: 83, SEQ ID NO: 89, SEQ ID NO: 92, and SEQ ID NO: 97. In some embodiments, an antibody or compound of this disclosure comprises SEQ ID NO: 78, SEQ ID NO: 83, SEQ ID NO: 89, SEQ ID NO: 95, and SEQ ID NO: 97. In some embodiments, an antibody or compound of this disclosure comprises SEQ ID NO: 78, SEQ ID NO: 83, SEQ ID NO: 92, SEQ ID NO: 95, and SEQ ID NO: 97. In some embodiments, an antibody or compound of this disclosure comprises SEQ ID NO: 78, SEQ ID NO: 89, SEQ ID NO: 92, SEQ ID NO: 95, and SEQ ID NO: 97. In some embodiments, an antibody or compound of this disclosure comprises SEQ ID NO: 83, SEQ ID NO: 89, SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, SEQ ID NO: 92, SEQ ID NO: 95, and SEQ ID NO: 97.

In some embodiments, an antibody or compound of this disclosure comprises SEQ ID NO: 79. In some embodiments, an antibody or compound of this disclosure comprises SEQ ID NO: 84. In some embodiments, an antibody or compound of this disclosure comprises SEQ ID NO: 90. In some embodiments, an antibody or compound of this disclosure comprises SEQ ID NO: 93. In some embodiments, an antibody or compound of this disclosure comprises SEQ ID NO: 96. In some embodiments, an antibody or compound of this disclosure comprises SEQ ID NO: 98. In some embodiments, an antibody or compound of this disclosure comprises SEQ ID NO: 86.

In some embodiments, an antibody or compound of this disclosure comprises SEQ ID NO: 79 and SEQ ID NO: 84. In some embodiments, an antibody or compound of this disclosure comprises SEQ ID NO: 79 and SEQ ID NO: 90. In some embodiments, an antibody or compound of this disclosure comprises SEQ ID NO: 79 and SEQ ID NO: 93. In some embodiments, an antibody or compound of this disclosure comprises SEQ ID NO: 79 and SEQ ID NO: 96. In some embodiments, an antibody or compound of this disclosure comprises SEQ ID NO: 79 and SEQ ID NO: 98. In some embodiments, an antibody or compound of this disclosure comprises SEQ ID NO: 84 and SEQ ID NO: 90. In some embodiments, an antibody or compound of this disclosure comprises SEQ ID NO: 84 and SEQ ID NO: 93. In some embodiments, an antibody or compound of this disclosure comprises SEQ ID NO: 84 and SEQ ID NO: 96. In some embodiments, an antibody or compound of this disclosure comprises SEQ ID NO: 84 and SEQ ID NO: 98. In some embodiments, an antibody or compound of this disclosure comprises SEQ ID NO: 90 and SEQ ID NO: 93. In some embodiments, an antibody or compound of this disclosure comprises SEQ ID NO: 90 and SEQ ID NO: 96. In some embodiments, an antibody or compound of this disclosure comprises SEQ ID NO: 90 and SEQ ID NO: 98. In some embodiments, an antibody or compound of this disclosure comprises SEQ ID NO: 93 and SEQ ID NO: 96. In some embodiments, an antibody or compound of this disclosure comprises SEQ ID NO: 93 and SEQ ID NO: 98. In some embodiments, an antibody or compound of this disclosure comprises SEQ ID NO: 96 and SEQ ID NO: 98. In some embodiments, an antibody or compound of this disclosure comprises SEQ ID NO: 79 and SEQ ID NO: 86. In some embodiments, an antibody or compound of this disclosure comprises SEQ ID NO: 86 and SEQ ID NO: 90. In some embodiments, an antibody or compound of this disclosure comprises SEQ ID NO: 86 and SEQ ID NO: 93. In some embodiments, an antibody or compound of this disclosure comprises SEQ ID NO: 86 and SEQ ID NO: 96. In some embodiments, an antibody or compound of this disclosure comprises SEQ ID NO: 86 and SEQ ID NO: 98.

In some embodiments, an antibody or compound of this disclosure comprises SEQ ID NO: 79, SEQ ID NO: 84, and SEQ ID NO: 90. In some embodiments, an antibody or compound of this disclosure comprises SEQ ID NO: 79, SEQ ID NO: 84, and SEQ ID NO: 93. In some embodiments, an antibody or compound of this disclosure comprises SEQ ID NO: 79, SEQ ID NO: 84, and SEQ ID NO: 96. In some embodiments, an antibody or compound of this disclosure comprises SEQ ID NO: 79, SEQ ID NO: 84, and SEQ ID NO: 98. In some embodiments, an antibody or compound of this disclosure comprises SEQ ID NO: 79, SEQ ID NO: 90, and SEQ ID NO: 93. In some embodiments, an antibody or compound of this disclosure comprises SEQ ID NO: 79, SEQ ID NO: 90, and SEQ ID NO: 96. In some embodiments, an antibody or compound of this disclosure comprises SEQ ID NO: 79, SEQ ID NO: 90, and SEQ ID NO: 98. In some embodiments, an antibody or compound of this disclosure comprises SEQ ID NO: 79, SEQ ID NO: 93, and SEQ ID NO: 96. In some embodiments, an antibody or compound of this disclosure comprises SEQ ID NO: 79, SEQ ID NO: 93, and SEQ ID NO: 98. In some embodiments, an antibody or compound of this disclosure comprises SEQ ID NO: 79, SEQ ID NO: 96, and SEQ ID NO: 98. In some embodiments, an antibody or compound of this disclosure comprises SEQ ID NO: 84, SEQ ID NO: 90, and SEQ ID NO: 93. In some embodiments, an antibody or compound of this disclosure comprises SEQ ID NO: 84, SEQ ID NO: 90, and SEQ ID NO: 96. In some embodiments, an antibody or compound of this disclosure comprises SEQ ID NO: 84, SEQ ID NO: 90, and SEQ ID NO: 98. In some embodiments, an antibody or compound of this disclosure comprises SEQ ID NO: 84, SEQ ID NO: 93, and SEQ ID NO: 96. In some embodiments, an antibody or compound of this disclosure comprises SEQ ID NO: 84, SEQ ID NO: 93, and SEQ ID NO: 98. In some embodiments, an antibody or compound of this disclosure comprises SEQ ID NO: 84, SEQ ID NO: 96, and SEQ ID NO: 98. In some embodiments, an antibody or compound of this disclosure comprises SEQ ID NO: 90, SEQ ID NO: 93, and SEQ ID NO: 96. In some embodiments, an antibody or compound of this disclosure comprises SEQ ID NO: 90, SEQ ID NO: 93, and SEQ ID NO: 98. In some embodiments, an antibody or compound of this disclosure comprises SEQ ID NO: 90, SEQ ID NO: 96, and SEQ ID NO: 98. In some embodiments, an antibody or compound of this disclosure comprises SEQ ID NO: 93, SEQ ID NO: 96, and SEQ ID NO: 98. In some embodiments, an antibody or compound of this disclosure comprises SEQ ID NO: 79, SEQ ID NO: 86, and SEQ ID NO: 90. In some embodiments, an antibody or compound of this disclosure comprises SEQ ID NO: 79, SEQ ID NO: 86, and SEQ ID NO: 93. In some embodiments, an antibody or compound of this disclosure comprises SEQ ID NO: 79, SEQ ID NO: 86, and SEQ ID NO: 96. In some embodiments, an antibody or compound of this disclosure comprises SEQ ID NO: 79, SEQ ID NO: 86, and SEQ ID NO: 98. In some embodiments, an antibody or compound of this disclosure comprises SEQ ID NO: 86, SEQ ID NO: 90, and SEQ ID NO: 93. In some embodiments, an antibody or compound of this disclosure comprises SEQ ID NO: 86, SEQ ID NO: 90, and SEQ ID NO: 96. In some embodiments, an antibody or compound of this disclosure comprises SEQ ID NO: 86, SEQ ID NO: 90, and SEQ ID NO: 98. In some embodiments, an antibody or compound of this disclosure comprises SEQ ID NO: 86, SEQ ID NO: 93, and SEQ ID NO: 96. In some embodiments, an antibody or compound of this disclosure comprises SEQ ID NO: 86, SEQ ID NO: 93, and SEQ ID NO: 98. In some embodiments, an antibody or compound of this disclosure comprises SEQ ID NO: 86, SEQ ID NO: 96, and SEQ ID NO: 98.

In some embodiments, an antibody or compound of this disclosure comprises SEQ ID NO: 79, SEQ ID NO: 84, SEQ ID NO: 90, and SEQ ID NO: 93. In some embodiments, an antibody or compound of this disclosure comprises SEQ ID NO: 79, SEQ ID NO: 84, SEQ ID NO: 90, and SEQ ID NO: 96. In some embodiments, an antibody or compound of this disclosure comprises SEQ ID NO: 79, SEQ ID NO: 84, SEQ ID NO: 90, and SEQ ID NO: 98. In some embodiments, an antibody or compound of this disclosure comprises SEQ ID NO: 79, SEQ ID NO: 84, SEQ ID NO: 93, and SEQ ID NO: 96. In some embodiments, an antibody or compound of this disclosure comprises SEQ ID NO: 79, SEQ ID NO: 84, SEQ ID NO: 93, and SEQ ID NO: 98. In some embodiments, an antibody or compound of this disclosure comprises SEQ ID NO: 79, SEQ ID NO: 84, SEQ ID NO: 96, and SEQ ID NO: 98. In some embodiments, an antibody or compound of this disclosure comprises SEQ ID NO: 79, SEQ ID NO: 90, SEQ ID NO: 93, and SEQ ID NO: 96. In some embodiments, an antibody or compound of this disclosure comprises SEQ ID NO: 79, SEQ ID NO: 90, SEQ ID NO: 93, and SEQ ID NO: 98. In some embodiments, an antibody or compound of this disclosure comprises SEQ ID NO: 79, SEQ ID NO: 90, SEQ ID NO: 96, and SEQ ID NO: 98. In some embodiments, an antibody or compound of this disclosure comprises SEQ ID NO: 79, SEQ ID NO: 93, SEQ ID NO: 96, and SEQ ID NO: 98. In some embodiments, an antibody or compound of this disclosure comprises SEQ ID NO: 84, SEQ ID NO: 90, SEQ ID NO: 93, and SEQ ID NO: 96. In some embodiments, an antibody or compound of this disclosure comprises SEQ ID NO: 84, SEQ ID NO: 90, SEQ ID NO: 93, and SEQ ID NO: 98. In some embodiments, an antibody or compound of this disclosure comprises SEQ ID NO: 84, SEQ ID NO: 90, SEQ ID NO: 96, and SEQ ID NO: 98. In some embodiments, an antibody or compound of this disclosure comprises SEQ ID NO: 84, SEQ ID NO: 93, SEQ ID NO: 96, and SEQ ID NO: 98. In some embodiments, an antibody or compound of this disclosure comprises SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, and SEQ ID NO: 93. In some embodiments, an antibody or compound of this disclosure comprises SEQ ID NO: 79, SEQ ID NO: 86, SEQ ID NO: 90, and SEQ ID NO: 96. In some embodiments, an antibody or compound of this disclosure comprises SEQ ID NO: 79, SEQ ID NO: 86, SEQ ID NO: 90, and SEQ ID NO: 98. In some embodiments, an antibody or compound of this disclosure comprises SEQ ID NO: 79, SEQ ID NO: 86, SEQ ID NO: 93, and SEQ ID NO: 96. In some embodiments, an antibody or compound of this disclosure comprises SEQ ID NO: 79, SEQ ID NO: 86, SEQ ID NO: 93, and SEQ ID NO: 98. In some embodiments, an antibody or compound of this disclosure comprises SEQ ID NO: 79, SEQ ID NO: 86, SEQ ID NO: 96, and SEQ ID NO: 98. In some embodiments, an antibody or compound of this disclosure comprises SEQ ID NO: 86, SEQ ID NO: 90, SEQ ID NO: 93, and SEQ ID NO: 96. In some embodiments, an antibody or compound of this disclosure comprises SEQ ID NO: 86, SEQ ID NO: 90, SEQ ID NO: 93, and SEQ ID NO: 98. In some embodiments, an antibody or compound of this disclosure comprises SEQ ID NO: 86, SEQ ID NO: 90, SEQ ID NO: 96, and SEQ ID NO: 98. In some embodiments, an antibody or compound of this disclosure comprises SEQ ID NO: 86, SEQ ID NO: 93, SEQ ID NO: 96, and SEQ ID NO: 98.

In some embodiments, an antibody or compound of this disclosure comprises SEQ ID NO: 79, SEQ ID NO: 84, SEQ ID NO: 90, SEQ ID NO: 93, and SEQ ID NO: 96. In some embodiments, an antibody or compound of this disclosure comprises SEQ ID NO: 79, SEQ ID NO: 84, SEQ ID NO: 90, SEQ ID NO: 93, and SEQ ID NO: 98. In some embodiments, an antibody or compound of this disclosure comprises SEQ ID NO: 79, SEQ ID NO: 84, SEQ ID NO: 90, SEQ ID NO: 96, and SEQ ID NO: 98. In some embodiments, an antibody or compound of this disclosure comprises SEQ ID NO: 79, SEQ ID NO: 84, SEQ ID NO: 93, SEQ ID NO: 96, and SEQ ID NO: 98. In some embodiments, an antibody or compound of this disclosure comprises SEQ ID NO: 79, SEQ ID NO: 90, SEQ ID NO: 93, SEQ ID NO: 96, and SEQ ID NO: 98. In some embodiments, an antibody or compound of this disclosure comprises SEQ ID NO: 84, SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, SEQ ID NO: 93, and SEQ ID NO: 96. In some embodiments, an antibody or compound of this disclosure comprises SEQ ID NO: 79, SEQ ID NO: 86, SEQ ID NO: 90, SEQ ID NO: 93, and SEQ ID NO: 98. In some embodiments, an antibody or compound of this disclosure comprises SEQ ID NO: 79, SEQ ID NO: 86, SEQ ID NO: 90, SEQ ID NO: 96, and SEQ ID NO: 98. In some embodiments, an antibody or compound of this disclosure comprises SEQ ID NO: 79, SEQ ID NO: 86, SEQ ID NO: 93, SEQ ID NO: 96, and SEQ ID NO: 98. In some embodiments, an antibody or compound of this disclosure comprises SEQ ID NO: 86, SEQ ID NO: 90, SEQ ID NO: 93, SEQ ID NO: 96, and SEQ ID NO: 98.

In some embodiments, an antibody or compound of this disclosure comprises SEQ ID NO: 79, SEQ ID NO: 84, SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, SEQ ID NO: 93, SEQ ID NO: 96, and SEQ ID NO: 98.

In some embodiments, an antibody or compound of this disclosure comprises SEQ ID NO: 80. In some embodiments, an antibody or compound of this disclosure comprises SEQ ID NO: 85. In some embodiments, an antibody or compound of this disclosure comprises SEQ ID NO: 89. In some embodiments, an antibody or compound of this disclosure comprises SEQ ID NO: 91. In some embodiments, an antibody or compound of this disclosure comprises SEQ ID NO: 96. In some embodiments, an antibody or compound of this disclosure comprises SEQ ID NO: 97. In some embodiments, an antibody or compound of this disclosure comprises SEQ ID NO: 87.

In some embodiments, an antibody or compound of this disclosure comprises SEQ ID NO: 80 and SEQ ID NO: 85. In some embodiments, an antibody or compound of this disclosure comprises SEQ ID NO: 80 and SEQ ID NO: 89. In some embodiments, an antibody or compound of this disclosure comprises SEQ ID NO: 80 and SEQ ID NO: 91. In some embodiments, an antibody or compound of this disclosure comprises SEQ ID NO: 80 and SEQ ID NO: 96. In some embodiments, an antibody or compound of this disclosure comprises SEQ ID NO: 80 and SEQ ID NO: 97. In some embodiments, an antibody or compound of this disclosure comprises SEQ ID NO: 85 and SEQ ID NO: 89. In some embodiments, an antibody or compound of this disclosure comprises SEQ ID NO: 85 and SEQ ID NO: 91. In some embodiments, an antibody or compound of this disclosure comprises SEQ ID NO: 85 and SEQ ID NO: 96. In some embodiments, an antibody or compound of this disclosure comprises SEQ ID NO: 85 and SEQ ID NO: 97. In some embodiments, an antibody or compound of this disclosure comprises SEQ ID NO: 89 and SEQ ID NO: 91. In some embodiments, an antibody or compound of this disclosure comprises SEQ ID NO: 89 and SEQ ID NO: 96. In some embodiments, an antibody or compound of this disclosure comprises SEQ ID NO: 89 and SEQ ID NO: 97. In some embodiments, an antibody or compound of this disclosure comprises SEQ ID NO: 91 and SEQ ID NO: 96. In some embodiments, an antibody or compound of this disclosure comprises SEQ ID NO: 91 and SEQ ID NO: 97. In some embodiments, an antibody or compound of this disclosure comprises SEQ ID NO: 96 and SEQ ID NO: 97. In some embodiments, an antibody or compound of this disclosure comprises SEQ ID NO: 80 and SEQ ID NO: 87. In some embodiments, an antibody or compound of this disclosure comprises SEQ ID NO: 87 and SEQ ID NO: 89. In some embodiments, an antibody or compound of this disclosure comprises SEQ ID NO: 87 and SEQ ID NO: 91. In some embodiments, an antibody or compound of this disclosure comprises SEQ ID NO: 87 and SEQ ID NO: 96. In some embodiments, an antibody or compound of this disclosure comprises SEQ ID NO: 87 and SEQ ID NO: 97.

In some embodiments, an antibody or compound of this disclosure comprises SEQ ID NO: 80, SEQ ID NO: 85, and SEQ ID NO: 89. In some embodiments, an antibody or compound of this disclosure comprises SEQ ID NO: 80, SEQ ID NO: 85, and SEQ ID NO: 91. In some embodiments, an antibody or compound of this disclosure comprises SEQ ID NO: 80, SEQ ID NO: 85, and SEQ ID NO: 96. In some embodiments, an antibody or compound of this disclosure comprises SEQ ID NO: 80, SEQ ID NO: 85, and SEQ ID NO: 97. In some embodiments, an antibody or compound of this disclosure comprises SEQ ID NO: 80, SEQ ID NO: 89, and SEQ ID NO: 91. In some embodiments, an antibody or compound of this disclosure comprises SEQ ID NO: 80, SEQ ID NO: 89, and SEQ ID NO: 96. In some embodiments, an antibody or compound of this disclosure comprises SEQ ID NO: 80, SEQ ID NO: 89, and SEQ ID NO: 97. In some embodiments, an antibody or compound of this disclosure comprises SEQ ID NO: 80, SEQ ID NO: 91, and SEQ ID NO: 96. In some embodiments, an antibody or compound of this disclosure comprises SEQ ID NO: 80, SEQ ID NO: 91, and SEQ ID NO: 97. In some embodiments, an antibody or compound of this disclosure comprises SEQ ID NO: 80, SEQ ID NO: 96, and SEQ ID NO: 97. In some embodiments, an antibody or compound of this disclosure comprises SEQ ID NO: 85, SEQ ID NO: 89, and SEQ ID NO: 91. In some embodiments, an antibody or compound of this disclosure comprises SEQ ID NO: 85, SEQ ID NO: 89, and SEQ ID NO: 96. In some embodiments, an antibody or compound of this disclosure comprises SEQ ID NO: 85, SEQ ID NO: 89, and SEQ ID NO: 97. In some embodiments, an antibody or compound of this disclosure comprises SEQ ID NO: 85, SEQ ID NO: 91, and SEQ ID NO: 96. In some embodiments, an antibody or compound of this disclosure comprises SEQ ID NO: 85, SEQ ID NO: 91, and SEQ ID NO: 97. In some embodiments, an antibody or compound of this disclosure comprises SEQ ID NO: 85, SEQ ID NO: 96, and SEQ ID NO: 97. In some embodiments, an antibody or compound of this disclosure comprises SEQ ID NO: 89, SEQ ID NO: 91, and SEQ ID NO: 96. In some embodiments, an antibody or compound of this disclosure comprises SEQ ID NO: 89, SEQ ID NO: 91, and SEQ ID NO: 97. In some embodiments, an antibody or compound of this disclosure comprises SEQ ID NO: 89, SEQ ID NO: 96, and SEQ ID NO: 97. In some embodiments, an antibody or compound of this disclosure comprises SEQ ID NO: 91, SEQ ID NO: 96, and SEQ ID NO: 97. In some embodiments, an antibody or compound of this disclosure comprises SEQ ID NO: 80, SEQ ID NO: 87, and SEQ ID NO: 89. In some embodiments, an antibody or compound of this disclosure comprises SEQ ID NO: 80, SEQ ID NO: 87, and SEQ ID NO: 91. In some embodiments, an antibody or compound of this disclosure comprises SEQ ID NO: 80, SEQ ID NO: 87, and SEQ ID NO: 96. In some embodiments, an antibody or compound of this disclosure comprises SEQ ID NO: 80, SEQ ID NO: 87, and SEQ ID NO: 97. In some embodiments, an antibody or compound of this disclosure comprises SEQ ID NO: 87, SEQ ID NO: 89, and SEQ ID NO: 91. In some embodiments, an antibody or compound of this disclosure comprises SEQ ID NO: 87, SEQ ID NO: 89, and SEQ ID NO: 96. In some embodiments, an antibody or compound of this disclosure comprises SEQ ID NO: 87, SEQ ID NO: 89, and SEQ ID NO: 97. In some embodiments, an antibody or compound of this disclosure comprises SEQ ID NO: 87, SEQ ID NO: 91, and SEQ ID NO: 96. In some embodiments, an antibody or compound of this disclosure comprises SEQ ID NO: 87, SEQ ID NO: 91, and SEQ ID NO: 97. In some embodiments, an antibody or compound of this disclosure comprises SEQ ID NO: 87, SEQ ID NO: 96, and SEQ ID NO: 97.

In some embodiments, an antibody or compound of this disclosure comprises SEQ ID NO: 80, SEQ ID NO: 85, SEQ ID NO: 89, and SEQ ID NO: 91. In some embodiments, an antibody or compound of this disclosure comprises SEQ ID NO: 80, SEQ ID NO: 85, SEQ ID NO: 89, and SEQ ID NO: 96. In some embodiments, an antibody or compound of this disclosure comprises SEQ ID NO: 80, SEQ ID NO: 85, SEQ ID NO: 89, and SEQ ID NO: 97. In some embodiments, an antibody or compound of this disclosure comprises SEQ ID NO: 80, SEQ ID NO: 85, SEQ ID NO: 91, and SEQ ID NO: 96. In some embodiments, an antibody or compound of this disclosure comprises SEQ ID NO: 80, SEQ ID NO: 85, SEQ ID NO: 91, and SEQ ID NO: 97. In some embodiments, an antibody or compound of this disclosure comprises SEQ ID NO: 80, SEQ ID NO: 85, SEQ ID NO: 96, and SEQ ID NO: 97. In some embodiments, an antibody or compound of this disclosure comprises SEQ ID NO: 80, SEQ ID NO: 89, SEQ ID NO: 91, and SEQ ID NO: 96. In some embodiments, an antibody or compound of this disclosure comprises SEQ ID NO: 80, SEQ ID NO: 89, SEQ ID NO: 91, and SEQ ID NO: 97. In some embodiments, an antibody or compound of this disclosure comprises SEQ ID NO: 80, SEQ ID NO: 89, SEQ ID NO: 96, and SEQ ID NO: 97. In some embodiments, an antibody or compound of this disclosure comprises SEQ ID NO: 80, SEQ ID NO: 91, SEQ ID NO: 96, and SEQ ID NO: 97. In some embodiments, an antibody or compound of this disclosure comprises SEQ ID NO: 85, SEQ ID NO: 89, SEQ ID NO: 91, and SEQ ID NO: 96. In some embodiments, an antibody or compound of this disclosure comprises SEQ ID NO: 85, SEQ ID NO: 89, SEQ ID NO: 91, and SEQ ID NO: 97. In some embodiments, an antibody or compound of this disclosure comprises SEQ ID NO: 85, SEQ ID NO: 89, SEQ ID NO: 96, and SEQ ID NO: 97. In some embodiments, an antibody or compound of this disclosure comprises SEQ ID NO: 85, SEQ ID NO: 91, SEQ ID NO: 96, and SEQ ID NO: 97. In some embodiments, an antibody or compound of this disclosure comprises SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, and SEQ ID NO: 91. In some embodiments, an antibody or compound of this disclosure comprises SEQ ID NO: 80, SEQ ID NO: 87, SEQ ID NO: 89, and SEQ ID NO: 96. In some embodiments, an antibody or compound of this disclosure comprises SEQ ID NO: 80, SEQ ID NO: 87, SEQ ID NO: 89, and SEQ ID NO: 97. In some embodiments, an antibody or compound of this disclosure comprises SEQ ID NO: 80, SEQ ID NO: 87, SEQ ID NO: 91, and SEQ ID NO: 96. In some embodiments, an antibody or compound of this disclosure comprises SEQ ID NO: 80, SEQ ID NO: 87, SEQ ID NO: 91, and SEQ ID NO: 97. In some embodiments, an antibody or compound of this disclosure comprises SEQ ID NO: 80, SEQ ID NO: 87, SEQ ID NO: 96, and SEQ ID NO: 97. In some embodiments, an antibody or compound of this disclosure comprises SEQ ID NO: 87, SEQ ID NO: 89, SEQ ID NO: 91, and SEQ ID NO: 96. In some embodiments, an antibody or compound of this disclosure comprises SEQ ID NO: 87, SEQ ID NO: 89, SEQ ID NO: 91, and SEQ ID NO: 97. In some embodiments, an antibody or compound of this disclosure comprises SEQ ID NO: 87, SEQ ID NO: 89, SEQ ID NO: 96, and SEQ ID NO: 97. In some embodiments, an antibody or compound of this disclosure comprises SEQ ID NO: 87, SEQ ID NO: 91, SEQ ID NO: 96, and SEQ ID NO: 97.

In some embodiments, an antibody or compound of this disclosure comprises SEQ ID NO: 80, SEQ ID NO: 85, SEQ ID NO: 89, SEQ ID NO: 91, and SEQ ID NO: 96. In some embodiments, an antibody or compound of this disclosure comprises SEQ ID NO: 80, SEQ ID NO: 85, SEQ ID NO: 89, SEQ ID NO: 91, and SEQ ID NO: 97. In some embodiments, an antibody or compound of this disclosure comprises SEQ ID NO: 80, SEQ ID NO: 85, SEQ ID NO: 89, SEQ ID NO: 96, and SEQ ID NO: 97. In some embodiments, an antibody or compound of this disclosure comprises SEQ ID NO: 80, SEQ ID NO: 85, SEQ ID NO: 91, SEQ ID NO: 96, and SEQ ID NO: 97. In some embodiments, an antibody or compound of this disclosure comprises SEQ ID NO: 80, SEQ ID NO: 89, SEQ ID NO: 91, SEQ ID NO: 96, and SEQ ID NO: 97. In some embodiments, an antibody or compound of this disclosure comprises SEQ ID NO: 85, SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, SEQ ID NO: 91, and SEQ ID NO: 96. In some embodiments, an antibody or compound of this disclosure comprises SEQ ID NO: 80, SEQ ID NO: 87, SEQ ID NO: 89, SEQ ID NO: 91, and SEQ ID NO: 97. In some embodiments, an antibody or compound of this disclosure comprises SEQ ID NO: 80, SEQ ID NO: 87, SEQ ID NO: 89, SEQ ID NO: 96, and SEQ ID NO: 97. In some embodiments, an antibody or compound of this disclosure comprises SEQ ID NO: 80, SEQ ID NO: 87, SEQ ID NO: 91, SEQ ID NO: 96, and SEQ ID NO: 97. In some embodiments, an antibody or compound of this disclosure comprises SEQ ID NO: 87, SEQ ID NO: 89, SEQ ID NO: 91, SEQ ID NO: 96, and SEQ ID NO: 97.

In some embodiments, an antibody or compound of this disclosure comprises SEQ ID NO: 80, SEQ ID NO: 85, SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, SEQ ID NO: 91, SEQ ID NO: 96, and SEQ ID NO: 97.

In some embodiments, an antibody or compound of this disclosure comprises any one of SEQ ID NOS: 99-113. In some embodiments, an antibody or compound of this disclosure comprises any one of SEQ ID NOS: 114-123. In some embodiments, an antibody or compound of this disclosure comprises any one of SEQ ID NOS: 124-131. In some embodiments, an antibody or compound of this disclosure comprises any one of SEQ ID NOS: 132-137. In some embodiments, an antibody or compound of this disclosure comprises any one of SEQ ID NOS: 138-143. In some embodiments, an antibody or compound of this disclosure comprises any one of SEQ ID NOS: 144-146.

In some embodiments, an antibody or compound of this disclosure comprises any one of SEQ ID NOS: 99-113 and any one of SEQ ID NOS: 114-123. In some embodiments, an antibody or compound of this disclosure comprises any one of SEQ ID NOS: 99-113 and any one of SEQ ID NOS: 124-131. In some embodiments, an antibody or compound of this disclosure comprises any one of SEQ ID NOS: 99-113 and any one of SEQ ID NOS: 132-137. In some embodiments, an antibody or compound of this disclosure comprises any one of SEQ ID NOS: 99-113 and any one of SEQ ID NOS: 138-143. In some embodiments, an antibody or compound of this disclosure comprises any one of SEQ ID NOS: 99-113 and any one of SEQ ID NOS: 144-146. In some embodiments, an antibody or compound of this disclosure comprises any one of SEQ ID NOS: 114-123 and any one of SEQ ID NOS: 124-131. In some embodiments, an antibody or compound of this disclosure comprises any one of SEQ ID NOS: 114-123 and any one of SEQ ID NOS: 132-137. In some embodiments, an antibody or compound of this disclosure comprises any one of SEQ ID NOS: 114-123 and any one of SEQ ID NOS: 138-143. In some embodiments, an antibody or compound of this disclosure comprises any one of SEQ ID NOS: 114-123 and any one of SEQ ID NOS: 144-146. In some embodiments, an antibody or compound of this disclosure comprises any one of SEQ ID NOS: 124-131 and any one of SEQ ID NOS: 132-137. In some embodiments, an antibody or compound of this disclosure comprises any one of SEQ ID NOS: 124-131 and any one of SEQ ID NOS: 138-143. In some embodiments, an antibody or compound of this disclosure comprises any one of SEQ ID NOS: 124-131 and any one of SEQ ID NOS: 144-146. In some embodiments, an antibody or compound of this disclosure comprises any one of SEQ ID NOS: 132-137 and any one of SEQ ID NOS: 138-143. In some embodiments, an antibody or compound of this disclosure comprises any one of SEQ ID NOS: 132-137 and any one of SEQ ID NOS: 144-146. In some embodiments, an antibody or compound of this disclosure comprises any one of SEQ ID NOS: 138-143 and any one of SEQ ID NOS: 144-146.

In some embodiments, an antibody or compound of this disclosure comprises any one of SEQ ID NOS: 99-113, any one of SEQ ID NOS: 114-123, and any one of SEQ ID NOS: 124-131. In some embodiments, an antibody or compound of this disclosure comprises any one of SEQ ID NOS: 99-113, any one of SEQ ID NOS: 114-123, and any one of SEQ ID NOS: 132-137. In some embodiments, an antibody or compound of this disclosure comprises any one of SEQ ID NOS: 99-113, any one of SEQ ID NOS: 114-123, and any one of SEQ ID NOS: 138-143. In some embodiments, an antibody or compound of this disclosure comprises any one of SEQ ID NOS: 99-113, any one of SEQ ID NOS: 114-123, and any one of SEQ ID NOS: 144-146. In some embodiments, an antibody or compound of this disclosure comprises any one of SEQ ID NOS: 99-113, any one of SEQ ID NOS: 124-131, and any one of SEQ ID NOS: 132-137. In some embodiments, an antibody or compound of this disclosure comprises any one of SEQ ID NOS: 99-113, any one of SEQ ID NOS: 124-131, and any one of SEQ ID NOS: 138-143. In some embodiments, an antibody or compound of this disclosure comprises any one of SEQ ID NOS: 99-113, any one of SEQ ID NOS: 124-131, and any one of SEQ ID NOS: 144-146. In some embodiments, an antibody or compound of this disclosure comprises any one of SEQ ID NOS: 99-113, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 124-131, and any one of SEQ ID NOS: 132-137. In some embodiments, an antibody or compound of this disclosure comprises any one of SEQ ID NOS: 114-123, any one of SEQ ID NOS: 124-131, and any one of SEQ ID NOS: 138-143. In some embodiments, an antibody or compound of this disclosure comprises any one of SEQ ID NOS: 114-123, any one of SEQ ID NOS: 124-131, and any one of SEQ ID NOS: 144-146. In some embodiments, an antibody or compound of this disclosure comprises any one of SEQ ID NOS: 114-123, any one of SEQ ID NOS: 132-137, and any one of SEQ ID NOS: 138-143. In some embodiments, an antibody or compound of this disclosure comprises any one of SEQ ID NOS: 114-123, any one of SEQ ID NOS: 132-137, and any one of SEQ ID NOS: 144-146. In some embodiments, an antibody or compound of this disclosure comprises any one of SEQ ID NOS: 114-123, any one of SEQ ID NOS: 138-143, and any one of SEQ ID NOS: 144-146. In some embodiments, an antibody or compound of this disclosure comprises any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 132-137, any one of SEQ ID NOS: 138-143, and any one of SEQ ID NOS: 144-146.

In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 132-137. In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 114-123, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 114-123, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 124-131, any one of SEQ ID NOS: 132-137, any one of SEQ ID NOS: 138-143, and any one of SEQ ID NOS: 144-146.

In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, any one of SEQ ID NOS: 138-143, and any one of SEQ ID NOS: 144-146.

In some embodiments, an antibody or compound of this disclosure comprises SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO 113, SEQ ID NO: 123, SEQ ID NO: 130, SEQ ID NO: 135, SEQ ID NO: 143, and SEQ ID NO: 145.

In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 113, SEQ ID NO: 123, SEQ ID NO: 130, SEQ ID NO: 135, SEQ ID NO: 143, and SEQ ID NO: 145. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 113, SEQ ID NO: 123, SEQ ID NO: 130, SEQ ID NO: 135, SEQ ID NO: 143, and SEQ ID NO: 145.

EXAMPLES

Example 1: A Tetravalent Bispecific Antibody Comprising Antibody HC2:LC and Aflibercept-Derived Sequences To generate a tetravalent bispecific antibody in which the heavy chain of antibody HC2:LC1 was fused to an aflibercept-derived VEGF-binding domain, an amino acid sequence was generated comprising the following appended amino acid sequences, from N-terminus to C-terminus:
1) SEQ ID NO: 14 (heavy chain of antibody HC2:LC1);
2) SEQ ID NO: 31 (linker peptide, underlined); and
3) SEQ ID NO: 22 (aflibercept-derived sequence).

The resulting polypeptide (SEQ ID NO: 149) was co-expressed with SEQ ID NO: 17, to provide tetravalent, bispecific antibody HC2-AFL:LC1, comprising the sequences shown in TABLE 33. Amino acids 1-19 of SEQ ID NO: 149 are the heavy chain signal peptide (SEQ ID NO: 11). Amino acids 1-20 of SEQ ID NO: 17 are the light chain signal peptide (SEQ ID NO: 12). In some embodiments, a mature HC2-AFL:LC1 does not comprise the signal peptides. For example, a mature HC2-AFL:LC1 of the disclosure can comprise SEQ ID NO: 254 and SEQ ID NO: 250.

TABLE 33

| SEQ ID NO: | Name | Amino acid sequence |
|---|---|---|
| 149 | signal peptide-HC2-AFL | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK<u>GGGGS</u>SDTGRPFVEMYSEIPEIIH MTEGRELVIPCRVTSPNI<u>TVT</u>LKKFPLDTLIPDGKRIIWDSRK GFIISNATYKEIGLLTCEATVNGHLYKTNYLTHRQTNTIIDVV LSPSHGIELSVGEKLVLNCTARTELNVGIDFNWEYPSSKHQH KKLVNRDLKTQSGSEMKKFLSTLTIDGVTRSDQGLYTCAAS SGLMTKKNSTFVRVHEK |
| 17 | Signal peptide-LC1 | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| 254 | HC2-AFL | EVQLVESGGGLVQPGGSLRLSCAASGFTFNANAMNWVRQA PGKGLEWVGRIRTKSNNYATYYAGSVKDRFTISRDDSKNSL YLQMNSLKTEDTAVYYCVRDYYGSSAWITYWGQGTLVTV SSASTKGPSVFPLAPCSRSTSESTAALGCLVKDYFPEPVTVS WNSGALTSGVHTFPAVLQSSGLYSLSSVVTVPSSSLGTKTYT CNVDHKPSNTKVDKRVESKYGPPCPPCPAPEFLGGPSVFLFP PKPKDTLMISRTPEVTCVVVDVSQEDPEVQFNWYVDGVEV HNAKTKPREEQFNSTYRVVSVLTVLHQDWLNGKEYKCKVS NKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLGKG <u>GGGGS</u>SDTGRPFVEMYSEIPEIIHMTEGRELVIPCRVTSP<u>NITVT LKK</u>FPLDTLIPDGKRIIWDSRKGFIISNATYKEIGLLTCEATVN GHLYKTNYLTHRQTNTIIDVVLSPSHGIELSVGEKLVLNCTA RTELNVGIDFNWEYPSSKHQHKKLVNRDLKTQSGSEMKKF LSTLTIDGVTRSDQGLYTCAASSGLMTKKNSTFVRVHEK |

Example 2: A Tetravalent Bispecific Antibody Comprising Antibody HC2:LC1 and Brolucizumab-Derived Sequences To generate a tetravalent bispecific antibody in which the heavy chain of antibody HC2:LC1 was fused to a brolucizumab-derived VEGF-binding domain, an amino acid sequence was generated comprising the following appended amino acid sequences, from N-terminus to C-terminus:
1) SEQ ID NO: 14 (heavy chain of antibody HC2:LC1);
2) SEQ ID NO: 31 (linker peptide, underlined); and
3) SEQ ID NO: 23 (brolucizumab-derived sequence).

The resulting polypeptide (SEQ ID NO: 150) was co-expressed with SEQ ID NO: 17, to provide tetravalent, bispecific antibody HC2-BRO:LC1, comprising the sequences shown in TABLE 34. Amino acids 1-19 of SEQ ID NO: 150 are the heavy chain signal peptide (SEQ ID NO: 11). Amino acids 1-20 of SEQ ID NO: 17 are the light chain signal peptide (SEQ ID NO: 12). In some embodiments, a mature HC2-BRO:LC1 does not comprise the signal peptides. For example, a mature HC2-BRO:LC1 of the disclosure can comprise SEQ ID NO: 255 and SEQ ID NO: 250.

TABLE 34

| SEQ ID NO: | Name | Amino acid sequence |
|---|---|---|
| 150 | signal peptide-HC2-BRO | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK<u>GGGGS</u>EIVMTQSPSTLSASVGDR VIITCQASEIIHSWLAWYQQKPGKAPKLLIYLASTLASGVPSR FSGSGSGAEFTLTISSLQPDDFATYYCQNVYLASTNGANFGQ |

TABLE 34-continued

| SEQ ID NO: | Name | Amino acid sequence |
|---|---|---|
| | | GTKLTVLGGGGSGGGGSGGGGSGGGGSEVQLVESGGGLV QPGGSLRLSCTASGFSLTDYYYMTWVRQAPGKGLEWVGFI DPDDDPYYATWAKGRFTISRDNSKNTLYLQMNSLRAEDTA VYYCAGGDHNSGWGLDIWGQGTLVTVSS |
| 17 | Signal peptide-LC1 | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| 255 | HC2-BRO | EVQLVESGGGLVQPGGSLRLSCAASGFTFNANAMNWVRQA PGKGLEWVGRIRTKSNNYATYYAGSVKDRFTISRDDSKNSL YLQMNSLKTEDTAVYYCVRDYYGSSAWITYWGQGTLVTV SSASTKGPSVFPLAPCSRSTSESTAALGCLVKDYFPEPVTVS WNSGALTSGVHTFPAVLQSSGLYSLSSVVTVPSSSLGTKTYT CNVDHKPSNTKVDKRVESKYGPPCPPCPAPEFLGGPSVFLFP PKPKDTLMISRTPEVTCVVVDVSQEDPEVQFNWYVDGVEV HNAKTKPREEQFNSTYRVVSVLTVLHQDWLNGKEYKCKVS NKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLGKG GGGSEIVMTQSPSTLSASVGDRVIITCQASEIIHSWLAWYQQ KPGKAPKLLIYLASTLASGVPSRFSGSGSGAEFTLTISSLQPD DFATYYCQNVYLASTNGANFGQGTKLTVLGGGGSGGGGS GGGGSGGGGSEVQLVESGGGLVQPGGSLRLSCTASGFSLTD YYYMTWVRQAPGKGLEWVGFIDPDDDPYYATWAKGRFTIS RDNSKNTLYLQMNSLRAEDTAVYYCAGGDHNSGWGLDIW GQGTLVTVSS |

Example 3: A Tetravalent Bispecific Antibody Comprising Antibody HC2:LC1 and Ranibizumab-Derived Sequences To generate a tetravalent bispecific antibody in which the heavy chain of antibody HC2:LC1 was fused to a ranibizumab-derived VEGF-binding domain, an amino acid sequence was generated comprising the following appended amino acid sequences, from N-terminus to C-terminus:
1) SEQ ID NO: 14 (heavy chain of antibody HC2:LC1);
2) SEQ ID NO: 31 (linker peptide, underlined); and
3) SEQ ID NO: 28 (ranibizumab-derived sequence).

The resulting polypeptide (SEQ ID NO: 151) was co-expressed with SEQ ID NO: 17, to provide tetravalent, bispecific antibody HC2-RAN:LC1, comprising the sequences shown in TABLE 35. Amino acids 1-19 of SEQ ID NO: 151 are the heavy chain signal peptide (SEQ ID NO: 11). Amino acids 1-20 of SEQ ID NO: 17 are the light chain signal peptide (SEQ ID NO: 12). In some embodiments, a mature HC2-RAN:LC1 does not comprise the signal peptides. For example, a mature HC2-RAN:LC1 of the disclosure can comprise SEQ ID NO: 256 and SEQ ID NO: 250.

TABLE 35

| SEQ ID NO: | Name | Amino acid sequence |
|---|---|---|
| 151 | Signal peptide-HC2-RAN | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGKGGGGSEVQLVESGGGLVQPGGSL RLSCAASGYDFTHYGMNWVRQAPGKGLEWVGWINTYTGE PTYAADFKRRFTFSLDTSKSTAYLQMNSLRAEDTAVYYCAK YPYYYGTSHWYFDVWGQGTLVTVSSGGGGSGGGGSGGGG SDIQLTQSPSSLSASVGDRVTITCSASQDISNYLNWYQQKPG KAPKVLIYFTSSLHSGVPSRFSGSGSGTDFTLTISSLQPEDFAT YYCQQYSTVPWTFGQGTKVEIK |
| 17 | Signal peptide-LC1 | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |

TABLE 35-continued

| SEQ ID NO:Name | | Amino acid sequence |
|---|---|---|
| 256 | HC2-RAN | EVQLVESGGGLVQPGGSLRLSCAASGFTFNANAMNWVRQA PGKGLEWVGRIRTKSNNYATYYAGSVKDRFTISRDDSKNSL YLQMNSLKTEDTAVYYCVRDYYGSSAWITYWGQGTLVTV SSASTKGPSVFPLAPCSRSTSESTAALGCLVKDYFPEPVTVS WNSGALTSGVHTFPAVLQSSGLYSLSSVVTVPSSSLGTKTYT CNVDHKPSNTKVDKRVESKYGPPCPPCPAPEFLGGPSVFLFP PKPKDTLMISRTPEVTCVVVDVSQEDPEVQFNWYVDGVEV HNAKTKPREEQFNSTYRVVSVLTVLHQDWLNGKEYKCKVS NKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLGKG GGGSEVQLVESGGGLVQPGGSLRLSCAASGYDFTHYGMNW VRQAPGKGLEWVGWINTYTGEPTYAADFKRRFTFSLDTSKS TAYLQMNSLRAEDTAVYYCAKYPYYYGTSHWYFDVWGQ GTLVTVSSGGGGSGGGGSGGGGSDIQLTQSPSSLSASVGDR VTITCSASQDISNYLNWYQQKPGKAPKVLIYFTSSLHSGVPS RFSGSGSGTDFTLTISSLQPEDFATYYCQQYSTVPWTFGQGT KVEIK |

Example 4: Characterization of Bispecific Compounds

The following multi-specific antibodies of the disclosure were generated: (i) HC2-RAN:LC1, (ii) HC2-AFL:LC1, (iii) HC2-BRO:LC1, (iv) HC2-ABI:LC1, (v) HC2:LC1-AFL, (vi) HC2:LC1-BRO, (vii) HC2:LC1-ABI, (viii) HC2-AFL:LC1-AFL, (ix) HC2-BRO:LC1-BRO, and (x) HC2-ABI:LC1-ABI. Enzyme-linked immunosorbent assays (ELISAs) were performed to determine binding of these antibodies to VEGF and HPTP-β (VE-PTP). Binding to HPTP-β (VE-PTP) was confirmed for all constructs, and binding to VEGF was confirmed for all constructs except for HC2-RAN:LC1.

Figure 16:
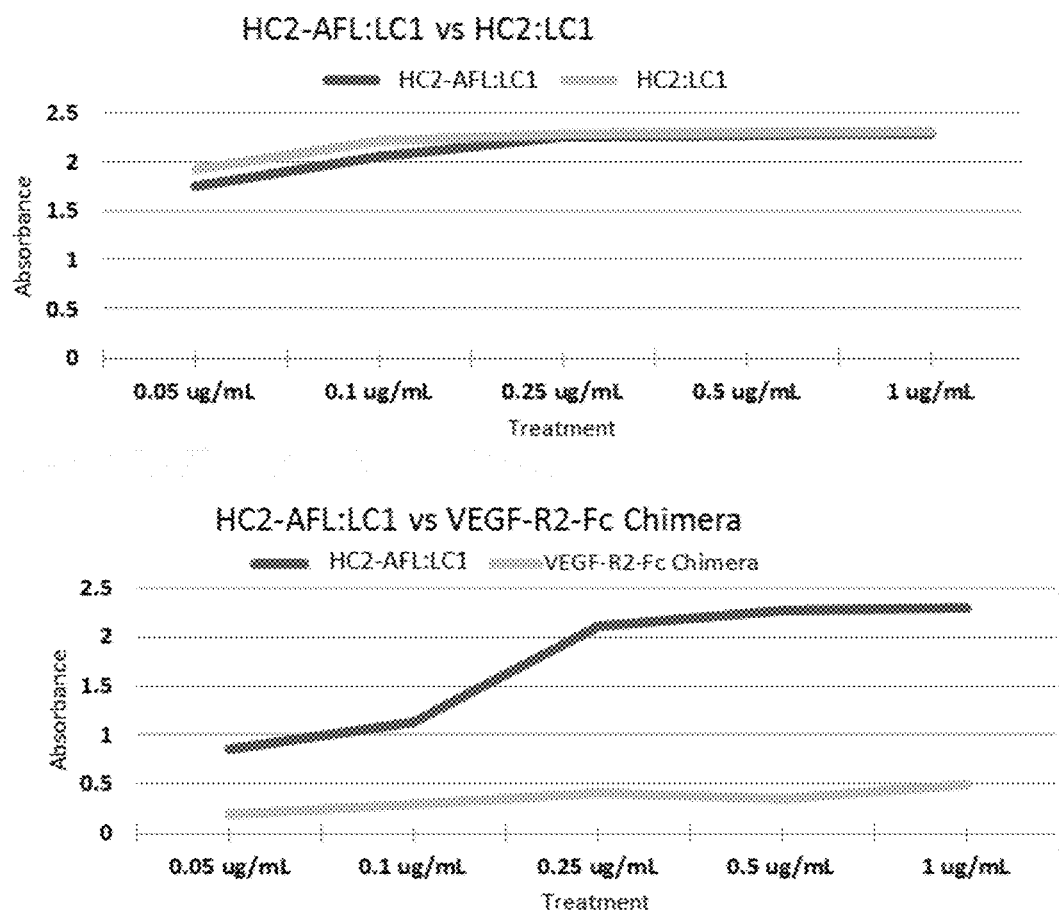
FIG. 16: ELISA data demonstrating binding of a tetravalent bispecific antibody HC2-AFL:LC1 to HPTP-β (top panel) and VEGF (bottom panel).
Figure 17:
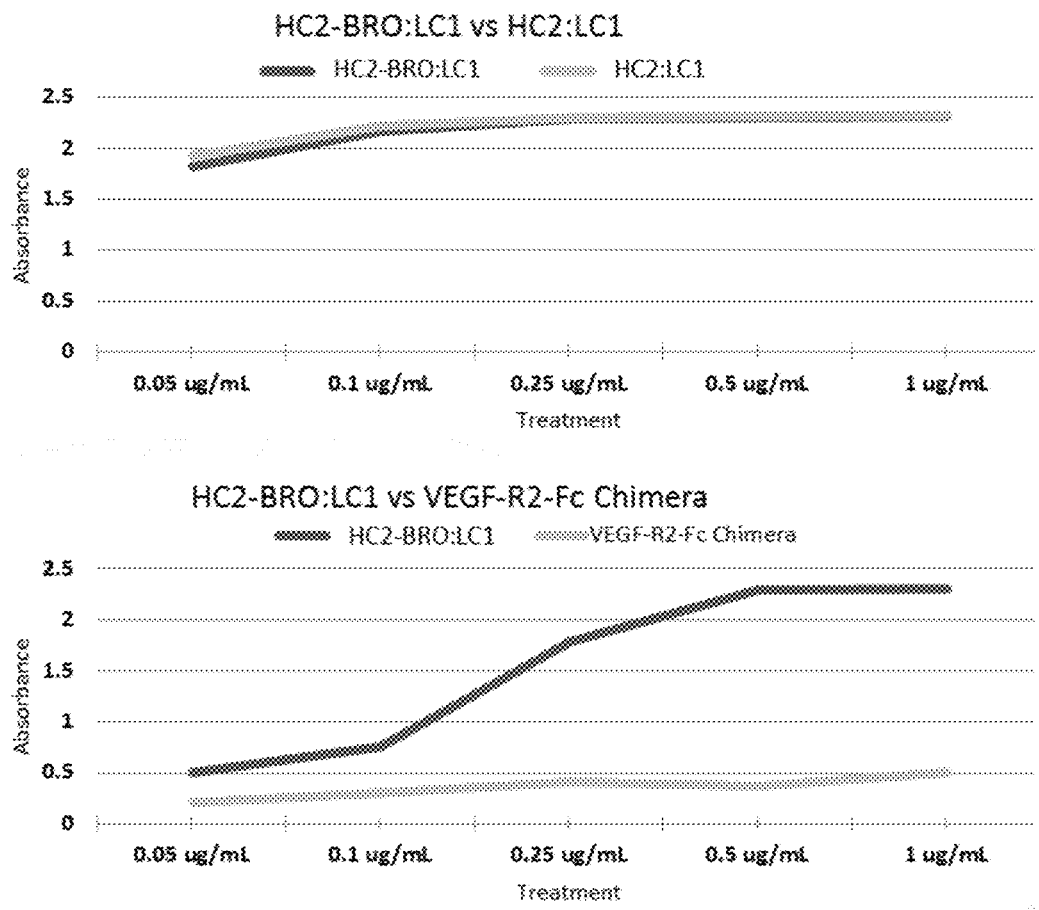
FIG. 17: ELISA data demonstrating binding of a tetravalent bispecific antibody HC2-BRO:LC1 to HPTP-β (top panel) and VEGF (bottom panel).
Figure 18:
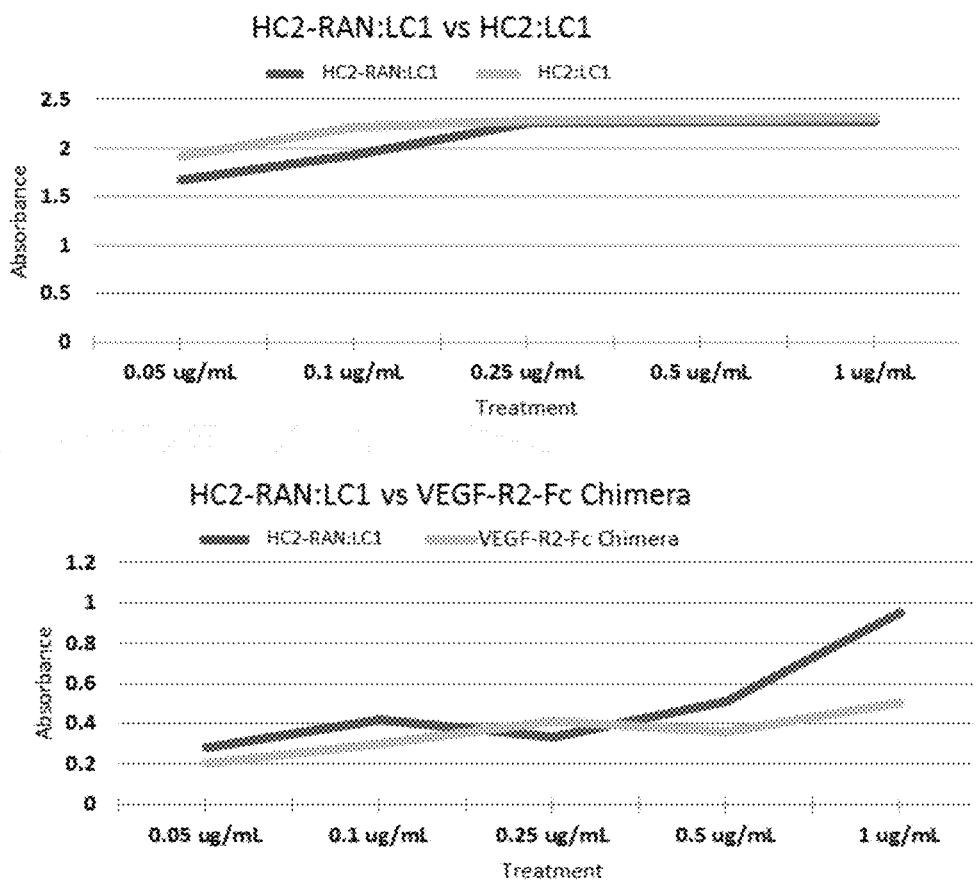
FIG. 18: ELISA data testing binding of a tetravalent bispecific antibody HC2-RAN:LC1 to HPTP-β (top panel) and VEGF (bottom panel).

The tetravalent, bispecific antibodies described in EXAMPLES 1-3 were produced and characterized as described in TABLE 36, FIG. 16, FIG. 17, and FIG. 18.

TABLE 36 provides results from small scale production and characterization of bispecific candidates.

TABLE 36

| Candidate Name | Yield (mg) | HC MW (Da)** | LC MW (Da)** | Intact MW (Da) |
|---|---|---|---|---|
| HC2-RAN:LC1 | 0.84 | 76113/76109 | 23400/23399 | 198981 |
| HC2-AFL:LC1 | 1.32 | 72756/72748 | 23400/23399 | 192270 |
| HC2-BRO:LC1 | 0.73 | 75882/75877 | 23400/23399 | 198532 |

**m/c = measured/calculated

FIG. 16 provides ELISA data demonstrating binding of a tetravalent bispecific antibody HC2-AFL:LC1 to HPTP-β (top panel) and VEGF (bottom panel). Binding is compared to controls (HC2:LC1 in top panel, VEGF-R2-Fc chimera in bottom panel).

FIG. 17 provides ELISA data demonstrating binding of a tetravalent bispecific antibody HC2-BRO:LC1 to HPTP-β (top panel) and VEGF (bottom panel). Binding is compared to controls (HC2:LC1 in top panel, VEGF-R2-Fc chimera in bottom panel).

FIG. 18 provides ELISA data evaluating binding of a tetravalent bispecific antibody HC2-RAN:LC1 to HPTP-β (top panel) and VEGF (bottom panel). Binding is compared to controls (HC2:LC1 in top panel, VEGF-R2-Fc chimera in bottom panel).

Example 5: A Tetravalent Bispecific Antibody Comprising Antibody HC2:LC1 and Abicipar-Derived Sequences To generate a tetravalent bispecific antibody in which the heavy chain of antibody HC2:LC1 was fused to an abicipar-derived VEGF-binding domain, an amino acid sequence was generated comprising the following appended amino acid sequences, from N-terminus to C-terminus:
1) Residues 1-467 of SEQ ID NO: 14 (heavy chain of antibody HC2:LC1);
2) SEQ ID NO:31 (linker peptide, underlined); and
3) SEQ ID NO: 244 (abicipar-derived sequence).

The resulting polypeptide (SEQ ID NO: 231) was co-expressed with SEQ ID NO: 17, to provide tetravalent, bispecific antibody HC2-ABI:LC1, comprising the sequences shown in TABLE 37. Amino acids 1-19 of SEQ ID NO: 231 are the heavy chain signal peptide (SEQ ID NO: 11). Amino acids 1-20 of SEQ ID NO: 17 are the light chain signal peptide (SEQ ID NO: 12). In some embodiments, a mature HC2-ABI:LC1 does not comprise the signal peptides. For example, a mature HC2-ABI:LC1 of the disclosure can comprise SEQ ID NO: 257 and SEQ ID NO: 250.

TABLE 37

| SEQ ID NO:Name | | Amino acid sequence |
|---|---|---|
| 231 | Signal peptide-HC2-ABI | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE |

TABLE 37-continued

| SEQ ID NO: | Name | Amino acid sequence |
|---|---|---|
| | | NNYKTTPPVLDSDGSFFLYSRLTVDKSRWQEGNVFSCSVMH<br>EALHNHYTQKSLSLSLGGGGGSDLDKKLLEAARAGQDDEV<br>RILMANGADVNARDSTG<u>W</u>TPLHLAAPWGHPEIVEVLLKNG<br>ADVNAADFQGWTPLHLAAAVGHLEIVEVLLKYGADVNAQ<br>DKFGKTAFDISIDNGNEDLAEILQKAA |
| 17 | Signal<br>peptide-<br>LC1 | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGEC |
| 257 | HC2-<br>ABI | EVQLVESGGGLVQPGGSLRLSCAASGFTENANAMNWVRQA<br>PGKGLEWVGRIRTKSNNYATYYAGSVKDRFTISRDDSKNSL<br>YLQMNSLKTEDTAVYYCVRDYYGSSAWITYWGQGTLVTV<br>SSASTKGPSVFPLAPCSRSTSESTAALGCLVKDYFPEPVTVS<br>WNSGALTSGVHTFPAVLQSSGLYSLSSVVTVPSSSLGTKTYT<br>CNVDHKPSNTKVDKRVESKYGPPCPPCPAPEFLGGPSVFLFP<br>PKPKDTLMISRTPEVTCVVVDVSQEDPEVQFNWYVDGVEV<br>HNAKTKPREEQFNSTYRVVSVLTVLHQDWLNGKEYKCKVS<br>NKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLGGG<br>GGSDLDKKLLEAARAGQDDEVRILMANGADVNARDSTG<u>W</u><br><u>TPL</u>HLAAPWGHPEIVEVLLKNGADVNAADFQGWTPLHLAA<br>AVGHLEIVEVLLKYGADVNAQDKFGKTAFDISIDNGNEDLA<br>EILQKAA |

Example 6: A Hexavalent Bispecific Antibody Comprising Antibody HC2:LC1 and Brolucizumab-Derived Sequences To generate a heavy chain with brolucizumab-derived VEGF-binding domains added at the C-terminus, an amino acid sequence was generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 23 (brolucizumab-derived sequence).

To generate a light chain with brolucizumab-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 23 (brolucizumab-derived sequence).

The resulting polypeptides, SEQ ID NO: 150 and SEQ ID NO: 218 were co-expressed to provide a hexavalent, bispecific antibody HC2-BRO:LC1-BRO shown in TABLE 38. Amino acids 1-19 of SEQ ID NO: 150 are the heavy chain signal peptide (SEQ ID NO: 11). Amino acids 1-20 of SEQ ID NO: 218 are the light chain signal peptide (SEQ ID NO: 12). In some embodiments, a mature HC2-BRO:LC1-BRO does not comprise the signal peptides. For example, a mature HC2-BRO:LC1-BRO of the disclosure can comprise SEQ ID NO: 255 and SEQ ID NO: 258.

TABLE 38

| SEQ ID NO: | Name | Amino acid sequence |
|---|---|---|
| 150 | Signal<br>peptide-<br>HC2-<br>BRO | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGKGGGGSEIVMTQSPSTLSASVGDR<br>VIITCQASEIIHSWLAWYQQKPGKAPKLLIYLASTLASGVPSR<br>FSGSGSGAEFTLTISSLQPDDFATYYCQNVYLASTNGANFGQ<br>GTKLTVLGGGGSGGGGSGGGGSGGGGSEVQLVESGGGLV<br>QPGGSLRLSCTASGFSLTDYYYMTWVRQAPGKGLEWVGFI<br>DPDDDPYYATWAKGRFTISRDNSKNTLYLQMNSLRAEDTA<br>VYYCAGGDHNSGWGLDIWGQGTLVTVSS |
| 218 | Signal<br>peptide-<br>LC1-<br>BRO | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ |

TABLE 38-continued

| SEQ ID NO:Name | | Amino acid sequence |
|---|---|---|
| | | WKVDNALQSGNSQESVTEQDSKDSTYSLSSTLTLSKADYEK
HKVYACEVTHQGLSSPVTKSFNRGECGGGGSEIVMTQSPST
LSASVGDRVIITCQASEIIHSWLAWYQQKPGKAPKLLIYLAS
TLASGVPSRFSGSGSGAEFTLTISSLQPDDFATYYCQNVYLA
STNGANFGQGTKLTVLGGGGSGGGGSGGGGSGGGGSEVQ
LVESGGGLVQPGGSLRLSCTASGFSLTDYYYMTWVRQAPG
KGLEWVGFIDPDDDPYYATWAKGRFTISRDNSKNTLYLQM
NSLRAEDTAVYYCAGGDHNSGWGLDIWGQGTLVTVSS |
| 258 | LC1-
BRO | DVVMTQSPSFLSASVGDRVTITCKASQHVGTAVAWYQQRP
GKAPKLLIYWASTRHTGVPSRFSGSGSGTEFTLTISSLQPEDF
ATYFCQQYSSYPFTFGGGTKLEIKRTVAAPSVFIFPPSDEQLK
SGTASVVCLLNNFYPREAKVQWKVDNALQSGNSQESVTEQ
DSKDSTYSLSSTLTLSKADYEKHKVYACEVTHQGLSSPVTK
SFNRGECGGGGSEIVMTQSPSTLSASVGDRVIITCQASEIIHS
WLAWYQQKPGKAPKLLIYLASTLASGVPSRFSGSGSGAEFT
LTISSLQPDDFATYYCQNVYLASTNGANFGQGTKLTVLGGG
GGSGGGGSGGGGSGGGGSEVQLVESGGGLVQPGGSLRLSC
TASGFSLTDYYYMTWVRQAPGKGLEWVGFIDPDDDPYYAT
WAKGRFTISRDNSKNTLYLQMNSLRAEDTAVYYCAGGDHN
SGWGLDIWGQGTLVTVSS |

Example 7: A Hexavalent Bispecifc Antibody Comprising Antibody HC2:LC1 and Aflibercept-Derived Sequences To generate a heavy chain with aflibercept-derived VEGF-binding domains added at the C-terminus, an amino acid sequence was generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 22 (aflibercept-derived sequence).

To generate a light chain with aflibercept-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptides, SEQ ID NO: 149 and SEQ ID NO: 219 were co-expressed to provide a hexavalent, bispecific antibody HC2-AFL:LC1-AFL shown in TABLE 39. Amino acids 1-19 of SEQ ID NO: 149 are the heavy chain signal peptide (SEQ ID NO: 11). Amino acids 1-20 of SEQ ID NO: 219 are the light chain signal peptide (SEQ ID NO: 12). In some embodiments, a mature HC2-AFL:LC1-AFL does not comprise the signal peptides. For example, a mature HC2-AFL:LC1-AFL of the disclosure can comprise SEQ ID NO: 254 and SEQ ID NO: 259.

TABLE 39

| SEQ ID NO:Name | | Amino acid sequence |
|---|---|---|
| 149 | Signal
peptide-
HC2-
AFL | MGWTLVFLFLLSVTAGVHSEVQLVESGGGLVQPGGSLRLSC
AASGFTFNANAMNWVRQAPGKGLEWVGRIRTKSNNYATY
YAGSVKDRFTISRDDSKNSLYLQMNSLKTEDTAVYYCVRD
YYGSSAWITYWGQGTLVTVSSASTKGPSVFPLAPCSRSTSES
TAALGCLVKDYFPEPVTVSWNSGALTSGVHTFPAVLQSSGL
YSLSSVVTVPSSSLGTKTYTCNVDHKPSNTKVDKRVESKYG
PPCPPCPAPEFLGGPSVFLFPPKPKDTLMISRTPEVTCVVVDV
SQEDPEVQFNWYVDGVEVHNAKTKPREEQFNSTYRVVSVL
TVLHQDWLNGKEYKCKVSNKGLPSSIEKTISKAKGQPREPQ
VYTLPPSQEEMTKNQVSLTCLVKGFYPSDIAVEWESNGQPE
NNYKTTPPVLDSDGSFFLYSRLTVDKSRWQEGNVFSCSVMH
EALHNHYTQKSLSLSLGKGGGGSSDTGRPFVEMYSEIPEIIH
MTEGRELVIPCRVTSPNITVTLKKFPLDTLIPDGKRIIWDSRK
GFIISNATYKEIGLLTCEATVNGHLYKTNYLTHRQTNTIIDVV
LSPSHGIELSVGEKLVLNCTARTELNVGIDFNWEYPSSKHQH
KKLVNRDLKTQSGSEMKKFLSTLTIDGVTRSDQGLYTCAAS
SGLMTKKNSTFVRVHEK |
| 219 | Signal
peptide-
LC1-
AFL | MVSSAQFLGLLLLCFQGTRCDVVMTQSPSFLSASVGDRVTIT
CKASQHVGTAVAWYQQRPGKAPKLLIYWASTRHTGVPSRF
SGSGSGTEFTLTISSLQPEDFATYFCQQYSSYPFTFGGGTKLEI
KRTVAAPSVFIFPPSDEQLKSGTASVVCLLNNFYPREAKVQ
WKVDNALQSGNSQESVTEQDSKDSTYSLSSTLTLSKADYEK
HKVYACEVTHQGLSSPVTKSFNRGECGGGGSSDTGRPFVEM
YSEIPEIIHMTEGRELVIPCRVTSPNITVTLKKFPLDTLIPDGK
RIIWDSRKGFIISNATYKEIGLLTCEATVNGHLYKTNYLTHR
QTNTIIDVVLSPSHGIELSVGEKLVLNCTARTELNVGIDFNW
EYPSSKHQHKKLVNRDLKTQSGSEMKKFLSTLTIDGVTRSD
QGLYTCAASSGLMTKKNSTFVRVHEK |

TABLE 39-continued

| SEQ ID NO: | Name | Amino acid sequence |
|---|---|---|
| 259 | LC1-AFL | DVVMTQSPSFLSASVGDRVTITCKASQHVGTAVAWYQQRP GKAPKLLIYWASTRHTGVPSRFSGSGSGTEFTLTISSLQPEDF ATYFCQQYSSYPFTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC<u>GGGGS</u>SDTGRPFVEMYSEIPEIMMTEGRELVIPCR VTSPNITVTLKKFPLDTLIPDGKRIIWDSRKGFIISNATYKEIG LLTCEATVNGHLYKTNYLTHRQTNTIIDVVLSPSHGIELSVG EKLVLNCTARTELNVGIDFNWEYPSSKHQHKKLVNRDLKT QSGSEMKKFLSTLTIDGVTRSDQGLYTCAASSGLMTKKNST FVRVHEK |

Example 8: A Hexavalent Bispecific Antibody Comprising Antibody HC2:LC1 and Ranibizumab-Derived Sequences To generate a heavy chain with ranibizumab-derived VEGF-binding domains added at the C-terminus, an amino acid sequence is generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 28 (ranibizumab-derived sequence).

To generate a light chain with ranibizumab-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 28 (ranibizumab-derived sequence).

The resulting polypeptides, SEQ ID NO: 151 and SEQ ID NO: 243 are co-expressed to provide a hexavalent, bispecific antibody HC2-RAN:LC1-RAN shown in TABLE 40. Amino acids 1-19 of SEQ ID NO: 151 are the heavy chain signal peptide (SEQ ID NO: 11). Amino acids 1-20 of SEQ ID NO: 243 are the light chain signal peptide (SEQ ID NO: 12). In some embodiments, a mature HC2-RAN:LC1-RAN does not comprise the signal peptides. For example, a mature HC2-RAN:LC1-RAN of the disclosure can comprise SEQ ID NO: 256 and SEQ ID NO: 260.

TABLE 40

| SEQ ID NO: | Name | Amino acid sequence |
|---|---|---|
| 151 | Signal peptide-HC2-RAN | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK<u>GGGGS</u>EVQLVESGGGLVQPGGSL RLSCAASGYDFTHYGMN<u>W</u>VRQAPGKGLEWVGWINTYTGE PTYAADFKRRFTFSLDTSKSTAYLQMNSLRAEDTAVYYCAK YPYYYGTSHWYFDVWGQGTLVTVSSGGGGSGGGGSGGGG SDIQLTQSPSSLSASVGDRVTITCSASQDISNYLNWYQQKPG KAPKVLIYFTSSLHSGVPSRFSGSGSGTDFTLTISSLQPEDFAT YYCQQYSTVPWTFGQGTKVEIK |
| 243 | Signal peptide-LC1-RAN | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC<u>GGGGS</u>EVQLVESGG GLVQPGGSLRLSCAASGYDFTHYGMN<u>W</u>VRQAPGKGLEWV GWINTYTGEPTYAADFKRRFTFSLDTSKSTAYLQMNSLRAE DTAVYYCAKYPYYYGTSHWYFDVWGQGTLVTVSSGGGGS GGGGSGGGGSDIQLTQSPSSLSASVGDRVTITCSASQDISNYL NWYQQKPGKAPKVLIYFTSSLHSGVPSRFSGSGSGTDFLTI SSLQPEDFATYYCQQYSTVPWTFGQGTKVEIK |
| 260 | LC1-RAN | DVVMTQSPSFLSASVGDRVTITCKASQHVGTAVAWYQQRP GKAPKLLIYWASTRHTGVPSRFSGSGSGTEFTLTISSLQPEDF ATYFCQQYSSYPFTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC<u>GGGGS</u>EVQLVESGGGLVQPGGSLRLSCAASGYDF THYGMNWVRQAPGKGLEWVGWINTYTGEPTYAADFKRRF TFSLDTSKSTAYLQMNSLRAEDTAVYYCAKYPYYYGTSHW |

TABLE 40-continued

| SEQ ID NO:Name | Amino acid sequence |
|---|---|
| | YFDVWGQGTLVTVSSGGGGSGGGGSGGGGSDIQLTQSPSSL SASVGDRVTITCSASQDISNYLNWYQQKPGKAPKVLIYFTSS LHSGVPSRFSGSGSGTDFTLTISSLQPEDFATYYCQQYSTVP WTFGQGTKVEIK |

Example 9: A Hexavalent Bispecific Antibody Comprising Antibody HC2:LC1 and Abicipar-Derived Sequences To generate a heavy chain with abicipar-derived VEGF-binding domains added at the C-terminus, an amino acid sequence was generated comprising the following appended amino acid sequences, from N-terminus to C-terminus:

1) Residues 1-467 of SEQ ID NO: 14 (heavy chain of antibody HC2:LC1);
2) SEQ ID NO: 31 (linker peptide, underlined); and
3) SEQ ID NO: 244 (abicipar-derived sequence).

To generate a light chain with abicipar-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 244 (abicipar-derived sequence).

The resulting polypeptides, SEQ ID NO: 231 and SEQ ID NO: 232, were co-expressed to provide a hexavalent, bispecific antibody HC2-ABI:LC1-ABI shown in TABLE 41. Amino acids 1-19 of SEQ ID NO: 231 are the heavy chain signal peptide (SEQ ID NO: 11). Amino acids 1-20 of SEQ ID NO: 232 are the light chain signal peptide (SEQ ID NO: 12). In some embodiments, a mature HC2-ABI:LC1-ABI does not comprise the signal peptides. For example, a mature HC2-ABI:LC1-ABI of the disclosure can comprise SEQ ID NO: 257 and SEQ ID NO: 261.

TABLE 41

| SEQ ID NO:Name | | Amino acid sequence |
|---|---|---|
| 231 | Signal peptide-HC2-ABI | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGGGGGSDLDKKLLEAARAGQDDEV RILMANGADVNARDSTGWTPLHLAAPWGHPEIVEVLLKNG ADVNAADFQGWTPLHLAAAVGHLEIVEVLLKYGADVNAQ DKFGKTAFDISIDNGNEDLAEILQKAA |
| 232 | Signal peptide-LC1-ABI | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSDLDKKLLEA ARAGQDDEVRILMANGADVNARDSTGWTPLHLAAPWGHP EIVEVLLKNGADVNAADFQGWTPLHLAAAVGHLEIVEVLL KYGADVNAQDKFGKTAFDISIDNGNEDLAEILQKAA |
| 261 | LC1-ABI | DVVMTQSPSFLSASVGDRVTITCKASQHVGTAVAWYQQRP GKAPKLLIYWASTRHTGVPSRFSGSGSGTEFTLTISSLQPEDF ATYFCQQYSSYPFTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGECGGGGSDLDKKLLEAARAGQDDEVRILMANGADV NARDSTGWTPLHLAAPWGHPEIVEVLLKNGADVNAADFQG WTPLHLAAAVGHLEIVEVLLKYGADVNAQDKFGKTAFDISI DNGNEDLAEILQKAA |

Example 10: A Tetravalent Bispecific Antibody Comprising Antibody HC2:LC1 and Brolucizumab-Derived Sequences To generate a light chain with brolucizumab-derived VEGF-binding domains added at the C-terminus, an amino acid sequence was generated comprising the following appended amino acid sequences, from N-terminus to C-terminus:
1) SEQ ID NO: 17 (light chain of antibody HC2:LC1);
2) SEQ ID NO: 31 (linker peptide, underlined); and
3) SEQ ID NO: 23 (brolucizumab-derived sequence).

The resulting polypeptide (SEQ ID NO: 218) was co-expressed with SEQ ID NO: 14, to provide tetravalent, bispecific antibody HC2:LC1-BRO, comprising the sequences shown in TABLE 42. Amino acids 1-19 of SEQ ID NO: 14 are the heavy chain signal peptide (SEQ ID NO: 11). Amino acids 1-20 of SEQ ID NO: 218 are the light chain signal peptide (SEQ ID NO: 12). In some embodiments, a mature HC2:LC1-BRO does not comprise the signal peptides. For example, a mature HC2:LC1-BRO of the disclosure can comprise SEQ ID NO: 247 and SEQ ID NO: 258.

TABLE 42

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK |
| 218 | Signal peptide-LC1-BRO | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSEIVMTQSPST LSASVGDRVIITCQASEIIHSWLAWYQQKPGKAPKWYLAS TLASGVPSRFSGSGSGAEFTLTISSLQPDDFATYYCQNVYLA STNGANFGQGTKLTVLGGGGSGGGGSGGGGSGGGGSEVQ LVESGGGLVQPGGSLRLSCTASGFSLTDYYYMTWVRQAPG KGLEWVGFIDPDDDPYYATWAKGRFTISRDNSKNTLYLQM NSLRAEDTAVYYCAGGDHNSGWGLDIWGQGTLVTVSS |

Example 11: A Tetravalent Bispecific Antibody Comprising Antibody HC2:LC1 and Aflibercept-Derived Sequences To generate a light chain with aflibercept-derived VEGF-binding domains added at the C-terminus, an amino acid sequence was generated comprising the following appended amino acid sequences, from N-terminus to C-terminus:
1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptide (SEQ ID NO: 219) was co-expressed with SEQ ID NO: 14, to provide tetravalent, bispecific antibody HC2:LC1-AFL, comprising the sequences shown in TABLE 43. Amino acids 1-19 of SEQ ID NO: 14 are the heavy chain signal peptide (SEQ ID NO: 11). Amino acids 1-20 of SEQ ID NO: 219 are the light chain signal peptide (SEQ ID NO: 12). In some embodiments, a mature HC2:LC1-AFL does not comprise the signal peptides. For example, a mature HC2:LC1-AFL of the disclosure can comprise SEQ ID NO: 247 and SEQ ID NO: 259.

TABLE 43

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL |

TABLE 43-continued

| SEQ ID NO: | Name | Amino acid sequence |
|---|---|---|
| | | YSLSSVVTVPSSSLGTKTYTCNVDHKPSNTKVDKRVESKYG PPCPPCPAPEFLGGPSVFLFPPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK |
| 219 | Signal peptide-LC1-AFL | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC<u>GGGGS</u>SDTGRPFVEM YSEIPEIIHMTEGRELVIPCRVTSPNITVTLKKFPLDTLIPDGK RIIWDSRKGFIISNATYKEIGLLTCEATVNGHLYKTNYLTHR QTNTIIDVVLSPSHGIELSVGEKLVLNCTARTELNVGIDFNW EYPSSKHQHKKLVNRDLKTQSGSEMKKFLSTLTIDGVTRSD QGLYTCAASSGLMTKKNSTFVRVHEK |

Example 12: A Tetravalent Bispecific Antibody Comprising Antibody HC2:LC1 and Ranibizumab-Derived Sequences To generate a light chain with ranibizumab-derived VEGF-binding domains added at the C-terminus, an amino acid sequence is generated comprising the following appended amino acid sequences, from N-terminus to C-terminus:
1) SEQ ID NO: 17 (light chain of antibody HC2:LC1);
2) SEQ ID NO: 31 (linker peptide, underlined); and
3) SEQ ID NO: 28 (ranibizumab-derived sequence).

The resulting polypeptide (SEQ ID NO: 243) is co-expressed with SEQ ID NO: 14, to provide tetravalent, bispecific antibody HC2:LC1-RAN, comprising the sequences shown in TABLE 44. Amino acids 1-19 of SEQ ID NO: 14 are the heavy chain signal peptide (SEQ ID NO: 11). Amino acids 1-20 of SEQ ID NO: 243 are the light chain signal peptide (SEQ ID NO: 12). In some embodiments, a mature HC2:LC1-RAN does not comprise the signal peptides. For example, a mature HC2:LC1-RAN of the disclosure can comprise SEQ ID NO: 247 and SEQ ID NO: 260.

TABLE 44

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK |
| 243 | Signal peptide-LC1-RAN | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC<u>GGGGS</u>EVQLVESGG GLVQPGGSLRLSCAASGYDFTHYGMNWVRQAPGKGLEWV GWINTYTGEPTYAADFKRRFTFSLDTSKSTAYLQMNSLRAE DTAVYYCAKYPYYYGTSHWYFDVWGQGTLVTVSSGGGGS GGGGSGGGGSDIQLTQSPSSLSASVGDRVTITCSASQDISNYL NWYQQKPGKAPKVLIYFTSSLHSGVPSRFSGSGSGTDFTLTI SSLQPEDFATYYCQQYSTVPWTFGQGTKVEIK |

Example 13: A Tetravalent Bispecific Antibody Comprising Antibody HC2:LC1 and Abicipar-Derived Sequences To generate a light chain with abicipar-derived VEGF-binding domains added at the C-terminus, an amino acid sequence was generated comprising the following appended amino acid sequences, from N-terminus to C-terminus:
1) SEQ ID NO: 17 (light chain of antibody HC2:LC1);
2) SEQ ID NO: 31 (linker peptide, underlined); and
3) SEQ ID NO: 244 (abicipar-derived sequence).

The resulting polypeptide (SEQ ID NO: 232) was co-expressed with SEQ ID NO: 245 (residues 1-467 of SEQ ID NO: 14), to provide tetravalent, bispecific antibody HC2:LC1-ABI, comprising the sequences shown in TABLE 45. Amino acids 1-19 of SEQ ID NO: 245 are the heavy chain signal peptide (SEQ ID NO: 11). Amino acids 1-20 of SEQ ID NO: 232 are the light chain signal peptide (SEQ ID NO: 12). In some embodiments, a mature HC2:LC1-ABI does not comprise the signal peptides. For example, a mature HC2:LC1-ABI of the disclosure can comprise SEQ ID NO: 247 and SEQ ID NO: 261.

19: (i) HC2:LC1, a humanized monoclonal antibody specific for HPTP-β; (ii) HC2-BRO:LC1, a tetravalent bispecific antibody comprising brolucizumab-derived VEGF-binding domains fused to the C-termini of the heavy chains of HC2:LC1; (iii) HC2-AFL:LC1, a tetravalent bispecific antibody comprising aflibercept-derived VEGF-binding domains fused to the C-termini of the heavy chains of HC2:LC1; (iv) HC2-BRO:LC1-BRO, a hexavalent antibody comprising brolucizumab-derived VEGF-binding domains fused to the C-termini of the heavy chains and the light chains of HC2:LC1; or (v) HC2-AFL:LC1-AFL, a hexavalent antibody comprising aflibercept-derived VEGF-binding domains fused to the C-termini of the heavy chains and the light chains of HC2:LC1. After treatment, the cells were rinsed with ice cold PBS containing 1 mM NaOV and lysed in Complete Triton X Lysis Buffer (20 mM Tris-HCl, 137 mM NaCl, 10% Glycerol, 1% Triton X-100, 2 mM EDTA, 1 mM NaOV, 1 mM NaF, 1 mM PMSF, 1 μg/mL leupeptin, 1 μg/mL pepstatin).

The lysates were immunoprecipitated with anti-Tie2 and anti-VEGFR2 antibodies. 1-10 μg of VEGFR2 antibody (MAB3573, #89109), TIE-2 antibody (Ab33), and 25 μL of

TABLE 45

| SEQ ID NO:Name | | Amino acid sequence |
|---|---|---|
| 245 | Signal peptide- HC2 | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLG |
| 232 | Signal peptide- LC1- ABI | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSDLDKKLLEA ARAGQDDEVRILMANGADVNARDSTGWTPLHLAAPWGHP EIVEVLLKNGADVNAADFQGWTPLHLAAAVGHLEIVEVLL KYGADVNAQDKFGKTAFDISIDNGNEDLAEILQKAA |
| 262 | HC2 | EVQLVESGGGLVQPGGSLRLSCAASGFTFNANAMNWVRQA PGKGLEWVGRIRTKSNNYATYYAGSVKDRFTISRDDSKNSL YLQMNSLKTEDTAVYYCVRDYYGSSAWITYWGQGTLVTV SSASTKGPSVFPLAPCSRSTSESTAALGCLVKDYFPEPVTVS WNSGALTSGVHTFPAVLQSSGLYSLSSVVTVPSSSLGTKTYT CNVDHKPSNTKVDKRVESKYGPPCPPCPAPEFLGGPSVFLFP PKPKDTLMISRTPEVTCVVVDVSQEDPEVQFNWYVDGVEV HNAKTKPREEQFNSTYRVVSVLTVLHQDWLNGKEYKCKVS NKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLG |

Example 14: Bispecific Antibodies that Activate Tie2

Human Umbilical Cord Endothelial Cells (HUVECs) were seeded onto T75 flasks coated with porcine gelatin. Cell maintenance was performed using complete medium (EGM or EGM-2) and sub-cultured using Trypsin/EDTA into 100 mm dishes. After 3 days, the 100 mm dishes were rinsed, and treated in basal medium (EBM, EBM-2, OptiMEM I) for 30 minutes at 37° C./5% CO₂ with one of the following antibodies at 5 or 50 nM as indicated in FIG.

Protein A/G agarose beads were added to 1 mL of HUVEC lysate, and the tubes were placed on a rotating platform for 1-3 days at 4° C. The IP reaction tubes were rinsed with 1 mL complete Triton-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween 20+Tris Buffered Saline (TBS) between steps. An ECL detection system was used to visualize bands. Re-probe was performed on lots treated with 200 mM Glycine for 24-48 h.

Figure 19:
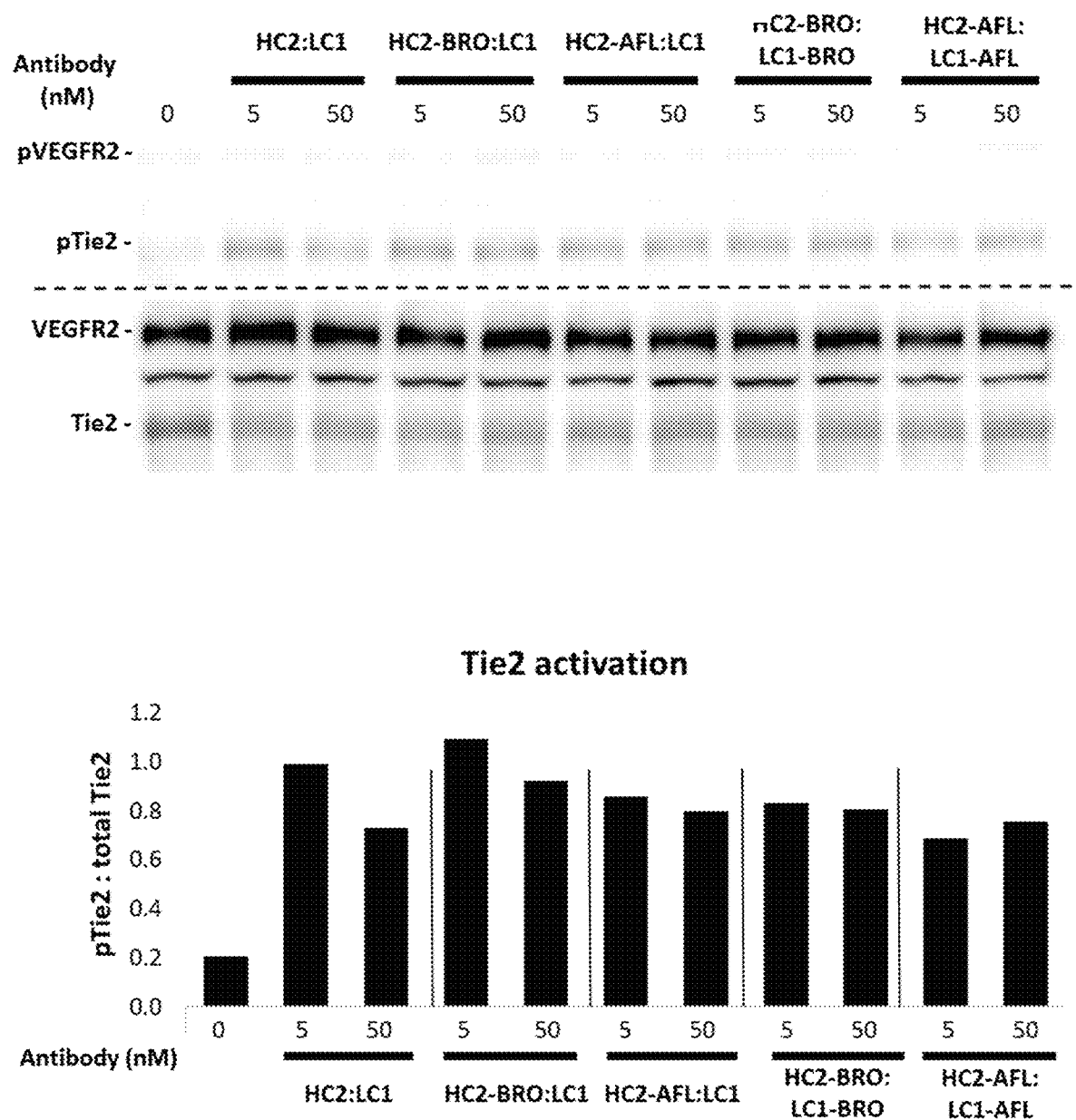
FIG. 19: Activation of Tie2 in HUVECs treated with tetravalent bispecific antibodies or hexavalent bispecific antibodies comprising brolucizumab-derived or aflibercept-derived VEGF-binding domains. As demonstrated by immunoprecipitation and western blot, all of the tested bispecific antibodies increased basal Tie2 activation (in the absence of exogenous Ang1 or Ang2), while basal VEGFR2 phosphorylation (in the absence of exogenous VEGF) was not affected.

As shown in FIG. 19, all of the tested bispecific antibodies increased basal Tie2 activation in HUVECS, while basal VEGFR2 phosphorylation was not affected. The top panel provides a western blot showing Tie2 activation and VEGFR2 activation as shown through detection of phospho-Tie2 and phospho-VEGFR2, respectively (top half), and total Tie2 and VEGFR2 (bottom half). The bottom panel provides the densitometric ratios of phosphorylated Tie2 to total Tie2.

The assay was repeated with the following antibodies of the disclosure, which also enhanced Tie2 activation in the absence of exogenous Ang1: (i) HC2-RAN:LC1, (ii) HC2-ABI:LC1, (iii) HC2:LC1-AFL, (iv) HC2:LC1-BRO, (v) HC2:LC1-ABI, and (vi) HC2-ABI:LC1-ABI.

Figure 20:
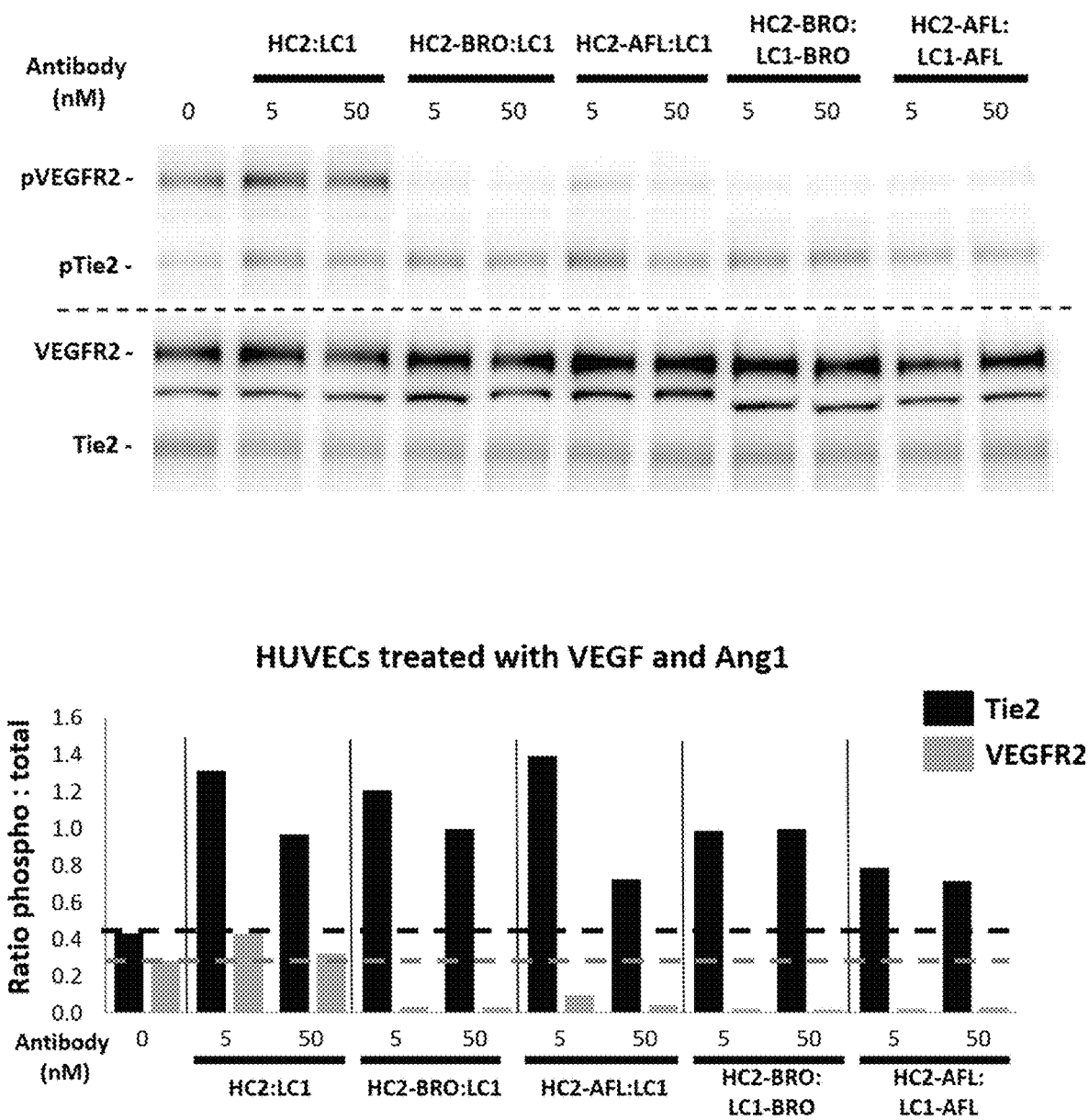
FIG. 20: Tetravalent bispecific and hexavalent bispecific antibodies comprising brolucizumab-derived or aflibercept-derived VEGF-binding domains enhance Tie2 activation and inhibit VEGFR2 activation in HUVECs treated with Ang1 and VEGF, as demonstrated by immunoprecipitation and western blot.

Example 15: Bispecific Antibodies Enhance Ang1-Mediated Tie2 Activation and Block VEGF-Mediated VEGFR2 Activation Human Umbilical Cord Endothelial Cells (HUVECs) were seeded onto T75 flasks coated with porcine gelatin. Cell maintenance was performed using complete medium (EGM or EGM-2) and sub-cultured using Trypsin/EDTA into 100 mm dishes. After 3 days, the 100 mm dishes were rinsed, and mock-pre-treated or pre-treated in basal medium (EBM, EBM-2, OptiMEM I) for 30 minutes at 37° C./5% $CO_2$ with one of the following antibodies at 5 or 50 nM as indicated in FIG. 20: (i) HC2:LC1, a humanized monoclonal antibody specific for HPTP-β; (ii) HC2-BRO:LC1, a tetravalent bispecific antibody comprising brolucizumab-derived VEGF-binding domains fused to the C-termini of the heavy chains of HC2:LC1; (iii) HC2-AFL:LC1, a tetravalent bispecific antibody comprising aflibercept-derived VEGF-binding domains fused to the C-termini of the heavy chains of HC2:LC1; (iv) HC2-BRO:LC1-BRO, a hexavalent antibody comprising brolucizumab-derived VEGF-binding domains fused to the C-termini of the heavy chains and the light chains of HC2:LC1; or (v) HC2-AFL:LC1-AFL, a hexavalent antibody comprising aflibercept-derived VEGF-binding domains fused to the C-termini of the heavy chains and the light chains of HC2:LC1. After pre-treatment, cells were treated with VEGF (5 ng/mL) and Ang1 (50 ng/mL) for 6 minutes at 37° C./5% $CO_2$ in basal medium (Phosphate buffered saline, PBS+0.2% Bovine Serum Albumin, or OptiMEM I). After treatment, the cells were rinsed with ice cold PBS containing 1 mM NaOV and lysed in Complete Triton X Lysis Buffer (20 mM Tris-HCl, 137 mM NaCl, 10% Glycerol, 1% Triton X-100, 2 mM EDTA, 1 mM NaOV, 1 mM NaF, 1 mM PMSF, 1 μg/mL leupeptin, 1 μg/mL pepstatin).

The lysates were immunoprecipitated with anti-Tie2 and anti-VEGFR2 antibodies. 1-10 μg of VEGFR2 antibody (MAB3573, #89109), TIE-2 antibody (Ab33), and 25 μL of Protein A/G agarose beads were added to 1 mL of HUVEC lysate, and the tubes were placed on a rotating platform for 1-3 days at 4° C. The IP reaction tubes were rinsed with 1 mL complete Triton-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween 20+Tris Buffered Saline (TBS) between steps. An ECL detection system was used to visualize bands. Re-probe was performed on lots treated with 200 mM Glycine for 24-48 h.

Treatment with VEGF and Ang1 resulted in increased phosphorylation of VEGFR2 and Tie2 (FIG. 20). Treatment with the HC2:LC1 antibody, specific for HPTP-β, enhanced Ang1-mediated Tie2 activation in cells treated with Ang1 and VEGF. Treatment with the bispecific antibodies enhanced Ang1-mediated Tie2 activation and blocked VEGF-mediated VEGFR2 activation in cells treated with Ang1 and VEGF. The top panel provides a western blot showing Tie2 activation and VEGFR2 activation as shown through detection of phospho-Tie2 and phospho-VEGFR2, respectively (top half), and total Tie2 and VEGFR2 (bottom half). The lower panel provides the densitometric ratios of phosphorylated Tie2 to total Tie2 and phosphorylated VEGFR2 to total VEGFR2.

Example 16: Bispecific Antibodies Enhance Ang1-Mediated Tie2 Activation and Block VEGF-Mediated VEGFR2 Activation (Immunoprecipitation and Western Blot Assays)

Human Umbilical Cord Endothelial Cells (HUVECs) were seeded onto T75 flasks coated with porcine gelatin. Cell maintenance was performed using complete medium (EGM or EGM-2) and sub-cultured using Trypsin/EDTA into 100 mm dishes. After 3 days, the 100 mm dishes were rinsed, and pre-treated in basal medium (EBM, EBM-2, OptiMEM I) for 30 minutes at 37° C./5% $CO_2$ with one of multi-specific antibodies of the disclosure as indicated for each figure. After pre-treatment, the cells were mock-treated or treated with VEGF and Ang1 for 6 minutes at 37° C./5% $CO_2$ in basal medium (Phosphate buffered saline, PBS+0.2% Bovine Serum Albumin, or OptiMEM I). After treatment, the cells were rinsed with ice cold PBS containing 1 mM NaOV and lysed in Complete Triton X Lysis Buffer (20 mM Tris-HCl, 137 mM NaCl, 10% Glycerol, 1% Triton X-100, 2 mM EDTA, 1 mM NaOV, 1 mM NaF, 1 mM PMSF, 1 μg/mL leupeptin, 1 μg/mL pepstatin).

The lysates were immunoprecipitated with anti-Tie2 and anti-VEGFR2 antibodies. 1-10 g of VEGFR2 antibody (MAB3573, #89109), TIE-2 antibody (Ab33), and 25 μL of Protein A/G agarose beads were added to 1 mL of HUVEC lysate, and the tubes were placed on a rotating platform for 1-3 days at 4° C. The IP reaction tubes were rinsed with 1 mL complete Triton-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween 20+Tris Buffered Saline (TBS) between steps. An ECL detection system was used to visualize bands. Re-probe was performed on lots treated with 200 mM Glycine for 24-48 h. The assay was repeated using different multi-specific antibodies of the disclosure, and different concentrations of VEGF and Ang1 as indicated for the following figures.

Figure 21A:
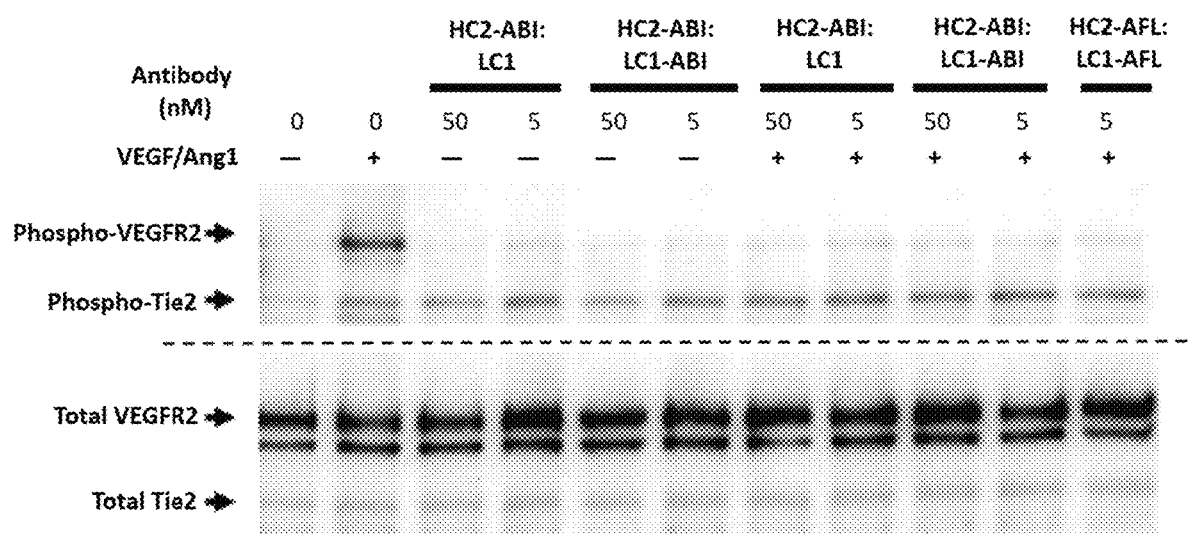
FIG. 21A, FIG. 21B, and FIG. 21C: Tetravalent bispecific and hexavalent bispecific antibodies comprising abicipar-derived or aflibercept-derived VEGF-binding domains enhance Tie2 activation and inhibit VEGFR2 activation in HUVECs, including HUVECs treated with Ang1 and VEGF.
Figure 21B:
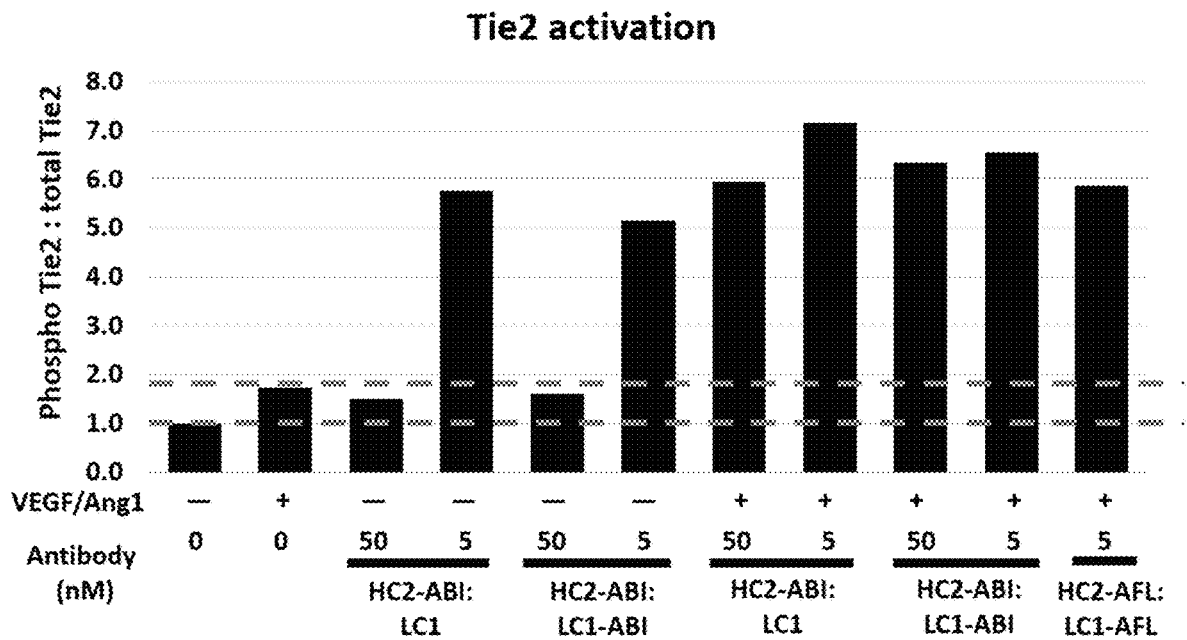
Figure 21C:
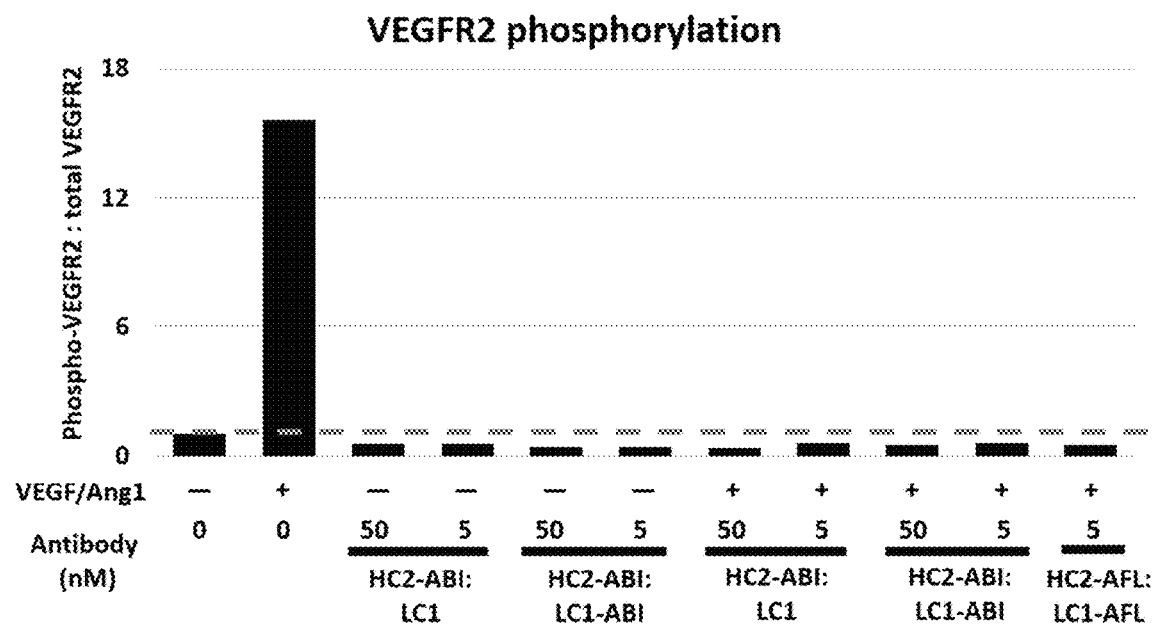

For FIG. 21A, FIG. 21B, and FIG. 21C, the cells were mock-pre-treated or pre-treated at 5 nM or 50 nM with one of: (i) HC2-ABI:LC1, a tetravalent bispecific antibody comprising abicipar-derived VEGF-binding domains fused to the C-termini of the heavy chains of HC2:LC1 (a humanized monoclonal antibody specific for HPTP-β); (ii) HC2-ABI:LC1-ABI, a hexavalent antibody comprising abicipar-derived VEGF-binding domains fused to the C-termini of the heavy chains and the light chains of HC2:LC1; or (iii) HC2-AFL:LC1-AFL, a hexavalent antibody comprising aflibercept-derived VEGF-binding domains fused to the C-termini of the heavy chains and the light chains of HC2:LC1. After pre-treatment, the cells were mock-treated (−) or treated (+) with VEGF (5 ng/mL) and Ang1 (50 ng/mL). Treatment with VEGF and Ang1 resulted in increased phosphorylation of VEGFR2 and Tie2 (FIG. 21A, FIG. 21B, and FIG. 21C). Treatment with the bispecific antibodies enhanced Tie2 activation and blocked VEGFR2 activation, including in cells treated with Ang1 and VEGF (FIG. 21A, FIG. 21B, and FIG. 21C). FIG. 21A provides a western blot showing Tie2 activation and VEGFR2 activation as shown through detection of phospho-Tie2 and phospho-VEGFR2, respectively (top half), and total Tie2 and VEGFR2 (bottom half). FIG. 21B provides the densitometric ratio of phosphorylated Tie2 to total Tie2, normalized to untreated cells. FIG. 21C provides the densitometric ratio of phosphorylated VEGFR2 to total VEGFR2, normalized to untreated cells.

Figure 22A:
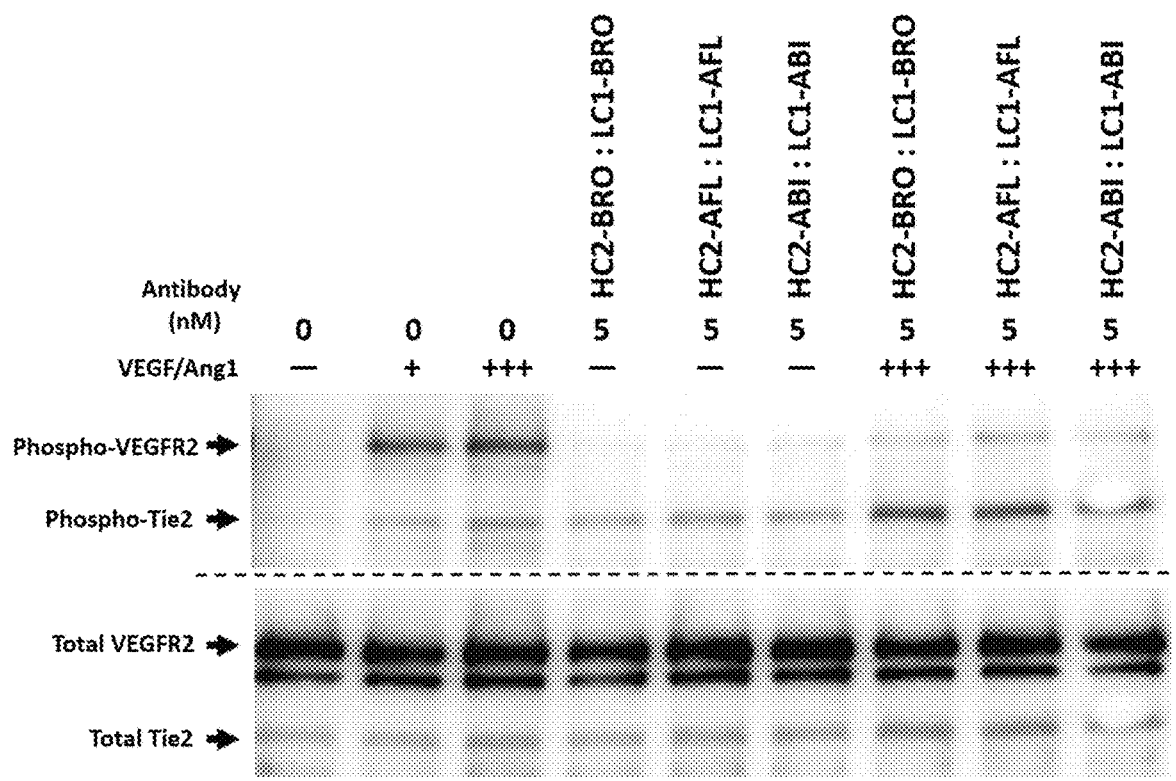
FIG. 22A, FIG. 22B, and FIG. 22C: Hexavalent bispecific antibodies comprising brolucizumab-derived, aflibercept-derived, or abicipar-derived VEGF-binding domains enhance Tie2 activation and inhibit VEGFR2 activation in HUVECs, including HUVECs treated with Ang1 and VEGF.
Figure 22B:
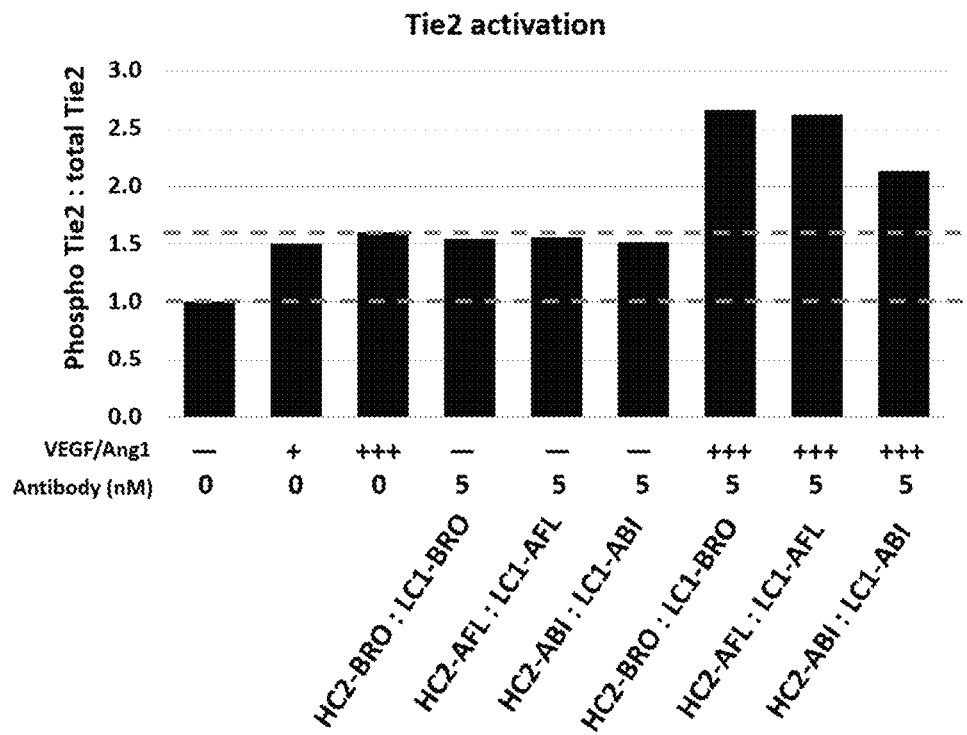
Figure 22C:
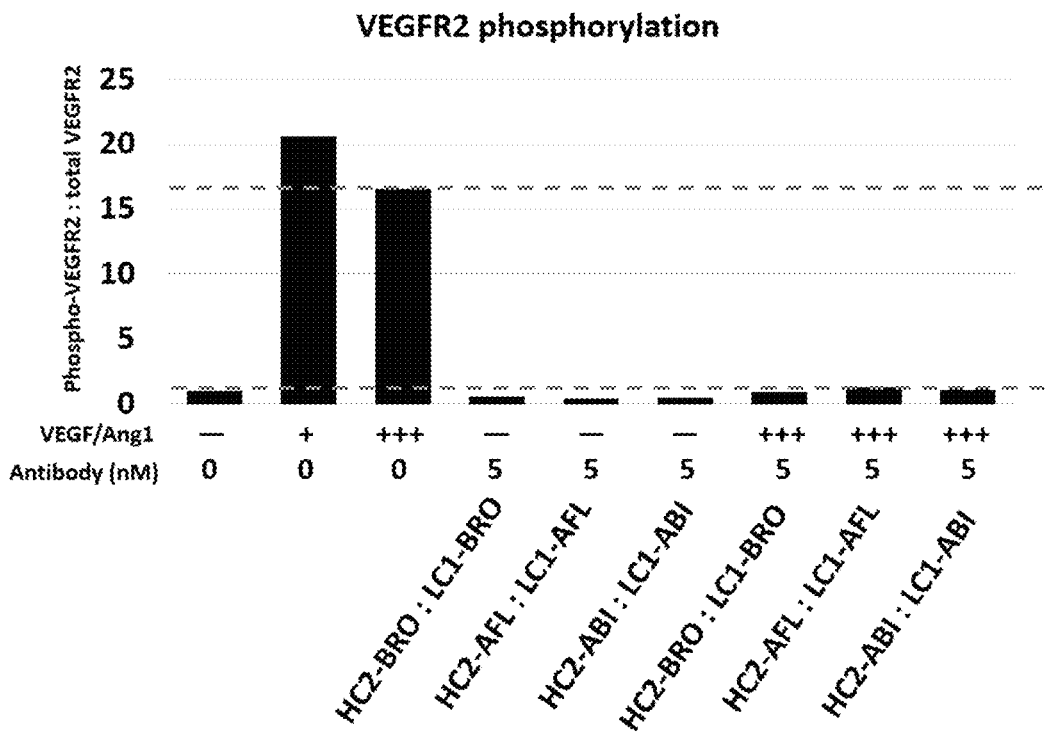

For FIG. 22A, FIG. 22B, and FIG. 22C, the cells were mock-pre-treated or pre-treated with one of the following antibodies at 5 nM: (i) HC2-BRO:LC1-BRO, a hexavalent antibody comprising brolucizumab-derived VEGF-binding domains fused to the C-termini of the heavy chains and the light chains of HC2:LC1 (a humanized monoclonal antibody specific for HPTP-β); (ii) HC2-AFL:LC1-AFL, a hexavalent antibody comprising aflibercept-derived VEGF-binding domains fused to the C-termini of the heavy chains and the light chains of HC2:LC1; or (iii) HC2-ABI:LC1:ABI, a hexavalent bispecific antibody comprising abicipar-derived VEGF-binding domains fused to the C-termini of the heavy chains and the light chains of HC2:LC1. After pre-treatment, the cells were mock-treated (−), treated with 5 ng/mL VEGF and 50 ng/mL Ang1 (+), or treated with 50 ng/mL VEGF and 250 ng/mL of Ang1 (+++). Treatment with VEGF and Ang1 resulted in increased phosphorylation of VEGFR2 and Tie2 (FIG. 22A, FIG. 22B, and FIG. 22C). Treatment with the bispecific antibodies enhanced Tie2 activation and blocked VEGFR2 activation, including in cells treated with Ang1 and VEGF. (FIG. 22A, FIG. 22B, and FIG. 22C). FIG. 22A provides a western blot showing Tie2 activation and VEGFR2 activation as shown through detection of phospho-Tie2 and phospho-VEGFR2, respectively (top half), and total Tie2 and VEGFR2 (bottom half). FIG. 22B provides the densitometric ratio of phosphorylated Tie2 to total Tie2, normalized to untreated cells. FIG. 22C provides the densitometric ratio of phosphorylated VEGFR2 to total VEGFR2, normalized to untreated cells.

Example 17: Bispecific Antibodies Enhance Ang1-Mediated Tie2 Activation and Block VEGF-Mediated VEGFR2 Activation (Electrochemiluminescence Assays)

Human Umbilical Cord Endothelial Cells (HUVECs) were seeded onto T75 flasks coated with porcine gelatin. Cell maintenance was performed using complete medium (EGM or EGM-2) and sub-cultured using Trypsin/EDTA into 100 mm dishes. After 3 days, the 100 mm dishes were rinsed, and mock-pre-treated or pre-treated in basal medium (EBM, EBM-2, OptiMEM I) for 30 minutes at 37° C./5% $CO_2$ with one the antibodies indicated below for each figure.

After pre-treatment, the cells were mock-treated or treated with VEGF and Ang1 for 6 minutes at 37° C./5% $CO_2$ in basal medium (Phosphate buffered saline, PBS+0.2% Bovine Serum Albumin, or OptiMEM I). After treatment, the cells were rinsed with ice cold PBS containing 1 mM NaOV and lysed in Complete Triton X Lysis Buffer (20 mM Tris-HCl, 137 mM NaCl, 10% Glycerol, 1% Triton X-100, 2 mM EDTA, 1 mM NaOV, 1 mM NaF, 1 mM PMSF, 1 µg/mL leupeptin, 1 µg/mL pepstatin).

Phosphorylated Tie2 and phosphorylated VEGFR2 were quantified by electrochemiluminescence. Primary or capture Antibodies were spotted onto 96 well Sector Imager plates. 5 µL of Tie2 antibody (30 µg/mL, AF313) or VEGFR2 antibody (30 µg/mL, 89109) were coated for 1 hour (at room temperature) or overnight (4° C.). Each plate was washed three times with TBS+0.02% Tween 20 (this was performed between each step). Wells were blocked with MSD Blocker A-3% in wash buffer for 1 hour on a rotating platform at room temperature. 25 µL of HUVEC lysates were added to each well directly and incubated for 1 hour on a rotating platform at room temperature. Detection antibody (1) was diluted to 2 µg/mL in 1% blocker/wash buffer (Ab33; AF2720/Y992; pTyr 1214; NB100 530), and 25 µL/well incubated for 1 hour on a rotating platform at room temperature. Detection antibody (2) was diluted to 1 µg/mL in 1% blocker/wash buffer (Goat anti-mouse, GAM; Goat anti-rabbit, GAR; both Sulfo Tag-labeled) and 25 µL/well incubated for 1 hour on a rotating platform at room temperature. Signal was captured using 150 µL of Meso Scale Discovery (MSD) read buffer in each well on an MSD imager instrument. The assay was repeated using different multi-specific antibodies of the disclosure, and different concentrations of VEGF and Ang1 as indicated for the following figures.

Figure 23A:
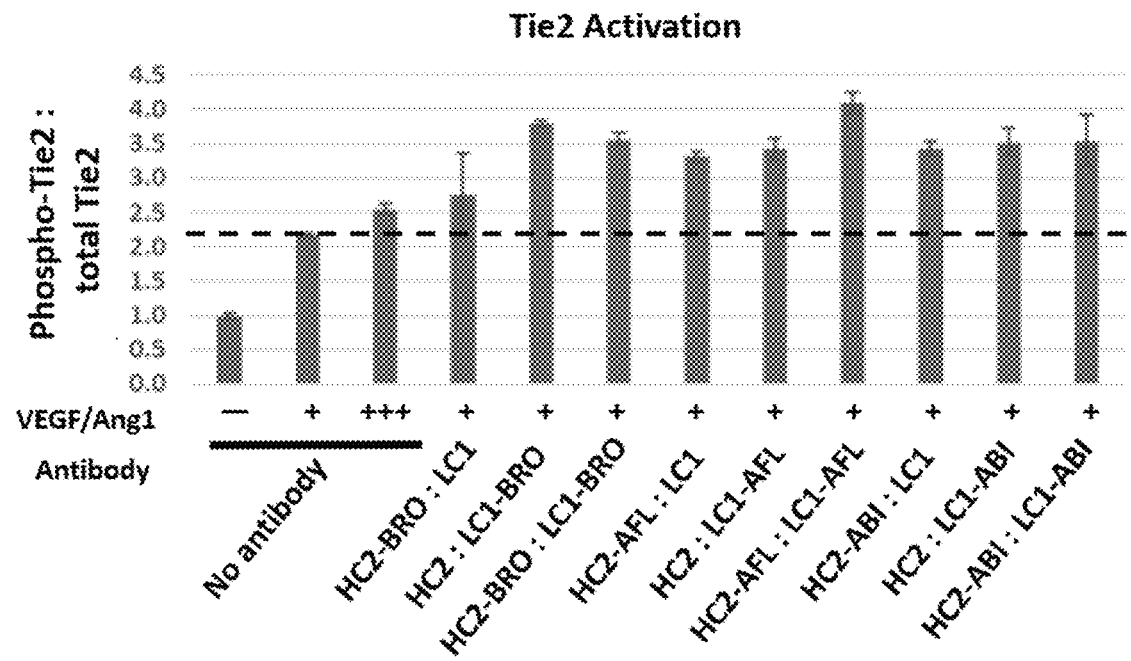
FIG. 23A and FIG. 23B: Tetravalent bispecific and hexavalent bispecific antibodies comprising brolucizumab-derived, aflibercept-derived, or abicipar-derived VEGF-binding domains enhance Tie2 activation and inhibit VEGFR2 activation in HUVECs treated with Ang1 and VEGF, as demonstrated by electrochemiluminescence signal quantification.
Figure 23B:
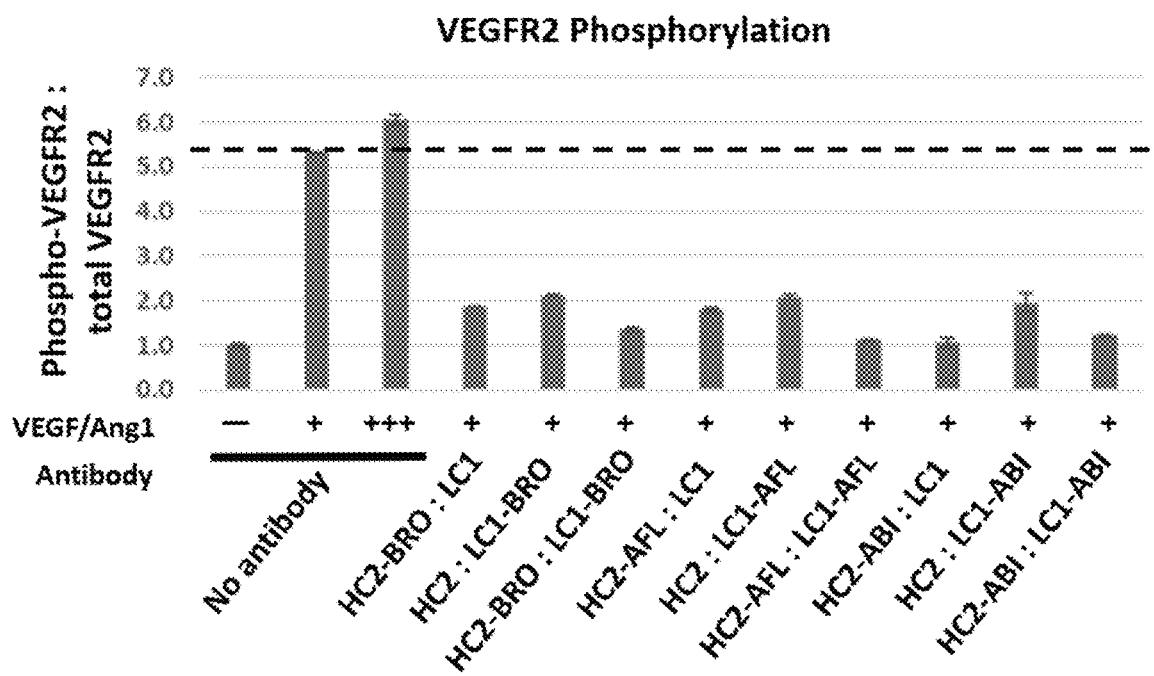

For FIG. 23A and FIG. 23B, the cells were mock-treated or pre-treated with one of the following antibodies at 5 nM: (i) HC2-BRO:LC1, a tetravalent bispecific antibody comprising brolucizumab-derived VEGF-binding domains fused to the C termini of the heavy chains of HC2:LC1 (a humanized monoclonal antibody specific for HPTP-β); (ii) HC2:LC1-BRO, a tetravalent bispecific antibody comprising brolucizumab-derived VEGF-binding domains fused to the C termini of the light chains of HC2:LC1; (iii) HC2-BRO:LC1-BRO, a hexavalent bispecific antibody comprising brolucizumab-derived VEGF-binding domains fused to the C termini of the heavy chains and the light chains of HC2:LC1; (iv) HC2-AFL:LC1, a tetravalent bispecific antibody comprising aflibercept-derived VEGF-binding domains fused to the C termini of the heavy chains of HC2:LC1; (v) HC2:LC1-AFL, a tetravalent bispecific antibody comprising aflibercept-derived VEGF-binding domains fused to the C termini of the light chains of HC2:LC1; (vi) HC2-AFL:LC1-AFL, a hexavalent bispecific antibody comprising aflibercept-derived VEGF-binding domains fused to the C termini of the heavy chains and the light chains of HC2:LC1; (vii) HC2-ABI:LC1, a tetravalent bispecific antibody comprising abicipar-derived VEGF-binding domains fused to the C termini of the heavy chains of HC2:LC1; (viii) HC2:LC1-ABI, a tetravalent bispecific antibody comprising abicipar-derived VEGF-binding domains fused to the C termini of the light chains of HC2:LC1; or (ix) HC2-ABI:LC1-ABI, a hexavalent bispecific antibody comprising abicipar-derived VEGF-binding domains fused to the C termini of the heavy chains and the light chains of HC2:LC1. FIG. 23A and FIG. 23B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL Ang1 (+++). Treatment with VEGF and Ang1 resulted in increased phosphorylation of Tie2 (FIG. 23A) and VEGFR2 (FIG. 23B). Pre-treatment with the multi-specific antibodies enhanced Tie2 activation (FIG. 23A) and inhibited VEGFR2 activation (FIG. 23B) in cells treated with Ang1 and VEGF.

Figure 24A:
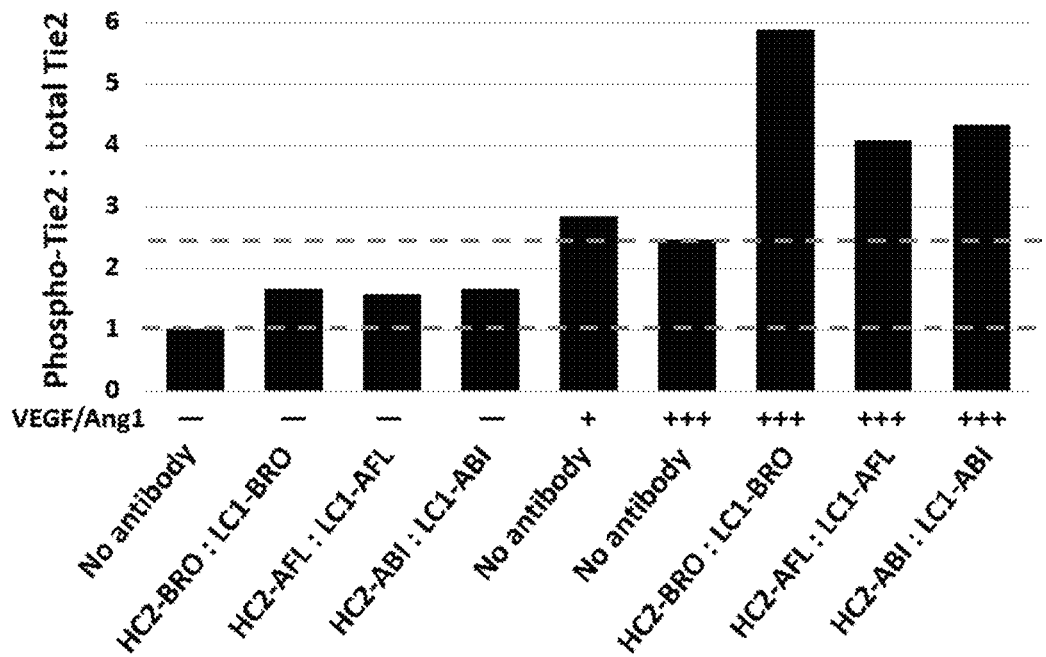
FIG. 24A and FIG. 24B: Hexavalent bispecific antibodies comprising brolucizumab-derived, aflibercept-derived, or abicipar-derived VEGF-binding domains enhance Tie2 activation and inhibit VEGFR2 activation in HUVECs treated with Ang1 and VEGF, as demonstrated by electrochemiluminescence signal quantification.
Figure 24B:
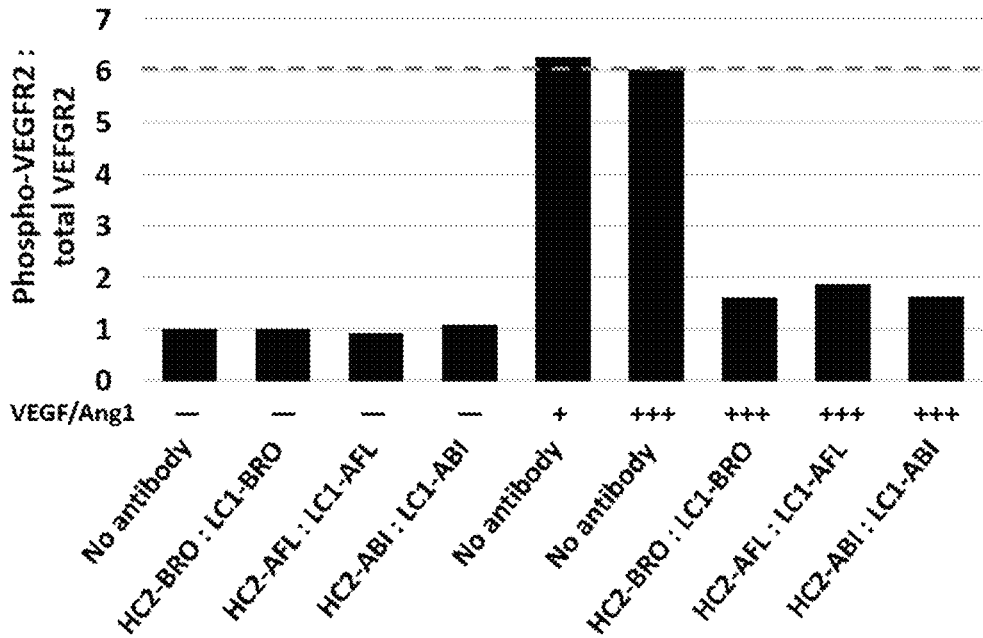

For FIG. 24A and FIG. 24B, the cells were mock-treated or pre-treated with one of the following antibodies at 5 nM: (i) HC2-BRO:LC1-BRO, a hexaavalent bispecific antibody comprising brolucizumab-derived VEGF-binding domains fused to the C termini of the heavy chains and the light chains of HC2:LC1 (a humanized monoclonal antibody specific for HPTP-β); (ii) HC2-AFL:LC1-AFL, a hexavalent bispecific antibody comprising aflibercept-derived VEGF-binding domains fused to the C termini of the heavy chains and the light chains of HC2:LC1; or (iii) HC2-ABI:LC1-ABI, a hexavalent bispecific antibody comprising abicipar-derived VEGF-binding domains fused to the C termini of the heavy chains and the light chains of HC2:LC1. FIG. 24A and FIG. 24B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL of Ang1 (+++). Treatment with VEGF and Ang1 resulted in increased phosphorylation of Tie2 (FIG. 24A) and VEGFR2 (FIG. 24B). Pre-treatment with the multi-specific antibodies enhanced Tie2 activation (FIG. 24A) and inhibited VEGFR2 activation (FIG. 24B) in cells treated with Ang1 and VEGF.

Figure 25A:
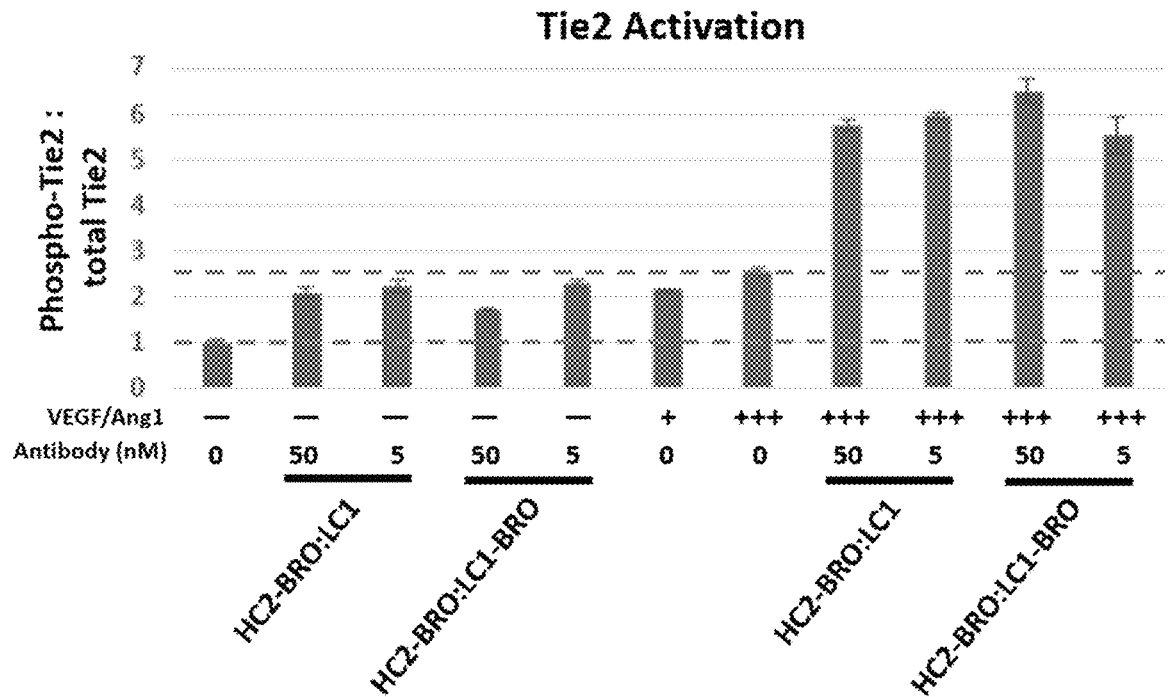
FIG. 25A and FIG. 25B: Tetravalent bispecific and hexavalent bispecific antibodies comprising brolucizumab-derived VEGF-binding domains enhance Tie2 activation and inhibit VEGFR2 activation in HUVECs treated with Ang1 and VEGF, as demonstrated by electrochemiluminescence signal quantification.
Figure 25B:
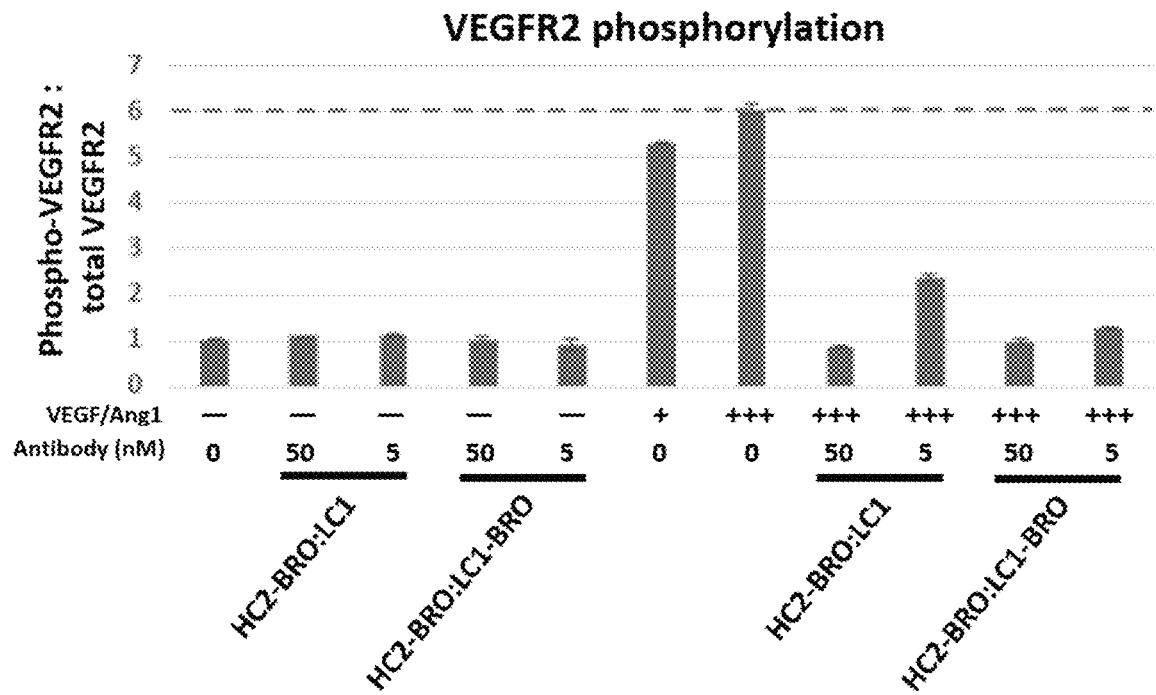

For FIG. 25A and FIG. 25B, the cells were mock-treated or pre-treated with one of the following antibodies at 5 or 50 nM: (i) HC2-BRO:LC1, a tetravalent bispecific antibody comprising brolucizumab-derived VEGF-binding domains fused to the C termini of the heavy chains of HC2:LC1 (a humanized monoclonal antibody specific for HPTP-β); or (ii) HC2-BRO:LC1-BRO, a hexavalent bispecific antibody comprising brolucizumab-derived VEGF-binding domains fused to the C termini of the heavy chains and the light chains of HC2:LC1. FIG. 25A and FIG. 25B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL of Ang1 (+++). Treatment with VEGF and Ang1 resulted in increased phosphorylation of Tie2 (FIG. 25A) and VEGFR2 (FIG. 25B). Pre-treatment with the multi-specific antibodies enhanced Tie2 activation (FIG. 25A) and inhibited VEGFR2 activation (FIG. 25B) in cells treated with Ang1 and VEGF.

Figure 26A:
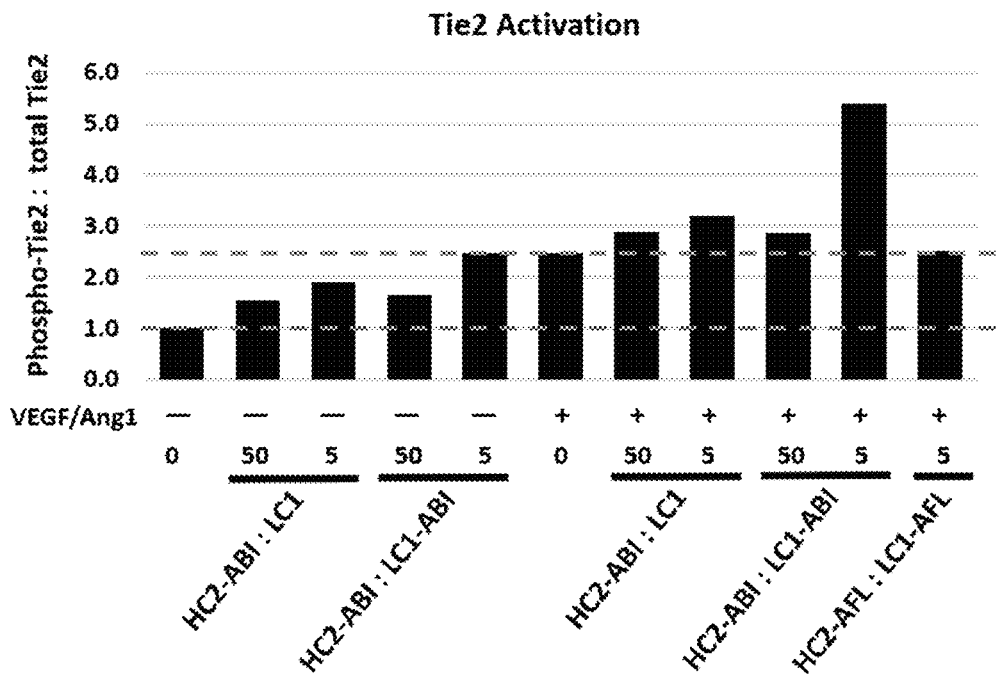
FIG. 26A and FIG. 26B: Tetravalent bispecific and hexavalent bispecific antibodies comprising abicipar-derived or aflibercept-derived VEGF-binding domains enhance Tie2 activation and inhibit VEGFR2 activation in HUVECs treated with Ang1 and VEGF, as demonstrated by electrochemiluminescence signal quantification.
Figure 26B:
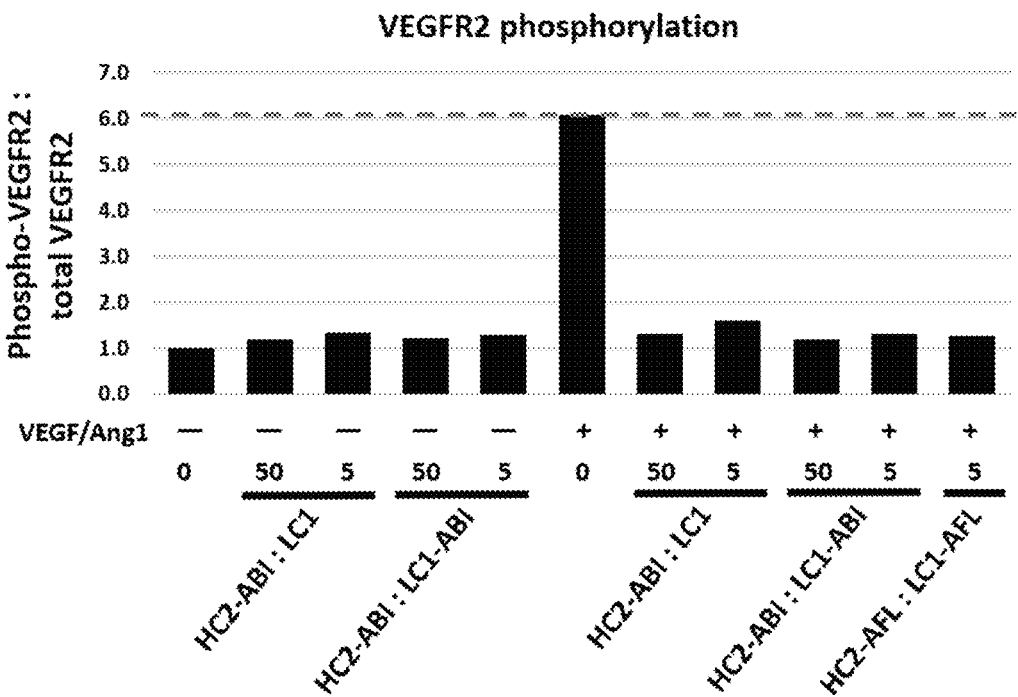

For FIG. 26A and FIG. 26B, the cells were mock-treated or pre-treated with one of the following antibodies at 5 nM or 50 nM: (i) HC2-ABI:LC1, a tetravalent bispecific antibody comprising abicipar-derived VEGF-binding domains fused to the C termini of the heavy chains of HC2:LC1 (a humanized monoclonal antibody specific for HPTP-β); (ii) HC2-ABI:LC1-ABI, a hexavalent bispecific antibody comprising abicipar-derived VEGF-binding domains fused to the C termini of the heavy chains and the light chains of HC2:LC1; or (iii) HC2-AFL:LC1:AFL, a hexavalent bispecific antibody comprising aflibercept-derived VEGF-binding domains fused to the C termini of the heavy chains and the light chains of HC2:LC1. FIG. 26A and FIG. 26B provide the ratio of phosphorylated Tie2 to total Tie2 and phosphorylated VEGFR2 to total VEGFR2, respectively, normalized to untreated cells. Treatments were as follows: mock-treated (−), or treated with 5 ng/mL VEGF and 50 ng/mL Ang1 (+). Treatment with VEGF and Ang1 resulted in increased phosphorylation of Tie2 (FIG. 26A) and VEGFR2 (FIG. 26B). Pre-treatment with the multi-specific antibodies enhanced Tie2 activation (FIG. 26A) and inhibited VEGFR2 activation (FIG. 26B) in cells treated with Ang1 and VEGF.

Figure 27A:
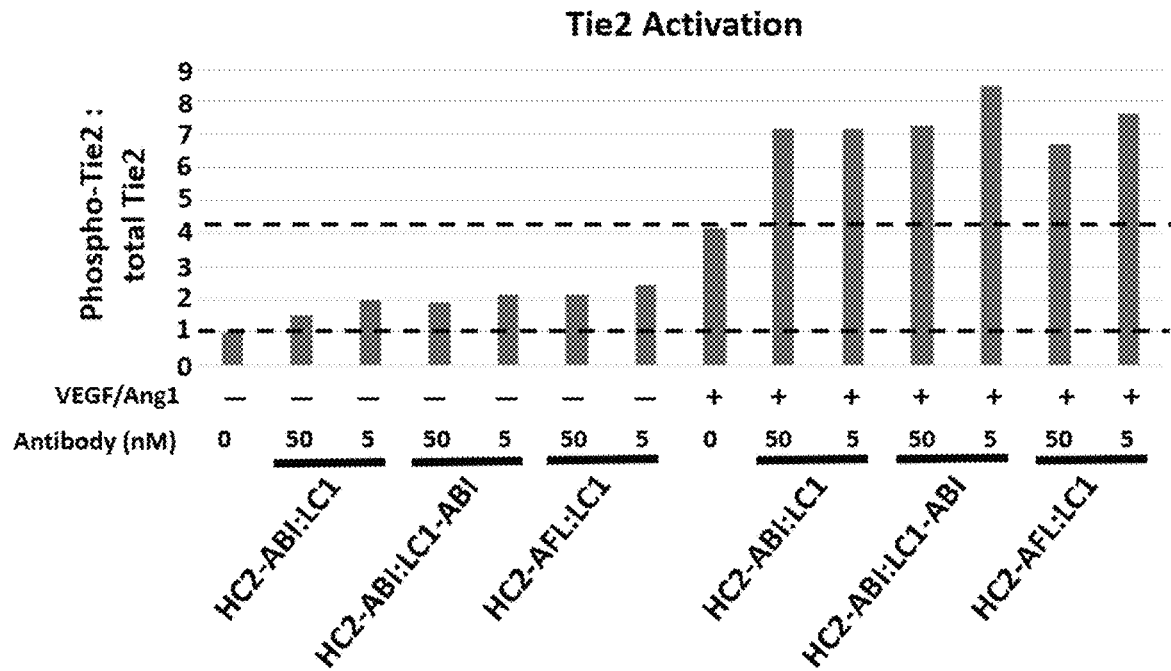
FIG. 27A and FIG. 27B: Tetravalent bispecific and hexavalent bispecific antibodies comprising abicipar-derived or aflibercept-derived VEGF-binding domains enhance Tie2 activation and inhibit VEGFR2 activation in HUVECs treated with Ang1 and VEGF, as demonstrated by electrochemiluminescence signal quantification.
Figure 27B:
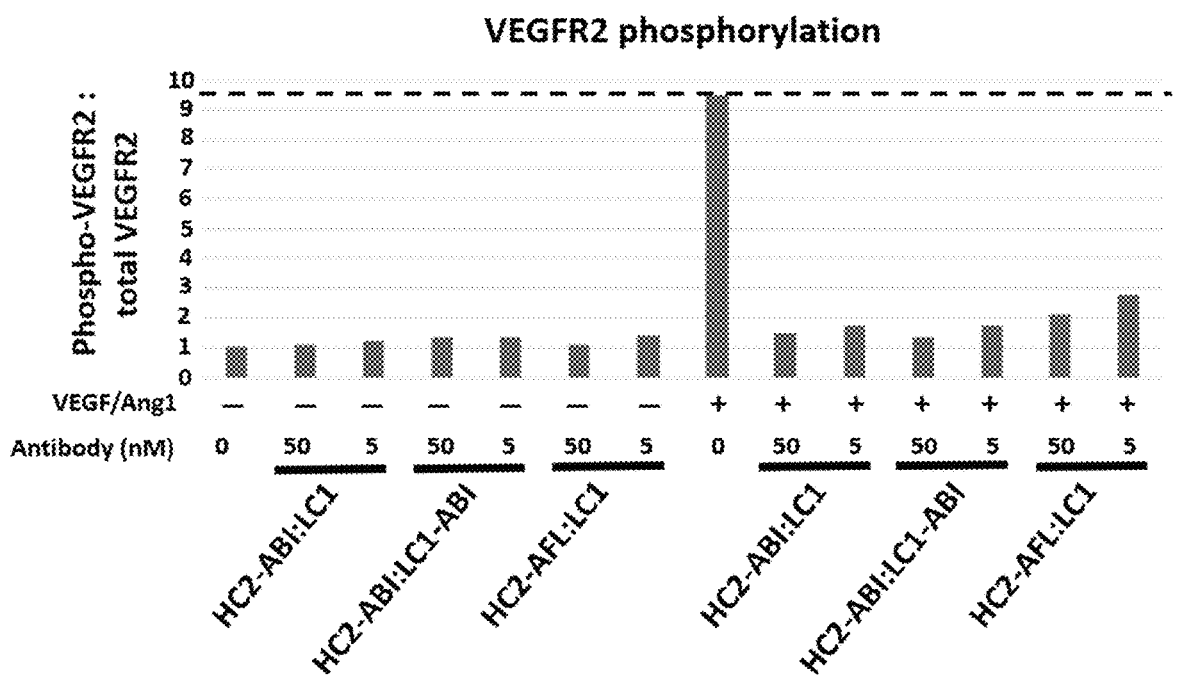

For FIG. 27A and FIG. 27B, the cells were mock-treated or pre-treated with one of the following antibodies at 5 nM or 50 nM: (i) HC2-ABI:LC1, a tetravalent bispecific antibody comprising abicipar-derived VEGF-binding domains fused to the C termini of the heavy chains of HC2:LC1 (a humanized monoclonal antibody specific for HPTP-β); (ii) HC2-ABI:LC1-ABI, a hexavalent bispecific antibody comprising abicipar-derived VEGF-binding domains fused to the C termini of the heavy chains and the light chains of HC2:LC1; or (iii) HC2-AFL:LC1, a tetravalent bispecific antibody comprising aflibercept-derived VEGF-binding domains fused to the C termini of the heavy chains of HC2:LC1. FIG. 27A and FIG. 27B provide the ratio of phosphorylated Tie2 to total Tie2 and phosphorylated VEGFR2 to total VEGFR2, respectively, normalized to untreated cells. Treatments were as follows: mock-treated (−), or treated with 25 ng/mL VEGF and 250 ng/mL Ang1 (+). Treatment with VEGF and Ang1 resulted in increased phosphorylation of Tie2 (FIG. 27A) and VEGFR2 (FIG. 27B). Pre-treatment with the multi-specific antibodies enhanced Tie2 activation (FIG. 27A) and inhibited VEGFR2 activation (FIG. 27B) in cells treated with Ang1 and VEGF.

Example 18: Multi-Specific Antibodies Bind HPTP-β and VEGF at High Affinity (Biacore Surface Plasmon Resonance Assays)

Biacore surface plasmon resonance assays were performed to determine the equilibrium dissociation constant ($K_D$) of antibodies of the disclosure for VEGF and HPTP-β (VE-PTP). Binding experiments were performed on Biacore 3000/Biacore T-200 instruments at 25° C.

The assay buffer contained 10 mM HEPES buffer (pH 7.4), 150 mM NaCl, 3 mM EDTA, and 0.05% P20 (polyoxyethylenesorbitan). The regeneration buffer contained 10 mM Glycine buffer (pH 1.75). The conjugation buffer contained 10 mM sodium acetate buffer (pH 5). A flow rate of 5 µL/minute was used for capturing ligand. A flow rate of 30 µL/minute was used for kinetic analysis.

For analysis of binding of antibodies to HPTP-β, polyhistidine tagged HPTP-β extracellular domain (ECD) 1/2 was immobilized on a chip surface via anti-His antibodies. Goat anti-His antibody was first immobilized on the surface of the chip by direct immobilization using EDC/NHS (N-ethyl-N'-(3-dimethyl aminopropyl carbodiimide)/N-hydroxy succinamide) coupling chemistry on flow cell 2 of the CM5 (Carboxymethylated dextran coated) chip. Unoccupied sites were blocked with 1M ethanolamine. The His-tagged ligand HPTP-β 1/2 ECD was captured at a response unit (RU) of 50. The analyte (antibody) was flowed over the chip at a single analyte concentration at a time. The binding of analyte to the ligand was monitored in real time to obtain on ($k_a$) and off ($k_d$) rates. The equilibrium constant ($K_D$) was calculated from the observed $k_a$ and $k_d$.

For analysis of binding of the antibodies to VEGF, the antibodies were immobilized on the surface of the chip by direct immobilization using EDC/Ni s coupling chemistry on flow cell 2 of the CM5 chip. Unoccupied sites were blocked with 1M ethanolamine. The analyte (VEGF) was flowed over the chip at a single analyte concentration at a time. The binding of analyte to the ligand was monitored in real time to obtain on ($k_a$) and off ($k_d$) rates. The equilibrium constant ($K_D$) was calculated from the observed $k_a$ and $k_d$.

Scouting analysis was performed using 10 nM of analyte to determine approximate $K_D$. Chi square analysis was carried out between the actual sensorgram and the sensorgram generated from the BIAnalysis software to confirm the accuracy of the analysis; values of 1-2 were considered accurate and below 1 highly accurate.

TABLE 46 provides equilibrium dissociation constants based on scouting experiments performed at a single ligand concentration. NB=no significant binding detected.

TABLE 46

| Construct | VEGF $K_D$ | VEGF chi sq | HPTP-β $K_D$ | HPTP-β chi sq |
|---|---|---|---|---|
| HC2:LC1 | NB | NB | 7.32E-11M (73.2 pM) | 0.0439 |
| Aflibercept | 1.60E-10M (160 pM) | 0.278 | NB | NB |
| HC2-AFL:LC1 | 3.50E-10M (350 pM) | 0.13 | 3.20E-10M (320 pM) | 0.336 |
| HC2-BRO:LC1 | 1.12E-13M (112 fM) | 0.148 | 3.25E-10M (325 pM) | 0.323 |
| HC2-ABI:LC1 | 1.10E-13M (110 fM) | 1.68 | 1.22E-10M (122 pM) | 1.38 |
| HC2-RBZ:LC1 | NB | | 5.86E-13M (586 fM) | 0.16 |
| HC2:LC1-AFL | 8.25E-10M (825 pM) | 0.189 | 4.67E-10M (467 pM) | 1.48 |
| HC2:LC1-BRO | 3.51E-14M (35.1 fM) | 0.185 | 3.09E-10M (309 pM) | 0.691 |
| HC2:LC1-ABI | 5.19E-10M (519 pM) | 3.09 | 6.10E-11M (61 pM) | 1.47 |
| HC2-AFL:LC1-AFL | 5.57E-10M (557 pM) | 2.53 | 6.94E-11M (69.4 pM) | 3.14 |
| HC2-BRO:LC1-BRO | 1.79E-12M (1.79 pM) | 0.809 | 3.50E-12M (3.5 pM) | 2.15 |
| HC2-ABI:LC1-ABI | 6.80E-10M (680 pM) | 8.02 | 2.05E-10M (205 pM) | 1.18 |

Full kinetic analysis was performed using 0 nM, 0.625 nM, 1.25 nM, 5 nM, and 10 nM of the analyte to determine $K_D$. Chi square analysis was carried out between the actual sensorgram and the sensorgram generated from the BIAnalysis software to confirm the accuracy of the analysis; values of 1-2 were considered accurate and below 1 highly accurate.

TABLE 47 provides equilibrium dissociation constants based on full kinetic experiments performed at multiple ligand concentrations. NB=no significant binding detected.

TABLE 47

| Construct | VEGF $K_D$ | VEGF chi sq | HPTP-β $K_D$ | HPTP-β chi sq |
|---|---|---|---|---|
| HC2:LC1 | NB | NB | 1.21E-10M (121 pM) | 0.123 |
| Aflibercept | 3.75E-11M (37.5 pM) | 0.106 | NB | NB |
| HC2-AFL:LC1 | 4.63E-11M (46.3 pM) | 0.0875 | 2.19E-10M (219 pM) | 0.0295 |
| HC2-BRO:LC1 | 2.18E-13M (218 fM) | 0.452 | 1.54E-10M (154 pM) | 0.0817 |
| HC2-ABI:LC1 | 4.00E-14M (40 fM) | 0.223 | 1.03E-12M (1.03 pM) | 0.113 |

These results demonstrate that the multi-specific antibodies HC2-AFL:LC1, HC2-BRO:LC1, HC2-ABI:LC1, HC2:LC1-AFL, HC2:LC1-BRO, HC2:LC1-ABI, HC2-AFL:LC1-AFL, HC2-BRO:LC1-BRO, and HC2-ABI:LC1-ABI bind to HPTP-β and VEGF with high affinity.

Example 19: A Hexavalent Antibody Comprising Antibody HC2:LC, Abicipar-Derived Sequences, and Brolucizumab-Derived Sequences To generate a heavy chain with abicipar-derived VEGF-binding domains added at the C-terminus, an amino acid sequence is generated comprising the following appended amino acid sequences, from N-terminus to C-terminus:

1) Residues 1-467 of SEQ ID NO: 14 (heavy chain of antibody HC2:LC1);

2) SEQ ID NO: 31 (linker peptide, underlined); and

3) SEQ ID NO: 244 (abicipar-derived sequence).

To generate a light chain with brolucizumab-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);

2) SEQ ID NO: 31 (linker peptide, underlined); and

3) SEQ ID NO: 23 (brolucizumab-derived sequence).

The resulting polypeptides, SEQ ID NO: 231 and SEQ ID NO: 218, are co-expressed to provide a hexavalent antibody HC2-ABI:LC1-BRO shown in TABLE 48. Amino acids 1-19 of SEQ ID NO: 231 are the heavy chain signal peptide (SEQ ID NO: 11). Amino acids 1-20 of SEQ ID NO: 218 are the light chain signal peptide (SEQ ID NO: 12). In some embodiments, a mature HC2-ABI:LC1-BRO does not comprise the signal peptides. For example, a mature HC2-ABI:LC1-BRO of the disclosure can comprise SEQ ID NO: 257 and SEQ ID NO: 258. The antibody is bispecific for target molecules, comprising a specificity for HPTP-β (VE-PTP) and VEGF. The antibody is trispecific for target epitopes, comprising a specificity for one HPTP-β (VE-PTP) epitope and for two VEGF epitopes.

TABLE 48

| SEQ ID NO: | Name | Amino acid sequence |
|---|---|---|
| 231 | Signal peptide-HC2-ABI | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGGGGGSDLDKKLLEAARAGQDDEV RILMANGADVNARDSTGWTPLHLAAPWGHPEIVEVLLKNG ADVNAADFQGWTPLHLAAAVGHLEIVEVLLKYGADVNAQ DKFGKTAFDISIDNGNEDLAEILQKAA |
| 218 | Signal peptide-LC1-BRO | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSEIVMTQSPST LSASVGDRVIITCQASEIIHSWLAWYQQKPGKAPKLLIYLAS TLASGVPSRFSGSGSGAEFTLTISSLQPDDFATYYCQNVYLA STNGANFGQGTKLTVLGGGGSGGGGSGGGGSGGGGSEVQ LVESGGGLVQPGGSLRLSCTASGFSLTDYYYMTWVRQAPG KGLEWVGFIDPDDDPYYATWAKGRFTISRDNSKNTLYLQM NSLRAEDTAVYYCAGGDHNSGWGLDIWGQGTLVTVSS |

Example 20: A Hexavalent Antibody Comprising Antibody HC2:LC, Aflibercept-Derived Sequences, and Brolucizumab-Derived Sequences To generate a heavy chain with brolucizumab-derived VEGF-binding domains added at the C-terminus, an amino acid sequence is generated comprising the following appended amino acid sequences, from N-terminus to C-terminus:
1) SEQ ID NO: 14 (heavy chain of antibody HC2:LC1);
2) SEQ ID NO: 31 (linker peptide, underlined); and
3) SEQ ID NO: 23 (brolucizumab-derived sequence).

To generate a light chain with aflibercept-derived VEGF-binding domains added at the C-terminus, an amino acid sequence is generated comprising the following appended amino acid sequences, from N-terminus to C-terminus:
1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptides, SEQ ID NO: 150 and SEQ ID NO: 219, are co-expressed to provide a hexavalent antibody HC2-BRO:LC1-AFL shown in TABLE 49. Amino acids 1-19 of SEQ ID NO: 150 are the heavy chain signal peptide (SEQ ID NO: 11). Amino acids 1-20 of SEQ ID NO: 219 are the light chain signal peptide (SEQ ID NO: 12). In some embodiments, a mature HC2-BRO:LC1-AFL does not comprise the signal peptides. For example, a mature HC2-BRO:LC1-AFL of the disclosure can comprise SEQ ID NO: 255 and SEQ ID NO: 259. The antibody is bispecific for target molecules, comprising a specificity for HPTP-β (VE-PTP) and VEGF. The antibody is trispecific for target epitopes, comprising a specificity for one HPTP-β (VE-PTP) epitope and for two VEGF epitopes.

TABLE 49

| SEQ ID NO: | Name | Amino acid sequence |
|---|---|---|
| 150 | Signal peptide-HC2-BRO | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGKGGGGSEIVMTQSPSTLSASVGDR VIITCQASEIIHSWLAWYQQKPGKAPKLLIYLASTLASGVPSR FSGSGSGAEFTLTISSLQPDDFATYYCQNVYLASTNGANFGQ GTKLTVLGGGGSGGGGSGGGGSGGGGSEVQLVESGGGLV QPGGSLRLSCTASGFSLTDYYYMTWVRQAPGKGLEWVGFI DPDDDPYYATWAKGRFTISRDNSKNTLYLQMNSLRAEDTA VYYCAGGDHNSGWGLDIWGQGTLVTVSS |

TABLE 49-continued

| SEQ ID NO:Name | Amino acid sequence |
|---|---|
| 219 Signal peptide-LC1- | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI AFLKRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSSDTGRPFVEM YSEIPEIIHMTEGRELVIPCRVTSPNITVTLKKFPLDTLIPDGK RIIWDSRKGFIISNATYKEIGLLTCEATVNGHLYKTNYLTHR QTNTIIDVVLSPSHGIELSVGEKLVLNCTARTELNVGIDFNW EYPSSKHQHKKLVNRDLKTQSGSEMKKFLSTLTIDGVTRSD QGLYTCAASSGLMTKKNSTFVRVHEK |

Embodiments

The following non-limiting embodiments provide illustrative examples of the disclosure, but do not limit the scope of the disclosure.

Embodiment 1

A compound comprising: (a) a first domain, wherein the first domain modulates a phosphatase, wherein the phosphatase modulates Tie2; and (b) a second domain that specifically binds a receptor tyrosine kinase agonist.

Embodiment 2

The compound of embodiment 1, wherein the compound is an antibody.

Embodiment 3

The compound of any one of embodiments 1-2, wherein the compound is a multispecific antibody.

Embodiment 4

The compound of any one of embodiments 1-3, wherein the compound is a tetravalent antibody.

Embodiment 5

The compound of any one of embodiments 1-3, wherein the compound is a hexavalent antibody.

Embodiment 6

The compound of any one of embodiments 1-5, wherein the compound is a bispecific antibody.

Embodiment 7

The compound of any one of embodiments 1-4 and 6, wherein the compound is a tetravalent bispecific antibody.

Embodiment 8

The compound of any one of embodiments 1-3 and 5-6, wherein the compound is a hexavalent bispecific antibody.

Embodiment 9

The compound of any one of embodiments 1-8, wherein the compound inhibits the phosphatase that modulates Tie2.

Embodiment 10

The compound of any one of embodiments 1-9, wherein the compound inhibits HPTP-β.

Embodiment 11

The compound of any one of embodiments 1-10, wherein the compound inhibits VE-PTP.

Embodiment 12

The compound of any one of embodiments 1-11, wherein the compound activates Tie2.

Embodiment 13

The compound of any one of embodiments 1-12, wherein the compound inhibits the receptor tyrosine kinase agonist.

Embodiment 14

The compound of any one of embodiments 1-13, wherein the compound inhibits VEGF receptor signaling.

Embodiment 15

The compound of any one of embodiments 1-14, wherein the compound inhibits a VEGF.

Embodiment 16

The compound of any one of embodiments 1-15, wherein the compound inhibits VEGF-A.

Embodiment 17

The compound of any one of embodiments 1-16, wherein the compound inhibits the phosphatase that modulates Tie2, and inhibits the receptor tyrosine kinase agonist.

Embodiment 18

The compound of any one of embodiments 1-17, wherein the phosphatase is HPTP-β, and the receptor tyrosine kinase agonist is a VEGF.

Embodiment 19

The compound of any one of embodiments 1-18, wherein the phosphatase is HPTP-β, and the receptor tyrosine kinase agonist is VEGF-A.

Embodiment 20

The compound of any one of embodiments 1-19, wherein the compound activates Tie2, and the receptor tyrosine kinase agonist is a VEGF.

Embodiment 21

The compound of any one of embodiments 1-20, wherein the compound activates Tie2, and the receptor tyrosine kinase agonist is VEGF-A.

Embodiment 22

The compound of any one of embodiments 1-21, wherein the phosphatase that modulates Tie2 signaling is a protein tyrosine phosphatase.

Embodiment 23

The compound of any one of embodiments 1-22, wherein the phosphatase that modulates Tie2 signaling is a receptor-like protein tyrosine phosphatase.

Embodiment 24

The compound of any one of embodiments 1-23, wherein the phosphatase that modulates Tie2 signaling is HPTP-β.

Embodiment 25

The compound of any one of embodiments 1-23, wherein the phosphatase that modulates Tie2 signaling is VE-PTP.

Embodiment 26

The compound of any one of embodiments 1-25, wherein the receptor tyrosine kinase agonist is a growth factor.

Embodiment 27

The compound of any one of embodiments 1-26, wherein the receptor tyrosine kinase agonist is a cysteine-knot growth factor superfamily member.

Embodiment 28

The compound of any one of embodiments 1-27, wherein the receptor tyrosine kinase agonist is a PDGF family member.

Embodiment 29

The compound of any one of embodiments 1-28, wherein the receptor tyrosine kinase agonist is a pro-angiogenic factor.

Embodiment 30

The compound of any one of embodiments 1-29, wherein the receptor tyrosine kinase agonist is a VEGF receptor agonist.

Embodiment 31

The compound of any one of embodiments 1-30, wherein the receptor tyrosine kinase agonist is a VEGF.

Embodiment 32

The compound of any one of embodiments 1-31, wherein the receptor tyrosine kinase agonist is VEGF-A.

Embodiment 33

The compound of any one of embodiments 1-32, wherein the first domain binds to HPTP-β.

Embodiment 34

The compound of any one of embodiments 1-33, wherein the first domain binds to VE-PTP.

Embodiment 35

The compound of any one of embodiments 1-34, wherein the first domain binds to an extracellular domain of HPTP-β.

Embodiment 36

The compound of any one of embodiments 1-34, wherein the first domain binds to a first FN3 repeat of an extracellular domain of HPTP-β.

Embodiment 37

The compound of any one of embodiments 1-36, wherein the second domain binds to a VEGF.

Embodiment 38

The compound of any one of embodiments 1-37, wherein the second domain binds to VEGF-A.

Embodiment 39

The compound of any one of embodiments 1-38, wherein the first domain binds to HPTP-β, and the receptor tyrosine kinase agonist is a VEGF.

Embodiment 40

The compound of any one of embodiments 1-39, wherein the first domain binds to HPTP-β, and the receptor tyrosine kinase agonist is VEGF-A.

Embodiment 41

The compound of any one of embodiments 1-40, wherein the first domain comprises a sequence that is at least 80% identical to any one of SEQ ID NOS: 76-98.

Embodiment 42

The compound of any one of embodiments 1-41, wherein the first domain comprises a sequence that is at least 80% identical to SEQ ID NO: 76, SEQ ID NO: 77, SEQ ID NO: 78, SEQ ID NO: 79, or SEQ ID NO: 80.

Embodiment 43

The compound of any one of embodiments 1-42, wherein the first domain comprises a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87.

Embodiment 44

The compound of any one of embodiments 1-43, wherein the first domain comprises a sequence that is at least 80% identical to SEQ ID NO: 88, SEQ ID NO: 89, or SEQ ID NO: 90.

Embodiment 45

The compound of any one of embodiments 1-44, wherein the first domain comprises a sequence that is at least 80% identical to SEQ ID NO: 91, SEQ ID NO: 92, or SEQ ID NO: 93.

Embodiment 46

The compound of any one of embodiments 1-45, wherein the first domain comprises a sequence that is at least 80% identical to SEQ ID NO: 94, SEQ ID NO: 95, or SEQ ID NO: 96.

Embodiment 47

The compound of any one of embodiments 1-46, wherein the first domain comprises a sequence that is at least 80% identical to SEQ ID NO: 97 or SEQ ID NO: 98.

Embodiment 48

The compound of any one of embodiments 1-47, wherein the first domain comprises: (a) a sequence that is at least 80% identical to SEQ ID NO: 76, SEQ ID NO: 77, SEQ ID NO: 78, SEQ ID NO: 79, or SEQ ID NO: 80; (b) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (c) a sequence that is at least 80% identical to SEQ ID NO: 88, SEQ ID NO: 89, or SEQ ID NO: 90; (d) a sequence that is at least 80% identical to SEQ ID NO: 91, SEQ ID NO: 92, or SEQ ID NO: 93; (e) a sequence that is at least 80% identical to SEQ ID NO: 94, SEQ ID NO: 95, or SEQ ID NO: 96; and (f) a sequence that is at least 80% identical to SEQ ID NO: 97 or SEQ ID NO: 98.

Embodiment 49

The compound of any one of embodiments 1-48, wherein the second domain comprises a sequence that is at least 80% identical to SEQ ID NO: 22, SEQ ID NO: 23, SEQ ID NO: 28, or SEQ ID NO: 244.

Embodiment 50

The compound of any one of embodiments 1-49, wherein the second domain comprises a sequence that is at least 80% identical to any one of SEQ ID NOS: 99-146.

Embodiment 51

The compound of any one of embodiments 1-50, wherein the second domain comprises a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113.

Embodiment 52

The compound of any one of embodiments 1-51, wherein the second domain comprises a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123.

Embodiment 53

The compound of any one of embodiments 1-52, wherein the second domain comprises a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131.

Embodiment 54

The compound of any one of embodiments 1-53, wherein the second domain comprises a sequence that is at least 80% identical to SEQ ID NO: 132, SEQ ID NO: 133, SEQ ID NO: 134, SEQ ID NO: 135, SEQ ID NO: 136, or SEQ ID NO: 137.

Embodiment 55

The compound of any one of embodiments 1-54, wherein the second domain comprises a sequence that is at least 80% identical to SEQ ID NO: 138, SEQ ID NO: 139, SEQ ID NO: 140, SEQ ID NO: 141, SEQ ID NO: 142, or SEQ ID NO: 143.

Embodiment 56

The compound of any one of embodiments 1-55, wherein the second domain comprises a sequence that is at least 80% identical to SEQ ID NO: 144, SEQ ID NO: 145, or SEQ ID NO: 146.

Embodiment 57

The compound of any one of embodiments 1-56, wherein the second domain comprises: (a) a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113; (b) a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123; (c) a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131; (d) a sequence that is at least 80% identical to SEQ ID NO: 132, SEQ ID NO: 133, SEQ ID NO: 134, SEQ ID NO: 135, SEQ ID NO: 136, or SEQ ID NO: 137; (e) a sequence that is at least 80% identical to SEQ ID NO: 138, SEQ ID NO: 139, SEQ ID NO: 140, SEQ ID NO: 141, SEQ ID NO: 142, or SEQ ID NO: 143; and (f) a sequence that is at least 80% identical to SEQ ID NO: 144, SEQ ID NO: 145, or SEQ ID NO: 146.

Embodiment 58

The compound of any one of embodiments 1-57, wherein the second domain comprises a sequence that is at least 80% identical to SEQ ID NO: 147, SEQ ID NO: 148, or any one of SEQ ID NOS: 233-242.

Embodiment 59

The compound of any one of embodiments 1-58, wherein: (a) the first domain comprises a sequence that is at least 80% identical to any one of SEQ ID NOS: 76-98; and (b) the second domain comprises a sequence that is at least 80% identical to any one of SEQ ID NOS: 99-148 or any one of SEQ ID NOS: 233-242.

Embodiment 60

The compound of any one of embodiments 1-59, wherein: (a) the first domain comprises: (i) a sequence that is at least 80% identical to SEQ ID NO: 76, SEQ ID NO: 77, SEQ ID NO: 78, SEQ ID NO: 79, or SEQ ID NO: 80; (ii) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (iii) a sequence that is at least 80% identical to SEQ ID NO: 88, SEQ ID NO: 89, or SEQ ID NO: 90; (iv) a sequence that is at least 80% identical to SEQ ID NO: 91, SEQ ID NO: 92, or SEQ ID NO: 93; (v) a sequence that is at least 80% identical to SEQ ID NO: 94, SEQ ID NO: 95, or SEQ ID NO: 96; and (vi) a sequence that is at least 80% identical to SEQ ID NO: 97 or SEQ ID NO: 98; and (b) the second domain comprises: (i) a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113; (ii) a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123; (iii) a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131; (iv) a sequence that is at least 80% identical to SEQ ID NO: 132, SEQ ID NO: 133, SEQ ID NO: 134, SEQ ID NO: 135, SEQ ID NO: 136, or SEQ ID NO: 137; (v) a sequence that is at least 80% identical to SEQ ID NO: 138, SEQ ID NO: 139, SEQ ID NO: 140, SEQ ID NO: 141, SEQ ID NO: 142, or SEQ ID NO: 143; and (vi) a sequence that is at least 80% identical to SEQ ID NO: 144, SEQ ID NO: 145, or SEQ ID NO: 146.

Embodiment 61

The compound of any one of embodiments 1-60, wherein: (a) the first domain comprises a sequence that is at least 80% identical to SEQ ID NO: 76, SEQ ID NO: 77, SEQ ID NO: 78, SEQ ID NO: 79, or SEQ ID NO: 80; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 62

The compound of any one of embodiments 1-61, wherein: (a) the first domain comprises a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 63

The compound of any one of embodiments 1-62, wherein: (a) the first domain comprises a sequence that is at least 80% identical to SEQ ID NO: 88, SEQ ID NO: 89, or SEQ ID NO: 90; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 64

The compound of any one of embodiments 1-63, wherein: (a) the first domain comprises a sequence that is at least 80% identical to SEQ ID NO: 91, SEQ ID NO: 92, or SEQ ID NO: 93; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 65

The compound of any one of embodiments 1-64, wherein: (a) the first domain comprises a sequence that is at least 80% identical to SEQ ID NO: 94, SEQ ID NO: 95, or SEQ ID NO: 96; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 66

The compound of any one of embodiments 1-65, wherein: (a) the first domain comprises a sequence that is at least 80% identical to SEQ ID NO: 97 or SEQ ID NO: 98; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 67

The compound of any one of embodiments 1-66, wherein: (a) the first domain comprises: (i) a sequence that is at least 80% identical to SEQ ID NO: 76, SEQ ID NO: 77, SEQ ID NO: 78, SEQ ID NO: 79, or SEQ ID NO: 80; (ii) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (iii) a sequence that is at least 80% identical to SEQ ID NO: 88, SEQ ID NO: 89, or SEQ ID NO: 90; (iv) a sequence that is at least 80% identical to SEQ ID NO: 91, SEQ ID NO: 92, or SEQ ID NO: 93; (v) a sequence that is at least 80% identical to SEQ ID NO: 94, SEQ ID NO: 95, or SEQ ID NO: 96; and (vi) a sequence that is at least 80% identical to SEQ ID NO: 97 or SEQ ID NO: 98; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 68

The compound of any one of embodiments 1-67, wherein the compound comprises: (a) a heavy chain sequence that is at least 80% identical to SEQ ID NO: 149, SEQ ID NO: 150, SEQ ID NO: 151, or SEQ ID NO: 231; and (b) a light chain sequence that is at least 80% identical to SEQ ID NO: 17, SEQ ID NO: 18, SEQ ID NO: 19, or SEQ ID NO: 20.

Embodiment 69

The compound of any one of embodiments 1-4, 6-7, and 9-68, wherein the compound is a tetravalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 13, SEQ ID NO: 14, SEQ ID NO: 15, or SEQ ID NO: 16; (c) a sequence that is at least 80% identical to any one of SEQ ID NOS: 31-75; and (d) a sequence that is at least 80% identical to SEQ ID NO: 17, SEQ ID NO: 18, SEQ ID NO: 19, or SEQ ID NO: 20.

Embodiment 70

The compound of any one of embodiments 1-4, 6-7 and 9-69, wherein the compound is a tetravalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 13, SEQ ID NO: 14, SEQ ID NO: 15, or SEQ ID NO: 16, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a sequence that is at least 80% identical to SEQ ID NO: 17, SEQ ID NO: 18, SEQ ID NO: 19, or SEQ ID NO: 20.

Embodiment 71

The compound of any one of embodiments 1-4, 6-7, 9-67, and 69, wherein the compound is a tetravalent bispecific antibody comprising: (a) a first chain, wherein the first chain comprises a sequence that is at least 80% identical to SEQ ID NO: 13, SEQ ID NO: 14, SEQ ID NO: 15, or SEQ ID NO: 16; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 17, SEQ ID NO: 18, SEQ ID NO: 19, or SEQ ID NO: 20, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 72

The compound of any one of embodiments 1-3, 5-6, and 8-67, wherein the compound is a hexavalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 13, SEQ ID NO: 14, SEQ ID NO: 15, or SEQ ID NO: 16; (c) a sequence that is at least 80% identical to any one of SEQ ID NOS: 31-75; and (d) a sequence that is at least 80% identical to SEQ ID NO: 17, SEQ ID NO: 18, SEQ ID NO: 19, or SEQ ID NO: 20.

Embodiment 73

The compound of any one of embodiments 1-3, 5-6, 8-67, and 72, wherein the compound is a hexavalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 13, SEQ ID NO: 14, SEQ ID NO: 15, or SEQ ID NO: 16, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 17, SEQ ID NO: 18, SEQ ID NO: 19, or SEQ ID NO: 20, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 74

The compound of any one of embodiments 1-67, wherein the compound comprises: (a) a heavy chain sequence that is at least 80% identical to SEQ ID NO: 245 or any one of SEQ ID NOS: 13-16; and (b) a light chain sequence that is at least 80% identical to SEQ ID NO: 218, SEQ ID NO: 219, SEQ ID NO: 232, or SEQ ID NO: 243.

Embodiment 75

The compound of any one of embodiments 1-67, wherein the compound comprises: (a) a heavy chain sequence that is at least 80% identical to SEQ ID NO: 149, SEQ ID NO: 150, SEQ ID NO: 151, or SEQ ID NO: 231; and (b) a light chain sequence that is at least 80% identical to SEQ ID NO: 218, SEQ ID NO: 219, SEQ ID NO: 232, or SEQ ID NO: 243.

Embodiment 76

The compound of any one of embodiments 1-75, wherein a binding affinity ($K_D$) of the compound to HPTP-β is about 30 fM to about 70 nM.

Embodiment 77

The compound of any one of embodiments 1-76, wherein a binding affinity ($K_D$) of the compound to the VEGF is about 30 fM to about 70 nM.

Embodiment 78

The compound of any one of embodiments 1-75, wherein a binding affinity ($K_D$) of the compound to HPTP-β is about 30 fM to about 70 nM, and a binding affinity ($K_D$) of the compound to VEGF is about 30 fM to about 70 nM.

Embodiment 79

A method of treating a condition in a subject in need thereof, the method comprising administering to the subject a therapeutically-effective amount of the compound of any one of embodiments 1-78.

Embodiment 80

The method of embodiment 79, wherein the condition is an ocular condition.

Embodiment 81

The method of any one of embodiments 79-80, wherein the condition is diabetic retinopathy.

Embodiment 82

The method of any one of embodiments 79-80, wherein the condition is neovascularization.

Embodiment 83

The method of any one of embodiments 79-80, wherein the condition is vascular leak.

Embodiment 84

The method of any one of embodiments 79-80, wherein the condition is increased intraocular pressure.

Embodiment 85

The method of any one of embodiments 79-80, wherein the condition is ocular edema.

Embodiment 86

The method of any one of embodiments 79-80 and 85, wherein the condition is diabetic macular edema.

Embodiment 87

The method of any one of embodiments 79-80, wherein the condition is ocular hypertension.

Embodiment 88

The method of any one of embodiments 79-80, wherein the condition is ocular inflammation.

Embodiment 89

The method of any one of embodiments 79-80, wherein the condition is glaucoma.

Embodiment 90

The method of any one of embodiments 79-89, wherein the administration is to an eye of the subject.

Embodiment 91

The method of any one of embodiments 79-90, wherein the administration is intravitreal.

Embodiment 92

The method of any one of embodiments 79-89, wherein the administration is subcutaneous.

Embodiment 93

The method of any one of embodiments 79-90, wherein the administration is topical.

Embodiment 94

The method of any one of embodiments 79-93, wherein the subject is human.

Embodiment 95

The method of any one of embodiments 79-94, wherein the therapeutically-effective amount is from about 0.25 mg to about 200 mg.

Embodiment 96

The method of any one of embodiments 79-95, wherein the therapeutically-effective amount is from about 1 mg/kg to about 10 mg/kg.

Embodiment 97

The method of any one of embodiments 79-95, wherein the therapeutically-effective amount is from about 1 mg to about 50 mg.

Embodiment 98

The method of any one of embodiments 79-95, wherein the therapeutically-effective amount is from about 50 mg to about 200 mg.

Embodiment 99

The compound of any one of embodiments 1-67, wherein the compound comprises: (a) a heavy chain sequence that is at least 80% identical to SEQ ID NO: 254, SEQ ID NO: 255, SEQ ID NO: 256, or SEQ ID NO: 257; and (b) a light chain sequence that is at least 80% identical to SEQ ID NO: 250, SEQ ID NO: 251, SEQ ID NO: 252, or SEQ ID NO: 253.

Embodiment 100

The compound of any one of embodiments 1-4, 6-7, and 9-68, wherein the compound is a tetravalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 246, SEQ ID NO: 247, SEQ ID NO: 248, or SEQ ID NO: 249; (c) a sequence that is at least 80% identical to any one of SEQ ID NOS: 31-75; and (d) a sequence that is at least 80% identical to SEQ ID NO: 250, SEQ ID NO: 251, SEQ ID NO: 252, or SEQ ID NO: 253.

Embodiment 101

The compound of any one of embodiments 1-4, 6-7 and 9-69, wherein the compound is a tetravalent bispecific antibody comprising: (a) a first chain, wherein the first chain comprises a linker, wherein the linker comprises a sequence

145 that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 246, SEQ ID NO: 247, SEQ ID NO: 248, or SEQ ID NO: 249, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a sequence that is at least 80% identical to SEQ ID NO: 250, SEQ ID NO: 251, SEQ ID NO: 252, or SEQ ID NO: 253.

Embodiment 102

The compound of any one of embodiments 1-4, 6-7, 9-67, and 69, wherein the compound is a tetravalent bispecific antibody comprising: (a) a first chain, wherein the first chain comprises a sequence that is at least 80% identical to SEQ ID NO: 246, SEQ ID NO: 247, SEQ ID NO: 248, or SEQ ID NO: 249; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 250, SEQ ID NO: 251, SEQ ID NO: 252, or SEQ ID NO: 253, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 103

The compound of any one of embodiments 1-3, 5-6, and 8-67, wherein the compound is a hexavalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 246, SEQ ID NO: 247, SEQ ID NO: 248, or SEQ ID NO: 249; (c) a sequence that is at least 80% identical to any one of SEQ ID NOS: 31-75; and (d) a sequence that is at least 80% identical to SEQ ID NO: 250, SEQ ID NO: 251, SEQ ID NO: 252, or SEQ ID NO: 253.

146

Embodiment 104

The compound of any one of embodiments 1-3, 5-6, 8-67, and 72, wherein the compound is a hexavalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 246, SEQ ID NO: 247, SEQ ID NO: 248, or SEQ ID NO: 249, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 250, SEQ ID NO: 251, SEQ ID NO: 252, or SEQ ID NO: 253, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 105

The compound of any one of embodiments 1-67, wherein the compound comprises: (a) a heavy chain sequence that is at least 80% identical to SEQ ID NO: 262 or any one of SEQ ID NOS: 246-249; and (b) a light chain sequence that is at least 80% identical to SEQ ID NO: 258, SEQ ID NO: 259, SEQ ID NO: 261, or SEQ ID NO: 260.

Embodiment 106

The compound of any one of embodiments 1-3, 5-6, and 8-67, wherein the compound comprises: (a) a heavy chain sequence that is at least 80% identical to SEQ ID NO: 254, SEQ ID NO: 255, SEQ ID NO: 256, or SEQ ID NO: 257; and (b) a light chain sequence that is at least 80% identical to SEQ ID NO: 258, SEQ ID NO: 259, SEQ ID NO: 261, or SEQ ID NO: 260.

---

What is claimed is:

1. A method of treating an ocular condition in a subject in need thereof, the method comprising administering to the subject a therapeutically effective amount of an antibody comprising:
   (a) a first domain that activates Tie2; and
   (b) a second domain that specifically binds a VEGF and inhibits VEGF function.

2. The method of claim 1, wherein the ocular condition is diabetic retinopathy.

3. The method of claim 1, wherein the ocular condition is neovascularization.

4. The method of claim 1, wherein the ocular condition is vascular leak.

5. The method of claim 1, wherein the ocular condition is increased intraocular pressure.

6. The method of claim 1, wherein the ocular condition is ocular edema.

7. The method of claim 1, wherein the ocular condition is diabetic macular edema.

8. The method of claim 1, wherein the ocular condition is wet age-related macular degeneration.

9. The method of claim 1, wherein the ocular condition is ocular inflammation.

10. The method of claim 1, wherein the ocular condition is retinal vein occlusion.

11. The method of claim 1, wherein the administration is to an eye of the subject.

12. The method of claim 1, wherein the administration is intravitreal.

13. The method of claim 1, wherein the administration is subcutaneous.

14. The method of claim 1, wherein the administration is systemic.

15. The method of claim 1, wherein the subject is a human.

16. The method of claim 1, wherein the therapeutically effective amount is from about 0.25 mg to about 200 mg.

17. The method of claim 1, wherein the therapeutically effective amount is from about 1 mg/kg to about 10 mg/kg.

18. The method of claim 1, wherein the therapeutically effective amount is from about 1 mg to about 50 mg.

19. The method of claim 1, wherein the therapeutically effective amount is from about 50 mg to about 200 mg.

\* \* \* \* \*